United States Patent
Konradi et al.

(10) Patent No.: US 10,676,470 B2
(45) Date of Patent: *Jun. 9, 2020

(54) INHIBITORS OF LYSINE GINGIPAIN

(71) Applicant: Cortexyme, Inc., South San Francisco, CA (US)

(72) Inventors: Andrei W. Konradi, Burlingame, CA (US); Stephen S. Dominy, Novato, CA (US); Casey Crawford Lynch, San Francisco, CA (US); Craig Coburn, San Rafael, CA (US); Joseph Vacca, Philadelphia, PA (US)

(73) Assignee: CORTEXYME, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/399,821

(22) Filed: Apr. 30, 2019

(65) Prior Publication Data

US 2019/0322659 A1 Oct. 24, 2019

Related U.S. Application Data

(60) Continuation of application No. 15/996,660, filed on Jun. 4, 2018, now Pat. No. 10,301,301, which is a continuation of application No. 15/683,348, filed on Aug. 22, 2017, now Pat. No. 9,988,375, which is a division of application No. 14/875,416, filed on Oct. 5, 2015, now Pat. No. 9,758,473.

(60) Provisional application No. 62/060,483, filed on Oct. 6, 2014.

(51) Int. Cl.
| | | |
|---|---|---|
| C07C 233/62 | (2006.01) | |
| C07C 233/78 | (2006.01) | |
| C07C 247/16 | (2006.01) | |
| C07D 417/12 | (2006.01) | |
| C07D 277/64 | (2006.01) | |
| C07D 409/12 | (2006.01) | |
| C07D 213/50 | (2006.01) | |
| C07C 247/18 | (2006.01) | |
| C07D 277/24 | (2006.01) | |
| C07D 213/53 | (2006.01) | |
| C07D 277/28 | (2006.01) | |

(52) U.S. Cl.
CPC .......... *C07D 417/12* (2013.01); *C07C 233/62* (2013.01); *C07C 233/78* (2013.01); *C07C 247/16* (2013.01); *C07C 247/18* (2013.01); *C07D 213/50* (2013.01); *C07D 213/53* (2013.01); *C07D 277/24* (2013.01); *C07D 277/28* (2013.01); *C07D 277/64* (2013.01); *C07D 409/12* (2013.01); *C07B 2200/07* (2013.01); *C07C 2601/08* (2017.05)

(58) Field of Classification Search
CPC .... C07C 233/62; C07C 233/78; C07C 247/16
See application file for complete search history.

(56) References Cited

U.S. PATENT DOCUMENTS

| | | | |
|---|---|---|---|
| 5,451,410 A | 9/1995 | Milstein et al. | |
| 5,523,308 A | 6/1996 | Costanzo | |
| 5,827,866 A | 10/1998 | Costanzo et al. | |
| 6,323,219 B1 | 11/2001 | Costanzo | |
| 7,183,260 B2 | 2/2007 | Karanewsky et al. | |
| 9,758,473 B2* | 9/2017 | Konradi | C07D 417/12 |
| 9,988,375 B2 | 6/2018 | Konradi et al. | |
| 10,301,301 B2* | 5/2019 | Konradi | C07D 417/12 |
| 2003/0008829 A1 | 1/2003 | Costanzo et al. | |
| 2005/0059607 A1 | 3/2005 | Breslav et al. | |

(Continued)

FOREIGN PATENT DOCUMENTS

| | | |
|---|---|---|
| AU | 2005/334458 A1 | 3/2007 |
| EP | 0 195 212 A2 | 9/1986 |
| EP | 0 272 671 A2 | 6/1988 |

(Continued)

OTHER PUBLICATIONS

Adang et al., "Unique Overlap in the Prerequisites for Thrombin Inhibition and Oral Bioavailability Resulting in Potent Oral Antithrombotics," J. Med. Chem., 2002, vol. 45, pp. 4419-4432.
Berg et al., "Design and evaluation of *Trypanosoma brucei* metacaspase inhibitors," Bioorg. Med. Chem. Lett., Mar. 15, 2010; 20(6): 2001-2006.
Bialas et al., "Exploring the Sn Binding Pockets in Gingipains by Newly Developed Inhibitors: Structure-Based Design, Chemistry, and Activity," Journal of Medicinal Chemistry, 2006, vol. 49, No. 5, pp. 1744-1753.
Bland et al. Journal of the Chemical Society D: Chemical Communications 1971, 17, 1024-1025.

(Continued)

*Primary Examiner* — Matthew P Coughlin
(74) *Attorney, Agent, or Firm* — Kilpatrick Townsend & Stockton LLP

(57) ABSTRACT

The present invention relates generally to therapeutics targeting the bacterium *Porphyromonas gingivalis*, including its protease Lysine gingipain (Kgp), and their use for the treatment of disorders associated with *P. gingivalis* infection, including brain disorders such as Alzheimer's disease. In certain embodiments, the invention provides compounds according to Formula I, as described herein, and pharmaceutically acceptable salts thereof.

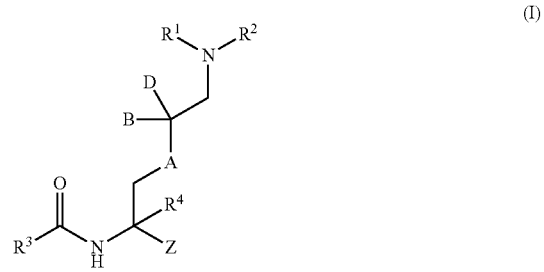

(I)

11 Claims, 8 Drawing Sheets

(56) References Cited

U.S. PATENT DOCUMENTS

2006/0084613 A1 4/2006 Ternansky et al.
2016/0096830 A1 4/2016 Konradi

FOREIGN PATENT DOCUMENTS

| EP | 530167 | A1 | 3/1993 |
|---|---|---|---|
| JP | 01-163162 | A1 | 6/1989 |
| RU | 2419626 | C2 | 5/2011 |
| WO | 92/04371 | A1 | 3/1992 |
| WO | 94/04172 | A1 | 3/1994 |
| WO | 93/00926 | A1 | 1/1996 |
| WO | 96/19483 | A1 | 6/1996 |
| WO | 96/30035 | A1 | 10/1996 |
| WO | 96/30396 | A1 | 10/1996 |
| WO | 96/37497 | A1 | 11/1996 |
| WO | 96/40741 | A1 | 12/1996 |
| WO | 96/40742 | A1 | 12/1996 |
| WO | 97/17363 | A1 | 5/1997 |
| WO | 98/05333 | A1 | 2/1998 |
| WO | 98/09987 | A1 | 3/1998 |
| WO | 99/26925 | A1 | 6/1999 |
| WO | 99/41276 | A1 | 8/1999 |
| WO | 00/44733 | A1 | 8/2000 |
| WO | 00/55124 | A2 | 9/2000 |
| WO | 2007/137080 | A2 | 11/2007 |
| WO | 2009/103432 | A2 | 8/2009 |
| WO | 2014/031784 | A1 | 2/2014 |
| WO | 2014/145257 | A2 | 9/2014 |
| WO | 2016/057413 | A2 | 4/2016 |

OTHER PUBLICATIONS

CAS Registry Entry for Registry No. 190903-94-7, which entered STN on Jul. 9, 1997.
CAS Registry Entry for Registry No. 190904-52-0, which entered STN on Jul. 9, 1997.
CAS Registry Entry for Registry No. 607393-00-0, which entered STN on Oct. 21, 2003.
Chauhan, Satendra S., "Enantioselective synthesis of (L)-Fmoc-α-Me-Lys(Boc)-OH via diastereoselective alkylation of oxazinone as a chiral auxiliary," Tetrahedron Letters, 2009, vol. 50, pp. 6913-6915.
Constanzo et al., "In-Depth Study of Tripeptide-Based α-Ketoheterocycles as Inhibitors of Thrombin. Effective Utilization of the $S_1$ Subsite and Its Implications to to Structure-Based Drug Design", Journal of Medicinal Chemistry, vol. 48, No. 6, Mar. 1, 2005, pp. 1-2.
Costanzo et al., "Potent, small-molecule inhibitors of human mast cell tryptase. Antiasthmatic action of a dipeptide-based transition-state analogue containing a benzothiazole keton," J. Med. Chem., Aug. 28, 2003;46(18), pp. 3865-3876.
Curtis et al., "Attenuation of the Virulence of *Porphyromonas gingivalis* by Using a Specific Synthetic Kgp Protease Inhibitor," Infection and Immunity, Dec. 2002, vol. 70., No. 12, pp. 6968-6975.
Duchene et al., "Analysis of Subpocket Selectivity and Identification of Potent Selective Inhibitors for Matriptase and Matriptasli-2," J. Med. Chem., vol. 57, Nov. 11, 2014, pp. 10198-10204.
Karukurichi et al., "Examination of the New A-(2'z-fluoro)vinyl Trigger With Lysine Decarboxylase: The Absolute Stereochemistry Dictates the Reaction Course", J.Am. Chem, Soc, vol. 129, No. 2, 2007, pp. 258-259.
Kataoka et al., "A novel, potent dual inhibitor of Arg-gingipains and Lys-gingipain as a promising agent for periodontal disease therapy," FASEB J, 2014, vol. 28, 3564-3578.
Ko et al., "Universal Peptidomimetics", J.Am. Chem. Soc, vol. 133, No. 3, 2011, pp. 462-477.
McGrath et al., "Structure-Guided Design of Peptide-Based Tryptase Inhibotors," Biochemistry, 2006, vol. 45, No. 19, pp. 5964-5973.
Mogami et al., "Effect of Thrombin on Human Amnion Mesenchymal Cells", Mouse Fetal Membranes, and Preterm Birth, The Journal of Biological Chemistry, vol. 289, No. 19, May 9, 2014, pp. 13295-13307.
PCT/US2015/054050, "International Search Report and Written Opinion", dated Jun. 30, 2016, 10 pages.
Sengupta et al., "Synthesis and biological evaluation of novel oxalamido derivatives as caspase-3 inhibitors," Indian J. Chem. Sec B, vol. 50B, Jul. 2011, pp. 901-905.
Singhrao et al., "Oral Inflammation, Tooth Loss, Risk Factors, and Association with Progression of Alzheimer's Disease," Journal of Alzheimer's Disease, 2014, vol. 42, pp. 723-737.
Teno et al., "Development of Active Center-Directed Inhibitors against Plasmin[1]," Chem. Pharm. Bull., 1991, vol. 39(9), pp. 2340-2346.
Wang et al., "Solid-Phase Synthesis of Peptide Vinyl Sulfones as Potential Inhibitors and Activity-Based Probes of Cysteine Proteases", Organic Letters. vol. 5, No. 5, Feb. 12, 2003, pp. 737-740.
Kadowaki et al., "Suppression of Pathogenicity of *Porphyromonas gingivalis* by Newly Developed Gingipain inhibitors," Mol Pharmacol, Dec. 2004, vol. 66, No. 6, pp. 1599-1606.

* cited by examiner

Compound 3

Compound 4

Compound 1

Compound 2

Compound 43

Compound 45

INHIBITORS OF LYSINE GINGIPAIN

CROSS-REFERENCES TO RELATED APPLICATIONS

The present application is a continuation of U.S. patent application Ser. No. 15/996,660, filed on Jun. 4, 2018, now U.S. Pat. No. 10,301,301 issued on May 28, 2019; which is a continuation of U.S. patent application Ser. No. 15/683,348 filed on Aug. 22, 2017, now U.S. Pat. No. 9,988,375 issued on Jun. 5, 2018; which is a division of U.S. patent application Ser. No. 14/875,416 filed on Oct. 5, 2015, now U.S. Pat. No. 9,758,473 issued on Sep. 12, 2017; which claims priority to U.S. Provisional Pat. Appl. No. 62/060,483 filed on Oct. 6, 2014, which applications are incorporated herein by reference in their entirety.

BACKGROUND OF THE INVENTION

Infection with the bacteria *Porphyromonas gingivalis* has been linked to the development of periodontal disease, Alzheimer's and other brain disorders, cardiovascular disease, diabetes, cancer, liver disease, kidney disease, preterm birth, arthritis, pneumonia and other disorders. *P. gingivalis* is an anaerobic asaccharolytic gram-negative rod bacterium that is known to infect the oral cavity and translocate systemically into coronary arteries, aorta, placental tissue, the brain, the kidneys, and the liver. The bacterium has also been identified in cancerous tissues and a mechanism has been proposed by which gingipains can trigger immortalization and metastasis. See: Gandhimadhi, et al. *Journal of Indian Society of Periodontology.* 2010; 14(2):114-120; Liao, et al., *Med Hypotheses,* 2009. 72(6): 732-5; Byrne, et al., *Oral Microbiol Immunol,* 2009. 24(6): 469-77; Mahendra, et al., *J Maxillofac Oral Surg,* 2009. 8(2): 108-13; Stelzel, et al., *J Periodontol,* 2002. 73(8): 868-70; Katz, et al., *Journal of Dental Research,* 2009. 88(6): 575-578; Poole, et al., *J Alzheimers Dis,* 2015, 43(1): 67-80; Ishikawa, et al., *Biochim Biophys Acta,* 2013. 1832(12): 2035-2043; Inaba, et al., *Cellular Microbiology,* 2014. 16(1): 131-145.

*P. gingivalis* produces extracellular proteases called gingipains, including Arginine Gingipain A (RgpA), Arginine Gingipain B (RgpB) and Lysine Gingipain (Kgp). Gingipains contribute to many functions of the organism including its survival and virulence. Gingipains can be secreted, transported to outer membrane surfaces of *P. gingivalis*, or released in outer membrane vesicles by the bacterium. Gingipains degrade a broad range of proteins (e.g., immunoglobulins, proteinase inhibitors, actin, and collagen) which can lead to cytoskeleton collapse and apoptosis in many types of cells. Recent research has demonstrated that small, peptide-derived inhibitors of Kgp can prevent gingipain-induced epithelial cell death. See: Travis, et al., *Adv Exp Med Biol,* 2000. 477: 455-65; Sheets, et al., *Infect Immun,* 2005. 73(3): 1543-52; Sheets, et al., *Infect Immun,* 2006. 74(10): 5667-78; Stathopoulou, et al., *BMC Microbiol,* 2009. 9: 107. New compounds for the inhibition of gingipain activity and the treatment of diseases associated with gingipain activity and *P. gingivalis* infection are needed. The present invention addresses this and other needs.

BRIEF SUMMARY OF THE INVENTION

In one aspect, the invention provides a compound according to Formula I:

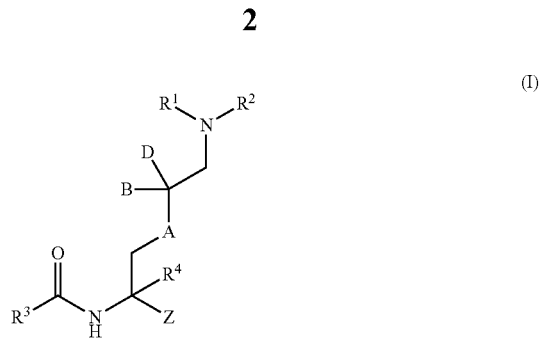

or a pharmaceutically acceptable salt thereof, wherein
Z is a thiol-reactive group or a masked thiol-reactive group;
A is selected from —$CH_2$— and —O—;
B and D are independently selected from hydrogen, halogen, $C_{1-4}$ haloalkyl, and $C_{1-4}$ haloalkoxy;
$R^1$ is selected from hydrogen and an amine protecting group;
$R^2$ is hydrogen; and
$R^3$ is selected from $C_{6-10}$ aryl, 5-to-12 membered heteroaryl, $C_{1-8}$ alkyl, $C_{3-8}$ cycloalkyl, 5-to-12 membered saturated heterocyclyl, -L-$R^5$, and —$OR^6$, wherein
L is selected from —O—, —NR—, $C_{1-4}$ alkylene, and 2- to 4-membered heteroalkylene, wherein R is selected from hydrogen and $C_{1-8}$ alkyl,
$R^5$ is selected from $C_{6-10}$ aryl, 5-to-12 membered heteroaryl, $C_{3-8}$ cycloalkyl, and 5-to-12 membered saturated heterocyclyl, and
—$OR^6$ and the carbonyl to which it is bonded form an amine protecting group,
and wherein $R^3$ is optionally substituted with one or more substituents selected from halo, —CN, —$NO_2$, —$N_3$, —OH, $R^a$, $R^b$, —$OR^a$, —$OR^b$, —$(CH_2)_kC(O)R^c$, —$NR^d(CH_2)_uC(O)R^c$, —$O(CH_2)_uC(O)R^c$, —$(CH_2)_k CONR^d R^d$, —$(CH_2)_k NR^d C(O)R^c$, —$NR^d(CH_2)_u CONR^d R^d$, —$NR^d(CH_2)_u NR^d C(O)R^c$, —$O(CH_2)_u CONR^d R^d$, —$O(CH_2)_u NR^d C(O)R^c$, —$(CH_2)_k S(O)_2 NR^d R^d$, —$(CH_2)_k NR^d S(O)_2 R^c$, —$(CH_2)_k S(O)_2 R^c$, —$(CH_2)_k S(O)R^c$, —$(CH_2)_k SR^d$, —$NR^d(CH_2)_u S(O)_2 NR^d R^d$, —$NR^d(CH_2)_u NR^d S(O)_2 R^c$, —$NR^d(CH_2)_u S(O)_2 R^c$, —$NR^d(CH_2)_u SR^d$, —$O(CH_2)_u S(O)_2 NR^d R^d$, —$O(CH_2)_u NR^d S(O)_2 R^c$, —$O(CH_2)_u S(O)_2 R^c$, —$O(CH_2)_u S(O)R^c$, and —$O(CH_2)_u SR^c$, wherein:
each $R^a$ is independently selected from $C_{1-4}$ alkyl and $C_{1-4}$ haloalkyl,
each $R^b$ is independently selected from $C_{3-6}$ cycloalkyl, $C_{3-6}$ halocycloalkyl, $C_{6-10}$ aryl, 5-to-12 membered heteroaryl, and 5-to-12 membered saturated heterocyclyl,
each $R^c$ is independently selected from —OH, $C_{1-8}$ alkyl, $C_{1-8}$ haloalkyl, $C_{3-8}$ cycloalkyl, $C_{3-8}$ halocycloalkyl, $C_{6-10}$ aryl, ($C_{6-10}$ aryl)-($C_{1-8}$ alkyl), 5-to-12 membered heteroaryl, and 5-to-12 membered saturated heterocyclyl,
each $R^d$ is independently selected from hydrogen and $C_{1-8}$ alkyl,
each subscript k is independently selected from 0, 1, 2, 3, 4, 5, and 6, and
each subscript u is independently selected from 1, 2, 3, 4, 5, and 6; and
$R^4$ is selected from hydrogen, halogen, $C_{1-4}$ alkyl, $C_{1-4}$ alkoxy, $C_{1-4}$ haloalkyl, and $C_{1-4}$ haloalkoxy;
provided that when Z is benzothiazol-2-yl-carbonyl, A is —$CH_2$—, and B, D, and $R^1$ are hydrogen, then $R^3$ is other than benzyloxy, substituted benzyloxy, or 1-(3-phenyl-propanoyl)piperidin-3-yl, and provided that when Z is phenoxymethyl-carbonyl or substituted phenoxymethyl-carbonyl, A is —CH$_2$—, and B and D are hydrogen, then R$^3$ is other than (2-phenyl)ethyl or substituted (2-phenyl)ethyl.

In some embodiments, the compound has a structure according to Formula Ic:

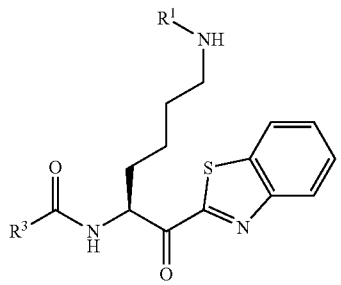

(Ic)

wherein R$^3$ is selected from C$_{6-10}$ aryl, 5-to-12 membered heteroaryl, C$_{3-8}$ cycloalkyl, 5-to-12 membered saturated heterocyclyl, and -L-R$^5$, wherein L is C$_{1-4}$ alkylene.

In some embodiments, the compound has a structure according to Formula Id:

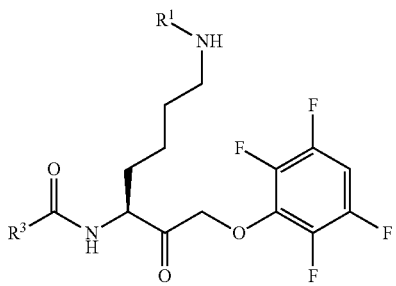

(Id)

wherein R$^3$ is selected from C$_{6-10}$ aryl, 5-to-12 membered heteroaryl, C$_{3-8}$ cycloalkyl, 5-to-12 membered saturated heterocyclyl, and -L-R$^5$, wherein L is C$_{1-4}$ alkylene.

In another aspect, the invention provides a pharmaceutical composition comprising a compound according to Formula I and a pharmaceutically acceptable excipient.

In another aspect, the invention provides a method of treating a disease or condition associated with *P. gingivalis* infection. The method includes administering to a subject an effective amount of a compound according to Formula Ie:

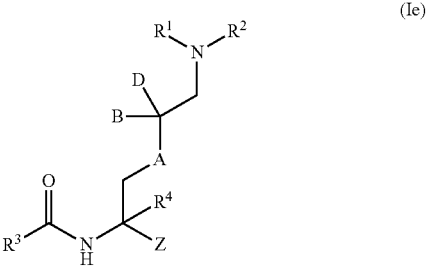

(Ie)

or a pharmaceutically acceptable salt thereof, wherein

Z is a thiol-reactive group or a masked thiol-reactive group;

A is selected from —CH$_2$— and —O—;

B and D are independently selected from hydrogen, halogen, C$_{1-4}$ haloalkyl, and C$_{1-4}$ haloalkoxy;

R$^1$ is selected from hydrogen and an amine protecting group;

R$^2$ is hydrogen; and

R$^3$ is selected from C$_{6-10}$ aryl, 5-to-12 membered heteroaryl, C$_{1-8}$ alkyl, C$_{3-8}$ cycloalkyl, 5-to-12 membered saturated heterocyclyl, -L-R$^5$, and —OR$^6$, wherein L is selected from —O—, —NR—, C$_{1-4}$ alkylene, and 2- to 4-membered heteroalkylene, wherein R is selected from hydrogen and C$_{1-8}$ alkyl, R$^5$ is selected from C$_{6-10}$ aryl, 5-to-12 membered heteroaryl, C$_{3-8}$ cycloalkyl, and 5-to-12 membered saturated heterocyclyl, and —OR$^6$ and the carbonyl to which it is bonded form an amine protecting group, and wherein R$^3$ is optionally substituted with one or more substituents selected from halo, —CN, —NO$_2$, —N$_3$, —OH, R$^a$, R$^b$, —OR$^a$, —OR$^b$, —(CH$_2$)$_k$C(O)R$^c$, —NR$^d$(CH$_2$)$_u$C(O)R$^c$, —O(CH$_2$)$_u$C(O)R$^c$, —(CH$_2$)$_k$CONR$^d$R$^d$, —(CH$_2$)$_k$NR$^d$C(O)R$^c$, —NR$^d$(CH$_2$)$_u$CONR$^d$R$^d$, —NR$^d$(CH$_2$)$_u$NR$^d$C(O)R$^c$, —O(CH$_2$)$_u$CONR$^d$R$^d$, —O(CH$_2$)$_u$NR$^d$C(O)R$^c$, —(CH$_2$)$_k$S(O)$_2$NR$^d$R$^d$, —(CH$_2$)$_k$NR$^d$S(O)$_2$R$^c$, —(CH$_2$)$_k$S(O)$_2$R$^c$, —(CH$_2$)$_k$S(O)R$^c$, —(CH$_2$)$_k$SR$^d$, —NR$^d$(CH$_2$)$_u$S(O)$_2$NR$^d$R$^d$, —NR$^d$(CH$_2$)$_u$NR$^d$S(O)$_2$R$^c$, —NR$^d$(CH$_2$)$_u$S(O)$_2$R$^c$, —NR$^d$(CH$_2$)$_u$S(O)R$^c$, —NR$^d$(CH$_2$)$_u$SR$^d$, —O(CH$_2$)$_u$S(O)$_2$NR$^d$R$^d$, —O(CH$_2$)$_u$NR$^d$S(O)$_2$R$^c$, —O(CH$_2$)$_u$S(O)$_2$R$^c$, —O(CH$_2$)$_u$S(O)R$^c$, and —O(CH$_2$)$_u$SR$^c$, wherein:

each R$^a$ is independently selected from C$_{1-4}$ alkyl and C$_{1-4}$ haloalkyl, each R$^b$ is independently selected from C$_{3-6}$ cycloalkyl, C$_{3-6}$ halocycloalkyl, C$_{6-10}$ aryl, 5-to-12 membered heteroaryl, and 5-to-12 membered saturated heterocyclyl, each R$^c$ is independently selected from —OH, C$_{1-8}$ alkyl, C$_{1-8}$ haloalkyl, C$_{3-8}$ cycloalkyl, C$_{3-8}$ halocycloalkyl, C$_{6-10}$ aryl, (C$_{6-10}$ aryl)-(C$_{1-8}$ alkyl), 5-to-12 membered heteroaryl, and 5-to-12 membered saturated heterocyclyl, each R$^d$ is independently selected from hydrogen and C$_{1-8}$ alkyl, each subscript k is independently selected from 0, 1, 2, 3, 4, 5, and 6, and each subscript u is independently selected from 1, 2, 3, 4, 5, and 6; and R$^4$ is selected from hydrogen, halogen, C$_{1-4}$ alkyl, C$_{1-4}$ alkoxy, C$_{1-4}$ haloalkyl, and C$_{1-4}$ haloalkoxy.

In some embodiments, the disease or condition associated with *P. gingivalis* infection is a brain disorder selected from Alzheimer's disease, Down's syndrome, epilepsy, autism, Parkinson's disease, essential tremor, fronto-temporal dementia, progressive supranuclear palsy, amyotrophic lateral sclerosis, Huntington's disease, multiple sclerosis, mild cognitive impairment, age associated memory impairment, chronic traumatic encephalopathy, stroke, Lewy Body disease, multiple system atrophy, schizophrenia, and depression. In some embodiments, the disease or condition associated with *P. gingivalis* infection is Alzheimer's disease.

BRIEF DESCRIPTION OF THE DRAWINGS

In FIG. 10, R represents a radionuclide or a radionuclide-substituted moiety (e.g., R=$^{18}$F-alkylene).

DETAILED DESCRIPTION OF THE INVENTION

I. General

Figure 1A:
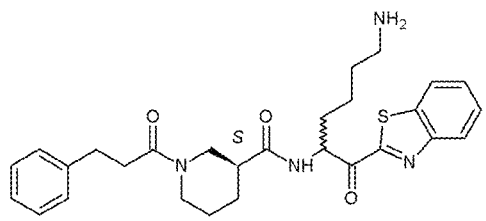
FIG. 1A shows the structure of 2-(N—[N-(3-phenylpropanoyl)-(S)-nipecotinyl]-(R)-lysinyl)-benzothiazole; compound 3.

Inhibition of Kgp with a variety of inhibitors has been shown to protect cells, prevent bacterial growth, increase immune system surveillance of the bacteria, and protect against reinfection. The present invention provides potent and selective nonpeptidic compounds with improved properties over previously described compounds. As demonstrated herein, Kgp inhibitors of the invention can prevent cell death caused by gingipains or *P. gingivalis* in an SH-SY5Y cell model. The compounds can be used to prevent cell death, inflammation, and other pathology in a variety of diseases associated with *P. gingivalis* infection, including aging-related conditions such as Alzheimer's disease.

II. Definitions

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. "Substituted alkyl" groups can be substituted with one or more groups selected from halo, hydroxy, amino, alkylamino, amido, acyl, nitro, cyano, and alkoxy.

As used herein, the term "alkoxy," by itself or as part of another substituent, refers to a group having the formula —OR, wherein R is alkyl. The term "lower alkoxyl" refers to an alkoxy radical having from one to seven carbons, e.g., methoxyl, ethoxyl, propoxyl, butoxyl, pentoxyl, hexoxyl, or heptoxyl radical.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. "Substituted cycloalkyl" groups can be substituted with one or more groups selected from halo, hydroxy, amino, alkylamino, amido, acyl, nitro, cyano, and alkoxy. The term "lower cycloalkyl" refers to a cycloalkyl radical having from three to seven carbons including, for example, cyclopropyl, cyclobutyl, cyclopentyl, cyclohexyl, and cycloheptyl.

As used herein, the term "alkylene" refers to an alkyl group, as defined above, linking at least two other groups (i.e., a divalent alkyl radical). The two moieties linked to the alkylene group can be linked to the same carbon atom or different carbon atoms of the alkylene group.

As used herein, the term "heteroalkyl," by itself or as part of another substituent, refers to an alkyl group of any suitable length and having from 1 to 3 heteroatoms such as N, O and S. For example, heteroalkyl can include ethers, thioethers and alkyl-amines. Additional heteroatoms can also be useful, including, but not limited to, B, Al, Si and P. The heteroatoms can be oxidized to form moieties such as, but not limited to, —S(O)— and —S(O)$_2$—. The heteroatom portion of the heteroalkyl can replace a hydrogen of the alkyl group to form a hydroxy, thio or amino group. Alternatively, the heteroatom portion can be the connecting atom, or be inserted between two carbon atoms.

As used herein, the term "heteroalkylene" refers to a heteroalkyl group, as defined above, linking at least two other groups (i.e., a divalent heteroalkyl radical). The two moieties linked to the heteroalkylene group can be linked to the same atom or different atoms of the heteroalkylene group.

As used herein, the terms "halo" and "halogen," by themselves or as part of another substituent, refer to a fluorine, chlorine, bromine, or iodine atom.

As used herein, the term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "haloalkoxy," by itself or as part of another substituent, refers to an alkoxy group where some or all of the hydrogen atoms are replaced with halogen atoms.

As used herein, the term "halocycloalkyl," by itself or as part of another substituent, refers to a cycloalkyl group where some or all of the hydrogen atoms are replaced with halogen atoms.

As used herein, the term "aryl," by itself or as part of another substituent, refers to an aromatic ring system having any suitable number of ring atoms and any suitable number of rings. Aryl groups can include any suitable number of ring atoms, such as 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. "Substituted aryl" groups can be substituted with one or more groups selected from halo, hydroxy, amino, alkylamino, amido, acyl, nitro, cyano, and alkoxy.

As used herein, the term "heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. "Substituted heteroaryl" groups can be substituted with one or more groups selected from halo, hydroxy, amino, alkylamino, amido, acyl, nitro, cyano, and alkoxy.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein the term "heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted. "Substituted heterocyclyl" groups can be substituted with one or more groups selected from halo, hydroxy, amino, oxo (=O), alkylamino, amido, acyl, nitro, cyano, and alkoxy.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "thiol-reactive group" refers to a functional group capable of forming a reversible or irreversible covalent bond with a thiol group (i.e., a group having the structure "—SH") such as the thiol group present in the α-sidechain of cysteine. Non-limiting examples of thiol reactive groups include thiazol-2-yl-carbonyl; benzothiazol-2-yl-carbonyl; oxazol-2-yl-carbonyl; benzooxazol-2-yl-carbonyl; pyridin-2-yl-carbonyl; pyrimidin-4-yl-carbonyl; pyrimidin-2-yl-carbonyl; isoxazol-5-yl-carbonyl; isoxazol-3-yl-carbonyl; 1,2,4-oxadiazol-3-yl-carbonyl; 1,2,4-oxadiazol-5-yl-carbonyl; maleimidyl; pyridinyldisulfanyl (including pyridin-2-yldisulfanyl); cyano; ethynyl; fluoromethyl-carbonyl; acyloxymethyl-carbonyl; aryloxymethyl-carbonyl; alkylsulfonyl-vinyl; and arylsulfonyl-vinyl. Other thiol-reactive groups are known to those of skill in the art including, for example, those described by Hermanson (*Bioconjugate Techniques*, 3$^{rd}$ Ed. 2013, Academic Press, San Diego).

A "masked thiol-reactive group" refers to a non-reactive precursor moiety that can be converted into a functional group capable of forming a reversible or irreversible covalent bond with a thiol group.

As used herein, the term "amine protecting group" refers to a chemical moiety that renders an amino group unreactive, but is also removable so as to restore the amino group. Examples of amine protecting groups include, but are not limited to, benzyloxycarbonyl, 9-fluorenylmethyloxycarbonyl (Fmoc), tert-butyloxycarbonyl (Boc), allyloxycarbonyl (Alloc), acetamido, phthalimido, and the like. Other amine protecting groups are known to those of skill in the art including, for example, those described by Green and Wuts (*Protective Groups in Organic Synthesis*, 4$^{th}$ Ed. 2007, Wiley-Interscience, New York).

As used herein, the term "carbonyl," by itself or as part of another substituent, refers to —C(O)—, i.e., a carbon atom double-bonded to oxygen and bound to two other groups in the moiety having the carbonyl.

As used herein, the term "amino" refers to a moiety —NR$_3$, wherein each R group is H or alkyl. An amino moiety can be ionized to form the corresponding ammonium cation.

As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)NR$_2$, wherein each R group is H or alkyl.

As used herein, the term "nitro" refers to the moiety —NO$_2$.

As used herein, the term "oxo" refers to an oxygen atom that is double-bonded to a compound (i.e., O═).

As used herein, the term "pharmaceutically acceptable excipient" refers to a substance that aids the administration of an active agent to a subject. By "pharmaceutically acceptable," it is meant that the excipient is compatible with the other ingredients of the formulation and is not deleterious to the recipient thereof. Pharmaceutical excipients useful in the present invention include, but are not limited to, binders, fillers, disintegrants, lubricants, glidants, coatings, sweeteners, flavors and colors.

As used herein, the term "salt" refers to acid or base salts of the compounds of the invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the terms "*Porphyromonas gingivalis*" and "*P. gingivalis*" refer to the gram-negative asaccharolytic bacterium that is recognized as a key causative microbe in the pathogenesis of periodontitis and related conditions. "*P. gingivalis* infection" refers to the invasion and colonization of *P. gingivalis* in a bodily tissue such as the gums or the brain. *P. gingivalis* infection is frequently characterized by subsequent tissue injury and disease.

As used herein, the term "gingipain" refers to cysteine proteases expressed by *P. gingivalis* having trypsin-like specificity (i.e., Lys-Xaa and Arg-Xaa). Gingipains are recognized as the major virulence factors of the *P. gingivalis* and contribute to bacterial attachment and colonization, nutrient acquisition, evasion of host defenses, and tissue invasion. The terms "lysine gingipain" and "Kgp" are used interchangeably to refer to the *P. gingivalis* lysine-specific gingipain known by EC number EC 3.4.22.47.

As used herein, the terms "treat," "treatment," and "treating" refer to any indicia of success in the treatment or amelioration of an injury, pathology, condition, or symptom (e.g., cognitive impairment), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom. The treatment or amelioration of symptoms can be based on any objective or subjective parameter; including, e.g., the result of a physical examination.

As used herein the terms "effective amount" and "therapeutically effective amount" refer to a dose of a compound such as a Kgp inhibitor that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); Goodman & Gilman's *The Pharmacological Basis of Therapeutics*, 11$^{th}$ Edition, 2006, Brunton, Ed., McGraw-Hill; and *Remington: The Science and Practice of Pharmacy*, 21$^{st}$ Edition, 2005, Hendrickson, Ed., Lippincott, Williams & Wilkins).

As used herein, the term "Alzheimer's disease" refers to a progressive disease of the central nervous system in humans and other mammals. It is manifested by dementia (especially in the elderly); disorientation; loss of memory; difficulty with language, calculation, or visual-spatial skills; and psychiatric manifestations. Alzheimer's disease is associated with progressive neurodegeneration and characteristic pathology, namely beta amyloid plaques and tau tangles.

As used herein, the term "subject" refers to animals such as mammals, including, but not limited to, primates (e.g., humans), cows, sheep, goats, horses, dogs, cats, rabbits, rats, mice and the like.

The terms "about" and "around," as used herein to modify a numerical value, indicate a close range surrounding that explicit value. If "X" were the value, "about X" or "around X" would indicate a value from 0.9X to 1.1X, and more preferably, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

III. Inhibitors of Lysine Gingipain

In one aspect, the invention provides a compound according to Formula I:

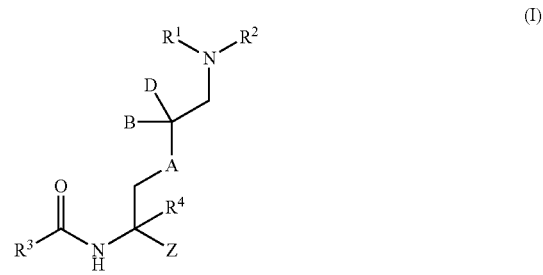

or a pharmaceutically acceptable salt thereof, wherein
Z is a thiol-reactive group or a masked thiol-reactive group;
A is selected from —CH$_2$— and —O—;
B and D are independently selected from hydrogen, halogen, C$_{1-4}$ haloalkyl, and C$_{1-4}$ haloalkoxy;
R$^1$ is selected from hydrogen and an amine protecting group;

R² is hydrogen; and
R³ is selected from C₆₋₁₀ aryl, 5-to-12 membered heteroaryl, C₁₋₈ alkyl, C₃₋₈ cycloalkyl, 5-to-12 membered saturated heterocyclyl, -L-R⁵, and —OR⁶, wherein
L is selected from —O—, —NR—, C₁₋₄ alkylene, and 2- to 4-membered heteroalkylene, wherein R is selected from hydrogen and C₁₋₈ alkyl,
R⁵ is selected from C₆₋₁₀ aryl, 5-to-12 membered heteroaryl, C₃₋₈ cycloalkyl, and 5-to-12 membered saturated heterocyclyl, and
—OR⁶ and the carbonyl to which it is bonded form an amine protecting group,
and wherein R³ is optionally substituted with one or more substituents selected from halo, —CN, —NO₂, —N₃, —OH, Rᵃ, Rᵇ, —ORᵃ, —ORᵇ, —(CH₂)ₖC(O)Rᶜ, —NRᵈ(CH₂)ᵤC(O)Rᶜ, —O(CH₂)ᵤC(O)Rᶜ, —(CH₂)ₖCONRᵈRᵈ, —(CH₂)ₖNRᵈC(O)Rᶜ, —NRᵈ(CH₂)ᵤCONRᵈRᵈ, —NRᵈ(CH₂)ᵤNRᵈC(O)Rᶜ, —O(CH₂)ᵤCONRᵈRᵈ, —O(CH₂)ᵤNRᵈC(O)Rᶜ, —(CH₂)ₖS(O)₂NRᵈRᵈ, —(CH₂)ₖNRᵈS(O)₂Rᶜ, —(CH₂)ₖS(O)₂Rᶜ, —(CH₂)ₖS(O)Rᶜ, —(CH₂)ₖSRᵈ, —NRᵈ(CH₂)ᵤS(O)₂NRᵈRᵈ, —NRᵈ(CH₂)ᵤNRᵈS(O)₂Rᶜ, —NRᵈ(CH₂)ᵤS(O)₂Rᶜ, —NRᵈ(CH₂)ᵤS(O)Rᶜ, —NRᵈ(CH₂)ᵤSRᵈ, —O(CH₂)ᵤS(O)NRᵈRᵈ, —O(CH₂)ᵤNRᵈS(O)₂Rᶜ, —O(CH₂)ᵤS(O)₂Rᶜ, —O(CH₂)ᵤS(O)Rᶜ, and —O(CH₂)ᵤSRᶜ, wherein:
each Rᵃ is independently selected from C₁₋₄ alkyl and C₁₋₄ haloalkyl,
each Rᵇ is independently selected from C₃₋₆ cycloalkyl, C₃₋₆ halocycloalkyl, C₆₋₁₀ aryl, 5-to-12 membered heteroaryl, and 5-to-12 membered saturated heterocyclyl,
each Rᶜ is independently selected from —OH, C₁₋₈ alkyl, C₁₋₈ haloalkyl, C₃₋₈ cycloalkyl, C₃₋₈ halocycloalkyl, C₆₋₁₀ aryl, (C₆₋₁₀ aryl)-(C₁₋₈ alkyl), 5-to-12 membered heteroaryl, and 5-to-12 membered saturated heterocyclyl,
each Rᵈ is independently selected from hydrogen and C₁₋₈ alkyl,
each subscript k is independently selected from 0, 1, 2, 3, 4, 5, and 6, and
each subscript u is independently selected from 1, 2, 3, 4, 5, and 6; and
R⁴ is selected from hydrogen, halogen, C₁₋₄ alkyl, C₁₋₄ alkoxy, C₁₋₄ haloalkyl, and C₁₋₄ haloalkoxy;
provided that when Z is benzothiazol-2-yl-carbonyl, A is —CH₂—, and B, D, and R¹ are hydrogen, then R³ is other than benzyloxy, substituted benzyloxy, or 1-(3-phenyl-propanoyl)piperidin-3-yl, and
provided that when Z is phenoxymethyl-carbonyl or substituted phenoxymethyl-carbonyl, A is —CH₂—, and B and D are hydrogen, then R³ is other than (2-phenyl) ethyl or substituted (2-phenyl)ethyl.

In some embodiments, the compound of Formula I has a structure according to Formula Ia:

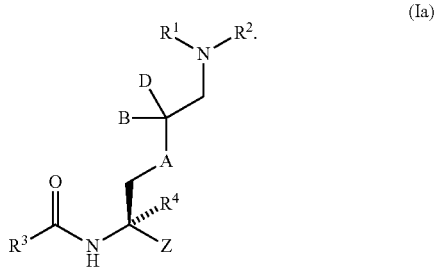

(Ia)

In some embodiments, the compound of Formula I has a structure according to Formula Ib:

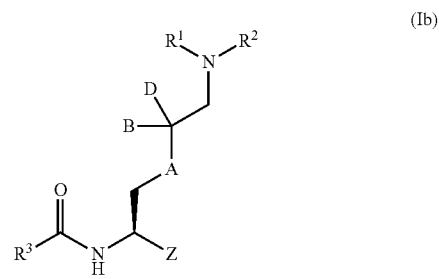

(Ib)

or a pharmaceutically acceptable salt thereof, wherein
B and D are independently selected from hydrogen, halogen, halomethyl, and halomethoxy.

In some embodiments, the invention provides compounds of Formula I, Formula Ia, or Formula Ib, and pharmaceutically acceptable salts thereof, wherein Z is selected from benzothiazol-2-yl-carbonyl; thiazol-2-yl-carbonyl; oxazol-2-yl-carbonyl; benzooxazol-2-yl-carbonyl; pyridin-2-yl-carbonyl; pyrimidin-4-yl-carbonyl; pyrimidin-2-yl-carbonyl; isoxazol-5-yl-carbonyl; isoxazol-3-yl-carbonyl; 1,2,4-oxadiazol-3-yl-carbonyl; 1,2,4-oxadiazol-5-yl-carbonyl; cyano; ethynyl; fluoromethyl-carbonyl; acyloxymethyl-carbonyl; aryloxymethyl-carbonyl; alkylsulfonyl-vinyl; and arylsulfonyl-vinyl; each of which is optionally substituted with one or more substituents selected from C₁₋₄ alkyl, C₁₋₄ alkoxy, C₁₋₄ haloalkyl, C₁₋₄ haloalkoxy, halogen, and —N₃.

In some embodiments, Z is selected from benzothiazol-2-yl-carbonyl, halogen-substituted aryloxymethyl-carbonyl, pyridin-2-yl-carbonyl, and thiazol-2-yl-carbonyl.

In some embodiments, the invention provides compounds of Formula I or Formula Ia as described above, and pharmaceutically acceptable salts thereof, wherein Z is selected from benzothiazol-2-yl-carbonyl; thiazol-2-yl-carbonyl; oxazol-2-yl-carbonyl; benzooxazol-2-yl-carbonyl; pyridin-2-yl-carbonyl; pyrimidin-4-yl-carbonyl; pyrimidin-2-yl-carbonyl; isoxazol-5-yl-carbonyl; isoxazol-3-yl-carbonyl; 1,2,4-oxadiazol-3-yl-carbonyl; 1,2,4-oxadiazol-5-yl-carbonyl; cyano; ethynyl; fluoromethyl-carbonyl; acyloxymethyl-carbonyl; aryloxymethyl-carbonyl; alkylsulfonyl-vinyl; and arylsulfonyl-vinyl; wherein Z is optionally substituted with one or more substituents selected from C₁₋₄ alkyl, C₁₋₄ alkoxy, C₁₋₄ haloalkyl, C₁₋₄ haloalkoxy, halogen, and —N₃; and wherein R³ is selected from C₆₋₁₀ aryl, 5-to-12 membered heteroaryl, C₃₋₈ cycloalkyl, 5-to-12 membered saturated heterocyclyl, and -L-R⁵. In some such embodiments, R¹ and R² are H; B and D are independently selected from hydrogen and fluoro; A is —CH₂—; and R⁴ is selected from hydrogen and C₁₋₄ alkyl.

In some embodiments, the invention provides compounds of Formula Ib as described above, and pharmaceutically acceptable salts thereof, wherein Z is selected from benzothiazol-2-yl-carbonyl; thiazol-2-yl-carbonyl; oxazol-2-yl-carbonyl; benzooxazol-2-yl-carbonyl; pyridin-2-yl-carbonyl; pyrimidin-4-yl-carbonyl; pyrimidin-2-yl-carbonyl; isoxazol-5-yl-carbonyl; isoxazol-3-yl-carbonyl; 1,2,4-oxadiazol-3-yl-carbonyl; 1,2,4-oxadiazol-5-yl-carbonyl; cyano; ethynyl; fluoromethyl-carbonyl; acyloxymethyl-carbonyl; aryloxymethyl-carbonyl; alkylsulfonyl-vinyl; and arylsulfonyl-vinyl; wherein Z is optionally substituted with one or more substituents selected from C₁₋₄ alkyl, C₁₋₄ alkoxy, C₁₋₄ haloalkyl, C₁₋₄ haloalkoxy, halogen, and —N₃;

and wherein $R^3$ is selected from $C_{6-10}$ aryl, 5-to-12 membered heteroaryl, $C_{3-8}$ cycloalkyl, 5-to-12 membered saturated heterocyclyl, and -L-$R^5$. In some such embodiments, $R^1$ and $R^2$ are H; B and D are independently selected from hydrogen and fluoro; and A is —CH$_2$—.

In some embodiments, the invention provides compounds of Formula I or Formula Ia as described above, and pharmaceutically acceptable salts thereof, wherein Z is selected from benzothiazol-2-yl-carbonyl, halogen-substituted aryloxymethyl-carbonyl, pyridin-2-yl-carbonyl, and thiazol-2-yl-carbonyl; and wherein $R^3$ is selected from $C_{6-10}$ aryl, 5-to-12 membered heteroaryl, $C_{3-8}$ cycloalkyl, 5-to-12 membered saturated heterocyclyl, and -L-$R^5$. In some such embodiments, $R^1$ and $R^2$ are H; B and D are independently selected from hydrogen and fluoro; A is —CH$_2$—; and $R^4$ is selected from hydrogen and $C_{1-4}$ alkyl.

In some embodiments, the invention provides compounds of Formula Ib as described above, and pharmaceutically acceptable salts thereof, wherein Z is selected from benzothiazol-2-yl-carbonyl, halogen-substituted aryloxymethyl-carbonyl, pyridin-2-yl-carbonyl, and thiazol-2-yl-carbonyl; and wherein $R^3$ is selected from $C_{6-10}$ aryl, 5-to-12 membered heteroaryl, $C_{3-8}$ cycloalkyl, 5-to-12 membered saturated heterocyclyl, and -L-$R^5$. In some such embodiments, $R^1$ and $R^2$ are H; B and D are independently selected from hydrogen and fluoro; and A is —CH$_2$—.

In some embodiments, the invention provides compounds of Formula I or Formula Ia as described above, and pharmaceutically acceptable salts thereof, wherein Z is selected from benzothiazol-2-yl-carbonyl; thiazol-2-yl-carbonyl; oxazol-2-yl-carbonyl; benzooxazol-2-yl-carbonyl; pyridin-2-yl-carbonyl; pyrimidin-4-yl-carbonyl; pyrimidin-2-yl-carbonyl; isoxazol-5-yl-carbonyl; isoxazol-3-yl-carbonyl; 1,2,4-oxadiazol-3-yl-carbonyl; 1,2,4-oxadiazol-5-yl-carbonyl; cyano; ethynyl; fluoromethyl-carbonyl; acyloxymethyl-carbonyl; aryloxymethyl-carbonyl; alkylsulfonyl-vinyl; and arylsulfonyl-vinyl; wherein Z is optionally substituted with one or more substituents selected from $C_{1-4}$ alkyl, $C_{1-4}$ alkoxy, $C_{1-4}$ haloalkyl, $C_{1-4}$ haloalkoxy, halogen, and —N$_3$; and wherein $R^3$ is selected from $C_{6-10}$ aryl, 5-to-12 membered heteroaryl, $C_{3-8}$ cycloalkyl, 5-to-12 membered saturated heterocyclyl, and -L-$R^5$. In some such embodiments, $R^1$ and $R^2$ are H; B and D are independently selected from hydrogen and fluoro; and A is —CH$_2$—. In some such embodiments, $R^4$ is selected from hydrogen and methyl.

In some embodiments, the invention provides compounds of Formula I or Formula Ia as described above, and pharmaceutically acceptable salts thereof, wherein Z is selected from benzothiazol-2-yl-carbonyl, halogen-substituted aryloxymethyl-carbonyl, pyridin-2-yl-carbonyl, and thiazol-2-yl-carbonyl; and wherein $R^3$ is selected from $C_{6-10}$ aryl, 5-to-12 membered heteroaryl, $C_{3-8}$ cycloalkyl, 5-to-12 membered saturated heterocyclyl, and -L-$R^5$. In some such embodiments, $R^1$ and $R^2$ are H; B and D are independently selected from hydrogen and fluoro; and A is —CH$_2$—. In some such embodiments, $R^4$ is selected from hydrogen and methyl.

In some embodiments, the invention provides compounds of Formula I or Formula Ia as described above, and pharmaceutically acceptable salts thereof, wherein:
A is —CH$_2$—;
B and D are hydrogen;
Z is selected from benzothiazol-2-yl-carbonyl, halogen-substituted aryloxymethyl-carbonyl, pyridin-2-yl-carbonyl, and thiazol-2-yl-carbonyl;
$R^1$ and $R^2$ are H; and
$R^3$ is selected from $C_{6-10}$ aryl, 5-to-12 membered heteroaryl, $C_{3-8}$ cycloalkyl, 5-to-12 membered saturated heterocyclyl, and -L-$R^5$. In some such embodiments, $R^4$ is hydrogen or methyl. In some such embodiments, $R^4$ is hydrogen.

In some embodiments, the invention provides compounds of Formula Ib as described above, and pharmaceutically acceptable salts thereof, wherein:
A is —CH$_2$—;
B and D are hydrogen;
Z is selected from benzothiazol-2-yl-carbonyl, halogen-substituted aryloxymethyl-carbonyl, pyridin-2-yl-carbonyl, and thiazol-2-yl-carbonyl;
$R^1$ and $R^2$ are H; and
$R^3$ is selected from $C_{6-10}$ aryl, 5-to-12 membered heteroaryl, $C_{3-8}$ cycloalkyl, 5-to-12 membered saturated heterocyclyl, and -L-$R^5$.

In some embodiments, the invention provides compounds of Formula I or Formula Ia as described above, and pharmaceutically acceptable salts thereof, wherein:
A is —CH$_2$—;
B is hydrogen;
D is fluoro;
Z is selected from benzothiazol-2-yl-carbonyl, halogen-substituted aryloxymethyl-carbonyl, pyridin-2-yl-carbonyl, and thiazol-2-yl-carbonyl;
$R^1$ and $R^2$ are H; and
$R^3$ is selected from $C_{6-10}$ aryl, 5-to-12 membered heteroaryl, $C_{3-8}$ cycloalkyl, 5-to-12 membered saturated heterocyclyl, and -L-$R^5$. In some such embodiments, $R^4$ is hydrogen or methyl. In some such embodiments, $R^4$ is hydrogen.

In some embodiments, the invention provides compounds of Formula Ib as described above, and pharmaceutically acceptable salts thereof, wherein:
A is —CH$_2$—;
B is hydrogen;
D is fluoro;
Z is selected from benzothiazol-2-yl-carbonyl, halogen-substituted aryloxymethyl-carbonyl, pyridin-2-yl-carbonyl, and thiazol-2-yl-carbonyl;
$R^1$ and $R^2$ are H; and
$R^3$ is selected from $C_{6-10}$ aryl, 5-to-12 membered heteroaryl, $C_{3-8}$ cycloalkyl, 5-to-12 membered saturated heterocyclyl, and -L-$R^5$.

In some embodiments, the invention provides compounds of Formula I or Formula Ia as described above, and pharmaceutically acceptable salts thereof, wherein:
A is —CH$_2$—;
B is hydrogen;
D is hydrogen or fluoro;
Z is benzothiazol-2-yl-carbonyl or halogen-substituted aryloxymethyl-carbonyl;
$R^1$ and $R^2$ are H;
$R^3$ is selected from cyclohexyl, cyclopentyl, morpholino, phenyl, piperidinyl, pyridinyl, tetrahydrofuranyl, tetrahydropyranyl, 1,2,3,4-tetrahydronaphthyl, and thiazolyl, each of which is optionally substituted with 1-3 members selected from the group consisting of methyl, methoxy, trifluoromethyl, acetyl, and —N$_3$; and
$R^4$ is hydrogen or methyl. In some such embodiments, $R^4$ is hydrogen. In some such embodiments, D and $R^4$ are hydrogen. In some such embodiments, D and $R^4$ are hydrogen, and Z is (2,3,5,6-tetrafluorophenoxy)methyl-carbonyl.

In some embodiments, the invention provides compounds of Formula Ib as described above, and pharmaceutically acceptable salts thereof, wherein:

A is —CH$_2$—;

B is hydrogen;

D is hydrogen or fluoro;

Z is benzothiazol-2-yl-carbonyl or halogen-substituted aryloxymethyl-carbonyl;

R$^1$ and R$^2$ are H; and

R$^3$ is selected from cyclohexyl, cyclopentyl, morpholino, phenyl, piperidinyl, pyridinyl, tetrahydrofuranyl, tetrahydropyranyl, 1,2,3,4-tetrahydronaphthyl, and thiazolyl, each of which is optionally substituted with 1-3 members selected from the group consisting of methyl, methoxy, trifluoromethyl, acetyl, and —N$_3$. In some such embodiments, D is hydrogen. In some such embodiments, D is hydrogen and Z is (2,3,5,6-tetrafluorophenoxy)methyl-carbonyl.

In some embodiments, the compound of Formula I has a structure according to Formula Ic:

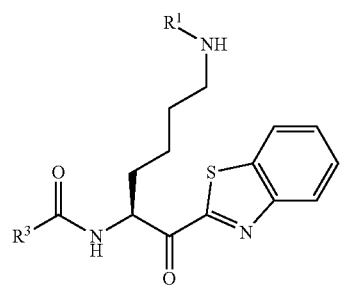

(Ic)

or a pharmaceutically acceptable salt thereof, wherein R$^3$ is selected from C$_{6-10}$ aryl, 5-to-12 membered heteroaryl, C$_{3-8}$ cycloalkyl, 5-to-12 membered saturated heterocyclyl, and -L-R$^5$, wherein L is C$_{1-4}$ alkylene.

In some embodiments, the invention provides a compound of Formula Ic, or a pharmaceutically acceptable salt thereof, wherein R$^3$ is selected from cyclohexyl, cyclopentyl, morpholino, phenyl, piperidinyl, pyridinyl, tetrahydrofuranyl, tetrahydropyranyl, 1,2,3,4-tetrahydronaphthyl, and thiazolyl, each of which is optionally substituted with 1-3 members selected from methyl, methoxy, trifluoromethyl, acetyl, and —N$_3$.

In some embodiments, the compound of Formula I, Formula Ia, Formula Ib, or Formula Ic is selected from:

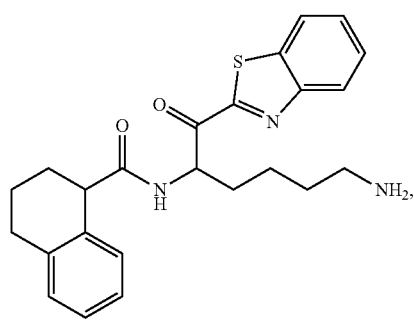

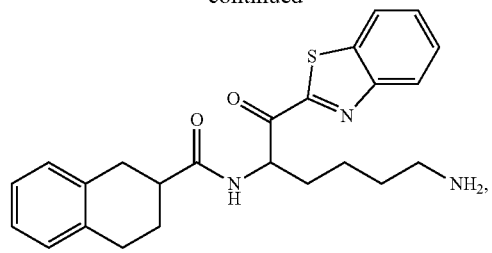

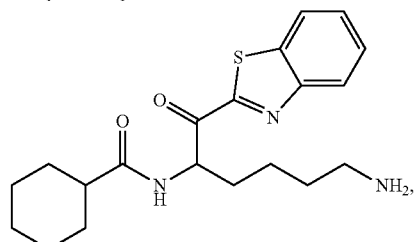

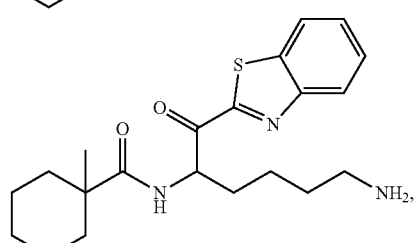

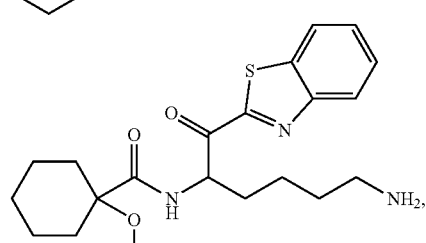

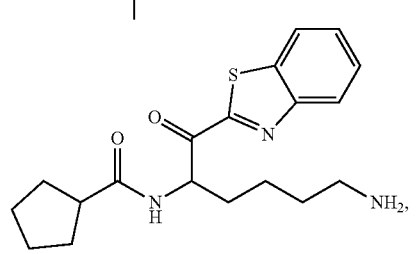

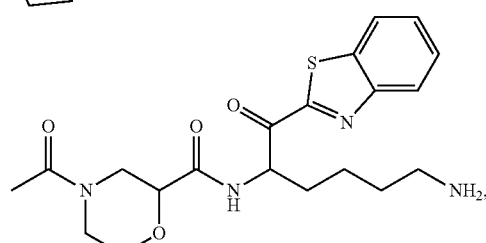

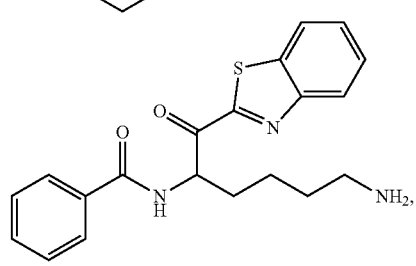

-continued
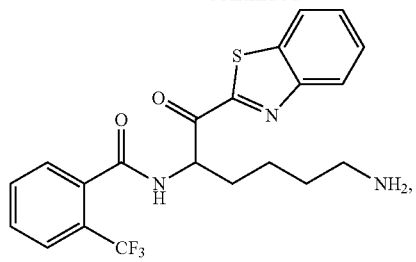
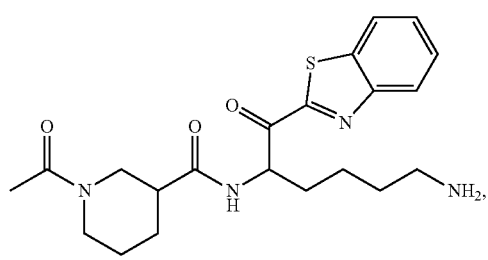
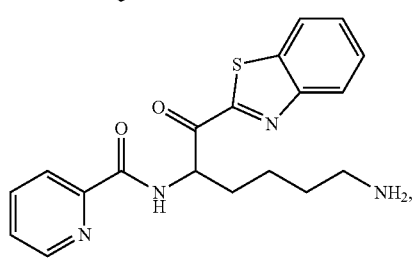
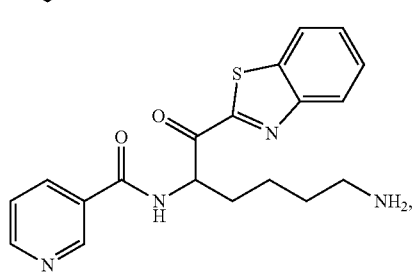
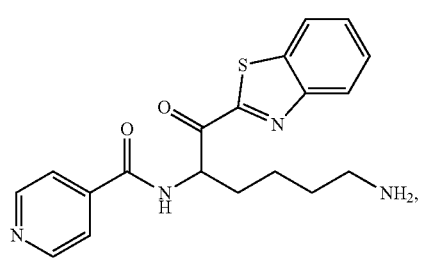
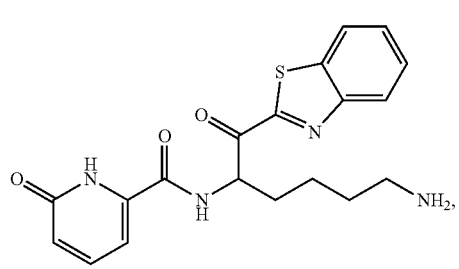
-continued
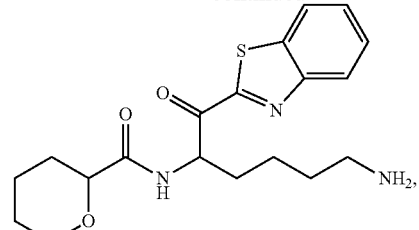
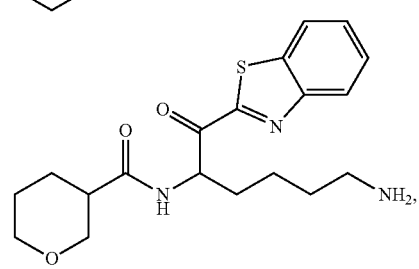
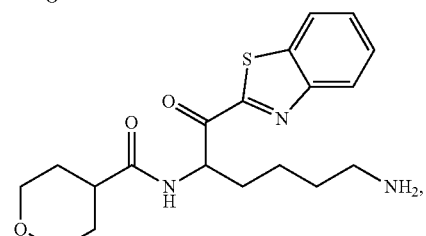
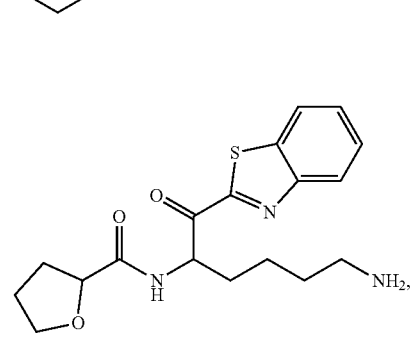
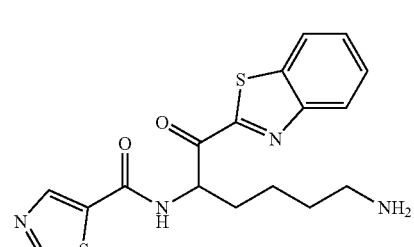
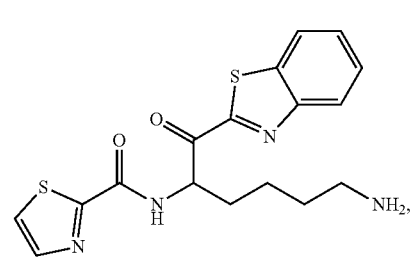
and pharmaceutically acceptable salts thereof.

In some embodiments, the compound of Formula I, Formula Ia, Formula Ib, or Formula Ic is selected from:
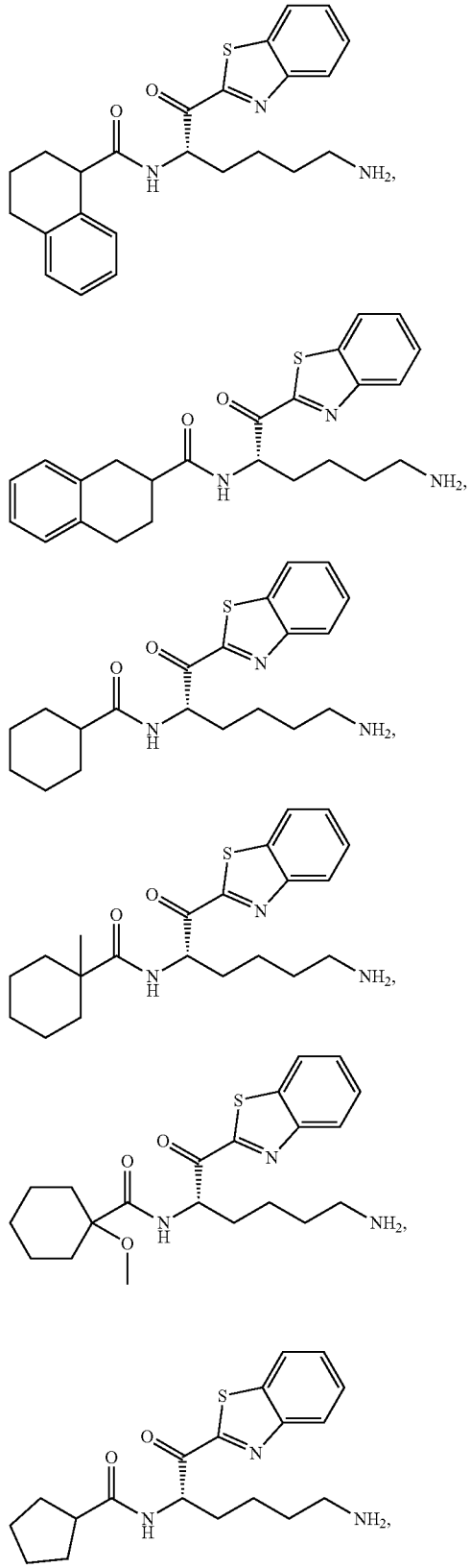
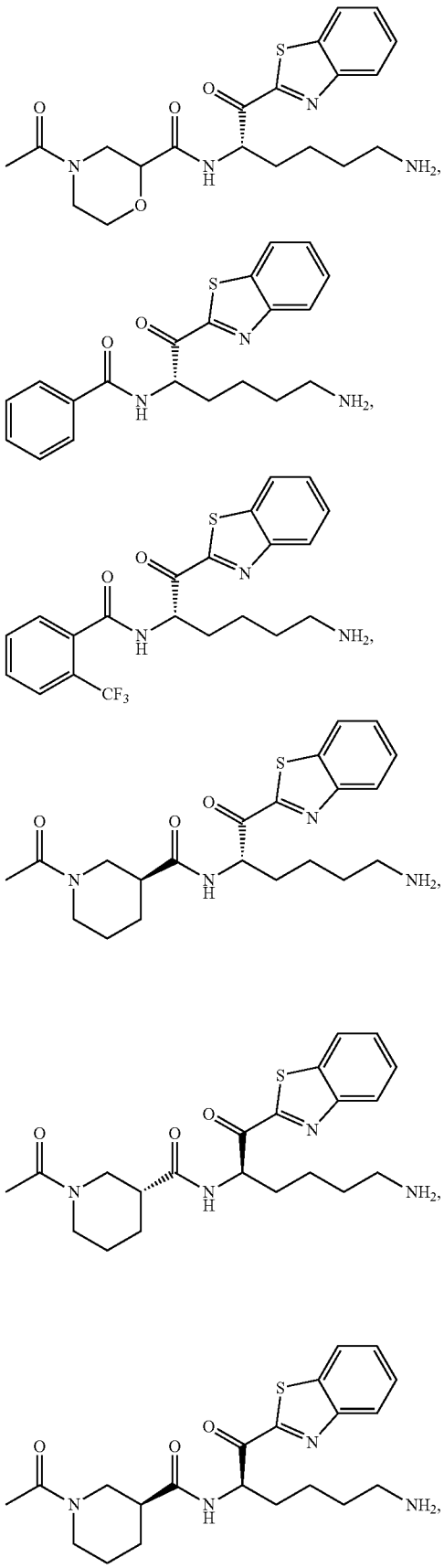

-continued
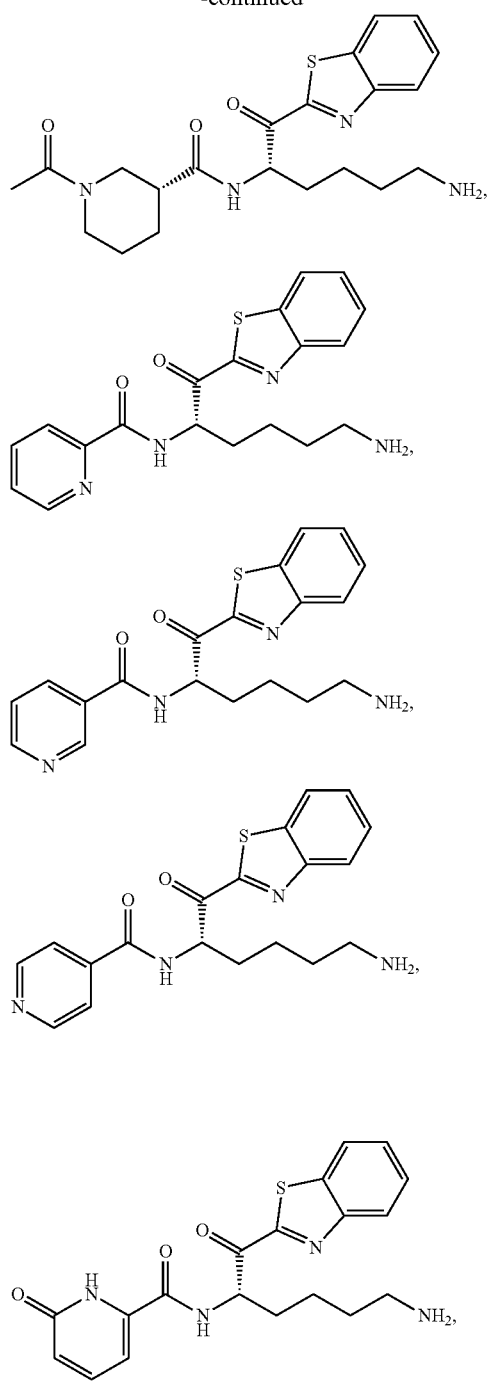
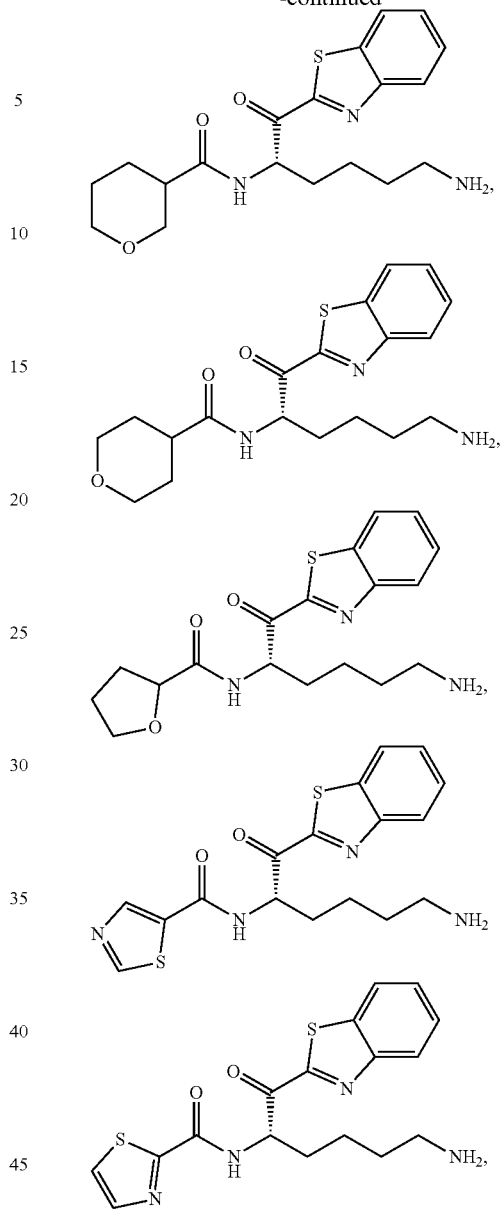
and pharmaceutically acceptable salts thereof.
In some embodiments, the invention provides compounds of Formula I, Formula Ia, or Formula Ib wherein A is —O—, including compounds according to Formula C1:
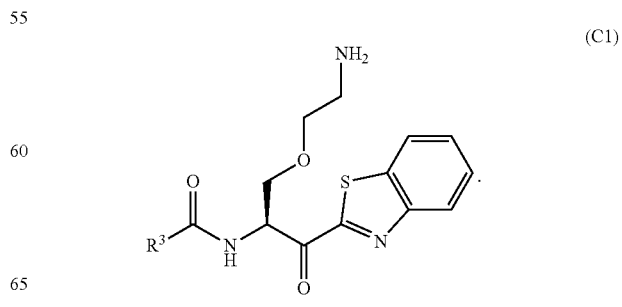

In some embodiments, the invention provides compounds of Formula I, Formula Ia, or Formula Ib wherein B is halo; D is halo; or B and D are halo; including compounds according to Formula C2, Formula C3, and Formula C4:

(C2)
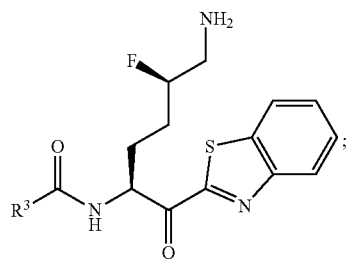

(C3)
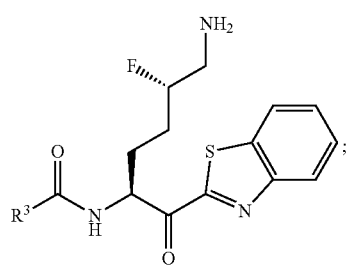

(C4)
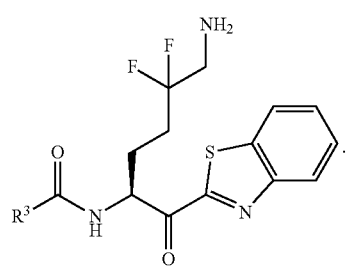

In some embodiments, the invention provides compounds of Formula I, Formula Ia, or Formula Ib wherein Z is selected from thiazol-2-yl-carbonyl; oxazol-2-yl-carbonyl; benzooxazol-2-yl-carbonyl; pyridin-2-yl-carbonyl; pyrimidin-4-yl-carbonyl; pyrimidin-2-yl-carbonyl; isoxazol-5-yl-carbonyl; isoxazol-3-yl-carbonyl; 1,2,4-oxadiazol-3-yl-carbonyl; 1,2,4-oxadiazol-5-yl-carbonyl; maleimidyl; pyridinyldisulfanyl (including pyridin-2-yldisulfanyl); cyano; ethynyl; fluoromethyl-carbonyl; acyloxymethyl-carbonyl; aryloxymethyl-carbonyl; alkylsulfonyl-vinyl; and arylsulfonyl-vinyl.

In some embodiments, the invention provides compounds of Formula I, Formula Ia, or Formula Ib wherein Z is selected from thiazol-2-yl-carbonyl; pyridin-2-yl-carbonyl; cyano; ethynyl; fluoromethylcarbonyl; and 2,3,5,6-tetrafluorophenoxymethyl-carbonyl; including compounds according to Formula B1, Formula B2, Formula B3, Formula B4, Formula B5, and Formula B6:

(B1)
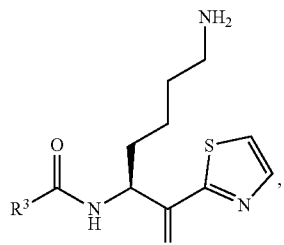

(B2)
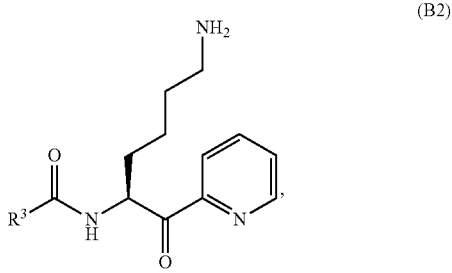

(B3)
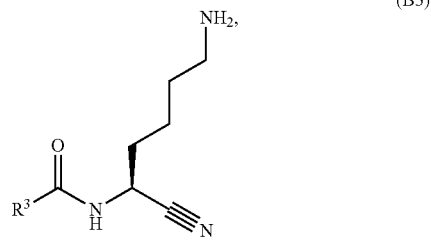

(B4)
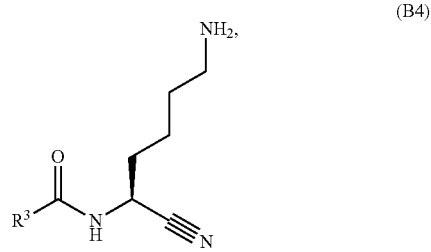

(B5)
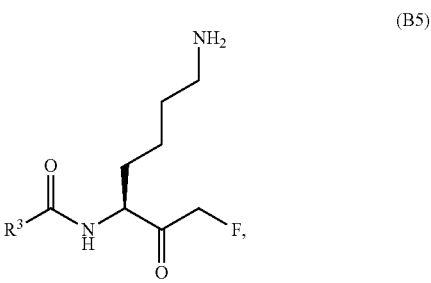

(B6)
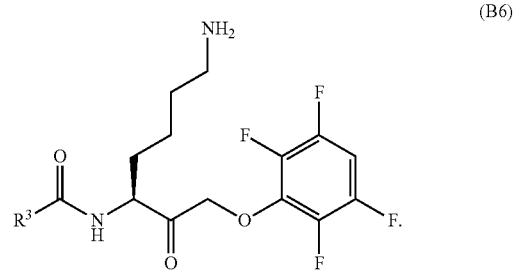

In some embodiments, the invention provides a compound having a structure according to Formula Id:

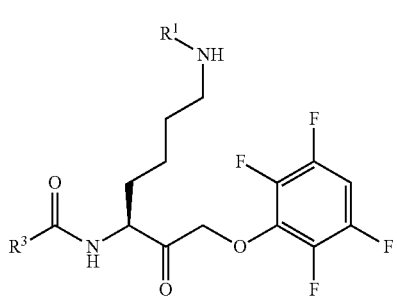

(Id)

or a pharmaceutically acceptable salt thereof, wherein $R^3$ is selected from $C_{6-10}$ aryl, 5-to-12 membered heteroaryl, $C_{3-8}$ cycloalkyl, 5-to-12 membered saturated heterocyclyl, and $-L-R^5$, wherein L is $C_{1-4}$ alkylene.

In some embodiments, the invention provides a compound of Formula Id, or a pharmaceutically acceptable salt thereof, wherein $R^3$ is selected from cyclohexyl, cyclopentyl, morpholino, phenyl, piperidinyl, pyridinyl, tetrahydrofuranyl, tetrahydropyranyl, 1,2,3,4-tetrahydronaphthyl, and thiazolyl, each of which is optionally substituted with 1-3 members selected from methyl, methoxy, trifluoromethyl, acetyl, and $-N_3$. In some such embodiments, $R^3$ is cyclopentyl.

In some embodiments, the compound of Formula Id is selected from:

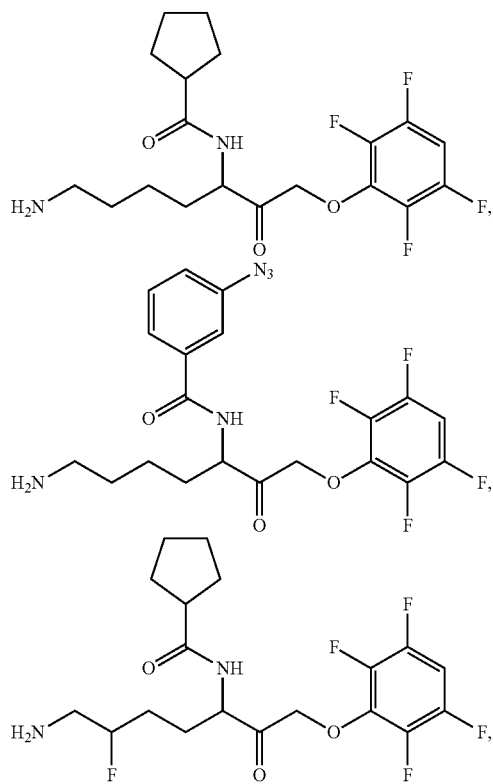

and pharmaceutically acceptable salts thereof.

In some embodiments, the compound of Formula Id is selected from:

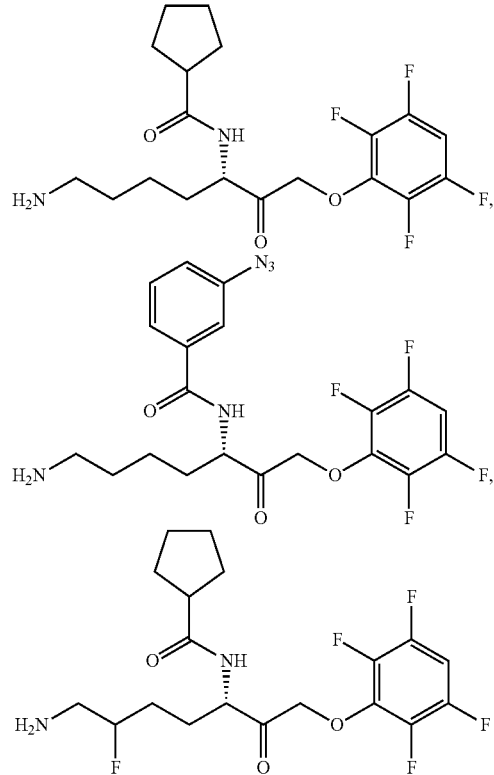

and pharmaceutically acceptable salts thereof.

In some embodiments, the compound of Formula Id is selected from:

and pharmaceutically acceptable salts thereof.

In some embodiments, the compound of Formula I, Formula Ia, or Formula Ib is selected from

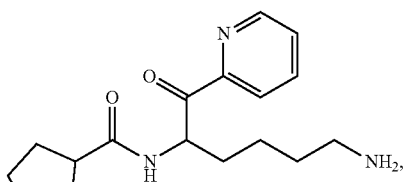

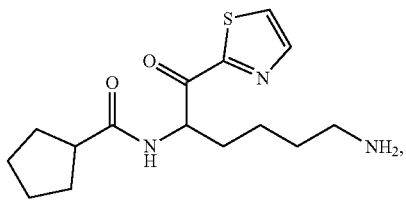

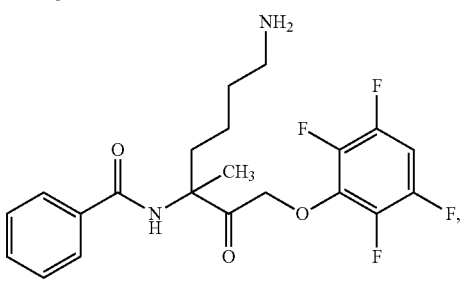

and pharmaceutically acceptable salts thereof.

In some embodiments, the invention provides compounds of Formula I, Formula Ia, or Formula Ib wherein Z is selected from pyridin-2-yl-carbonyl and thiazol-2-yl-carbonyl, and $R^3$ is selected from $C_{6-10}$ aryl and $C_{3-8}$ cycloalkyl. In some such embodiments, the compound is selected from:

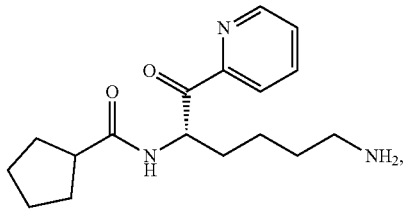

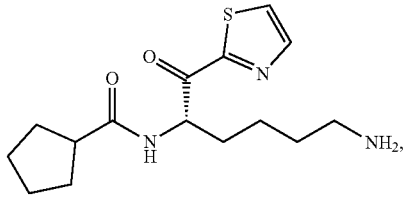

and pharmaceutically acceptable salts thereof.

In some embodiments, the invention provides compounds of Formula I or Formula Ia, wherein $R^4$ is selected from $C_{1-4}$ alkyl and $C_{1-4}$ haloalkyl. In some such embodiments, the compound is:

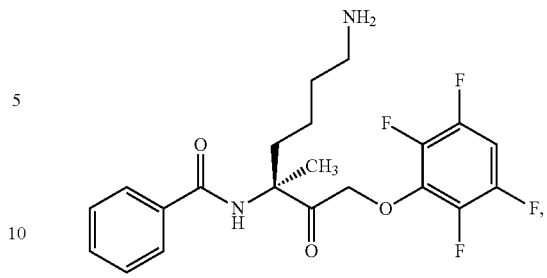

or a pharmaceutically acceptable salt thereof.

In some embodiments, the invention provides a compound of Formula I, Formula Ia, Formula Ib, Formula Ic, or Formula Id, or a pharmaceutically acceptable salt thereof, wherein $R^3$ is selected from cyclohexyl; 1-methylcyclohexyl; 1-methoxycyclohexyl; cyclopentyl; morpholin-2-yl; 4-acetylmorpholin-2-yl; phenyl; 2-trifluoromethylphenyl; 3-azidophenyl; piperidine-3-yl; 1-acetyl-piperidine-3-yl; pyridin-2-yl; pyridin-3-yl; pyridin-4-yl; 6-oxo-1,6-dihydropyridin-2-yl; tetrahydrofuran-2-yl; tetrahydro-2H-pyran-2-yl; tetrahydro-2H-pyran-3-yl; tetrahydro-2H-pyran-4-yl; 1,2,3,4-tetrahydronaphth-1-yl; 1,2,3,4-tetrahydronaphth-2-yl; thiazol-5-yl; and thiazol-2-yl.

In some embodiments, the invention provides a compound of Formula I, Formula Ia, Formula Ib, Formula Ic, or Formula Id, or a pharmaceutically acceptable salt thereof, wherein $R^3$ is selected from cyclohexyl; 1-methylcyclohexyl; 1-methoxycyclohexyl; cyclopentyl; 1,2,3,4-tetrahydronaphth-1-yl; and 1,2,3,4-tetrahydronaphth-2-yl; which radicals are shown below. In some such embodiments, $R^3$ is cyclopentyl.

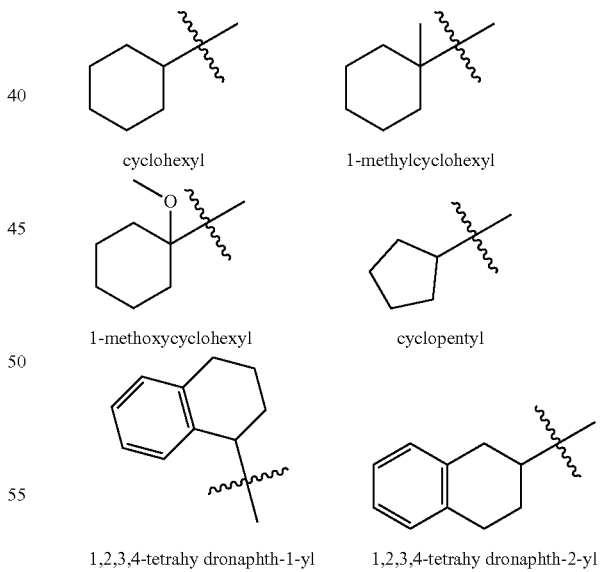

In some embodiments, the invention provides a compound of Formula I, Formula Ia, Formula Ib, Formula Ic, or Formula Id, or a pharmaceutically acceptable salt thereof, wherein $R^3$ is selected from morpholin-2-yl; 4-acetylmorpholin-2-yl; piperidine-3-yl; 1-acetyl-piperidine-3-yl; tetrahydrofuran-2-yl; tetrahydro-2H-pyran-2-yl; tetrahydro-2H-pyran-3-yl; and tetrahydro-2H-pyran-4-yl; which radicals are shown below.

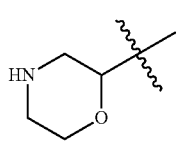
morpholin-2-yl

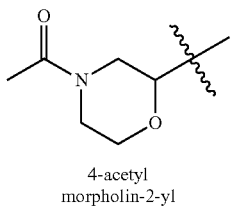
4-acetyl morpholin-2-yl

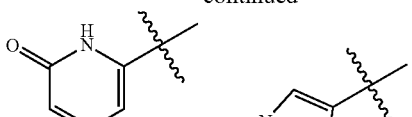
6-oxo-1,6-dihydropyridin-2-yl thiazol-5-yl

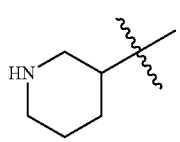
piperidine-3-yl

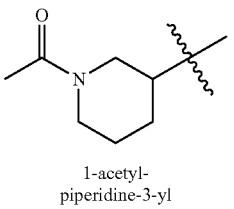
1-acetyl-piperidine-3-yl

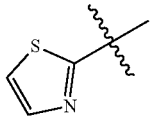
thiazol-2-yl

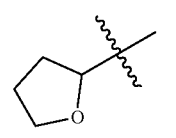
tetrahydrofuran-2-yl

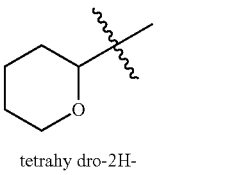
tetrahydro-2H-pyran-2-yl

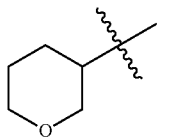
tetrahydro-2H-pyran-3-yl

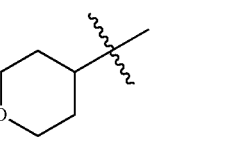
tetrahydro-2H-pyran-4-yl

In some embodiments, the invention provides a compound of Formula I, Formula Ia, Formula Ib, Formula Ic, or Formula Id, or a pharmaceutically acceptable salt thereof, wherein $R^3$ is selected from phenyl; 2-trifluoromethylphenyl; 3-azidophenyl; pyridin-2-yl; pyridin-3-yl; pyridin-4-yl; 6-oxo-1,6-dihydropyridin-2-yl; thiazol-5-yl; and thiazol-2-yl; which radicals are shown below.

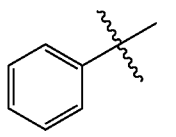
phenyl

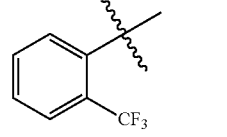
2-trifluoromethylphenyl

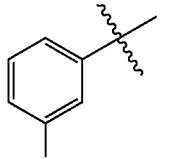
3-azidophenyl

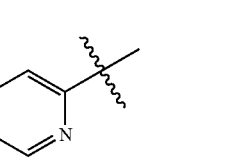
pyridin-2-yl

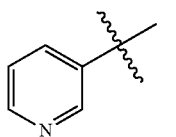
pyridin-3-yl

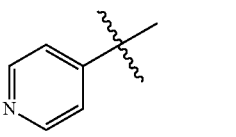
pyridin-4-yl

The compounds described herein and methods of using them encompass the preparation and use of therapeutically active enantiomers or diastereoisomers of the described compounds. All such enantiomers and diastereoisomers of these compounds are included in the scope of the invention. Such compounds can be used as mixtures (e.g., racemic mixtures) or as isolated enantiomers or diastereoisomers.

Compounds of the invention can be prepared so as to include radionuclides for use in diagnostic imaging application such as positron emission tomography (PET) and single-photon emission computed tomography (SPECT). For example, Kgp inhibitors as described herein can be prepared so as to include one or more radionuclides selected from oxygen-15 ($^{15}O$), nitrogen-13 ($^{13}N$), carbon-11 ($^{11}C$), iodine-131 ($^{131}I$), and fluorine-18 ($^{18}F$). Such radiolabeled compounds can be used for PET imagining. Compounds of the invention can also be prepared in deuterated form (i.e., having one or more deuterium atoms, $^2H$, in place of one more hydrogen atoms), tritiated form (i.e., having one or more tritium atoms, $^3H$, in place of one more hydrogen atoms), or $^{14}C$-labeled form (i.e., having one or more $^{14}C$ atoms in place of one more carbon atoms).

In further embodiments, the invention provides compounds according to Formula Ie:

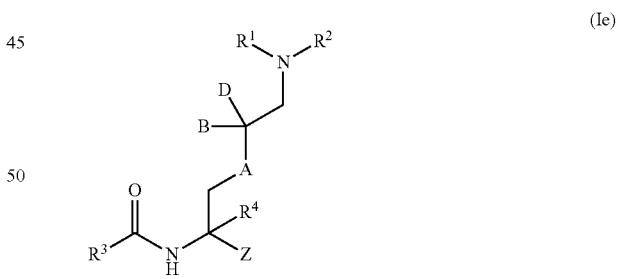

(Ie)

and pharmaceutically acceptable salts thereof, wherein
Z is a thiol-reactive group or a masked thiol-reactive group;
A is selected from —CH$_2$— and —O—;
B and D are independently selected from hydrogen, halogen, C$_{1-4}$ haloalkyl, and C$_{1-4}$ haloalkoxy;
$R^1$ is selected from hydrogen and an amine protecting group;
$R^2$ is hydrogen; and
$R^3$ is selected from C$_{6-10}$ aryl, 5-to-12 membered heteroaryl, C$_{1-8}$ alkyl, C$_{3-8}$ cycloalkyl, 5-to-12 membered saturated heterocyclyl, -L-R$^5$, and —OR$^6$, wherein L is selected from —O—, —NR—, $C_{1-4}$ alkylene, and 2- to 4-membered heteroalkylene, wherein R is selected from hydrogen and $C_{1-8}$ alkyl, $R^5$ is selected from $C_{6-10}$ aryl, 5-to-12 membered heteroaryl, $C_{3-8}$ cycloalkyl, and 5-to-12 membered saturated heterocyclyl, and —$OR^6$ and the carbonyl to which it is bonded form an amine protecting group, and wherein $R^3$ is optionally substituted with one or more substituents selected from halo, —CN, —$NO_2$, —$N_3$, —OH, $R^a$, $R^b$, —$OR^a$, —$OR^b$, —$(CH_2)_kC(O)R^c$, —$NR^d(CH_2)_uC(O)R^c$, —$O(CH_2)_uC(O)R^c$, —$(CH_2)_k CONR^dR^d$, —$(CH_2)_kNR^dC(O)R^c$, —$NR^d(CH_2)_u CONR^dR^d$, —$NR^d(CH_2)_uNR^dC(O)R^c$, —$O(CH_2)_u CONR^dR^d$, —$O(CH_2)_uNR^dC(O)R^c$, —$(CH_2)_kS(O)_2 NR^dR^d$, —$(CH_2)_kNR^dS(O)_2R^c$, —$(CH_2)_kS(O)_2R^c$, —$(CH_2)_kS(O)R^c$, —$(CH_2)_kSR^d$, —$NR^d(CH_2)_uS(O)_2 NR^dR^d$, —$NR^d(CH_2)_uNR^dS(O)_2R^c$, —$NR^d(CH_2)_uS (O)_2R^c$, —$NR^d(CH_2)_uS(O)R^c$, —$NR^d(CH_2)_uSR^d$, —$O(CH_2)_uS(O)_2NR^dR^d$, —$O(CH_2)_uNR^dS(O)_2R^c$, —$O(CH_2)_uS(O)_2R^c$, —$O(CH_2)_uS(O)R^c$, and —$O(CH_2)_uSR^c$, wherein:

each $R^a$ is independently selected from $C_{1-4}$ alkyl and $C_{1-4}$ haloalkyl, each $R^b$ is independently selected from $C_{3-6}$ cycloalkyl, $C_{3-6}$ halocycloalkyl, $C_{6-10}$ aryl, 5-to-12 membered heteroaryl, and 5-to-12 membered saturated heterocyclyl, each $R^c$ is independently selected from —OH, $C_{1-8}$ alkyl, $C_{1-8}$ haloalkyl, $C_{3-8}$ cycloalkyl, $C_{3-8}$ halocycloalkyl, $C_{6-10}$ aryl, ($C_{6-10}$ aryl)-($C_{1-8}$ alkyl), 5-to-12 membered heteroaryl, and 5-to-12 membered saturated heterocyclyl, each $R^d$ is independently selected from hydrogen and $C_{1-8}$ alkyl, each subscript k is independently selected from 0, 1, 2, 3, 4, 5, and 6, and each subscript u is independently selected from 1, 2, 3, 4, 5, and 6; and $R^4$ is selected from hydrogen, halogen, $C_{1-4}$ alkyl, $C_{1-4}$ alkoxy, $C_{1-4}$ haloalkyl, and $C_{1-4}$ haloalkoxy.

In some embodiments, the compound of Formula Ie has a structure according to Formula If:

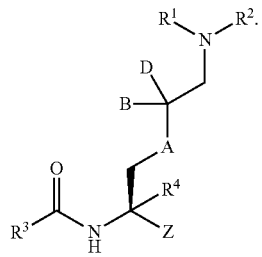

It is to be understood that compounds of the invention do not include 1-(3-phenylpropionyl)piperidine-3(R,S)-carboxylic acid-[4-amino-1(S)-(benzothiazole-2-carbonyl butyl] amide (i.e., A71561).

The compounds of the invention are highly active Kgp inhibitors, typically exhibiting Kgp Ki values and Kgp $IC_{50}$ values well below 1 µM.

The term "Ki" refers to inhibition constant. The Ki value for a particular test compound can be measured as follows. Fifty microliters (µl) of an enzyme such as Kgp (1 nM in 50 mM bis-Tris propane [pH 8.0] containing 1% [vol/vol] Triton X-100 and 5 mM 2-mercaptoethanol) is added to columns 1 to 11 of a 96-well plate, and 100 µl is added to column 12. Two µl of the test compound (100 µl in 100% DMSO) is added to column 12, and the sample is mixed three times by pipetting. Then, a doubling dilution is prepared across the plate by serial transfer into adjacent wells. 50 µl of succinyl-Ala-Phe-Lys-(7-amido-4-methylcoumarin ("AMC;" 40 µM in buffer) is added to all wells, and the contents are mixed. The reaction is monitored for AMC fluorescence for 15 min at 25° C., and the progress curves are automatically converted to rates by the Fluoroskan Ascent software.

The method can be used to assay enzymes including Kgp, RgpB, RgpA, trypsin, and cathepsin B. For RgpA and RgpB, the substrate can be Z-Arg-AMC. For trypsin, the buffer can contain 10 mM Tris and 10 mM $CaCl_2$) (pH 8.0), and the substrate can be Z-Gly-Gly-Arg-AMC. For cathepsin B, the buffer can contain 50 mM sodium phosphate, 1 mM EDTA, and 10 mM 2-mercaptoethanol (pH 6.25), and the substrate can be Z-Arg-Arg-AMC.

The inhibition constants can then be calculated by using the following equation, with an assumption that inhibition is fully competitive:

$$V_i = (V_{max}[S])/([S]+K_m(1+[I]/K_i)$$

where $V_i$ is the observed residual activity, [S] is the substrate concentration used in the assay, $V_{max}$ is the maximal velocity at an inhibitor concentration of zero, $K_i$ is the inhibitor dissociation constant, and [I] is the inhibitor concentration. Curves can then be fitted by nonlinear regression analysis by using fixed values for the substrate concentration and the value of the Michaelis constant ($K_m$). Data analysis can be carried out by using Prism v 2.01 (GraphPad, San Diego, Calif.).

The term "$IC_{50}$" indicates how much of a compound is needed to inhibit a given biological process (or component of a process, e.g., an enzyme, cell, cell receptor, or microorganism) by one half (50%). The $IC_{50}$ of a compound can be determined by constructing a dose-response curve and examining the effect of different concentrations of the compound on reversing the activity of the enzyme. From the dose-response curve, $IC_{50}$ values can be calculated for a given compound by determining the concentration needed to inhibit half of the maximum biological response of the enzyme.

In general, the Kgp Ki value for compounds of the invention ranges from about 0.001 nM to about 500 nM. The Kgp Ki value for a compound of the invention can range, for example, from about 1 nM to about 20 nM, or from about 20 nM to about 40 nM, or from about 40 nM to about 60 nM, or from about 60 nM to about 80 nM, or from about 80 nM to about 100 nM, or from about 100 nM to about 150 nM, or from about 150 nM to about 200 nM, or from about 200 nM to about 250 nM, or from about 250 nM to about 300 nM, or from about 300 nM to about 350 nM, or from about 350 nM to about 400 nM, or from about 400 nM to about 450 nM, or from about 450 nM to about 500 nM. The Kgp Ki value for a compound of the invention can range from about 0.001 nM to about 0.025 nM, or from about 0.025 nM to about 0.050 nM, or from about 0.050 nM to about 0.075 nM, or from about 0.075 nM to about 0.100 nM, or from about 0.100 nM to about 0.250 nM, or from about 0.250 nM to about 0.500 nM, or from about 0.500 nM to about 0.750 nM, or from about 0.750 nM to about 1 nM.

In general, the Kgp $IC_{50}$ value for compounds of the invention ranges from about 0.001 nM to about 500 nM. The Kgp IC50 value for a compound of the invention can range, for example, from about 1 nM to about 20 nM, or from about 20 nM to about 40 nM, or from about 40 nM to about 60 nM, or from about 60 nM to about 80 nM, or from about 80 nM to about 100 nM, or from about 100 nM to about 150 nM, or from about 150 nM to about 200 nM, or from about 200 nM to about 250 nM, or from about 250 nM to about 300 nM, or from about 300 nM to about 350 nM, or from about 350 nM to about 400 nM, or from about 400 nM to about 450 nM, or from about 450 nM to about 500 nM. The Kgp IC50 value for a compound of the invention can range from about 0.001 nM to about 0.025 nM, or from about 0.025 nM to about 0.050 nM, or from about 0.050 nM to about 0.075 nM, or from about 0.075 nM to about 0.100 nM, or from about 0.100 nM to about 0.250 nM, or from about 0.250 nM to about 0.500 nM, or from about 0.500 nM to about 0.750 nM, or from about 0.750 nM to about 1 nM.

In some embodiments, a Kgp inhibitor according to the invention has a Kgp Ki of 100 nM or less. In some embodiments, the Kgp inhibitor has a Kgp Ki of 50 nM or less.

In some embodiments, a Kgp inhibitor according to the invention has a Kgp $IC_{50}$ of 50 nM or less. In some embodiments, the Kgp inhibitor has a Kgp $IC_{50}$ of 15 nM or less.

Compounds having Kgp Ki values of 15 nM or less can be particularly useful for systemic administration. For example, such compounds can have Kgp Ki values ranging from about 1 picomolar (pM) to about 15 nanomolar (nM), from about 10 pM to about 12 nM, from about 100 pM to about 11 nM, or from about 100 pM to about 10 nM. Such compounds can have Kgp Ki values of less than 10 nanomolar (nM), less than 8 nM, less than 6 nM, or less than 4 nM.

Compounds having Kgp Ki values of 45 nM or less can be particularly useful for topical administration. For example, such compounds can have Kgp Ki values ranging from about 1 picomolar (pM) to about 40 nanomolar (nM), from about 10 pM to about 35 nM, from about 100 pM to about 30 nM, or from about 100 pM to about 25 nM.

In certain embodiments, Kgp inhibitors according to the invention are selective for Kgp. As used herein, a "selective" Kgp inhibitor is a compound that does not substantially affect the activity of proteases other than Kgp, RgpA, and RgpB when administered at a therapeutically effective dose for treating a disease or condition associated with *P. gingivalis* infection. Typically, a protease that is not substantially affected by a particular compound exhibits at least 90% of its normal enzymatic activity in the presence of the compound under physiological conditions. Selective Kgp inhibitors include those compounds that do not affect the activity of proteases other than Kgp when administered at a therapeutically effective dose for treating a brain disorder, periodontal disease, diabetes, a cardiovascular disease, arthritis, preterm birth, pneumonia, cancer, a kidney disease, a liver disease, a retinal disorder, or glaucoma associated with *P. gingivalis* infection. Preferably, selective Kgp inhibitors do not adversely affect the coagulation cascade when administered at therapeutically effective levels.

In some embodiments, the invention provides a Kgp inhibitor having a Kgp Ki of less than 50 nM. In some such embodiments, the trypsin Ki is greater than 60 nM. In the some embodiments, the Kgp inhibitor has a Ki for Kgp of less than 15 nM, and a (trypsin Ki)/(Kgp Ki) ratio of greater than 100.

In some embodiments, the invention provides compounds that are at least 30 times more selective for Kgp than for trypsin or cathepsin B. For some such compounds, the Kgp Ki is 0.9 nM, and the trypsin Ki and/or the cathepsin B Ki are 30 nM or more. In some embodiments, the Kgp Ki is 0.9 nM, and the trypsin Ki and/or the cathepsin B Ki are 115 μM or more. For some such compounds, the Kgp $IC_{50}$ is 50 nM or less and the trypsin $IC_{50}$ trypsin is 100 nM or more. For some such compounds, the Kgp $IC_{50}$ is 15 nM or less and the trypsin $IC_{50}$ trypsin is 1 μM or more.

IV. Methods of Making Compounds

Certain examples of compounds of Formula (I) can be prepared starting with certain lysine derivatives D1 and D6, which are described below and are commercially available or can be prepared following published procedures.

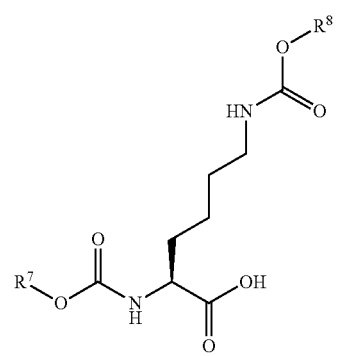

D1

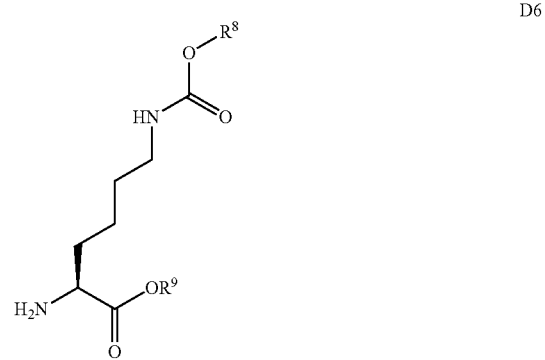

D6

In D1, preferred $R^7$ and $R^8$ each can be removed by chemical conditions that do not remove the other. For example, $R^7$=benzyl can be removed by hydrogen and a palladium-carbon catalyst, but $R^7$ is not affected by trifluoroacetic acid, whereas $R^8$=t-butyl can be removed by trifluoroacetic acid, but $R^8$ is not affected by hydrogen and a palladium-carbon catalyst. Other appropriate, complimentary combinations of $R^7$ and $R^8$ have been published. Similarly, in D6, complimentary, removable $R^8$ and $R^9$ are preferred, and several appropriate combinations have been published.

Certain D5 can be prepared by a sequence of transformations D1 to D2 to D3 to D4 to D5. See, Scheme 1.

Scheme 1

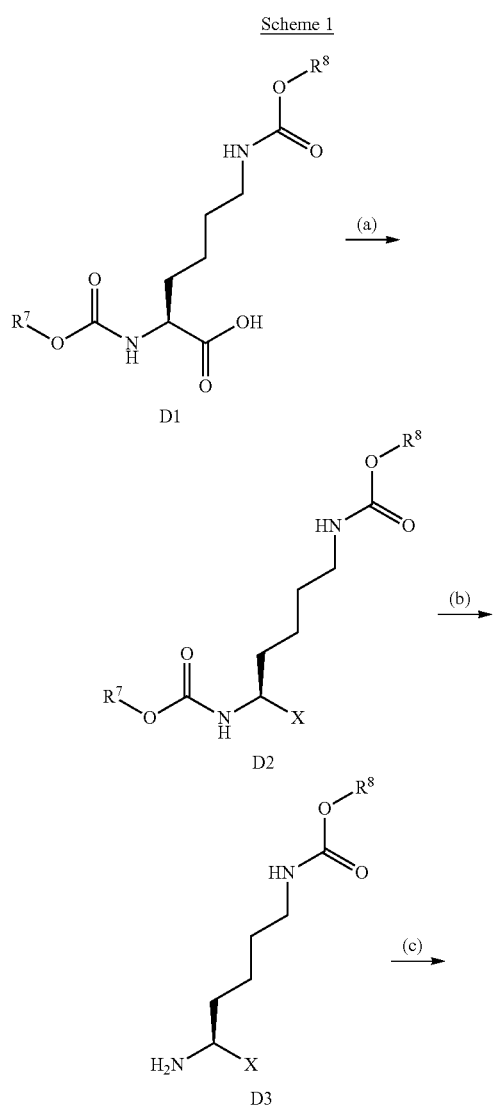

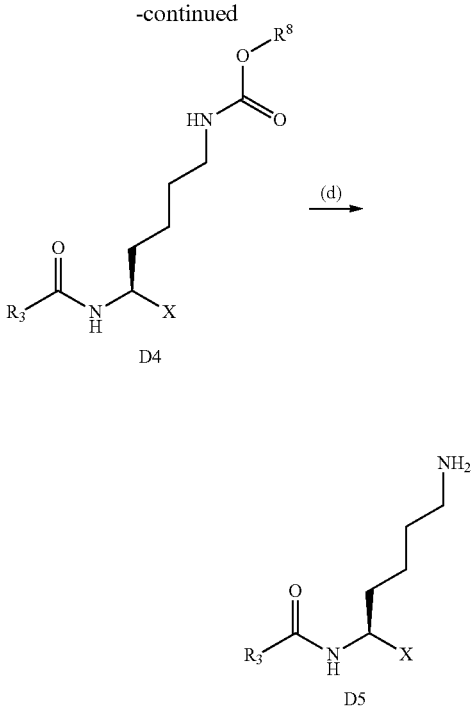

In most instances, the transformation of D1 to D2 will involve more than one chemical reaction. Following published procedures, the following chemical reactions can be applied to transform D1 to D2. D1 can be converted to E1 by treatment with N-methyl-O-methylhydroxylamine hydrochloride, an organic base (for example $Et_3N$), a racemization inhibitor (for example HOBt), and a dehydrating agent (for example EDAC), in an organic solvent (for example DMF). See, Scheme 2, step (a). E1 can be converted to D2.5 by treatment with a lithiated heterocycle (for example 2-lithiobenzothiazole, 2-lithiothiazole, or 2-lithiopyridine), in an organic solvent (for example THF), to install the corresponding $R^{10}$ (2-benzothiazolyl, 2-thiazolyl, or 2-pyridyl). See, Scheme 2, step (b).

Scheme 2

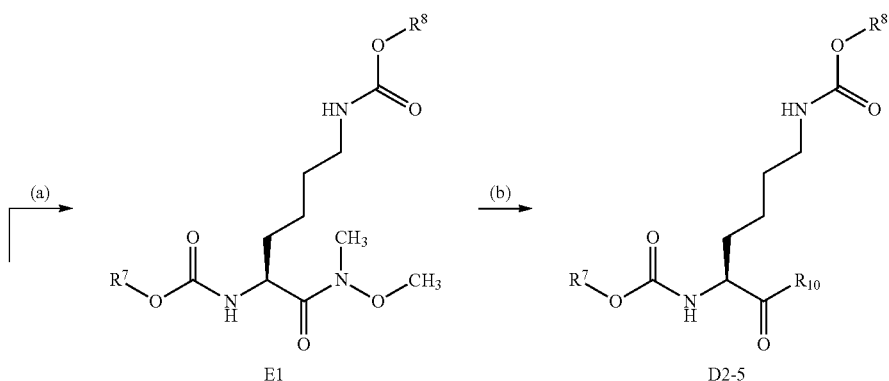

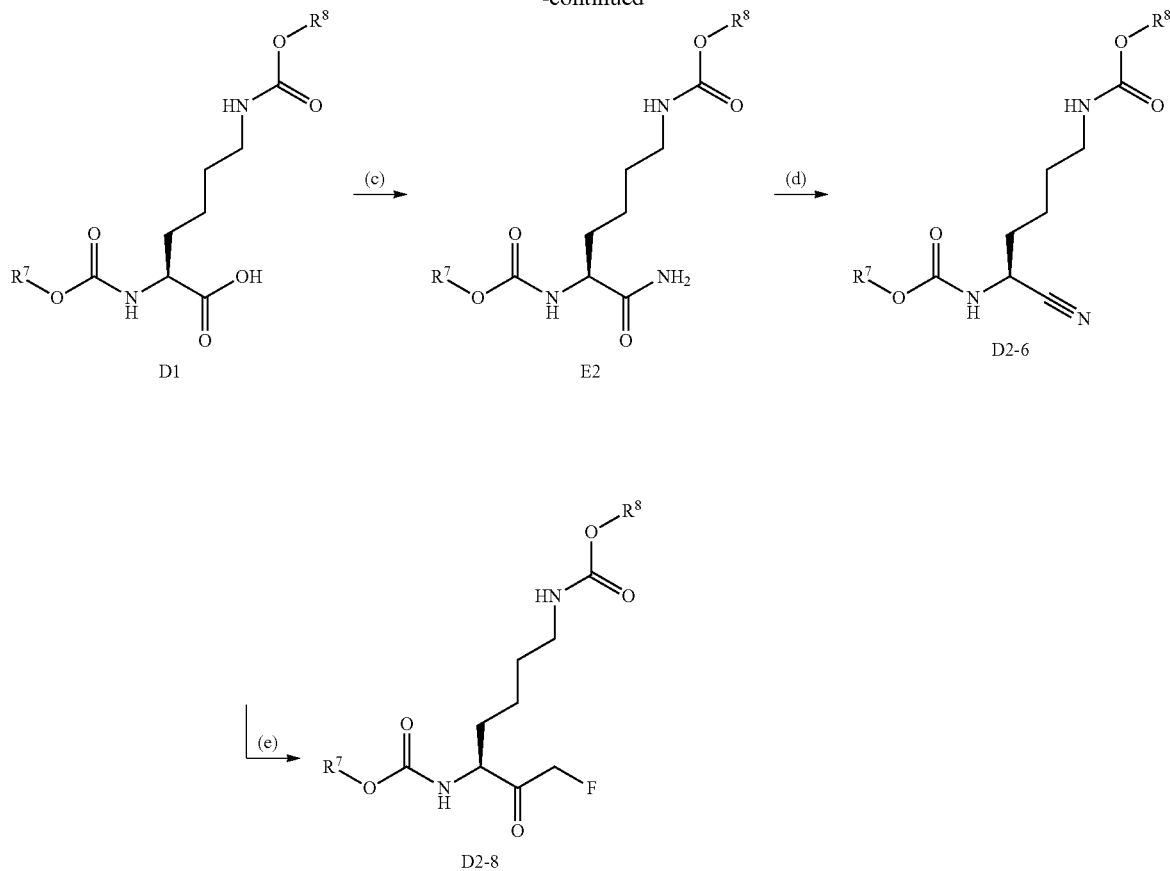

D1 can be converted to E2 by treatment with ammonium hydrochloride, an organic base (for example Et₃N), a racemization inhibitor (for example HOBt), and a dehydrating agent (for example EDAC), in an organic solvent (for example DMF). See, Scheme 2, step (c). E2 can be converted to D2-6 by treatment with an organic base (for example Et₃N), and a strong dehydrating agent (for example pyridine-sulfur trioxide complex), in an organic solvent (for example $CH_2Cl_2$). See, Scheme 2, step (d).

D1 can be converted to D2-8 by treatment with fluoroacetic anhydride, and Et3N, and DMAP, in an organic solvent (for example DMF). See, Scheme 2, step (e).

D1 can be converted to E3 by treatment with borane-dimethylsulfide complex, in an organic solvent (for example THF). See, Scheme 3, step (a). E3 can be converted to E7 by treatment with an organic base (for example Et₃N), a strong dehydrating agent (for example oxalyl chloride), and dimethylsulfoxide, in an organic solvent (for example $CH_2Cl_2$). See, Scheme 3, step (b). E7 can be converted to D2-10 by treatment with trimethyl diazo phosphonacetate and $K_2CO_3$, in an alcohol solvent (for example methanol). See, Scheme 3, step (c).

Scheme 3

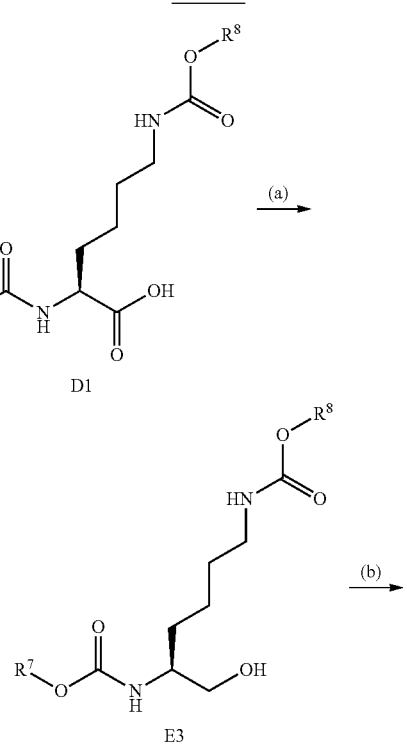

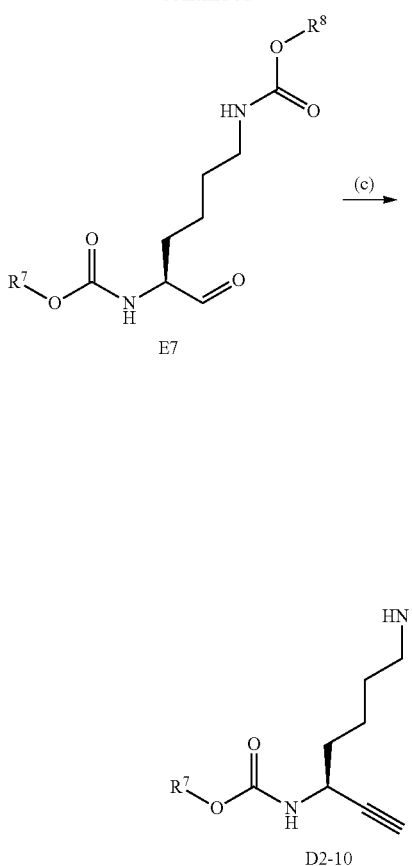

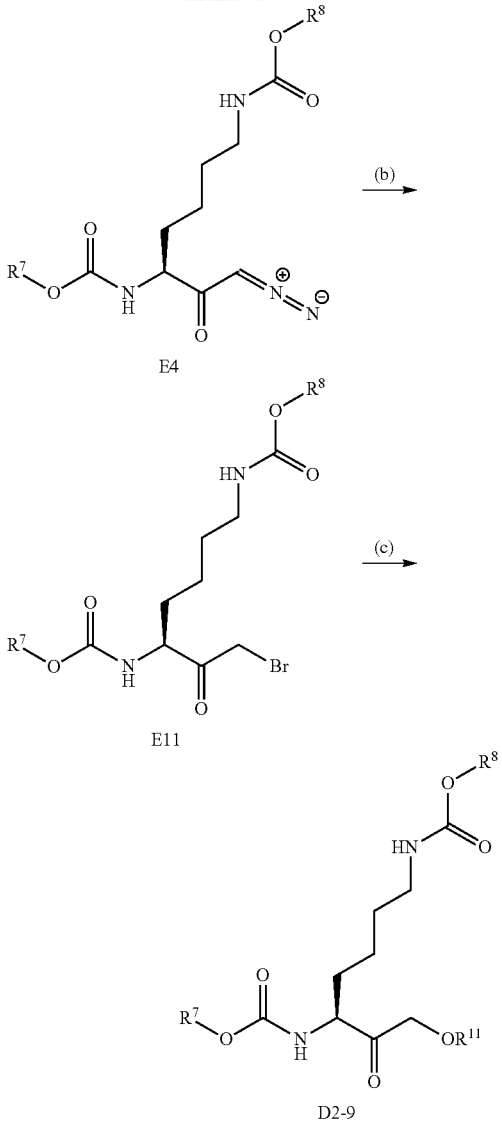

D1 can be converted to E4 by treatment with an organic base (for example Et$_3$N), a chloroformate (for example EtO$_2$CCl), and diazomethane, in an organic solvent (for example diethyl ether). See, Scheme 4, step (a). E4 can be converted to E11 by treatment with HBr, and acetic acid, in an organic solvent (for example THF). See, Scheme 4, step (b). E11 can be converted to D2-9 by treatment with an alcohol HOR$^{11}$ (for example 2,3,5,6-tetrafluorophenol), and KF, in an organic solvent (for example DMF), to install the corresponding —OR$^{11}$ (for example 2,3,5,6-tetrafluorophenoxy). See, Scheme 4, step (c).

Scheme 4

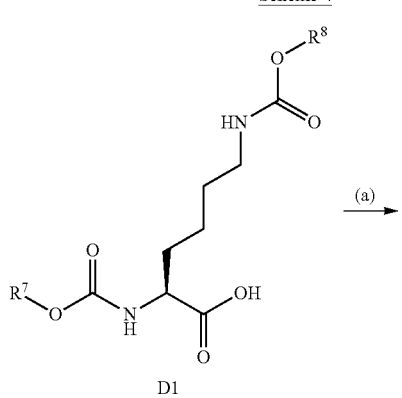

Furthermore, a wide variety of additional published procedures can be applied to transform D1 to other D2, in which X is a thiol-reactive group that is not illustrated.

After transformation of D1 to D2 (e.g., to D2-5, D2-6, D2-8, D2-9, or D2-10), R$^7$ can be removed by appropriate chemical conditions, generating D3 after spontaneous decarboxylation. D3 or a salt of D3 (e.g., the hydrochloride salt of D3) can be used in further synthetic steps. D3 can be treated with a carboxylic acid R$^3$CO2H, and a racemization inhibitor (for example HOBt), and a dehydrating agent (for example EDAC), in an organic solvent (for example DMF), generating D4. Alternatively, D3 can be treated with R$^3$COX, wherein X is a leaving group (for example chloride), and an organic base (for example Et$_3$N), in an organic solvent (for example CH$_2$Cl$_2$), generating D4. Alternatively, D3 can be treated with an isocyanate in organic solvent (for example CH$_2$Cl$_2$), generating D4. A wide variety of applicable R$^3$CO$_2$H, R$^3$COX, and isocyanates are commercially available, or can be prepared by published procedures. R$^8$ can be removed by an appropriate chemical conditions, generating D5 after spontaneous decarboxylation.

Other D5 can be prepared by a sequence of transformations D6 to D7 to D8 to D4 to D5. See, Scheme 5.

Scheme 5

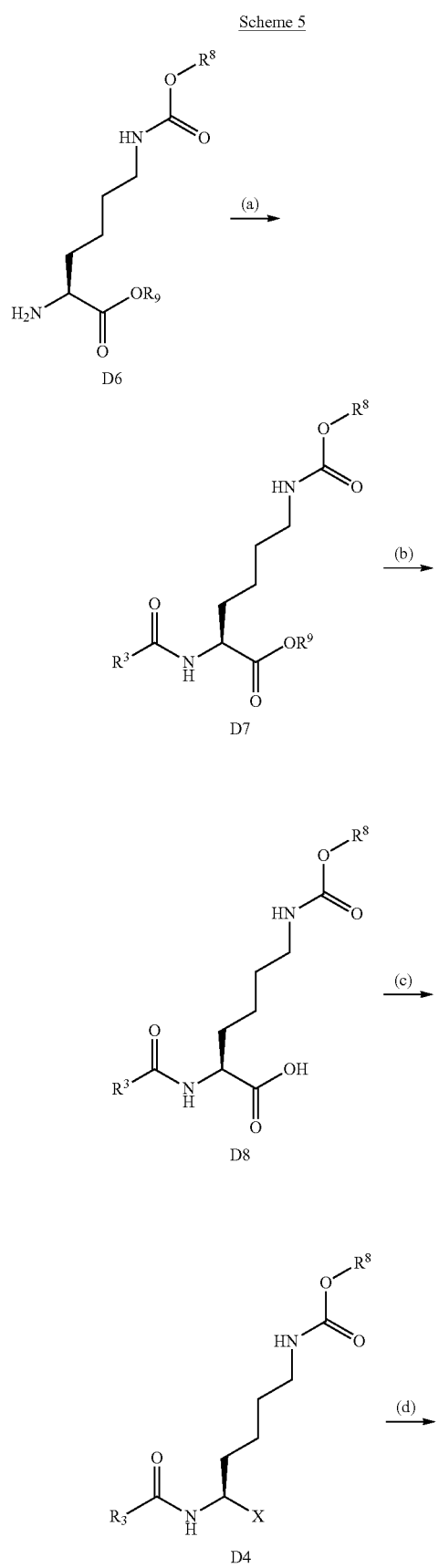

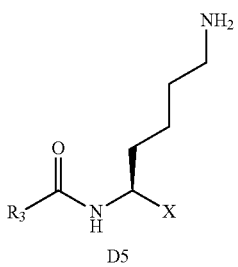

D6 can be treated with a carboxylic acid $R^3CO_2H$, and a racemization inhibitor (for example HOBt), and a dehydrating agent (for example EDAC), in an organic solvent (for example DMF), generating D7. See, Scheme 5, step (a). Alternatively, D6 can be treated with $R^3COX$, wherein X is a leaving group (for example chloride), and an organic base (for example $Et_3N$), in an organic solvent (for example $CH_2Cl_2$), generating D7. Alternatively, D3 as shown in Scheme 1 can be treated with an isocyanate in organic solvent (for example $CH_2Cl_2$), generating D7. A wide variety of applicable $R^3CO_2H$, $R^3COX$, and isocyanates are commercially available, or can be prepared by published procedures. $R^9$ can be removed by appropriate chemical conditions generating D8. See, Scheme 5, step (b).

D8 can be transformed to D4 by sequences of reactions similar to those described for transformation of D1 to D2. See, Scheme 5, step (c). In some embodiments, D8 is transformed to D4-9 as shown in Scheme 6, steps (a)-(c). In some embodiments, $-OR^{11}$ in D4-9 is 2,3,5,6-tetrafluorophenoxy.

Scheme 6

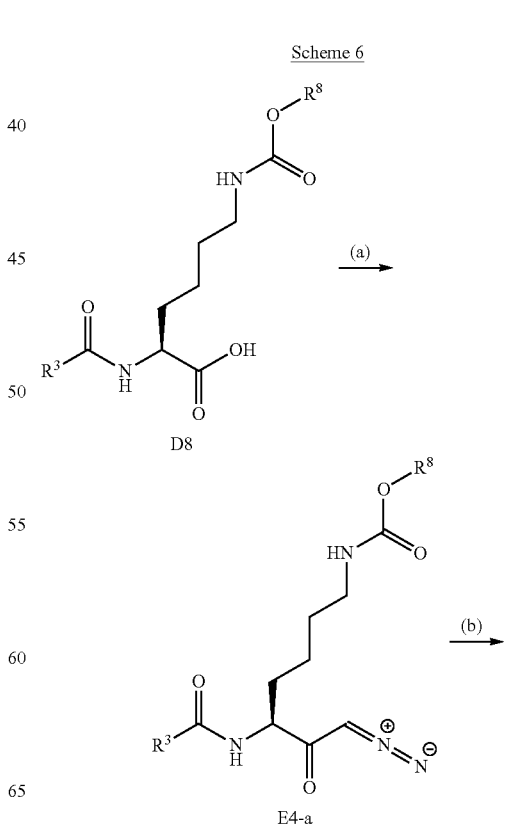

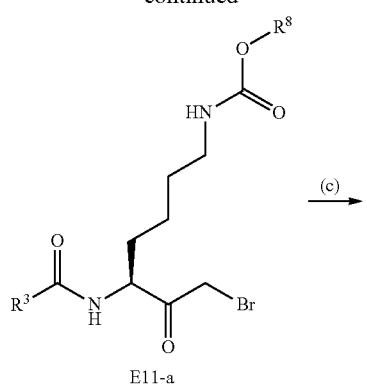

E11-a

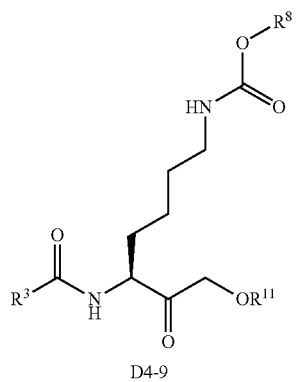

D4-9

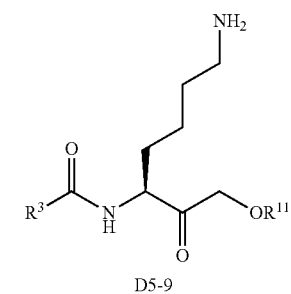

D5-9

Furthermore, a wide variety of additional published procedures can be applied to transform D8 to other D4, in which X is a thiol-reactive group that is not illustrated. Following the alternative sequence to D4, $R^8$ can be removed by appropriate chemical conditions, generating D5 after spontaneous decarboxylation. See, Scheme 5, step (d).

Preparation of certain examples of Formula (I) will require initial preparation of unnatural amino acids that feature side-chains that are not present in any of the amino acids that occur in proteins. A wide variety of methods have been published for preparation of amino acids that feature unnatural side-chains, including the most useful and important methods F1-4:

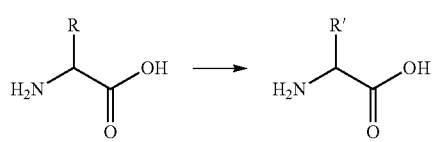

F1

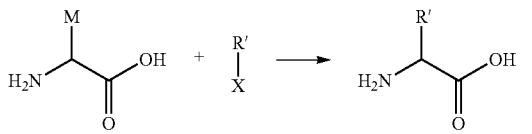

F2

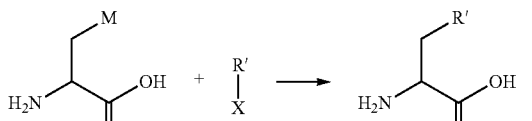

F3

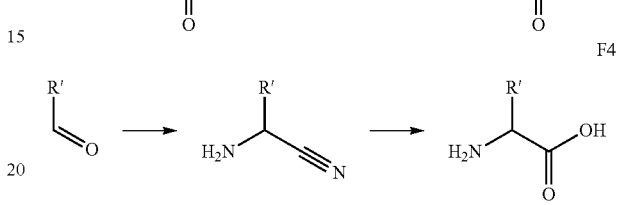

F4

Although not illustrated in F1-3, the amine and carboxylate groups are typically protected before application of these methods, and the protection is removed after construction of the unnatural side-chain. In F1, a natural side-chain (R) is modified to form an unnatural side-chain (R'). The natural amino acids serine, glutamic acid, and methionine would be especially for preparation of certain examples of Formulas (I) and (II). In F2, a metalated glycine derivative is treated with an alkylating agent (R'X) to install the unnatural side-chain (R'). In some instances, the metalated glycine derivative is generated by treating a glycine derivative with a strongly basic metalating agent (for example lithium diisopropylamide or potassium t-butoxide). In other instances, the starting glycine derivative is sufficiently acidic that a much less basic metalating agent (for example potassium carbonate) is satisfactory. In the latter instances the metalated glycine derivative may exist as a dissociated ion pair, rather than as the covalently bonded species illustrated in F2. In F3, a metalated alanine derivative is treated with an alkylating agent (R'X) to install the unnatural side-chain (R'). In most instances, the metalated alanine derivative is generated by treating a halogenated alanine derivative with a low valent metal (for example zinc dust). In many instances, a soluble palladium catalyst is utilized to facilitate F3. In F4, an aldehyde (R'CHO) is reacted with a source of ammonia and a source of cyanide, to generate an aminonitrile, which is subsequently hydrolyzed to generate an amino-acid featuring an unnatural sidechain (R'). Such methods can be used to prepared intermediates C1, C2, C3, and C4 set forth above.

After application of appropriate methods to prepare amino acids that feature unnatural sidechains, these amino acids can be appropriately protected, as described for D1 and D6, and then appropriate methods can be applied, as described for D2-4 and D7-9, to generate analogs of D5, wherein the lysine side-chain has been replaced with an unnatural side-chain. Thus, suitable methods are available to provide the variations of the $R^3$, Z, and $CH_2AC(B)(D)CH_2NH_2$ that are specified for Formulas (I) and (II).

V. Compositions/Administration

In a related aspect, the invention provides a pharmaceutical composition comprising a compound of Formula I and a pharmaceutically acceptable excipient.

The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

Pharmaceutical compositions containing compounds of the invention can be formulated for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semipermeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

Kgp inhibitors can also be administered topically as a solution, ointment, cream, gel, or suspension, as well as in mouth washes, eye-drops, and the like. Still further, transdermal delivery of Kgp inhibitors can be accomplished by means of iontophoretic patches and the like.

Pharmaceutical compositions containing Kgp inhibitors can also be in the form of a sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butane diol. In addition, sterile, fixed oils can be used as a solvent or suspending medium. For this purpose any bland fixed oil can be employed including synthetic monoglycerides, diglycerides, or triglycerides.

Aqueous suspensions can contain one or more Kgp inhibitors in admixture with excipients including, but not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate. Dispersible powders and granules (suitable for preparation of an aqueous suspension by the addition of water) can contain one or more Kbp inhibitors in admixture with a dispersing agent, wetting agent, suspending agent, or combinations thereof. Oily suspensions can be formulated by suspending a Kgp inhibitor in a vegetable oil (e.g., *arachis* oil, olive oil, sesame oil or coconut oil), or in a mineral oil (e.g., liquid paraffin). Oily suspensions can contain one or more thickening agents, for example beeswax, hard paraffin, or cetyl alcohol. These compositions can be preserved by the addition of an anti-oxidant such as ascorbic acid.

The pharmaceutical compositions of the invention can also be in the form of oil-in-water emulsions. The oily phase can be a vegetable oil, for example olive oil or *arachis* oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Additionally, the present invention encompasses various administration modes by which the compounds can be delivered to increase bioavailability or blood brain barrier penetration, including but not limited to, intravenous, intranasal, intrathecal, subcutaneous, intracranial and oral. Time release technology can be used to increase bioavailability including formulations for sustained-release (SR), sustained-action (SA), extended-release (ER, XR, XL) timed-release (TR), controlled-release (CR), modified release (MR), continuous-release, osmotic release and slow release implants. These alternative routes of administration were not previously considered for these molecules, which were primarily contemplated to be formulated for topical gingival delivery and not systemically.

The use of hybrid molecules to promote active transport or nanoparticles can be used in certain embodiments to increase blood brain barrier transport. For example liposomes, proteins, engineered peptide compounds or antibodies that bind to the receptors that transport proteins across the blood brain barrier including LPR-1 receptor, transferrin receptor, EGF-like growth factor or glutathione transporter can be used to increase penetration into the brain. Physical techniques including osmotic opening, ultrasound, lasers, sphenopalantine ganglion stimulation, direct intracranial, intrathecal, or intraventricular delivery via a pump can be used.

Pharmaceutical compositions according to the invention can also include one or more additional active agents useful in the treatment of conditions associated with *P. gingivalis* infection. In certain embodiments, the invention provides a pharmaceutical composition comprising one or more Kgp inhibitors as described herein in combination with one or more additional active agents for treatment of Alzheimer's disease. Several therapeutics are in development and in clinical use for treatment of Alzheimer's disease. Therapeutic strategies include lowering circulating levels of β-amyloid and tau (as described in more detail below), stabilizing microtubules, removing atherosclerotic plaques, modulating autophagy, modulating neurotransmitter levels, and inhibiting GABA(A) α5 receptors. Such therapeutics can maintain and/or restore cognitive function in subjects with Alzheimer's disease; slow the decline of cognitive function; and promote neuroplasticity and recovery of the brain.

Active agents that can be combined with Kgp inhibitors in pharmaceutical compositions include, but are not limited to, antibiotics (i.e., bacteriocidal compounds and bacteriostatic compounds), cholinesterase inhibitors, alpha-7 nicotinic receptor modulators, serotonin modulators, NMDA modulators, Aβ-targeted therapies, ApoE-targeted therapies, microglia-targeted therapies, blood/brain barrier-targeted therapies, tau-targeted therapies, complement-targeted therapies, and anti-inflammatories.

Any suitable antibiotic can be combined with one or more Kgp inhibitors in the pharmaceutical compositions of the invention. In certain embodiments, the invention provides a pharmaceutical composition containing one more Kgp inhibitors and an antibiotic having a P. gingivalis $MIC_{50}$ of less than 25 µg/ml. For example, the P. gingivalis $MIC_{50}$ of the antibiotic can be less than 20 µg/ml, less than 15 µg/ml, less than 10 µg/ml, less than 8 g/ml, less than 6 µg/ml, or less than 5 µg/ml. In some embodiments, the P. gingivalis $MIC_{50}$ of the antibiotic is less than 1 µg/ml. In some embodiments, the P. gingivalis $MIC_{50}$ of the antibiotic is less than 0.2 µg/ml.

Examples of bacteriocidal and bacteriostatic compounds include, but are not limited to: quinolones (e.g., moxifloxacin, gemifloxacin, ciprofloxacin, ofloxacin, trovafloxacin, sitafloxacin, and the like), β-lactams (e.g., penicillins such as amoxicillin, amoxacilin-clavulanate, piperacillin-tazobactam, penicillin G, and the like; and cephalosporins such as ceftriaxone and the like), macrolides (e.g., erythromycin, azithromycin, clarithromycin, and the like), carbapenems (e.g., doripenem, imipenem, meropinem, ertapenem, and the like), thiazolides (e.g, tizoxanidine, nitazoxanidine, RM 4807, RM 4809, and the like), tetracyclines (e.g., tetracycline, minocycline, doxycycline, eravacycline, and the like), clindamycin, metronidazole, and satranidazole. Bacteriocidal and bacteriostatic compounds also include agents that inhibit or otherwise interfere with formation of biofilms by anaerobic, gram-negative bacteria; such agents include oxantel, morantel, thiabendazole, and the like. Compositions of the invention can contain one or more Kgp inhibitors with one or more (e.g., two, three, four, five, six, or more) bacteriocidal/bacteriostatic compounds. Compositions containing bacteriocidal/bacteriostatic compounds can further contain a chlorhexidine (e.g., chlorhexidine digluconate) alone or in combination with a zinc compound (e.g., zinc acetate), can also be used in combination with the administered antibiotics.

In some embodiments, a combination of a penicillin (e.g., amoxicillin) and metronidazole or a combination of penicillin (e.g., amoxicillin), metronidazole and a tetracycline is used. In some embodiments, the antibiotic is selected from minocycline, doxycycline, metronidazole, amoxicillin, clindamycin, augmentin, satranidazole, and combinations thereof.

Examples of suitable cholinesterase inhibitors include, but are not limited to, donepezil, donepezil/memantine, galantamine, rivastigmine, and tacrine, as well as pharmaceutically acceptable salts thereof. Examples of suitable serotonin modulators include, but are not limited to, idalopirdine, RVT-101, citalopram, escitalopram, fluoxetine, fluvoxamine, paroxetine, and sertraline, as well as pharmaceutically acceptable salts thereof. Examples of suitable alpha-7 nicotinic receptor modulators include, but are not limited to, alpha-7 agonists such as encenicline and APN1125. Suitable NMDA modulators include, but are not limited to, NMDA receptor antagonists such as memantine and derivatives thereof.

Pharmaceutical compositions of the invention can also contain active agents that are directed to biomolecular targets associated with neurological diseases. Such targets include beta amyloid peptides (also referred to as beta amyloid, abeta, or Aβ), apolipoprotein E (also referred to as ApoE), and microtubule-associated tau (also referred to as tau proteins, or simply as tau).

Aβ-targeted therapies include inhibitors of Aβ production (such as beta-secretase inhibitors, gamma-secretase inhibitors, alpha-secretase activators), inhibitors of Aβ aggregation, inhibitors of Aβ oligomerization, and upregulators of Aβ clearance, among others (see, e.g., Jia, et al. *BioMed Research International*, 2014. Article ID 837157, doi: 10.1155/2014/837157). Examples of Aβ-targeted therapies include but are not limited to, antibodies, pioglitazone, begacestat, atorvastatin, simvastatin, etazolate, and tramiprosate, as well as pharmaceutically acceptable salts thereof.

Examples of ApoE-targeted therapies include, but are not limited to retinoid X receptor agonists (see, Cramer, et al., *Science* 2012. 335(6075): 1503-1506) and others described by Liu et al. (*Nat Rev Neurol*. 2013. 9(2): 106-118). Tau-targeted therapies include, but are not limited to, methylthioninium, leuco-methylthioninium, antibodies and those described by Lee, et al. (*Cold Spring Harb Perspect Med* 2011; 1:a006437).

Pharmaceutical compositions of the invention can also contain complement-targeted therapies. Such therapies target components of the complement system involved in the innate immune response. Complement targeted therapies include, but are not limited to, those described by Ricklin and Lambris (*Nat. Biotechnology* 2007. 25(11): 1265-1275).

Examples of suitable anti-inflammatories include, but are not limited to, NSAIDs such as apazone, diclofenac, ibuprofen, indomethacin, ketoprofen, nabumetone, naproxen, piroxicam, and sulindac, as well as pharmaceutically acceptable salts thereof.

VI. Methods of Treatment

As described above, infection with *P. gingivalis* and gingipain activity have been linked to the development of periodontal disease, Alzheimer's and other brain disorders, cardiovascular disease, diabetes, cancer, liver disease, kidney disease, preterm birth, arthritis, pneumonia and other disorders. See: Bostanci, et al. FEMS Microbiol Lett, 2012. 333(1): 1-9; Ghizoni, et al. *J Appl Oral Sci*, 2012. 20(1): 104-12; Gatz, et al. *Alzheimers Dement*, 2006. 2(2): 110-7; Stein, et al. *J Am Dent Assoc*, 2007. 138(10): 1314-22; quiz 1381-2; Noble, et al. *J Neurol Neurosurg Psychiatry*, 2009. 80(11): 1206-11; Sparks Stein, et al. *Alzheimers Dement*, 2012. 8(3): 196-203; Velsko, et al. *PLoS ONE*, 2014. 9(5): e97811; Demmer, et al. *J Dent Res*, 2015. 94(9S): 201-S-11S; Atanasova and Yilmaz. *Molecular Oral Microbiology*, 2014. 29(2): 55-66; Yoneda, et al. *BMC Gastroenterol*, 2012. 12: 16. Kgp inhibitors can therefore be used to diseases and conditions, such as brain disorders, caused by or otherwise affected by *P. gingivalis*.

Accordingly, another aspect of the invention provides a method of treating a disease or condition associated with *P.* gingivalis infection. The method includes administering to a subject an effective amount of a compound according to Formula Ie:

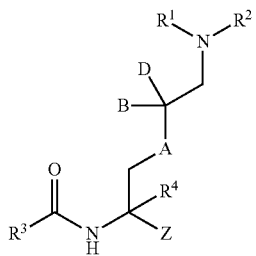

(Ie)

or a pharmaceutically acceptable salt thereof, wherein

Z is a thiol-reactive group or a masked thiol-reactive group;

A is selected from —$CH_2$— and —O—;

B and D are independently selected from hydrogen, halogen, $C_{1-4}$ haloalkyl, and $C_{1-4}$ haloalkoxy;

$R^1$ is selected from hydrogen and an amine protecting group;

$R^2$ is hydrogen; and $R^3$ is selected from $C_{6-10}$ aryl, 5-to-12 membered heteroaryl, $C_{1-8}$ alkyl, $C_{3-8}$ cycloalkyl, 5-to-12 membered saturated heterocyclyl, -L-$R^5$, and —$OR^6$, wherein L is selected from —O—, —NR—, $C_{1-4}$ alkylene, and 2- to 4-membered heteroalkylene, wherein R is selected from hydrogen and $C_{1-8}$ alkyl, $R^5$ is selected from $C_{6-10}$ aryl, 5-to-12 membered heteroaryl, $C_{3-8}$ cycloalkyl, and 5-to-12 membered saturated heterocyclyl, and —$OR^6$ and the carbonyl to which it is bonded form an amine protecting group, and wherein $R^3$ is optionally substituted with one or more substituents selected from halo, —CN, —$NO_2$, —$N_3$, —OH, $R^a$, $R^b$, —$OR^a$, —$OR^b$, —$(CH_2)_kC(O)R^c$, —$NR^d(CH_2)_uC(O)R^c$, —$O(CH_2)_uC(O)R^c$, —$(CH_2)_kCONR^dR^d$, —$(CH_2)_kNR^dC(O)R^c$, —$NR^d(CH_2)_uCONR^dR^d$, —$NR^d(CH_2)_uNR^dC(O)R^c$, —$O(CH_2)_uCONR^dR^d$, —$O(CH_2)_uNR^dC(O)R^c$, —$(CH_2)_kS(O)_2NR^dR^d$, —$(CH_2)_kNR^dS(O)_2R^c$, —$(CH_2)_kS(O)_2R^c$, —$(CH_2)_kS(O)R^c$, —$(CH_2)_kSR^d$, —$NR^d(CH_2)_uS(O)_2NR^dR^d$, —$NR^d(CH_2)_uNR^dS(O)_2R^c$, —$NR^d(CH_2)_uS(O)_2R^c$, —$NR^d(CH_2)_uS(O)R^c$, —$NR^d(CH_2)_uSR^d$, —$O(CH_2)_uS(O)_2NR^dR^d$, —$O(CH_2)_uNR^dS(O)_2R^c$, —$O(CH_2)_uS(O)_2R^c$, —$O(CH_2)_uS(O)R^c$, and —$O(CH_2)_uSR^c$, wherein:

each $R^a$ is independently selected from $C_{1-4}$ alkyl and $C_{1-4}$ haloalkyl, each $R^b$ is independently selected from $C_{3-6}$ cycloalkyl, $C_{3-6}$ halocycloalkyl, $C_{6-10}$ aryl, 5-to-12 membered heteroaryl, and 5-to-12 membered saturated heterocyclyl, each $R^c$ is independently selected from —OH, $C_{1-8}$ alkyl, $C_{1-8}$ haloalkyl, $C_{3-8}$ cycloalkyl, $C_{3-8}$ halocycloalkyl, $C_{6-10}$ aryl, ($C_{6-10}$ aryl)-($C_{1-8}$ alkyl), 5-to-12 membered heteroaryl, and 5-to-12 membered saturated heterocyclyl, each $R^d$ is independently selected from hydrogen and $C_{1-8}$ alkyl, each subscript k is independently selected from 0, 1, 2, 3, 4, 5, and 6, and each subscript u is independently selected from 1, 2, 3, 4, 5, and 6; and $R^4$ is selected from hydrogen, halogen, $C_{1-4}$ alkyl, $C_{1-4}$ alkoxy, $C_{1-4}$ haloalkyl, and $C_{1-4}$ haloalkoxy.

In some embodiments, the method includes administering one or more compounds from Table 1 to a subject.

TABLE 1

Compounds for use in the treatment of conditions associated with *P. Gingivalis* infection.

| Compound No. | Compound Structure |
|---|---|
| 1 | 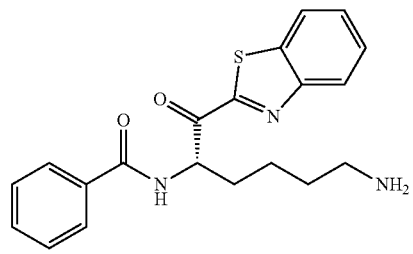 [SMILES: NCCCC[C@H](NC(=O)c1ccccc1)C(=O)c1nc2ccccc2s1] |
| 2 | 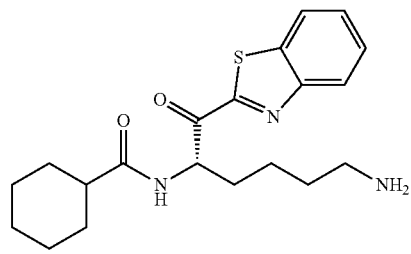 |

TABLE 1-continued

Compounds for use in the treatment of conditions associated with *P. Gingivalis* infection.

| Compound No. | Compound Structure |
|---|---|
| 3 | 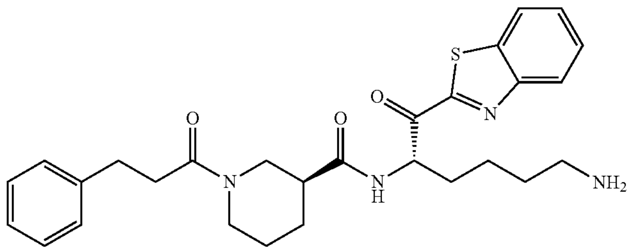 [SMILES: NCCCC[C@H](NC(=O)[C@H]1CCCN(C(=O)CCc2ccccc2)C1)C(=O)c1nc2ccccc2s1] |
| 4 | 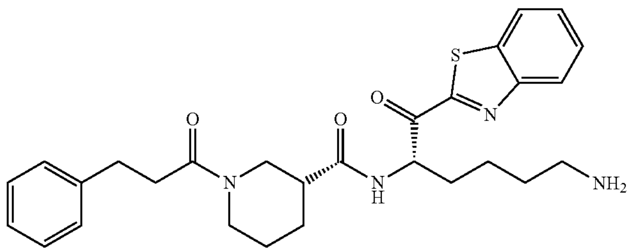 |
| 5/6 | 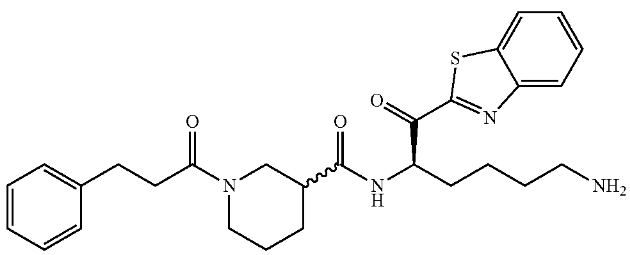 [SMILES: NCCCC[C@@H](NC(=O)C1CCCN(C(=O)CCc2ccccc2)C1)C(=O)c1nc2ccccc2s1] |
| 7 | 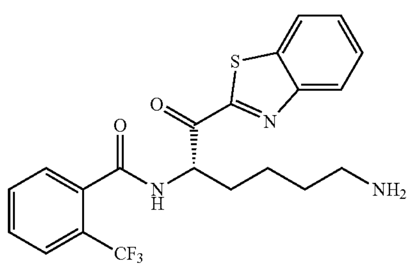 [SMILES: NCCCC[C@H](NC(=O)c1ccccc1C(F)(F)F)C(=O)c1nc2ccccc2s1] |
| 8 | 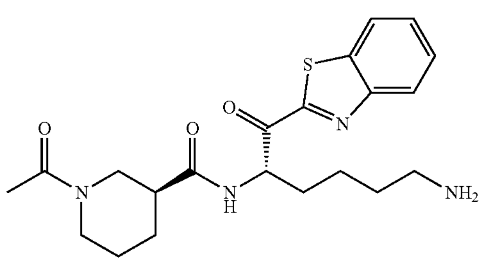 [SMILES: CC(=O)N1CCC[C@H](C(=O)N[C@@H](CCCCN)C(=O)c2nc3ccccc3s2)C1] |
| 9 | 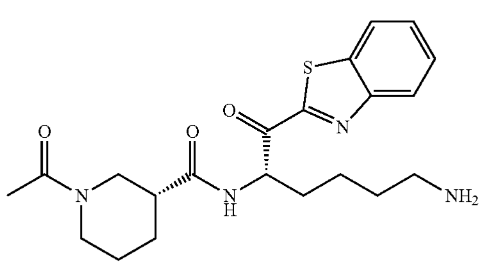 [SMILES: CC(=O)N1CCC[C@@H](C(=O)N[C@@H](CCCCN)C(=O)c2nc3ccccc3s2)C1] |

TABLE 1-continued
Compounds for use in the treatment of conditions associated with *P. Gingivalis* infection.
| Compound No. | Compound Structure |
|---|---|
| 10 | 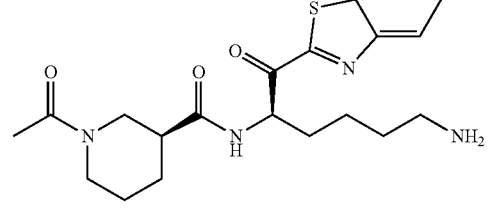 |
| 11 | 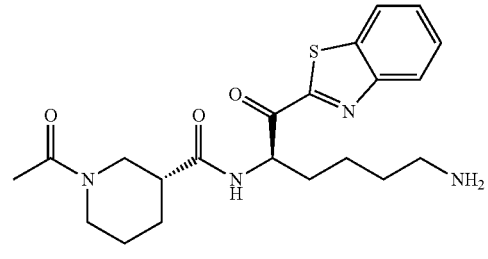 [SMILES: CC(=O)N1CCC[C@@H](C(=O)N[C@H](CCCCN)C(=O)c2nc3ccccc3s2)C1] |
| 12 | 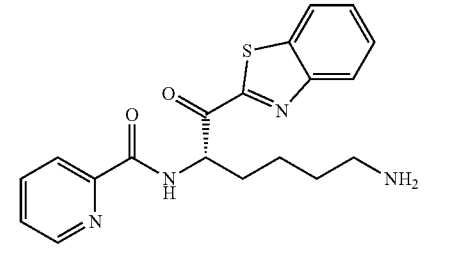 [SMILES: NCCCC[C@H](NC(=O)c1ccccn1)C(=O)c1nc2ccccc2s1] |
| 13 | 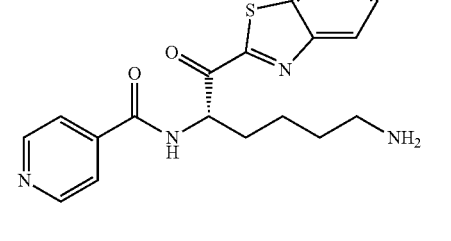 |
| 14/15 | 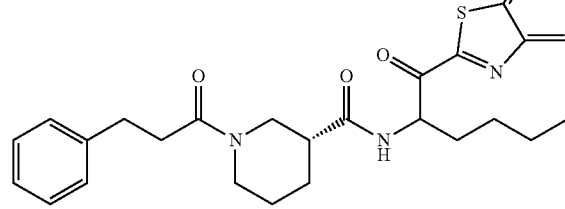 |

TABLE 1-continued

Compounds for use in the treatment of conditions associated with *P. Gingivalis* infection.

| Compound No. | Compound Structure |
|---|---|
| 16/17 | 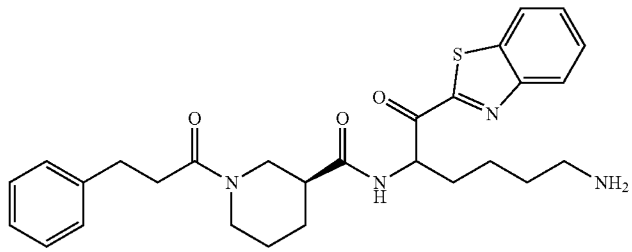 [SMILES: NCCCCC(NC(=O)[C@H]1CCCN(C(=O)CCc2ccccc2)C1)C(=O)c1nc2ccccc2s1] |
| 18/19 | 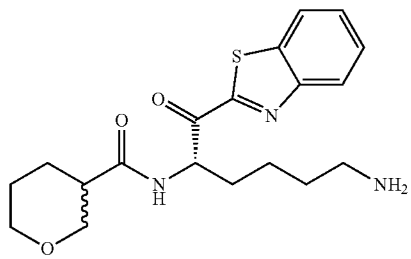 [SMILES: NCCCC[C@H](NC(=O)C1CCCOC1)C(=O)c1nc2ccccc2s1] |
| 20/21 | 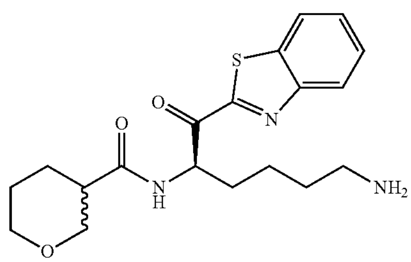 [SMILES: NCCCC[C@@H](NC(=O)C1CCCOC1)C(=O)c1nc2ccccc2s1] |
| 22 | 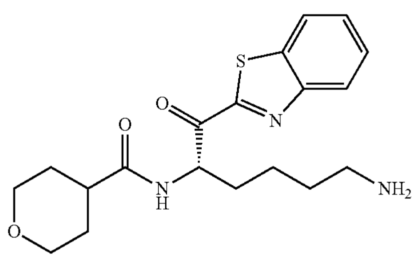 [SMILES: NCCCC[C@H](NC(=O)C1CCOCC1)C(=O)c1nc2ccccc2s1] |
| 23 | 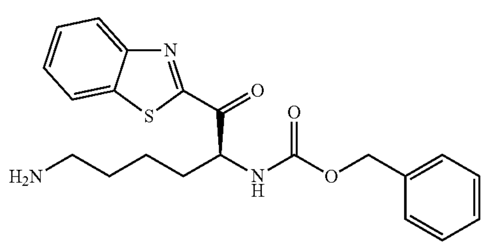 [SMILES: NCCCC[C@H](NC(=O)OCc1ccccc1)C(=O)c1nc2ccccc2s1] |
| 24 | 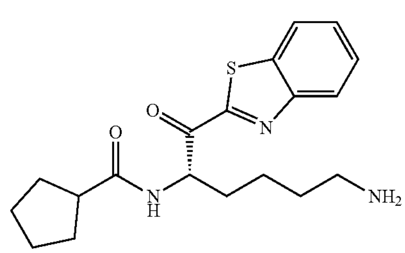 [SMILES: NCCCC[C@H](NC(=O)C1CCCC1)C(=O)c1nc2ccccc2s1] |

TABLE 1-continued

Compounds for use in the treatment of conditions associated with *P. Gingivalis* infection.

| Compound No. | Compound Structure |
| --- | --- |
| 25/26 | 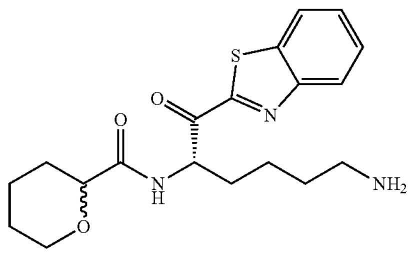 [SMILES: NCCCC[C@H](NC(=O)C1CCCCO1)C(=O)c1nc2ccccc2s1] |
| 27/28 | 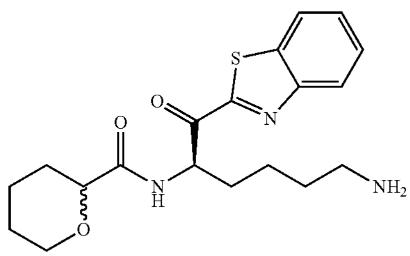 [SMILES: NCCCC[C@@H](NC(=O)C1CCCCO1)C(=O)c1nc2ccccc2s1] |
| 29 | 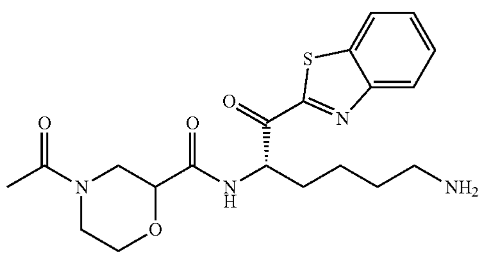 |
| 30 | 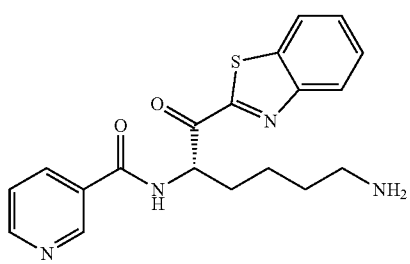 [SMILES: NCCCC[C@H](NC(=O)c1cccnc1)C(=O)c1nc2ccccc2s1] |
| 31 | 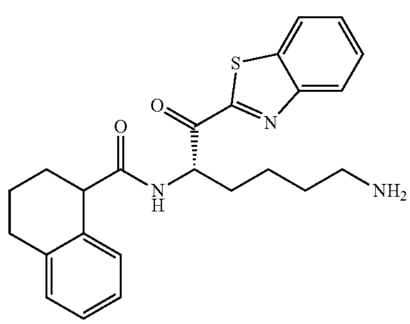 [SMILES: NCCCC[C@H](NC(=O)C1CCCc2ccccc21)C(=O)c1nc2ccccc2s1] |

TABLE 1-continued

Compounds for use in the treatment of conditions associated with *P. Gingivalis* infection.

| Compound No. | Compound Structure |
|---|---|
| 32 | 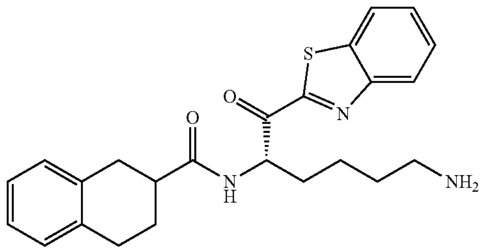 [SMILES: NCCCC[C@H](NC(=O)C1CCc2ccccc2C1)C(=O)c1nc2ccccc2s1] |
| 33 | 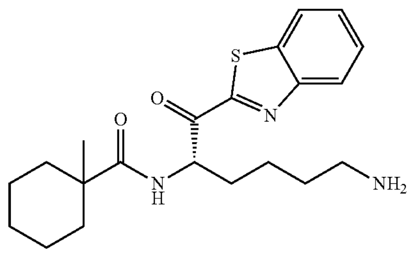 [SMILES: CC1(C(=O)N[C@@H](CCCCN)C(=O)c2nc3ccccc3s2)CCCCC1] |
| 34/35 | 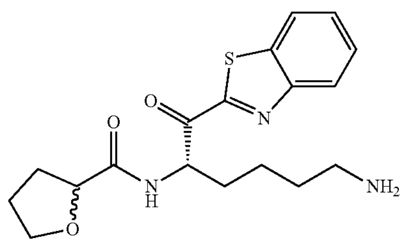 [SMILES: NCCCC[C@H](NC(=O)C1CCCO1)C(=O)c1nc2ccccc2s1] |
| 36/37 | 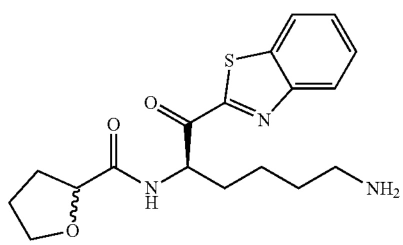 [SMILES: NCCCC[C@@H](NC(=O)C1CCCO1)C(=O)c1nc2ccccc2s1] |
| 38 | 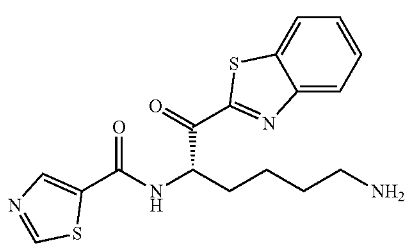 [SMILES: NCCCC[C@H](NC(=O)c1cncs1)C(=O)c1nc2ccccc2s1] |
| 39 | 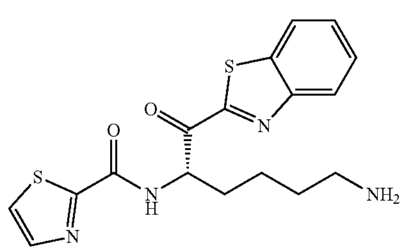 [SMILES: NCCCC[C@H](NC(=O)c1nccs1)C(=O)c1nc2ccccc2s1] |

TABLE 1-continued

Compounds for use in the treatment of conditions associated with *P. Gingivalis* infection.

| Compound No. | Compound Structure |
|---|---|
| 40 | 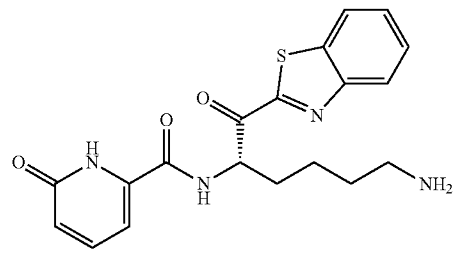 [SMILES: NCCCC[C@H](NC(=O)c1cccc(=O)[nH]1)C(=O)c1nc2ccccc2s1] |
| 41 | 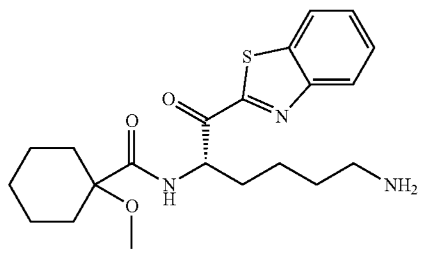 [SMILES: COC1(C(=O)N[C@@H](CCCCN)C(=O)c2nc3ccccc3s2)CCCCC1] |
| 42 | 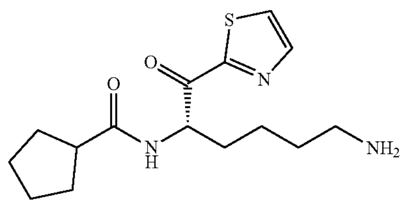 [SMILES: NCCCC[C@H](NC(=O)C1CCCC1)C(=O)c1nccs1] |
| 43 | 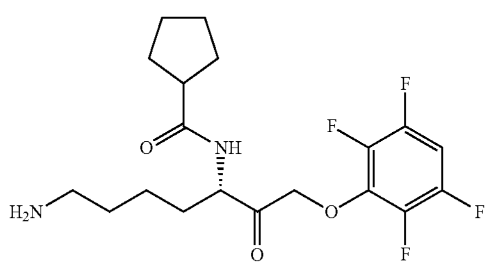 [SMILES: NCCCC[C@H](NC(=O)C1CCCC1)C(=O)COc1c(F)c(F)cc(F)c1F] |
| 44 | 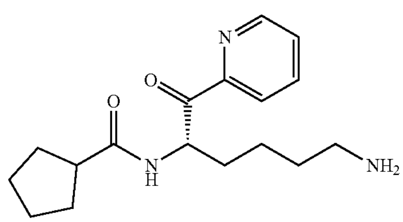 [SMILES: NCCCC[C@H](NC(=O)C1CCCC1)C(=O)c1ccccn1] |
| 45 | 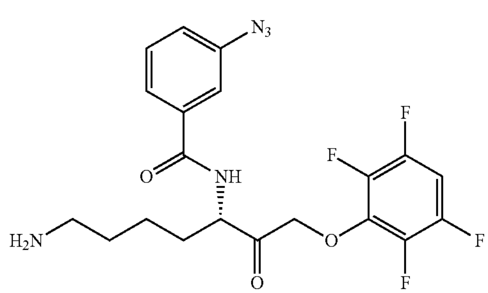 [SMILES: [N-]=[N+]=Nc1cccc(C(=O)N[C@@H](CCCCN)C(=O)COc2c(F)c(F)cc(F)c2F)c1] |

TABLE 1-continued

Compounds for use in the treatment of conditions associated with *P. Gingivalis* infection.

| Compound No. | Compound Structure |
|---|---|
| 46 | *(structure: cyclopentanecarbonyl-NH group on a chain with H₂N-CHF-CH₂CH₂-C*(NHC(O)cyclopentyl)-C(O)-CH₂-O-2,3,5-trifluorophenyl)* |
| 47 | *(structure: benzoyl-NH-C(CH₃)(CH₂CH₂CH₂CH₂NH₂)-C(O)-CH₂-O-2,3,5-trifluorophenyl)* |
| 48 | *(structure: methylsulfonyl-piperidin-3-yl-C(O)-NH-CH(CH₂CH₂CH₂CH₂NH₂)-C(O)-benzothiazol-2-yl)* |

In some embodiments, the invention provides a method of treating a disease or condition associated with *P. gingivalis* infection as described above, wherein the subject is a human or a canine.

In some embodiments, the invention provides a method of treating a disease or condition associated with *P. gingivalis* infection as described above, wherein the compound of Formula Ie has a structure according to Formula If:

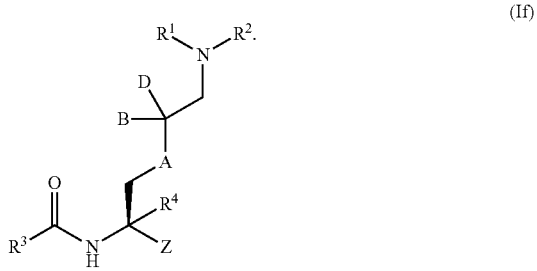

(If)

In some embodiments, the invention provides a method of treating a disease or condition associated with *P. gingivalis* infection as described above, wherein $R^4$ is hydrogen and B and D are independently selected from hydrogen, halogen, halomethyl, and halomethoxy.

In some embodiments, Z is selected from benzothiazol-2-yl-carbonyl; thiazol-2-yl-carbonyl; oxazol-2-yl-carbonyl; benzooxazol-2-yl-carbonyl; pyridin-2-yl-carbonyl; pyrimidin-4-yl-carbonyl; pyrimidin-2-yl-carbonyl; isoxazol-5-yl-carbonyl; isoxazol-3-yl-carbonyl; 1,2,4-oxadiazol-3-yl-carbonyl; 1,2,4-oxadiazol-5-yl-carbonyl; cyano; ethynyl; fluoromethyl-carbonyl; acyloxymethyl-carbonyl; aryloxymethyl-carbonyl; alkylsulfonyl-vinyl; and arylsulfonyl-vinyl; each of which is optionally substituted with one or more substituents selected from $C_{1-4}$ alkyl, $C_{1-4}$ alkoxy, $C_{1-4}$ haloalkyl, $C_{1-4}$ haloalkoxy, halogen, and $-N_3$.

In some embodiments, Z is selected from benzothiazol-2-yl-carbonyl, halogen-substituted aryloxymethyl-carbonyl, pyridin-2-yl-carbonyl, and thiazol-2-yl-carbonyl.

In some embodiments, the method includes administering a compound having a structure according to Formula Ic:

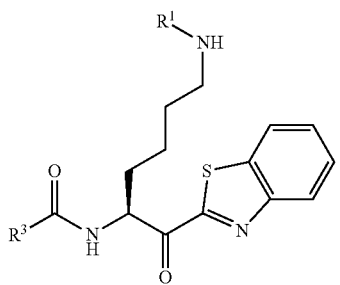
(Ic)

or a pharmaceutically acceptable salt thereof, wherein $R^3$ is selected from $C_{6-10}$ aryl, 5-to-12 membered heteroaryl, $C_{3-8}$ cycloalkyl, 5-to-12 membered saturated heterocyclyl, and -L-$R^5$, wherein L is $C_{1-4}$ alkylene.

In some embodiments, the compound used in the method is a compound of Formula Ic, or a pharmaceutically acceptable salt thereof, wherein $R^3$ is selected from cyclohexyl, cyclopentyl, morpholino, phenyl, piperidinyl, pyridinyl, tetrahydrofuranyl, tetrahydropyranyl, 1,2,3,4-tetrahydronaphthyl, and thiazolyl, each of which is optionally substituted with 1-3 members selected from methyl, methoxy, trifluoromethyl, acetyl, and —$N_3$.

In some embodiments, the compound used in the method is selected from:

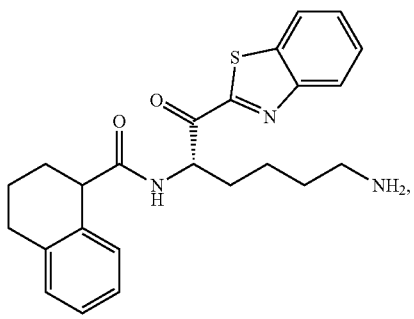

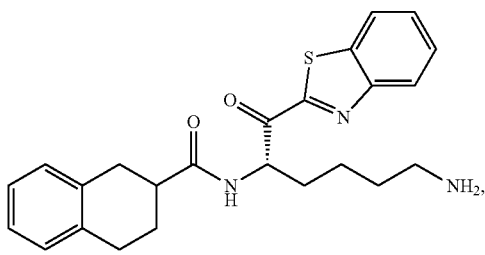

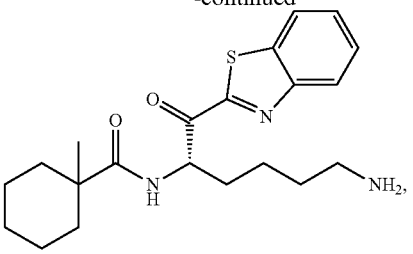

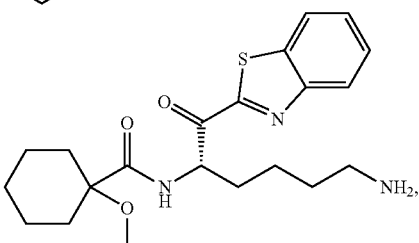

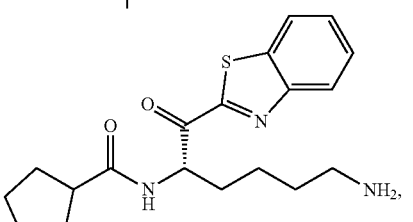

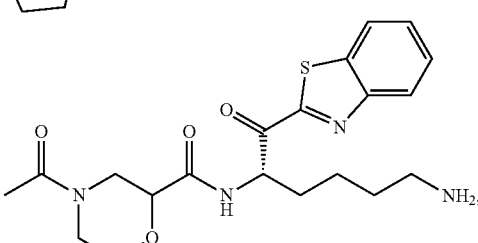

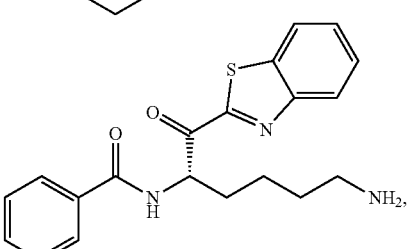

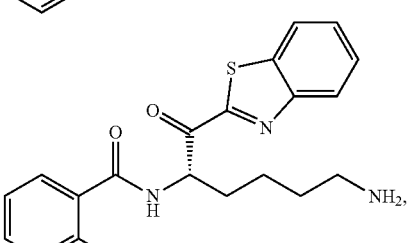

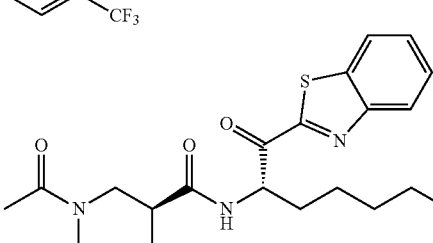

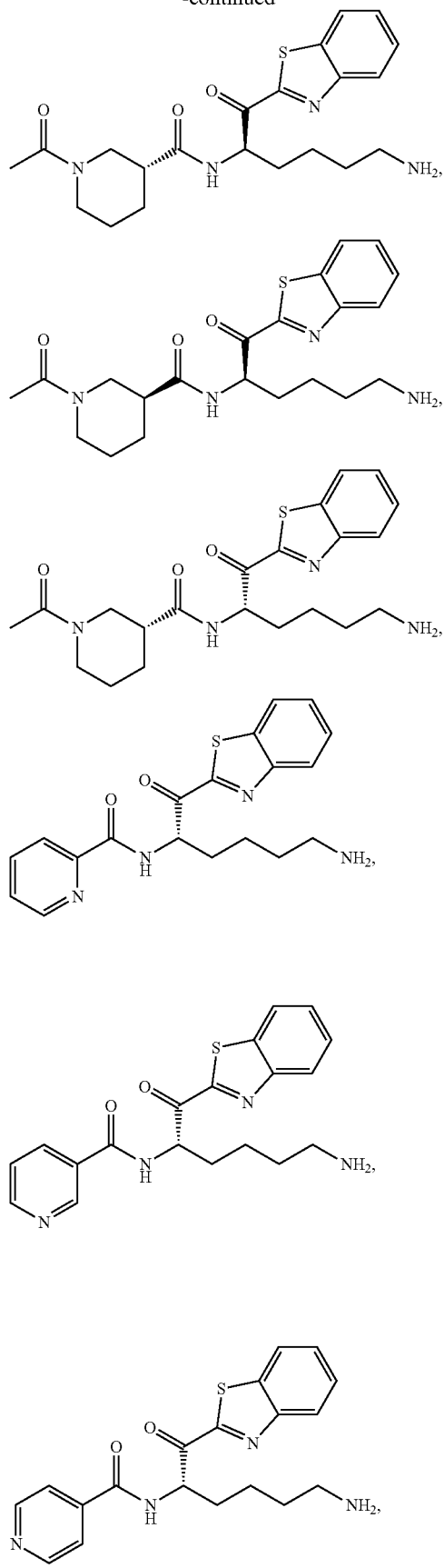
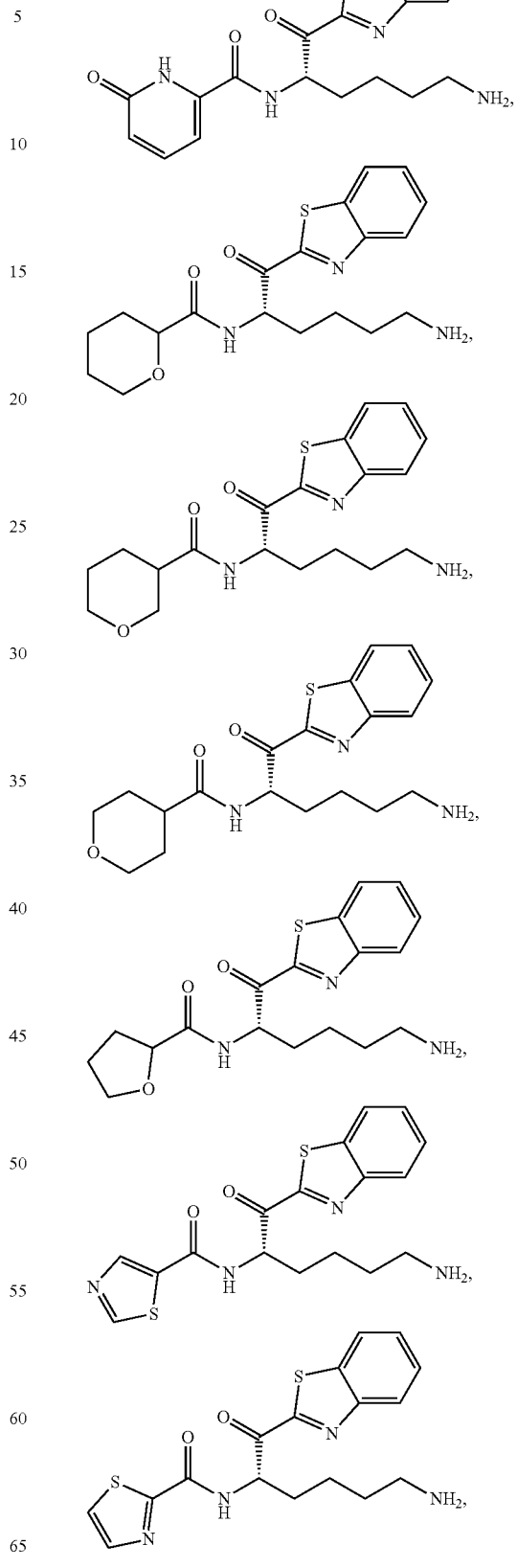
and pharmaceutically acceptable salts thereof.

In some embodiments, the method includes administering a compound having a structure according to Formula Id:

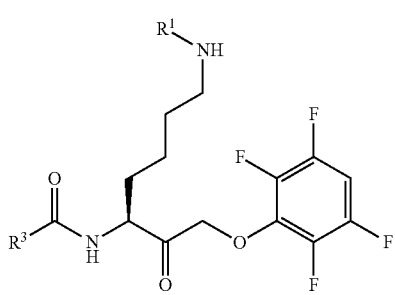
(Id)

or a pharmaceutically acceptable salt thereof,
wherein $R^3$ is selected from $C_{6-10}$ aryl, 5-to-12 membered heteroaryl, $C_{3-8}$ cycloalkyl, 5-to-12 membered saturated heterocyclyl, and -L-$R^5$,
wherein L is $C_{1-4}$ alkylene.

In some embodiments, the compound used in the method is a compound of Formula Id, or a pharmaceutically acceptable salt thereof, wherein $R^3$ is selected from cyclohexyl, cyclopentyl, morpholino, phenyl, piperidinyl, pyridinyl, tetrahydrofuranyl, tetrahydropyranyl, 1,2,3,4-tetrahydronaphthyl, and thiazolyl, each of which is optionally substituted with 1-3 members selected from methyl, methoxy, trifluoromethyl, acetyl, and —$N_3$.

In some embodiments, the compound used in the method is selected from:

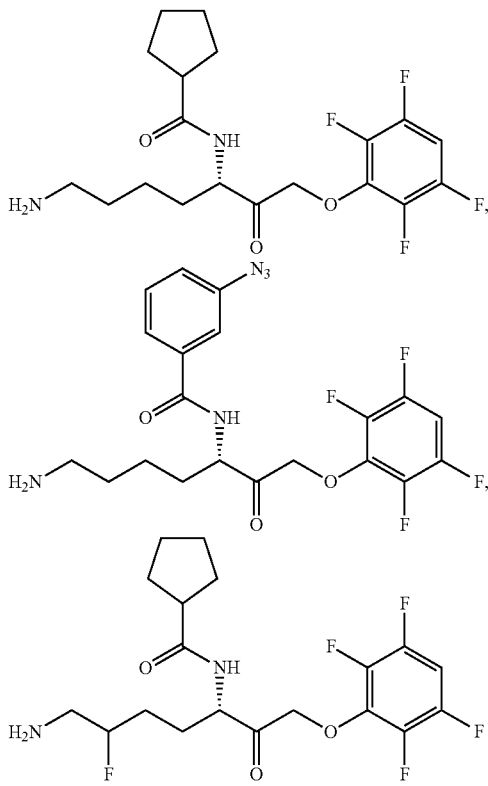

and pharmaceutically acceptable salts thereof.

In some embodiments, the compound used in the method is selected from:

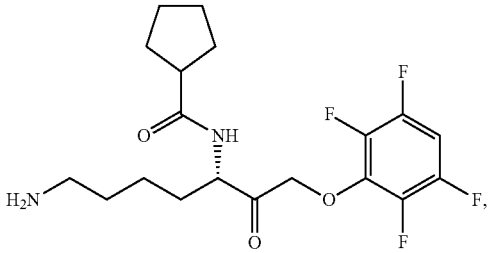

and pharmaceutically acceptable salts thereof.

In some embodiments, the compound used in the method of the invention is a compound of Formula I, wherein Z is selected from pyridin-2-yl-carbonyl and thiazol-2-yl-carbonyl, and $R^3$ is selected from $C_{6-10}$ aryl and $C_{3-8}$ cycloalkyl. In some such embodiments, the compound used in the method is selected from:

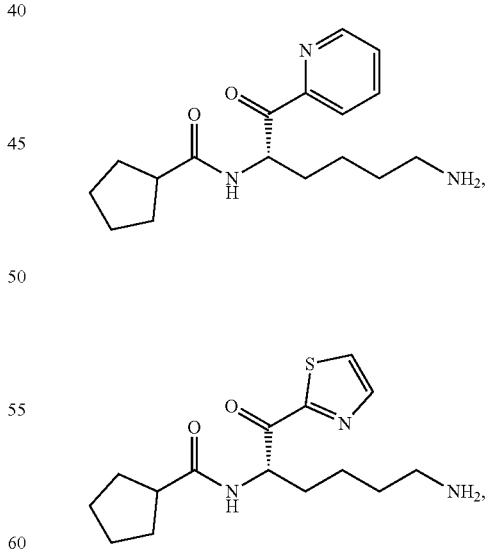

and pharmaceutically acceptable salts thereof.

In some embodiments, the compound used in the method of the invention is a compound of Formula I, wherein $R^4$ is selected from $C_{1-4}$ alkyl and $C_{1-4}$ haloalkyl. In some embodiments, the compound used in the method is

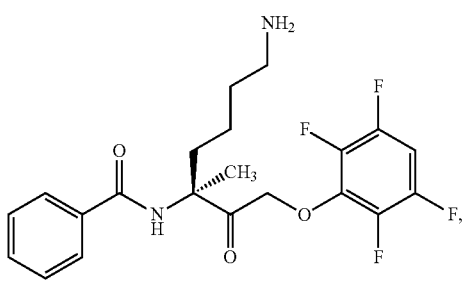 [SMILES: C[C@@](CCCCN)(NC(=O)c1ccccc1)C(=O)COc1c(F)c(F)cc(F)c1F]

or a pharmaceutically acceptable salt thereof.

In some embodiments, the compound used in the method is selected from:

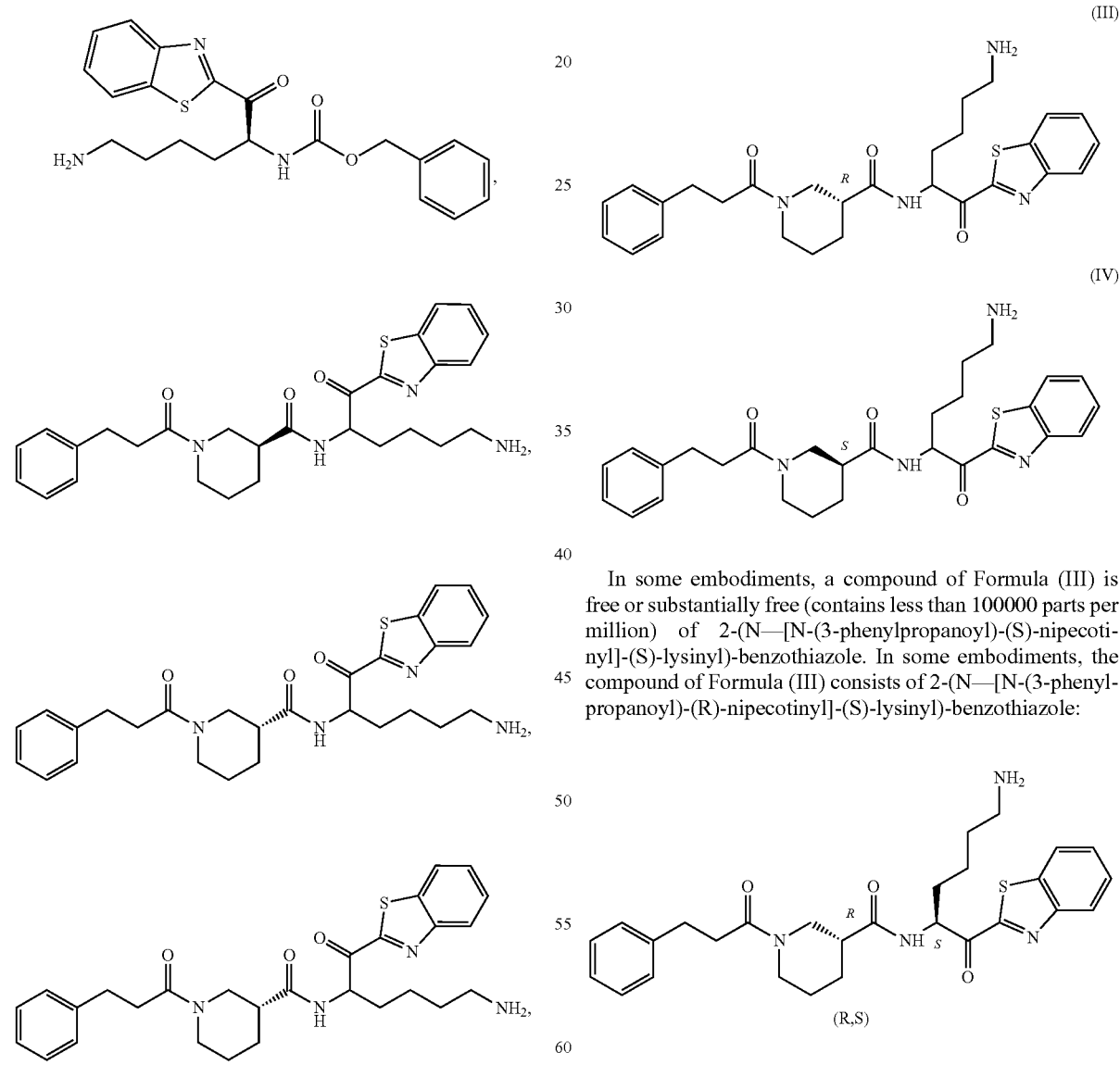

and pharmaceutically acceptable salts thereof.

Curtis et al. have described a compound dubbed A71561 (see, *Infection and Immunity,* 2002. 70(12): 6968-6975). A71561 is a mixture of two diastereomers: 2-(N—[N-(3-phenylpropanoyl)-(S)-nipecotinyl]-(S)-lysinyl)-benzothiazole and 2-(N—[N-(3-phenylpropanoyl)-(R)-nipecotinyl]-(S)-lysinyl)-benzothiazole. A71561 is not a selective inhibitor for Kgp, as its affinity to human Trypsin (Ki=30 nM) is too close to the affinity for Kgp (Ki=0.9 nM). There is no suggestion by Curtis that A71561 or structurally similar compounds may be used to treat brain disorders (e.g., Alzheimer's disease), diabetes, cardiovascular disease, arthritis or retinal disorders.

The method of the invention specifically encompasses the use of 2-(N—[N-(3-phenylpropanoyl)-(R)-nipecotinyl]-lysinyl)-benzothiazole, 2-(N—[N-(3-phenylpropanoyl)-(S)-nipecotinyl]-lysinyl)-benzothiazole (compounds of Formula (III) and (IV), respectively, and mixtures thereof, and pharmaceutically acceptable salts thereof, In some embodiments, a compound of Formula (III) is free or substantially free (contains less than 100000 parts per million) of 2-(N—[N-(3-phenylpropanoyl)-(S)-nipecotinyl]-(S)-lysinyl)-benzothiazole. In some embodiments, the compound of Formula (III) consists of 2-(N—[N-(3-phenylpropanoyl)-(R)-nipecotinyl]-(S)-lysinyl)-benzothiazole:

In some embodiments, a compound of Formula (III) would comprise (and in some embodiments, consist of) a mixture of the of 2-(N—[N-(3-phenylpropanoyl)-(R)-nipecotinyl]-(S)-lysinyl)-benzothiazole and of 2-(N—[N-(3-phenylpropanoyl)-(R)-nipecotinyl]-(R)-lysinyl)-benzothiazole stereoisomers:

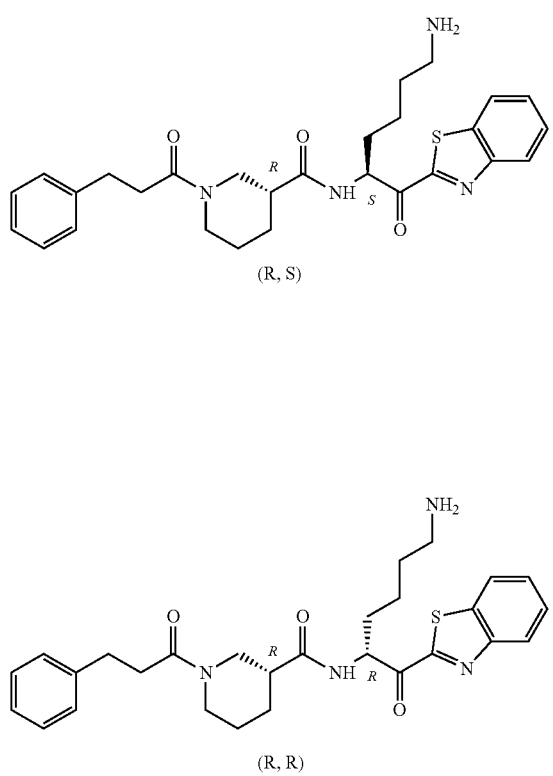

(R, S)

(R, R)

The 2-(N—[N-(3-phenylpropanoyl)-(R)-nipecotinyl]-(S)-lysinyl)-benzothiazole and of 2-(N—[N-(3-phenylpropanoyl)-(R)-nipecotinyl]-(R)-lysinyl)-benzothiazole stereoisomers may, e.g., be in a ratio greater than 20:1. In some embodiments, the ratio would be between 20:1 and 2:1. In some embodiments, the ratio would be less than 2:1.

In some embodiments, a compound of Formula (IV) would comprise (and in certain preferred embodiments, consist of) 2-(N—[N-(3-phenylpropanoyl)-(S)-nipecotinyl]-(S)-lysinyl)-benzothiazole:

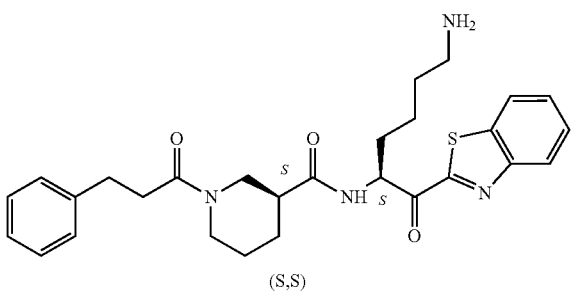

(S,S)

Thus, the invention encompasses use of a compound of Formula (IV) which is free or substantially free (contains less than 100000 parts per million) of 2-(N—[N-(3-phenylpropanoyl)-(S)-nipecotinyl]-(R)-lysinyl)-benzothiazole.

In some embodiments, a compound of Formula (IV) comprises a mixture of 2-(N—[N-(3-phenylpropanoyl)-(S)-nipecotinyl]-(S)-lysinyl)-benzothiazole and 2-(N—[N-(3-phenylpropanoyl)-(S)-nipecotinyl]-(R)-lysinyl)-benzothiazole:

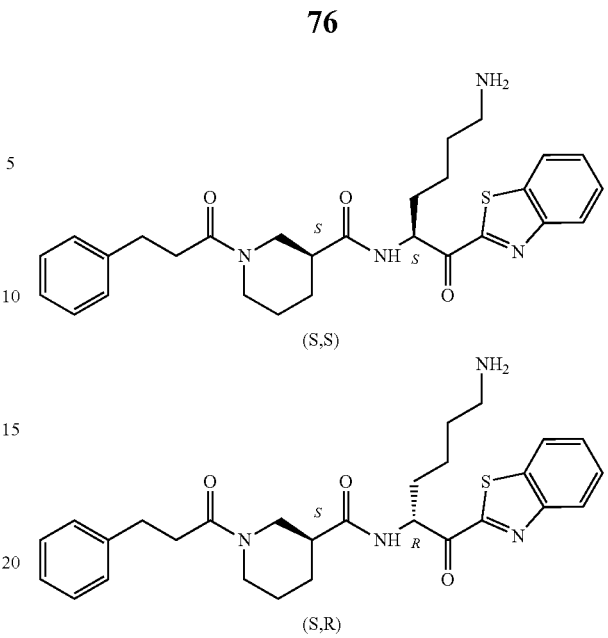

(S,S)

(S,R)

The 2-(N—[N-(3-phenylpropanoyl)-(S)-nipecotinyl]-(S)-lysinyl)-benzothiazole and 2-(N—[N-(3-phenylpropanoyl)-(S)-nipecotinyl]-(R)-lysinyl)-benzothiazole can, for example, be in a ratio greater than 20:1. In some embodiments, the ratio is between 20:1 and 2:1. In some embodiments, the ratio is less than 2:1.

In some embodiments, the disease or condition is selected from a brain disorder, periodontal disease, diabetes, a cardiovascular disease, arthritis, preterm birth, pneumonia, cancer, a kidney disease, a liver disease, a retinal disorder, and glaucoma.

In some embodiments, the disease or condition is a brain disorder.

In some embodiments, the brain disorder is selected from Alzheimer's disease, Down's syndrome, epilepsy, autism, Parkinson's disease, essential tremor, fronto-temporal dementia, progressive supranuclear palsy, amyotrophic lateral sclerosis, Huntington's disease, multiple sclerosis, mild cognitive impairment, age associated memory impairment, chronic traumatic encephalopathy, stroke, Lewy Body disease, multiple system atrophy, schizophrenia, and depression.

In some embodiments, the brain disorder is Alzheimer's disease.

In some embodiments, the method further includes administering to the subject one or more active agents selected from a cholinesterase inhibitor, a serotonin modulator, an NMDA modulator, an Aβ targeted therapy, an ApoE targeted therapy, a microglia targeted therapy, a blood brain barrier targeted therapy, a tau targeted therapy, a complement targeted therapy, and an anti-inflammatory.

In some embodiments, the disease or condition is periodontal disease. In some embodiments, the disease or condition is a liver disease. In some embodiments, the liver disease is non-alcoholic steatohepatitis. In some embodiments, the disease or condition is a retinal disorder. In some embodiments, the retinal disorder is age-related macular degeneration.

In some embodiments, the disease or condition is cancer. In some embodiments, the cancer is breast cancer, oral cancer, pancreatic cancer, or glioblastoma multiforme.

In certain embodiments, compounds of the invention inhibit active Kgp in the brain of a mammal, e.g., a human or an animal (e.g., a dog), and are cytoprotective or neuroprotective. By "neuroprotective," it is meant that the compounds prevent aberrant changes to neurons or death of neurons. Compounds of the invention are therefore useful, e.g., in treatment of a brain disorder (e.g., a neurodegenerative disease (e.g., Alzheimer's disease, Down's syndrome, epilepsy, autism, Parkinson's disease, essential tremor, fronto-temporal dementia, progressive supranuclear palsy, amyotrophic lateral sclerosis, Huntington's disease, multiple sclerosis, mild cognitive impairment, age associated memory impairment, chronic traumatic encephalopathy, stroke, Lewy Body disease, multiple system atrophy, schizophrenia and depression, etc.), diabetes, cardiovascular disease, arthritis, retinal disorders (e.g., age related macular degeneration) and glaucoma.

Figure 1B:
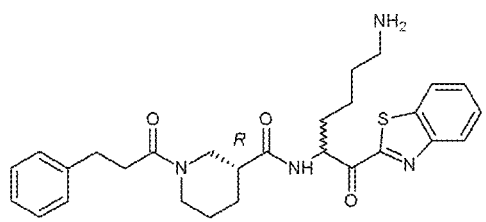
FIG. 1B shows the structure of 2-(N—[N-(3-phenylpropanoyl)-(R)-nipecotinyl]-(R)-lysinyl)-benzothiazole; compound 4.
Figure 1C:
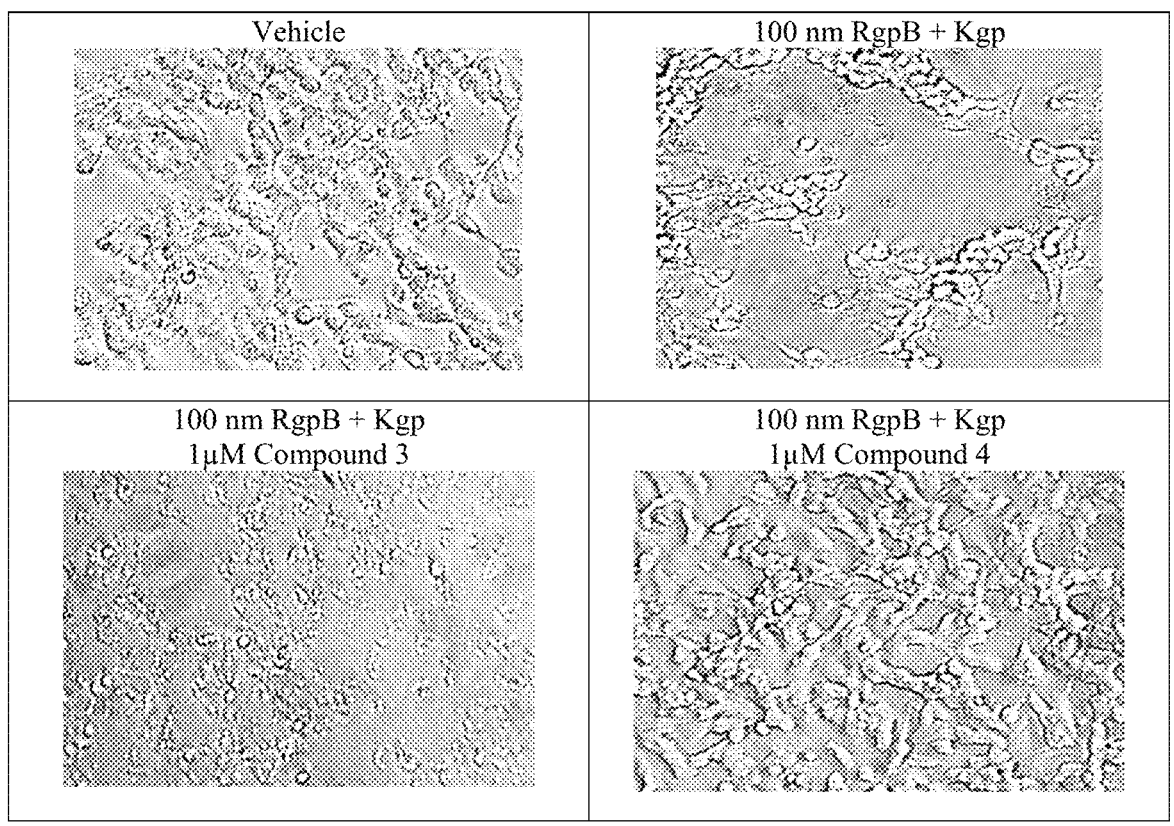
FIG. 1C shows that compound 4 prevents gingipain-induced death of differentiated SHSY-5Y cells, but compound 3 does not. Compound 3 exhibits a Kgp $IC_{50}$ between 10 and 25 nM, and compound 4 exhibits a Kgp $IC_{50}$ between 1 and 10 nM.
Figure 2A:
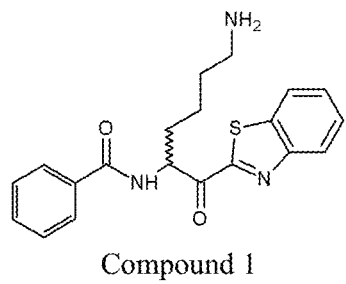
FIG. 2A shows the structure of compound 1.
Figure 2B:
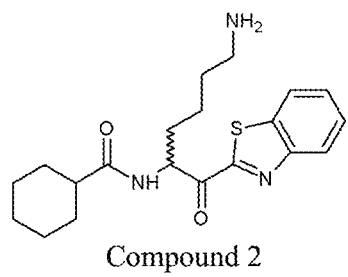
FIG. 2B shows the structure of compound 2.

As evidenced by FIG. 1, 2-(N—[N-(3-phenylpropanoyl)-(R)-nipecotinyl]-(R)-lysinyl)-benzothiazole is effective at preventing cell death. As evidenced by FIG. 2, compound 1 and compound 2 are effective at preventing cell death. In addition, modifications to these 1-(3-phenylpropionyl)piperidine-3-carboxylic acid-[4-amino-1-(benzothiazole-2-carbonyl butyl] amides can improve the properties (e.g., neuroprotective properties) of the compounds of the invention and/or make compounds of the invention more suitable for systemic administration. Data from in vitro assays demonstrates that this type of compounds can be used to protect cells from gingipain induced cell death (FIG. 2).

Kgp inhibitors as described herein can be administered at any suitable dose in the methods of the invention. In general, a Kgp inhibitor is administered at a dose ranging from about 0.1 milligrams to about 1000 milligrams per kilogram of a subject's body weight (i.e., about 0.1-1000 mg/kg). The dose of Kgp inhibitor can be, for example, about 0.1-1000 mg/kg, or about 1-500 mg/kg, or about 25-250 mg/kg, or about 50-100 mg/kg. The dose of Kgp inhibitor can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg. The dosages can be varied depending upon the requirements of the patient, the severity of the disorder being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat the disorder.

Kgp inhibitors can be administered for periods of time which will vary depending upon the nature of the particular disorder, its severity, and the overall condition of the subject to whom the Kgp inhibitor is administered. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a subject can be monitored for changes in his or her condition and for alleviation of the symptoms of the disorder. The dosage of the Kgp inhibitor can either be increased in the event the subject does not respond significantly to a particular dosage level, or the dose can be decreased if an alleviation of the symptoms of the disorder is observed, or if the disorder has been remedied, or if unacceptable side effects are seen with a particular dosage.

A therapeutically effective amount of a Kgp inhibitor can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 144, 168, 192, 216, or 240 hours (i.e., 3, 4, 5, 6, 7, 8, 9, or 10 days). In certain embodiments, administration of one or more Kgp inhibitors is conducted in a chronic fashion over periods ranging from several months to several years. Accordingly, some embodiments of the invention provide a method of treating a disease or condition associated with *P. gingivalis* infection as described above, wherein the compound is administered to the subject for at least one year. In some embodiments, the compound is administered to the subject for at least 10 years. In some embodiments, the compound is administered to the subject for at least 60 years.

Administration of Kgp inhibitors according to the methods of the invention typically results in the reduction of circulating levels of active Kgp in a subject and/or the reduction of active Kgp in the brain. In certain embodiments, administration of a Kgp inhibitor according to the methods of the invention results in at least a 20% reduction of circulating levels of active Kgp and/or at least a 20% reduction of active Kgp in the brain. For example, the circulating levels of Kgp and/or the levels of Kgp in the brain are preferably reduced by from about 25% to about 95%, or from about 35% to about 95%, or from about 40% to about 85%, or from about 40% to about 80% as compared to the corresponding levels of Kgp 24 hours prior to the first administration of the Kgp inhibitor.

Kgp inhibitors can be administered alone or in combination with one or more additional therapeutically active agents, as described above. The one or more additional therapeutically effective agents include, e.g., (i) a pharmaceutically acceptable agent which inhibits Arginine Gingipain A (RgpA) and/or Arginine Gingipain B (RgpB) production, translocation of RgpB and/or Kgp into systemic circulation or brain and/or pathological (e.g., neurotoxic effects) of RgpA, RgpB and or Kgp in a mammal; (ii) an antibacterial agent which is bacteriostatic or bacteriocidal with respect to *P. gingivalis*; (iii) one or more antibodies which bind to RgpA, RgpB and/or Kgp (e.g., 18E6, which binds to the first half of the immunoglobulin domain of RgpB; Kgp-specific monoclonal antibody, 7B9, which recognizes an epitope within the Kgp catalytic domain; the RgpA antibody 61Bg 1.3, humanized versions of any of the foregoing, etc.); (iv) epitopes of antibodies which bind to RgpA, RgpB and/or Kgp or other proteins expressed by *P. gingivalis*; and (v) combinations of any of the foregoing.

The additional therapeutically active agents also include Aβ peptides level reducers, pathogenic level tau reducers, microtubule stabilizers, agents capable or removing atherosclerotic plaques, agents that lower circulating levels of β-amyloid and tau, modulators of autophagy, neurotransmitter level regulators, GABA(A) α5 receptors inhibitors, and additional agents that help maintain and/or restore cognitive function and functional deficits of Alzheimer's disease, and/or slow down decline in cognitive functions and functional deficits in Alzheimer's disease.

Figure 9:
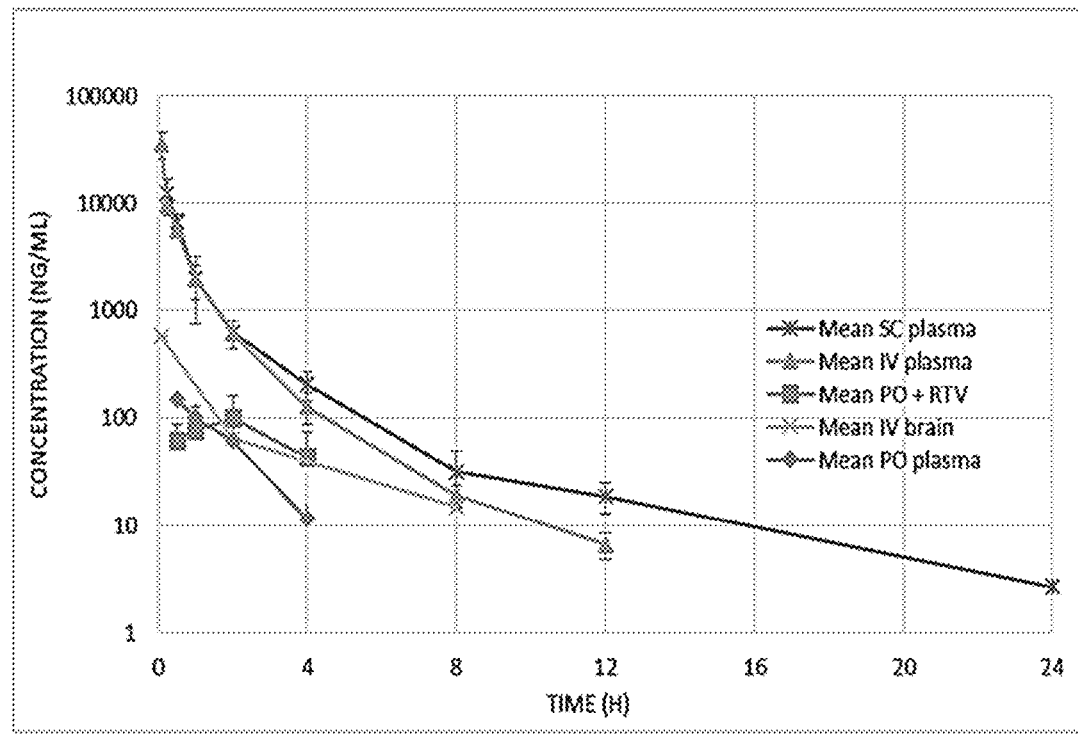
FIG. 9 shows phamacokinetic data for a Kgp inhibitor, Kyt-36, demonstrating that ritonavir (RTC) increases the half-life of orally administered Kyt-36.

Pharmaceutical compositions of the invention can contain one or more Kgp inhibitors as described herein in combination with ritonavir (RTV), which can increase bioavailability and increase blood brain barrier penetration. For example, ritonavir is commonly combined with oral peptidic HIV protease inhibitors to increase plasma levels by inhibiting the P450 3A4 enzyme and thus decreasing first-pass metabolism (see, Walmsley, et al., *N Engl J Med,* 2002. 346(26): 2039-46). In addition, RTV binds to P-glycoprotein, a transmembrane efflux pump that is found in many tissues, including the blood brain barrier, allowing co-administered compounds better access to the brain (see, Marzolini, et al., *Mol Pharm,* 2013. 10(6): 2340-9). Therefore, a combination of RTV and Kgp inhibitors can be used to increase plasma concentrations and brain levels of the gingipain inhibitors. It is shown herein that oral administration of RTV 15 minutes prior to the Kgp inhibitor, Kyt-36 increases the half life (FIG. 9) therefore it is expected that RTV will also increase the half life of other Kgp inhibitors.

In some embodiments, compounds of the invention can be administered with natural gingipain inhibitors including melabaricone C, isolated from nutmeg or polyphenolic compounds derived from plants, such as cranberry, green tea, apple, and hops can be administered in conjunction for treatment or prevention of brain disorders. Naturally and unnaturally occurring antimicrobial peptides including: κ-casein peptide (109-137) 34, histatin 5, and CL(14-25), CL(K25A) and CL(R24A, K25A), can also be administered in conjunction with the Kgp inhibitors of the invention. (see, e.g., Taniguchi et al., *Biopolymers,* 2014. 102(5): 379-89).

Kgp inhibitors as described herein can be administered with antibodies targeting gingipains or other *P. gingivalis* proteins. Antibodies may rely on damage to the blood brain barrier for access to the brain or peripheral interference with gingpains and *P. gingivalis* propagation. Antibodies can also help to stimulate the efficacy of the immune system in clearing the bacteria. New or existing antibodies to RgpA, RgpB, or Kgp can be utilized including 18E6 and 7B9. An RgpA antibody 61BG 1.3 has previously demonstrated efficacy topically in prevention of recolonization by *P. gingivalis* after periodontal treatment. See, Booth et al., *Infect Immun,* 1996. 64(2): 422-7. Antibodies would preferably be humanized for use in humans. Methods known to those in the field for delivery of biologics to improve half-life and brain penetration can be used including, but not limited to, intravenous delivery, subcutaneous delivery, intranasal delivery, intrathecal delivery, vector transport, and direct brain delivery.

The methods of the invention also encompass administration of Kgp inhibitors as described herein with one or more of the following additional therapeutically active agents or pharmaceutically acceptable salts thereof: an arginine derivative; histatin 5; baculovirus p35; a single point mutant of cowpox viral cytokine-response modifier (CrmA (Asp>Lys)); phenylalanyl-ureido-citrullinyl-valyl-cycloarginal (FA-70C1); (acycloxy)methyl ketone (Cbz-Phe-Lys-CH$_2$OCO-2,4,6-Me3Ph); peptidyl chloro-methyl ketones (e.g., chloromethyl ketone derivatives of arginine, chloromethyl ketone derivatives of lysine, and the like); fluoromethyl ketones; bromo-methyl ketones; ketopeptides; 1-(3-phenylpropionyl)piperidine-3(R,S)-carboxylic acid [4-amino-1(S)-(benzothiazole-2-carbonyl)butyl]amide (A71561); azapeptide fumaramide; aza-peptide Michael acceptors; benzamidine compounds; acyclomethylketone; activated factor X inhibitors (e.g., DX-9065a); cranberry nondialysable fraction; cranberry polyphenol fraction; pancreatic trypsin inhibitor; Cbz-Phe-Lys-CH$_2$O—CO-2,4,6-Me3-Ph; E-64; chlorhexidine; zinc (e.g., zinc acetate); or a combination of two, three or more of any of foregoing.

In some of these embodiments, Zn can enhance potency and selectivity of the compounds (e.g., chlorhexidine, benzamidine, etc.) used in the methods of the invention. Benzamidine compounds include, e.g., the following compounds and derivatives thereof:

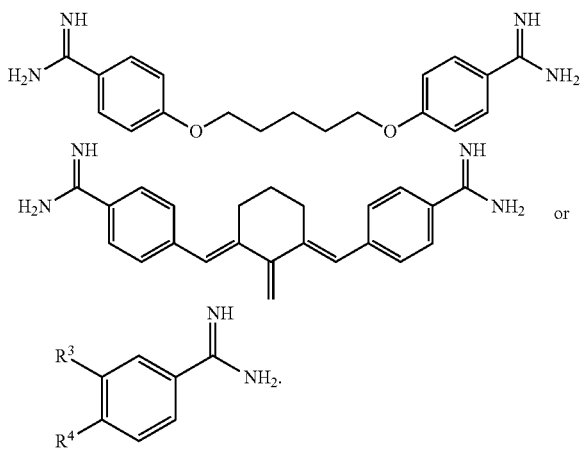

A lysine gingipain inhibitor of the invention can be administered in the same composition as an additional therapeutically active agent. Alternatively, the additional therapeutically active agent can be administered separately before, concurrently with, or after administration of the lysine gingipain inhibitor.

Similar to humans, *P. gingivalis* infection and periodontal disease is one of the most common infectious diseases affecting adult dogs and cats. Using adult beagle dogs, researchers demonstrated the existence of Rgp in plaque samples taken from beagle dogs given a specific soft diet to increase plaque formation on tooth surfaces. (See, e.g., Davis and Head, Front *Pharmacol,* 2014. 5: 47; Reichart, et al., *Journal of Periodontal Research,* 1984. 19(1): 67-75; Kataoka, S., et al., *FASEB J,* 2014 28(8): 3564-78.) Dogs and cats with *P. gingivalis* infection and gingipains in their brain and circulatory system may experience periodontal disease, mild cognitive impairment, age associated memory impairments, damage or generalized accelerated aging due to gingipain induced cell death, which could be treated or prevented with compositions of Formula I, II, III, IV or V.

VII. Methods of Detecting *P. gingivalis* and Diagnosing Conditions Associated with *P. gingivalis* Infection The present invention also provides for a diagnostic test for gingipains or *P. gingivalis* in the brain or patient samples in order to diagnose or predict brain disorders, or to determine who would be the best candidates for treatment with compounds described herein. Prior art has noted changes in serum profiles based on infection with *P. gingivalis*. A novel assay to diagnose or predict risk of development of brain disorders is to conduct an ELISA on saliva, cerebral spinal fluid or blood, for example, to detect one or both gingipains. Saliva, blood and CSF levels of gingipain or other *P. gingivalis* markers would be expected to be higher in at risk patients and patients who are good candidates for treatment. Development of an ELISA is a fairly simple process known to those skilled in the art utilizing one antibody against the target to capture the target and a second labeled antibody against a different epitope on the target to obtain a quantitative readout. Commercially available or newly generated antibodies could be used for this purpose. Immobilized or labeled compounds described herein (for example with biotin or HRP) could be utilized to substitute for one or both antibodies. Click chemistry compounds such as those depicted in FIG. 10 could be utilized for this purpose. The diagnostic could include detection of one or more gingipains. Biotinylation of the detection antibody can be used to increase sensitivity.

Alternatively, instead of detecting the presence or absence of the gingipains, an assay for their activity in saliva, CSF or blood could be used. This would provide the benefit of providing a readout on the most biologically relevant factor (e.g., activity) in the presence or absence of treatment, for example. Methods for developing enzyme assays are known to those skilled in the art. A salivary test known as the BANA Test is commercially available for dental applications to test for proteases from *P. gingivalis* and 2 other oral bacteria. The BANA test is a small plastic card to which is attached two separate reagent matrices, seen as strips on the card. The lower white reagent matrix is impregnated with N-benzoyl-DL-arginine-B-naphthylamide (BANA). Subgingival plaque samples are applied to the lower matrix, and then distilled water is applied to the upper matrix. Then the lower matrix is folded back to make contact with the upper matrix. The upper buff reagent matrix contains a chromogenic diazo reagent which reacts with one of the hydrolytic products of the enzyme reaction forming a blue color. The reaction occurs when the plastic strip is inserted into an incubator set at 35 degrees C. for 5 minutes. The BANA substrate detects at least 3 different oral bacteria however and is not specific to *P. gingivalis*. The BANA test could be used to identify people at risk for brain disorders or eligible for treatment. Alternatively, the BANA substrate can be substituted in similar formats or in a liquid assay with an RgpA, RgpB and/or KGP specific substrate.

Reagents that bind to active gingipains, including but not limited to those described in this application, can be used to precipitate only active gingipains followed by detection with a monoclonal for example. Alternatively, an antibody or other high affinity binding agent could be used to precipitate the gingipain from the CSF followed by a protease assay with a labeled substrate, which allows for increased fluorescence or colorometric readout as the labeled substrate is digested.

Figure 10:
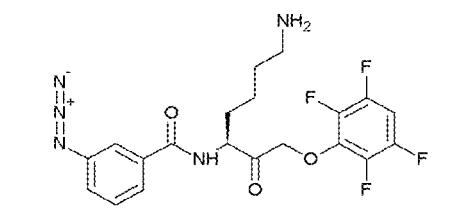
FIG. 10 shows an example of a "click chemistry" compound that can be used to create radiolabeled PET/SPECT imaging agents or capture agents for in vitro assays or diagnostics.
Figure 10:
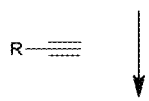
Figure 10:
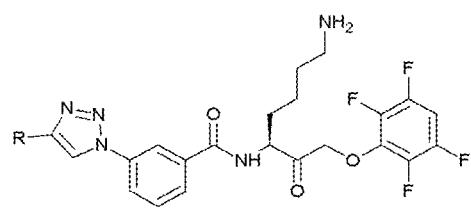

The present invention also provides for a diagnostic based on imaging *P. gingivalis* or its gingpains in the human brain. Any agent that binds to gingipains, including but not limited to compounds of the present invention and other compounds described elsewhere, can be labeled with F18 or other radiological markers and visualized using PET or SPECT scanning. A positive signal would indicate treatment with compounds described herein. In a preferred and non limiting embodiment, compound 45 as described herein is modified via "click chemistry" to install a radiolabel that can be imaged with PET or SPECT (FIG. 10).

VIII. Examples

Example 1

Figure 2C:
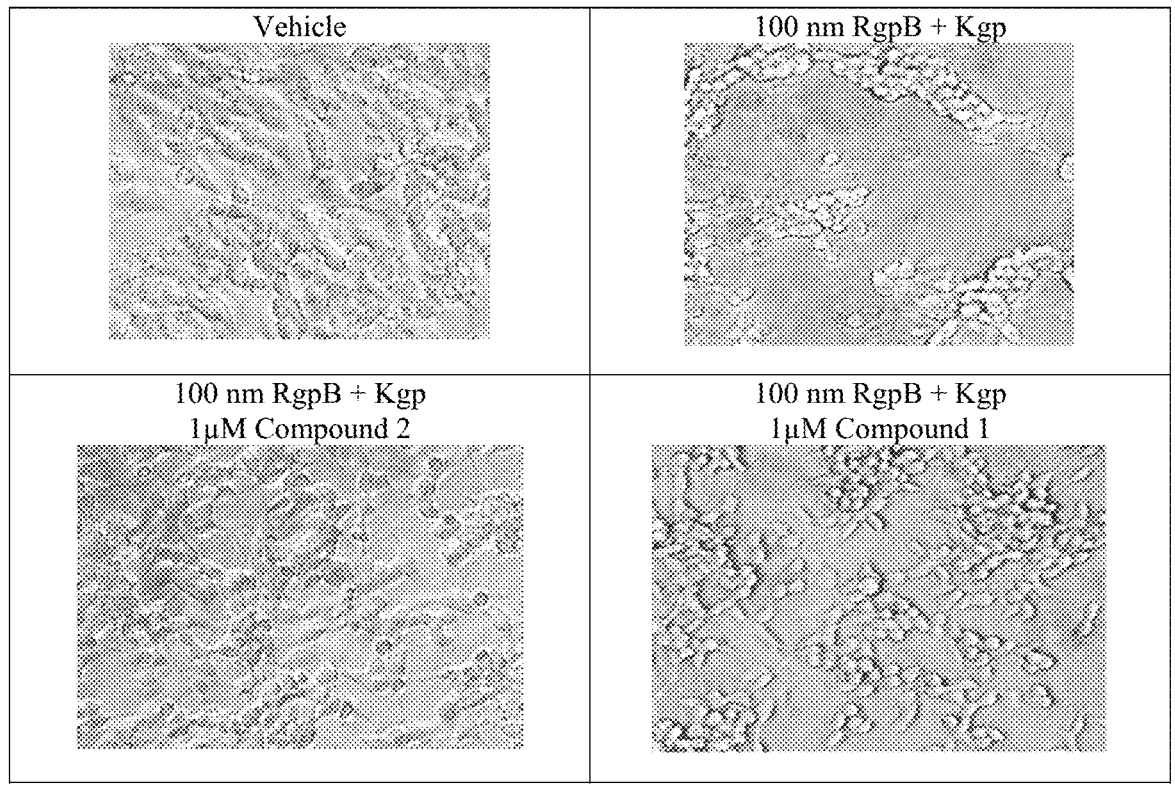
FIG. 2C shows that either compound 1 or compound 2 prevents gingipain-induced death of differentiated SHSY-5Y cells, but that compound 2 is more effective. Compound 2 a Kgp $IC_{50}$ between 1 and 10 nM and a trypsin $IC_{50}$ of 5,000 nM.
Figure 3A:
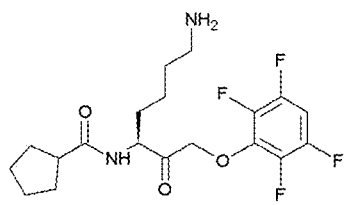
FIG. 3A shows the structure of Compound 43.
Figure 3B:
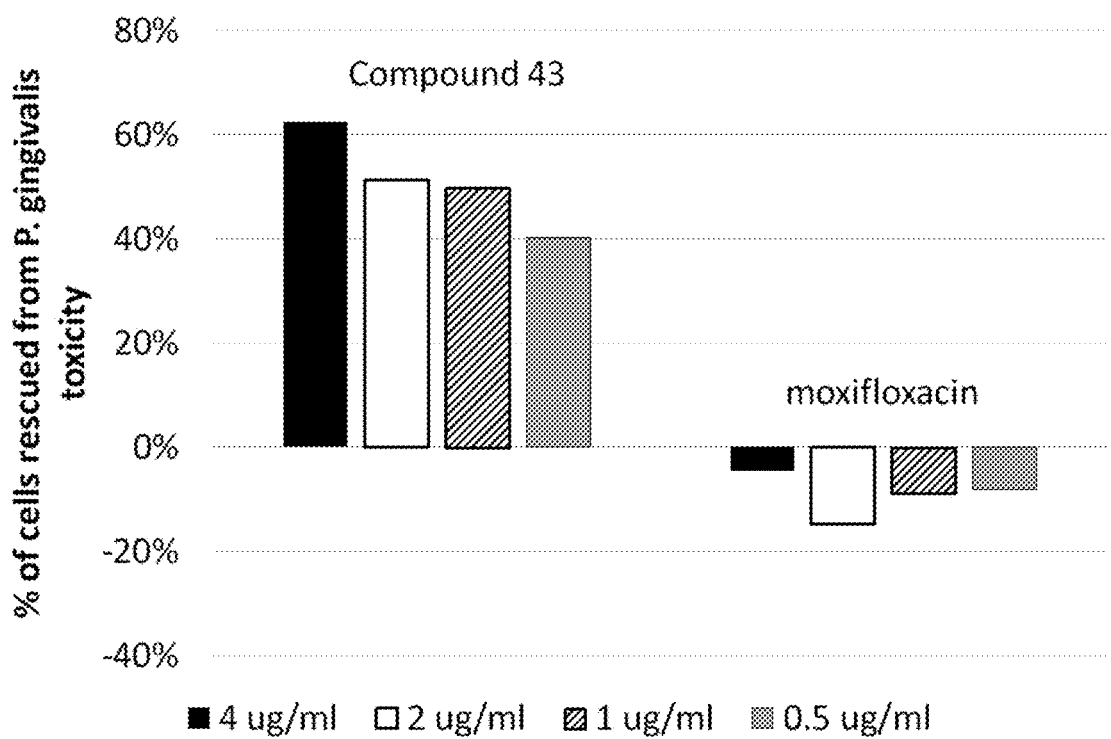
FIG. 3B shows that Compound 43, an irreversible covalent lysine gingipain inhibitor having a sub-nanomolar $IC_{50}$ value, protects SHSY5Y cells from *P. gingivalis*-induced toxicity in vitro compared to the antibiotic moxifloxacin.

SH-SY5Y neuroblastoma cells were cultured and differentiated in the presence of 5 uM retinoic acid based on established methods [Saberi S., et al. *Cell Mol Neurobiol* 2013. 33: 747-751]. Differentiation into neuronal cells was verified by observation of neurite outgrowth. The differentiated cells were exposed to 100 nM Kgp and/or RgpB for 24 hours, in the presence or absence of Kgp inhibitors. Results were recorded using a digital microscope camera (FIG. 1C, FIG. 2C). Gingipains are toxic to cells while COR compounds prevent the cytotoxicity.

Example 2

Adult male mice (CD-1, 25 g approximately) n=6 per group were anaesthetized and injected unilaterally intrahippocampally using standard stereotaxic techniques. Gingipains RgpB and Kgp, purified from *P. gingivalis* were diluted prior to injection to 10 µg/ml. Seven days post-surgery the animals were anaesthetized, perfused and humanely killed and brains removed and sectioned for histological analysis. Fluoro-Jade staining was then be performed on sections of hippocampus to assess for neurodegeneration (Schmued L C and Hopkins K J, 2000). Fluoro-Jade staining identifies cell bodies, dendrites, axons and axons terminals of degenerating neurons but does not stain healthy neurons, myelin, or vascular elements.

Figure 4:
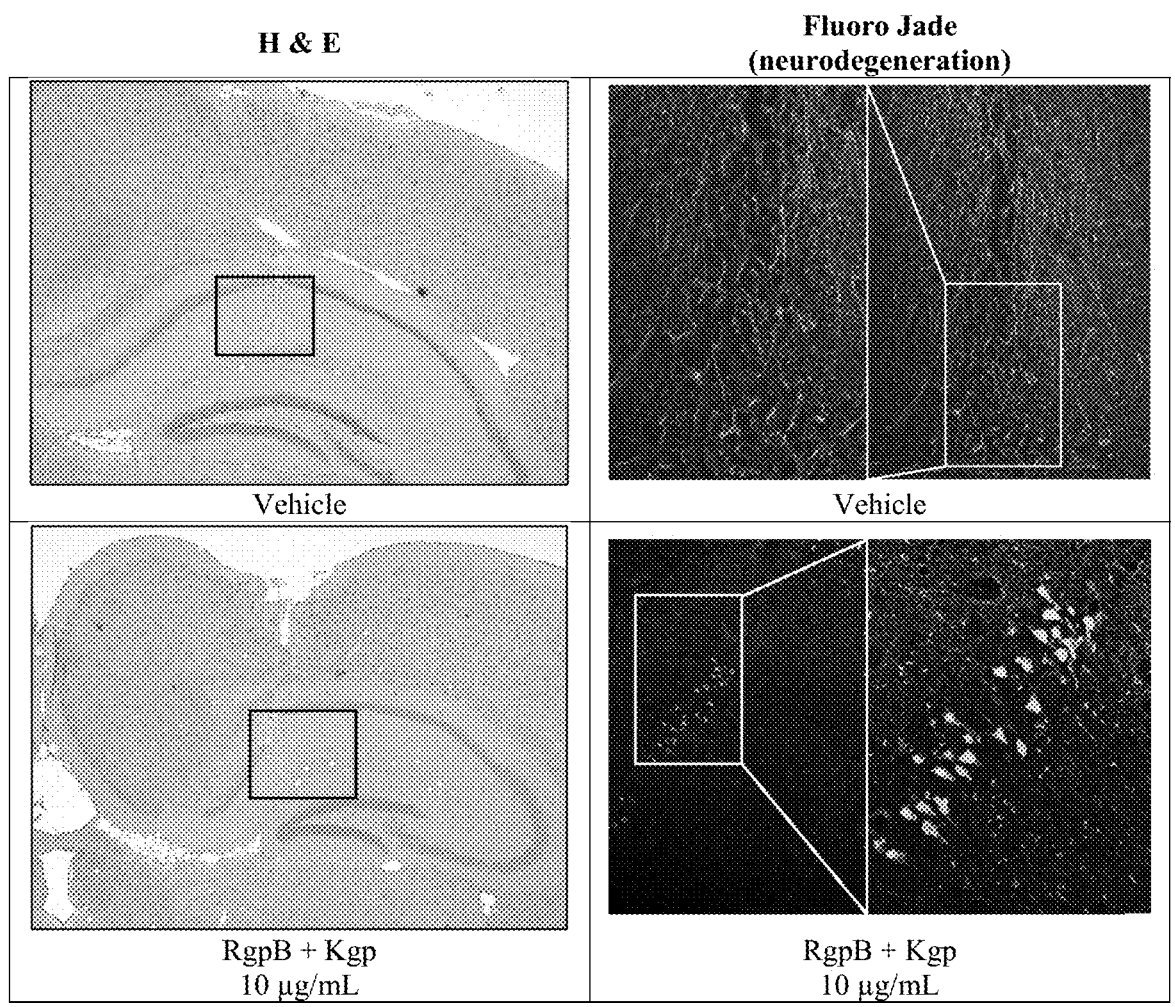
FIG. 4 shows that intrahippocampal injection of gingipains into mouse brain causes neurodegeneration after 7 days.

Brain sections were examined with an epifluorescence microscope (Nikon Microphot FXA) using a filter system suitable for visualizing fluorescein or fluorescein isothiocyanate (FITC). Images were acquired with a Leica DC Camera and an Image Analysis software (Leica IM50). Fluoro-Jade C-positive degenerating neurons appeared bright yellow-green against a dark background and were clearly identified in the animal groups treated with Gingipains. No Fluoro-Jade C-positive cells were observed in vehicle-treated group (FIG. 4).

Example 3

Figure 5:
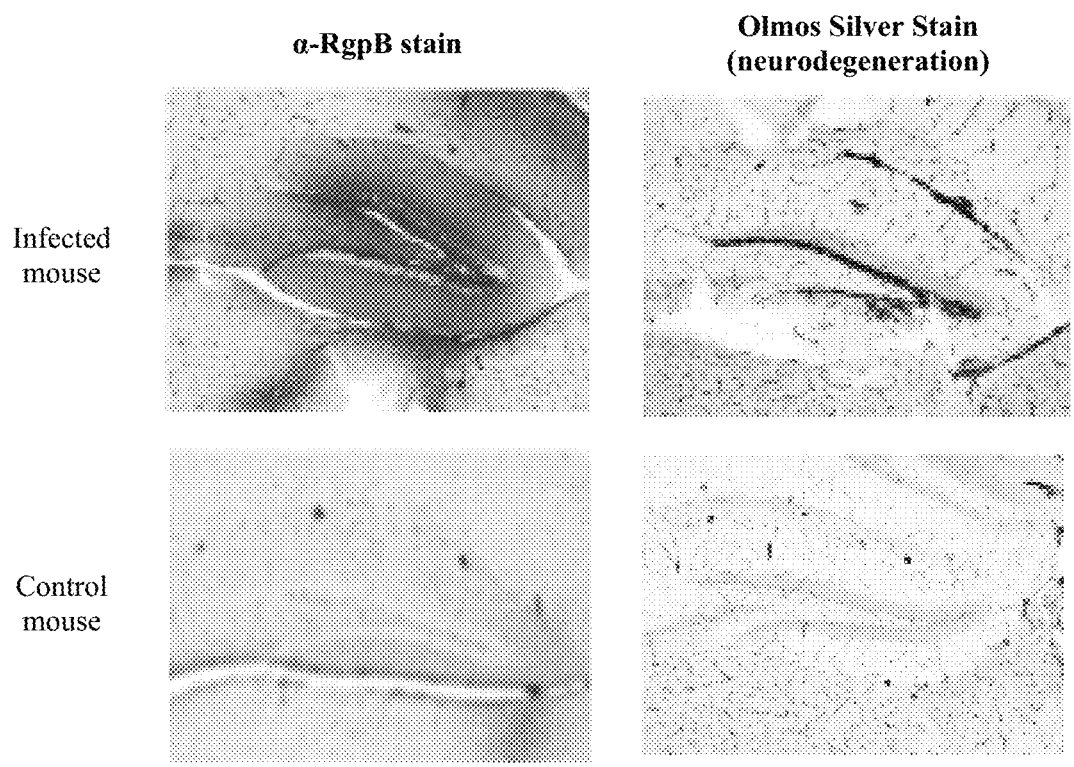
FIG. 5 shows that RgpB brain infiltration overlaps with neurodegeneration of the subgranular zone in the hippocampus of BalbC mice infected with *P. gingivalis* orally for 6 weeks.

Female Balb/c mice were obtained from Harlan Laboratories (USA) and allowed to acclimate. 8 week old mice were challenged orally with $10^9$ CFU W83 *P. gingivalis* in 2% Na-CMC, 2 times per week for 6 weeks. Control mice received mock challenge with 2% Na-CMC only. 6 weeks after initial infection, mice were sacrificed, perfused and brains dissected. Brains were embedded and sectioned. 18E6 immunohistochemistry for RgpB showed brain infiltration in 3/6 mice. De Olmos silver stain for neurodegeneration showed staining in 2 of the 3 mice with infiltration (FIG. 5).

Example 4

Female Balb/cJ mice were obtained from Taconic and allowed to acclimate. 8 week old mice were challenged orally with $10^9$ CFU W83 *P. gingivalis* every $3^{rd}$ day for 4 administrations.

Figure 6A:
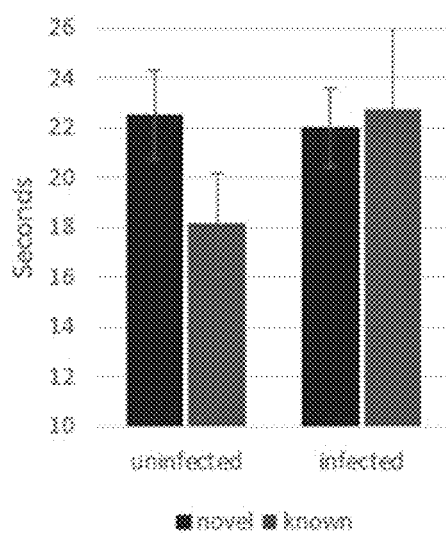
FIG. 6A shows that wild-type mice infected with *P. gingivalis* show cognitive impairment on the Novel Object Recognition task at the 6 week time point. Infected mice spend equal amounts of time exploring a novel and familiar object, while normal mice spend increased time on the novel object.
Figure 6B:
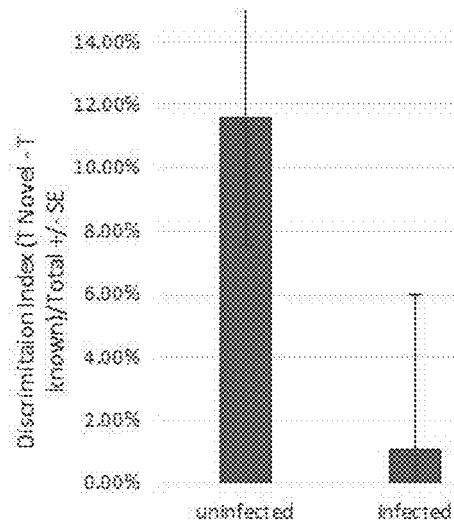
FIG. 6B shows the discrimination index $(T_{Novel}-T_{familiar})/T_{total}$ for the uninfected mice and the infected mice.

Novel object recognition test for cognitive function was initiated 6 weeks after the initial infection. Mice were familiarized with the test cage for 2 min the day prior to object familiarization. On the day of familiarization, mice were presented with two wooden blue rectangles for 5 minutes. 24 h later mice were presented with one blue rectangle (right side) and one pink heart (left side, both objects made of wood) for the duration of 3 min. The time during which the mouse directed its nose within 2 cm of an object was recorded. Mock infected mice on average spent more time exploring the novel object compared to infected mice who on average spent equal time on both objects indicating cognitive dysfunction (FIG. 6).

Example 5

Figure 7:
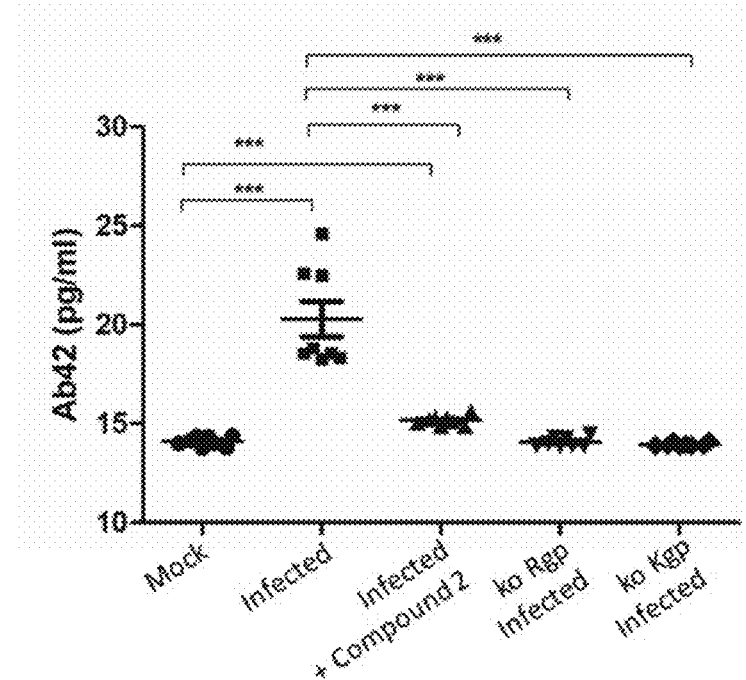
FIG. 7 shows brain levels of abeta 42 ("Ab42") measured with ELISA, indicating that infection increases brain abeta and this can be resolved by treatment with compound 2 mid-way through the infection. Additionally, the rise in abeta 42 is prevented when the bacteria used for infection does not express Kgp.

Female Balb/cJ mice were obtained from Taconic and allowed to acclimate. 43-44 week old mice were challenged orally with $10^9$ CFU W83 *P. gingivalis* or a *P. gingivalis* strain lacking expression of Kgp every other day for 42 days. Compound 2 or vehicle (2% DMSO) was given subcutaneously three times per day on days 21-42. On day 42 mice were sacrificed and the brain removed and frozen. A sample including hippocampal tissue was lysed in RIPA buffer with protease inhibitors and analyzed for Abeta42 expression with the Amyloid beta 42 ELISA Kit, Mouse (Life Technologies). Infected mice showed an increase in abeta42 that was not apparently in Kgp knock out mice or mice treated with compound 2 (FIG. 7).

Example 6

Figure 8:
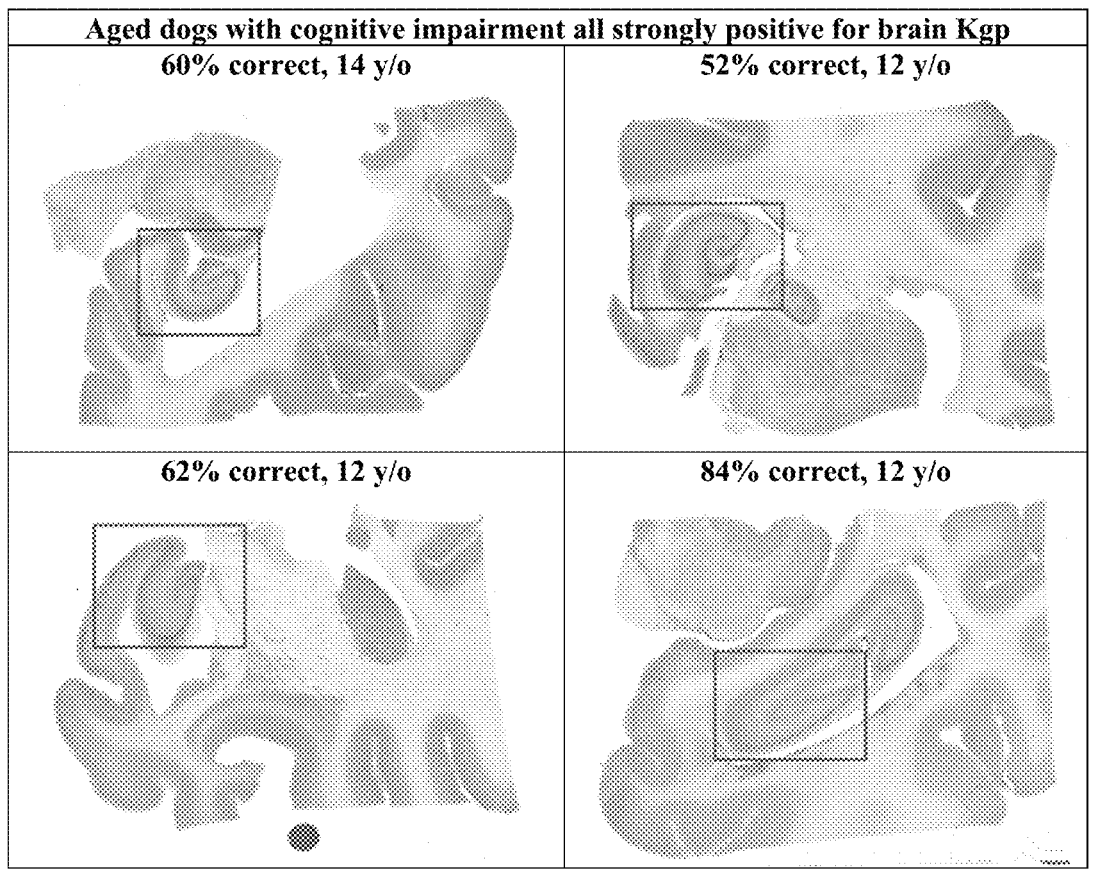
FIG. 8 shows that aged dogs with cognitive impairment are strongly positive for brain Kgp.
Figure 8:
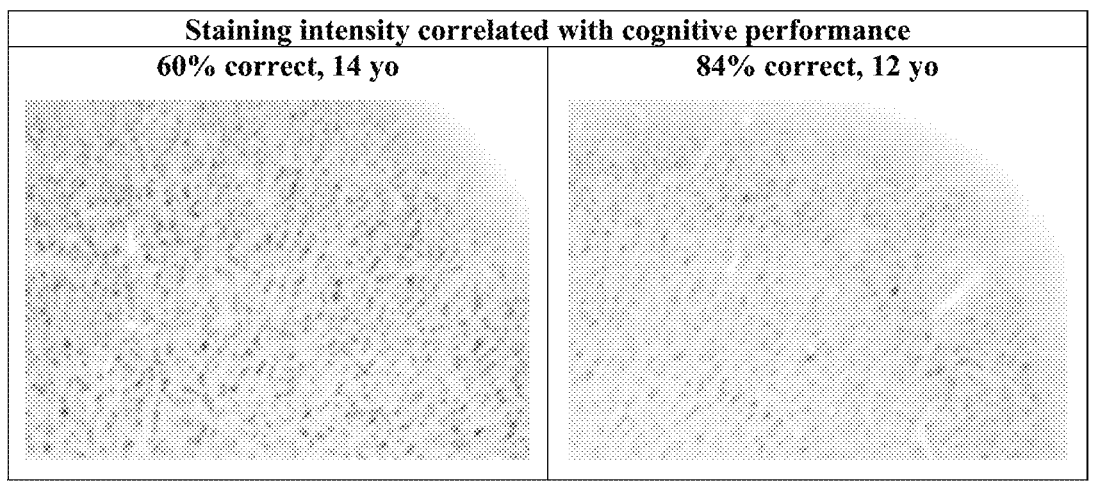

Aged dogs were assessed for cognitive impairment as described by Araujo et al. [*J Alzheimers Dis*, 2011. 26(1): 143-55]. Brains were embedded and sliced and assessed for gingipain infiltration as described in Example 1 with 7B9 antibody for Kgp (FIG. 8).

Example 7. Preparation of benzyl-N-[(5S)-5-amino-6-(1,3-benzothiazol-2-yl)-6-oxo-hexyl]carbamate

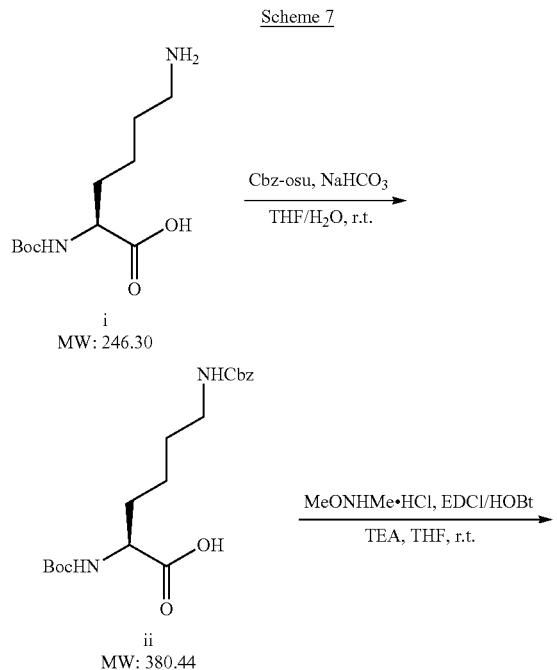

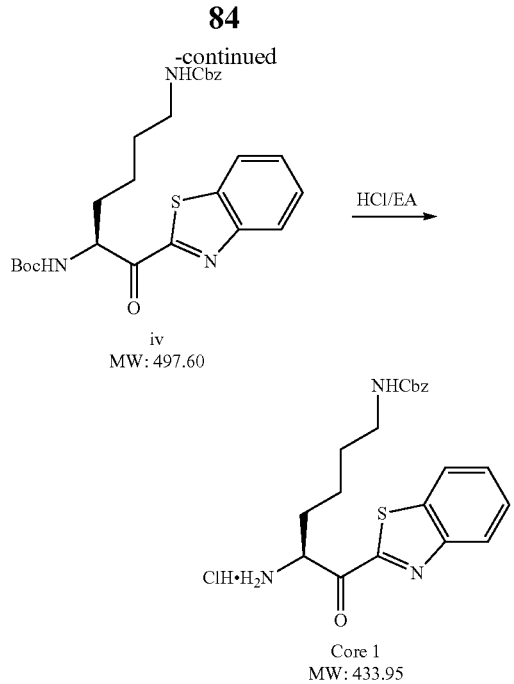

(2S)-6-(benzyloxycarbonylamino)-2-(tert-butoxycarbonylamino)hexanoic Acid (ii)

To a solution of (2S)-6-amino-2-(tert-butoxycarbonylamino)hexanoic acid (100.00 g, 406.01 mmol, 1.00 eq), NaHCO₃ (102.33 g, 1.22 mol, 3.00 eq) in THF (1000 mL) and H₂O (1000 mL) was added CbzOSu (101.19 g, 406.01 mmol, 1.00 eq) at 0° C. Then the mixture was stirred at 30° C. for 16 hr. The mixture was adjusted to pH=5-6 with 1N HCl, extracted with EA (600 mL×3), dried over Na₂SO₄, concentrated to give (2S)-6-(benzyloxycarbonylamino)-2-(tert-butoxycarbonyl-amino)hexanoic acid (142.00 g, 373.26 mmol, 91.9% yield) as a yellow oil.

Tert-butyl-N-[(1S)-5-(benzyloxycarbonylamino)-1-[methoxy(methyl)-carbamoyl]pentyl]carbamate (iii)

To a solution of (2S)-6-(benzyloxycarbonylamino)-2-(tert-butoxycarbonylamino) hexanoic acid (142.00 g, 373.26 mmol, 1.00 eq), N-methoxymethanamine (54.61 g, 559.89 mmol, 1.50 eq), EDCI (93.02 g, 485.24 mmol, 1.30 eq), HOBt (65.57 g, 485.24 mmol, 1.30 eq) in DCM (2 L) was added TEA (113.31 g, 1.12 mol, 3.00 eq) dropwise at 0° C. over 0.5 hr. Then the mixture was stirred at 30° C. for 16 hr. TLC indicated the reaction completed. Then the mixture was diluted with water (1000 mL) and separated. The organic layer was washed with HCl (aq, 1M, 500 mL) and saturated NaHCO₃ (aq, 500 mL) in sequence, dried over Na₂SO₄ and concentrated to give the crude, which was purified by column chromatography on silica gel (PE:EA=5:1 to PE:EA=1:1) to give tert-butyl-N-[(1S)-5-(benzyloxycarbonyl-amino)-1-[methoxy(methyl)carbamoyl]pentyl]carbamate (110.00 g, 259.74 mmol, 69.6% yield) as a light yellow oil.

Tert-butyl-N-[(1R)-1-(1,3-benzothiazole-2-carbonyl)-5-(benzyloxycarbonyl-amino)pentyl]-carbamate (iv)

To a mixture of 1,3-benzothiazole (9.58 g, 70.83 mmol, 3.00 eq) in THF (50 mL) was added n-BuLi (2.5 M in THF, 28.3 mL) dropwise at −65° C. under N₂. The mixture was stirred at −65° C. under N₂ for 1 hr. Then tert-butyl-N-[(1R)-5-(benzyloxycarbonylamino)-1-[methoxy(methyl)carbamoyl]pentyl]carbamate (10.00 g, 23.61 mmol, 1.00 eq) in THF (50 mL) was added dropwise at −65° C. under N₂ and the reaction mixture was stirred at −65° C. under N₂ for another 3 hr. TLC indicated the reaction completed. The mixture was quenched by saturated NH₄Cl (aq, 10 mL), then the mixture was extracted with EA (100 mL×3), dried over Na₂SO₄ and concentrated to give the crude, which was purified by column chromatography on silica gel (PE:EA=5:1 to PE:EA=3:1) to give tert-butyl-N-[(1R)-1-(1,3-benzothiazole-2-carbonyl)-5-(benzyloxycarbonylamino)pentyl]-carbamate (6.20 g, 12.46 mmol, 52.8% yield) as a light yellow oil.

Benzyl-N-[(5S)-5-amino-6-(1,3-benzothiazol-2-yl)-6-oxo-hexyl]carbamate (Core 1)

To a solution of tert-butyl-N-[(1S)-1-(1,3-benzothiazole-2-carbonyl)-5-(benzyloxycarbonylamino) pentyl]carbamate (10.84 g, 21.78 mmol, 1.00 eq) in EA (140 mL) was added HCl/EA (4 M, 12 mL). Then the reaction was stirred at 30° C. for 15 hr. The reaction mixture was filtered and the filter cake was washed with EA (80 mL) and dried in vacuo to afford benzyl-N-[(5S)-5-amino-6-(1,3-benzothiazol-2-yl)-6-oxo-hexyl]carbamate hydrochloride (7.52 g, 17.33 mmol, 79.6% yield) as a yellow solid.

Example 8. Preparation of N-[(1S)-5-amino-1-(1,3-benzothiazole-2-carbonyl)pentyl]benzamide (1)

Scheme 8

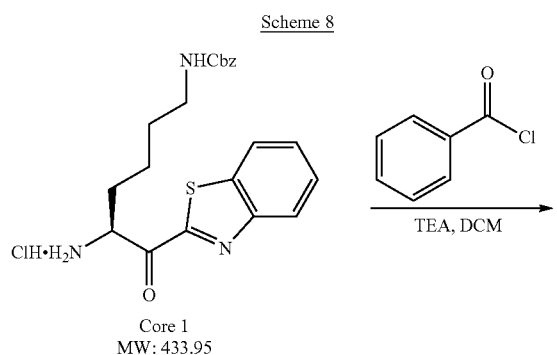

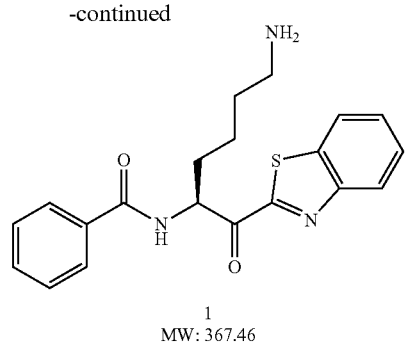

Benzyl-N-[(5S)-5-benzamido-6-(1,3-benzothiazol-2-yl)-6-oxo-hexyl]carbamate (1a)

To a mixture of benzyl-N-[(5S)-5-amino-6-(1,3-benzothiazol-2-yl)-6-oxo-hexyl]-carbamate; hydrochloride (400 mg, 921.77 μmol, 1.00 eq), TEA (280 mg, 2.77 mmol, 3.00 eq) in DCM (10 mL) was added benzoyl chloride (156 mg, 1.11 mmol, 1.20 eq) dropwise at 0° C. under N₂. The mixture was stirred at 0° C. for another 0.5 hr. TLC (PE:EA=5:1) indicated the reaction completed. The mixture was washed with water (5 mL×3), dried over Na₂SO₄, concentrated to give benzyl-N-[(5S)-5-benzamido-6-(1,3-benzothiazol-2-yl)-6-oxo-hexyl]carbamate (300 mg, 598.09 μmol, 64.9% yield) as a light yellow solid.

N-[(1S)-5-amino-1-(1,3-benzothiazole-2-carbonyl)pentyl]benzamide (1)

A mixture of benzyl-N-[(5S)-5-benzamido-6-(1,3-benzothiazol-2-yl)-6-oxo-hexyl]carbamate (250 mg, 498.41 μmol, 1.00 eq) in AcOH (1 mL) was added HBr/AcOH (5.5 M, 1 mL). The mixture was stirred at 30° C. for 0.5 h. LC-MS indicated the reaction completed. Water (20 mL) was added and extracted with MTBE (5 mL×2). Then the aqueous layer was lyophilized to give the crude, which was purified by prep-HPLC (CH₃CN/H₂O/TFA) to give N-[(1S)-5-amino-1-(1,3-benzothiazole-2-carbonyl)pentyl]benzamide trifluoroacetate (20 mg, 41.54 μmol, 8.33% yield) as a light yellow solid. MS m/z=368.1 (MH⁺).

Example 9. Preparation of N-[(1S)-5-amino-1-(1,3-benzothiazole-2-carbonyl)pentyl]cyclohexanecarboxamide (2)

Scheme 9

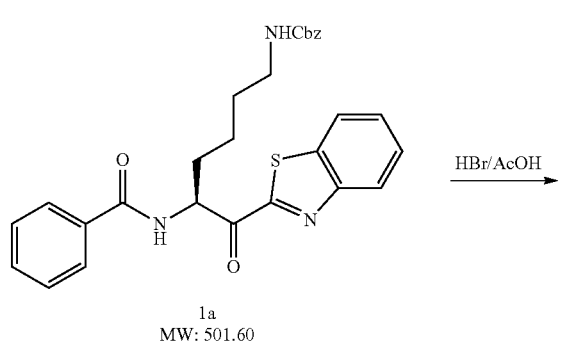

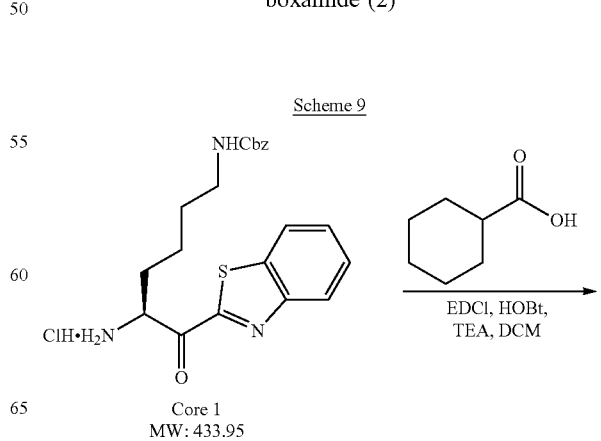

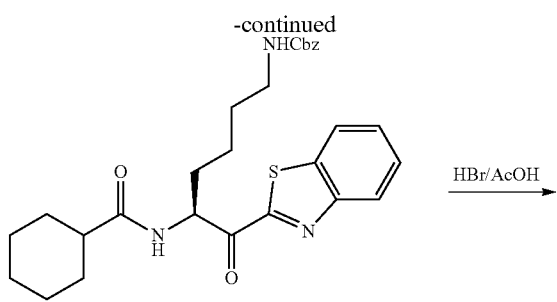

2a
MW: 507.64

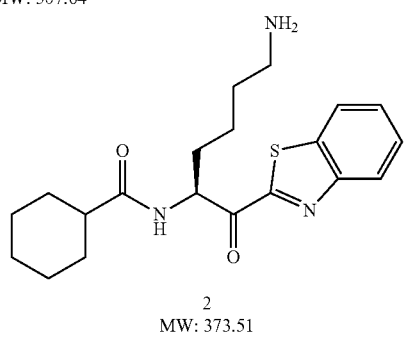

2
MW: 373.51

Benzyl-N-[(5S)-6-(1,3-benzothiazol-2-yl)-5-(cyclohexanecarbonylamino)-6-oxo-hexyl]carbamate (2a)

To a mixture of benzyl-N-[(5S)-5-amino-6-(1,3-benzothiazol-2-yl)-6-oxo-hexyl]carbamate; hydrochloride (400 mg, 921.77 μmol, 1.00 eq), cyclohexanecarboxylic acid (142 mg, 1.11 mmol, 1.20 eq), EDCI (230 mg, 1.20 mmol, 1.30 eq), HOBt (162 mg, 1.20 mmol, 1.30 eq) in DCM (10 mL) was added TEA (280 mg, 2.77 mmol, 3.00 eq) dropwised at 0° C. The mixture was stirred at 30° C. for 16 h. LC-MS indicated the reaction completed. Water (10 mL) was added, then extracted with DCM (10 mL×2), washed with water (10 mL), then saturated NaHCO$_3$ (aq, 10 mL×2), dried over Na$_2$SO$_4$, concentrated to give a crude, which was purified by flash chromatography to give benzyl-N-[(5S)-6-(1,3-benzothiazol-2-yl)-5-(cyclohexanecarbonylamino)-6-oxo-hexyl] carbamate (2a; 210 mg, crude) as a yellow solid.

N-[(1S)-5-amino-1-(1,3-benzothiazole-2-carbonyl)pentyl]cyclohexanecarboxamide (2)

To a mixture of benzyl-N-[(5S)-6-(1,3-benzothiazol-2-yl)-5-(cyclohexanecarbonylamino)-6-oxo-hexyl]carbamate (200 mg, 393.98 μmol, 1.00 eq) in AcOH (1 mL) was added HBr/AcOH (5.5 M, 1 mL). The mixture was stirred at 30° C. for 0.5 hr. LC-MS indicated the reaction completed. Water (20 mL) was added and extracted with MTBE (5 mL×2). Then the aqueous layer was lyophilized to give a crude, which was purified by prep-HPLC to give N-[(1S)-5-amino-1-(1,3-benzothiazole-2-carbonyl)pentyl]cyclohexanecarboxamide trifluoroacetate (2; 10 mg, 20.51 μmol, 5.21% yield) as a light yellow solid. MS m/z=374 (MH$^+$). $^1$H NMR (CD$_3$OD, 400 MHz) d 8.20 (dd, J=7.6, J=0.4, 1H), 8.14 (dd, J=7.6, J=1.2, 1H), 7.66-7.61 (m, 2H), 5.64 (dd, J=4.0, J=10.0, 1H), 3.02-2.93 (m, 2H), 2.38-2.35 (m, 1H), 2.18-2.10 (m, 1H), 1.84-1.55 (m, 9H), 1.48-1.17 (m, 6H).

Example 10. Preparation of (3S)—N-[(1S)-5-amino-1-(1,3-benzothiazole-2-carbonyl)pentyl]-1-(3-phenylpropanoyl)piperidine-3-carboxamide (3)

Scheme 10

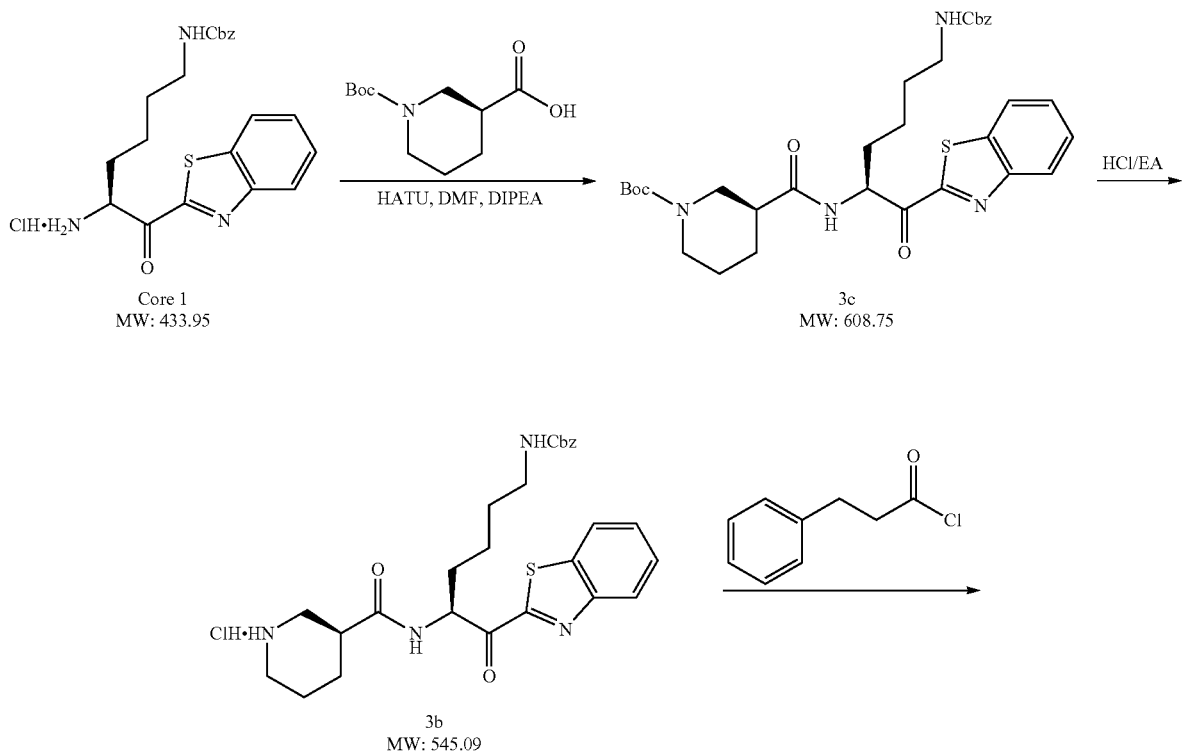

-continued

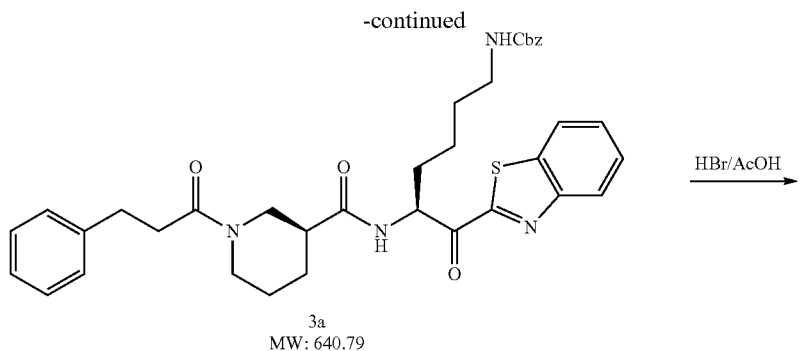

3a
MW: 640.79

HBr/AcOH →

3
MW: 506.77

Tert-butyl-(3S)-3-[[(1S)-1-(1,3-benzothiazole-2-carbonyl)-5-(benzyloxycarbonylamino)pentyl]carbamoyl]piperidine-1-carboxylate (3c)

A mixture of (3S)-1-tert-butoxycarbonylpiperidine-3-carboxylic acid (190 mg, 829.59 μmol, 1.20 eq), HATU (315 mg, 829.59 μmol, 1.20 eq), DIPEA (268 mg, 2.07 mmol, 3.00 eq) in DMF (5 mL) was stirred at 0° C. for 1 h. Then benzyl-N-[(5S)-5-amino-6-(1,3-benzothiazol-2-yl)-6-oxohexyl]carbamate hydrochloride (300 mg, 691.32 μmol, 1.00 eq) was added and the mixture was stirred at 30° C. for 16 h. TLC (PE:EA=3:1) indicated the reaction completed. EA (20 mL) was added and washed with water (10 mL×3), dried over Na$_2$SO$_4$, concentrated to give tert-butyl-(3S)-3-[[(1S)-1-(1,3-benzothiazole-2-carbonyl)-5-(benzyloxycarbonylamino)pentyl]carbamoyl]piperidine-1-carboxylate (250 mg, 410.68 μmol, 59.4% yield, 55% de) as a yellow solid.

Benzyl-N-[(5S)-6-(1,3-benzothiazol-2-yl)-6-oxo-5-[[(3S)-piperidine-3-carbonyl]amino]hexyl]carbamate (3b)

To a mixture of tert-butyl-(3S)-3-[[(1S)-1-(1,3-benzothiazole-2-carbonyl)-5-(benzyloxycarbonylamino)pentyl]carbamoyl]piperidine-1-carboxylate (250 mg, 410.68 μmol, 1.00 eq) in EA (2 mL) was added HCl/EtOAc (4M, 2 mL). The mixture was stirred at 30° C. for 1.5 h. TLC (PE:EA=3:1) indicated the reaction completed. The reaction mixture was filtered to give benzyl-N-[(5S)-6-(1,3-benzothiazol-2-yl)-6-oxo-5-[[(3S)-piperidine-3-carbonyl]amino]hexyl]carbamate (3b; 200 mg, crude, 67% de) as a white solid.

Benzyl-N-[(5S)-6-(1,3-benzothiazol-2-yl)-6-oxo-5-[[(3S)-1-(3-phenylpropanoyl)-piperidine-3-carbonyl]amino]hexyl]carbamate (3a)

To a mixture of benzyl-N-[(5S)-6-(1,3-benzothiazol-2-yl)-6-oxo-5-[[(3 S)-piperidine-3-carbonyl]amino]hexyl]carbamate (200 mg, 393.21 μmol, 1.00 eq), TEA (119 mg, 1.18 mmol, 3.00 eq) in DCM (5 mL) was added 3-phenylpropanoyl chloride (80 mg, 471.85 μmol, 1.20 eq) at 0° C. under N$_2$. The mixture was stirred at 0° C. for another 0.5 h. LC-MS indicated the reaction completed. DCM (10 mL) was added and washed with water (5 mL×3), dried over Na$_2$SO$_4$, concentrated to give benzyl-N-[(5S)-6-(1,3-benzothiazol-2-yl)-6-oxo-5-[[(3S)-1-(3-phenylpropanoyl)piperidine-3-carbonyl]amino]hexyl]carbamate (3a; 220 mg, crude) as a yellow solid.

(3S)—N-[(1S)-5-amino-1-(1,3-benzothiazole-2-carbonyl)pentyl]-1-(3-phenyl-propanoyl)piperidine-3-carboxamide; 2,2,2-trifluoroacetic Acid (3)

To a mixture of benzyl-N-[(5S)-6-(1,3-benzothiazol-2-yl)-6-oxo-5-[[(3S)-1-(3-phenylpropanoyl) piperidine-3-carbonyl]amino]hexyl]carbamate (220 mg, 343.33 μmol, 1.00 eq) in AcOH (1 mL) was added HBr/AcOH (5.5 M, 1 mL) at 30° C. under N$_2$. The mixture was stirred at 30° C. under N$_2$ for another 0.5 h. LC-MS indicated the reaction completed. Water (20 mL) was added and extracted with MTBE (5 mL×2). Then the aqueous layer was lyophilized to give a crude, which was purified by prep-HPLC (CH$_3$CN/H$_2$O/TFA) to give (3S)—N-[(1S)-5-amino-1-(1,3-benzothiazole-2-carbonyl)pentyl]-1-(3-phenylpropanoyl)piperidine-3-carboxamide (3; 15 mg, 29.61 μmol, 8.62% yield) as a light yellow solid. MS m/z=507.2 (MH$^+$).

Example 11. Preparation of (3R)—N-[(1S)-5-amino-1-(1,3-benzothiazole-2-carbonyl)pentyl]-1-(3-phenylpropanoyl)piperidine-3-carboxamide (4)

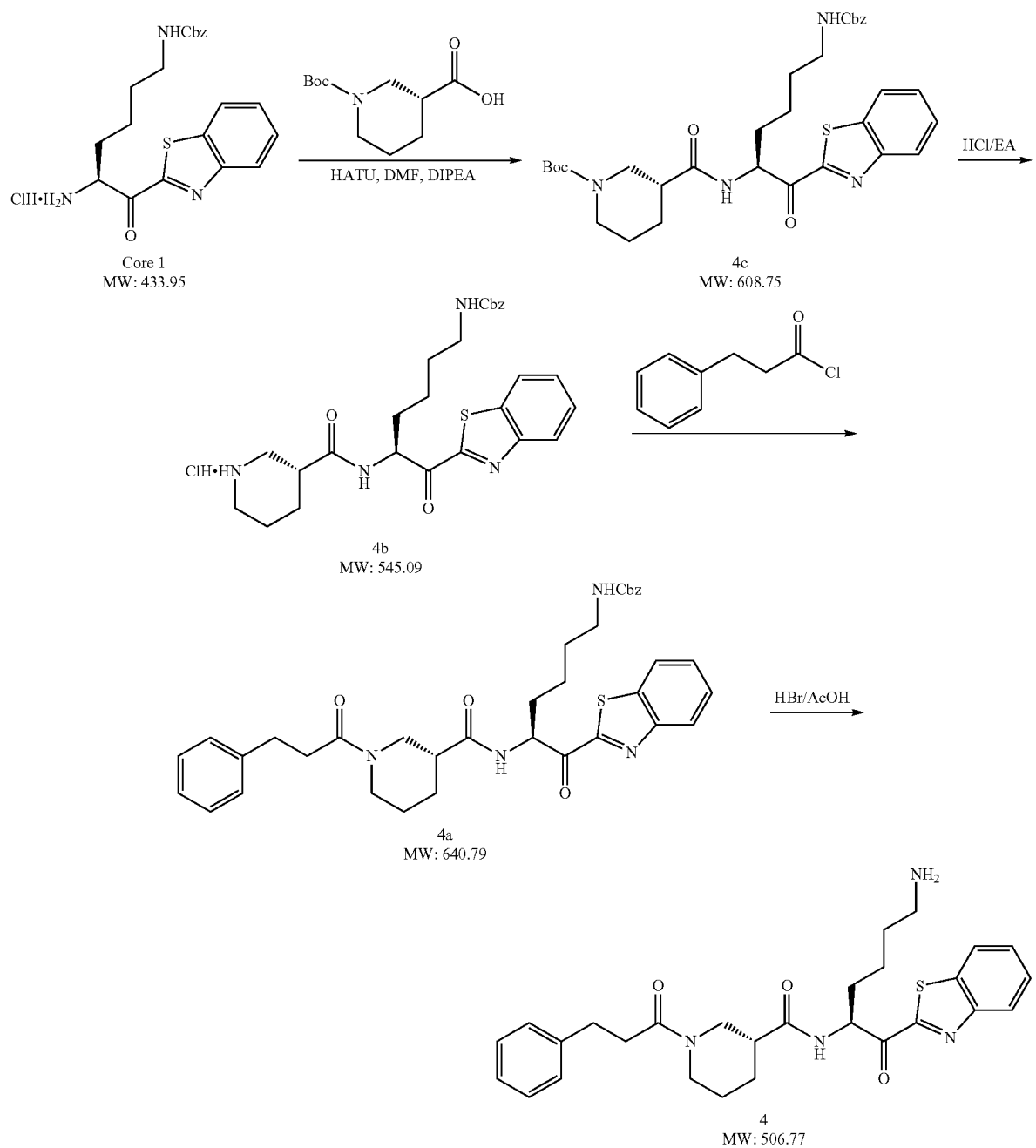

Scheme 11

Tert-butyl-(3R)-3-[[(1S)-1-(1,3-benzothiazole-2-carbonyl)-5-(benzyloxycarbonylamino)pentyl]carbamoyl]piperidine-1-carboxylate (4c)

To a solution of (3R)-1-tert-butoxycarbonylpiperidine-3-carboxylic acid (190 mg, 828.72 μmol, 1.20 eq) in DMF (10 mL) were added HATU (320 mg, 841.60 μmol, 1.22 eq) and DIPEA (267 mg, 2.07 mmol, 2.99 eq) under 0° C. After stirring for 0.5 h under 0° C., benzyl-N-[(5S)-5-(aminochloranyl)-6-(1,3-benzothiazol-2-yl)-6-oxo-hexyl]carbamate hydrochloride (300 mg, 691.32 μmol, 1.00 eq) was added and the resulting mixture was stirred at 30° C. for 3 h. TLC (PE:EA=3:1) indicated the reaction completed. The mixture was diluted with H$_2$O (15 mL×2) and extracted with EA (20 mL×2). The combined organic layers were washed with H$_2$O (20 mL×2), dried over Na$_2$SO$_4$, filtered and concentrated to give tert-butyl-(3R)-3-[[(1S)-1-(1,3-benzothiazole-2-carbonyl)-5-(benzyloxycarbonylamino)pentyl]carbamoyl]piperidine-1-carboxylate (4c; 600 mg, crude) as a oil, which was used directly for next step without further purification.

Benzyl-N-[(5S)-6-(1,3-benzothiazol-2-yl)-6-oxo-5-[[(3R)-piperidine-3-carbonyl]amino]hexyl]carbamate (4b)

To a solution of tert-butyl-(3R)-3-[[(1S)-1-(1,3-benzothiazole-2-carbonyl)-5-(benzyloxycarbonylamino)pentyl]carbamoyl]piperidine-1-carboxylate (600 mg, 985.63 µmol, 1.00 eq) in EA (10 mL) was added HCl/EA (4 M, 4 mL, 16.23 eq). The reaction mixture was stirred at 30° C. for 1 h. The suspension was filtered and the filter cake was collected to afford benzyl-N-[(5S)-6-(1,3-benzothiazol-2-yl)-6-oxo-5-[[(3R)-piperidine-3-carbonyl]amino]hexyl]carbamate hydrochloride (4b; 700 mg, crude), which was used directly for next step without purification. It was confirmed by LC-MS.

Benzyl-N-[(5S)-6-(1,3-benzothiazol-2-yl)-6-oxo-5-[[(3R)-1-(3-phenylpropanoyl)piperidine-3-carbonyl]amino]hexyl]carbamate (4a)

To a solution of benzyl-N-[(5S)-6-(1,3-benzothiazol-2-yl)-6-oxo-5-[[(3R)-piperidine-3-carbonyl]amino]hexyl]carbamate; hydrochloride (700 mg, 1.28 mmol, 1.00 eq) in DCM (10 mL) was added TEA (2.19 g, 21.64 mmol, 16.91 eq). The mixture was cooled to 0° C., and then 3-phenylpropanoyl chloride (1.14 g, 6.76 mmol, 5.28 eq) was added dropwise. The resulting mixture was stirred at 0° C. for 30 min. LC-MS indicated the reaction completed. The reaction was quenched by H$_2$O (20 mL) and extracted with DCM (20 mL×2). The combined organic layers were dried over Na$_2$SO$_4$, filtered and concentrated to give benzyl-N-[(5S)-6-(1,3-benzothiazol-2-yl)-6-oxo-5-[[(3R)-1-(3-phenylpropanoyl)piperidine-3-carbonyl]amino]hexyl]carbamate (4a; 600 mg, crude), which was used directly for next step without purification.

(3R)—N-[(1S)-5-amino-1-(1,3-benzothiazole-2-carbonyl)pentyl]-1-(3-phenylpropanoyl)piperidine-3-carboxamide (4)

To a solution of benzyl-N-[(5S)-6-(1,3-benzothiazol-2-yl)-6-oxo-5-[[(3R)-1-(3-phenylpropanoyl)piperidine-3-carbonyl]amino]hexyl]carbamate (600 mg, 936.34 µmol, 1.00 eq) in AcOH (10 mL) was added HBr/AcOH (936.34 µmol, 1.00 eq) (2 mL, 33% purity) under N$_2$. The reaction mixture was stirred at 32° C. for 30 min. LC-MS indicated the desired product was detected. The mixture was diluted with H$_2$O (100 mL) and MeOH (20 mL), washed with MTBE (50 mL×2). The resulting solution was lyophilized to give a residue, which was purified by prep-HPLC (mobile phase: CH$_3$CN, H$_2$O/TFA) to give (3R)—N-[(1S)-5-amino-1-(1,3-benzothiazole-2-carbonyl)pentyl]-1-(3-phenylpropanoyl)piperidine-3-carboxamide; 2,2,2-trifluoroacetic acid trifluoroacetate (4; 30 mg, 40.83 µmol, 4.36% yield) as a yellow solid. MS m/z=507.2 (MH$^+$).

Example 12. Preparation of N-[(1S)-5-amino-1-(1,3-benzothiazole-2-carbonyl)pentyl]-2-(trifluoromethyl)benzamide (7)

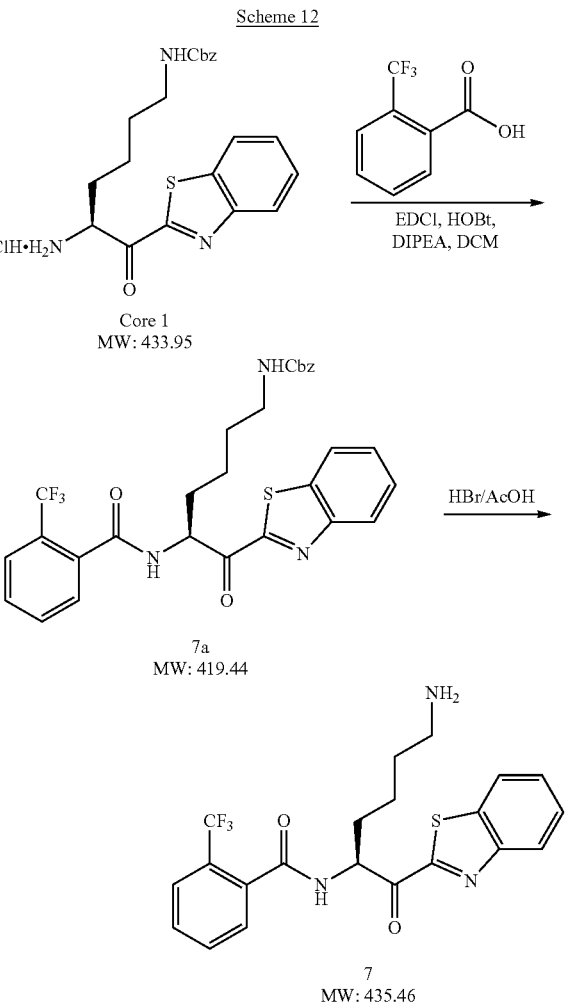

Scheme 12

Benzyl-N-[(5S)-6-(1,3-benzothiazol-2-yl)-6-oxo-5-[[2-(trifluoromethyl)benzoyl]amino]hexyl]carbamate (7a)

To a mixture of benzyl-N-[(5S)-5-amino-6-(1,3-benzothiazol-2-yl)-6-oxo-hexyl]carbamate (400 mg, 921.77 µmol, 1.00 eq), 2-(trifluoromethyl)benzoic acid (210 mg, 1.11 mmol, 1.20 eq), HOBt (162 mg, 1.20 mmol, 1.30 eq), EDCI (230 mg, 1.20 mmol, 1.30 eq) in DCM (10 mL) was added DIPEA (358 mg, 2.77 mmol, 3.00 eq) at 0° C. Then the mixture was stirred at 30° C. for 16 h. LC-MS indicated the reaction completed. The mixture was washed with water (5 mL×3), dried over Na$_2$SO$_4$, concentrated to give benzyl-N-[(5S)-6-(1,3-benzothiazol-2-yl)-6-oxo-5-[[2-(trifluoromethyl)benzoyl]amino]hexyl]carbamate (7a; 500 mg, crude) as a yellow solid.

N-[(1S)-5-amino-1-(1,3-benzothiazole-2-carbonyl)pentyl]-2-(trifluoromethyl) benzamide (7)

To a mixture of benzyl-N-[(5S)-6-(1,3-benzothiazol-2-yl)-6-oxo-5-[[2-(trifluoromethyl) benzoyl]amino]hexyl]carbamate (300 mg, 526.69 μmol, 1.00 eq) in AcOH (1 mL) was added HBr/AcOH (5.5 M, 1 mL). The mixture was stirred at 30° C. under N₂ for 0.5 h. LC-MS indicated the reaction completed. Water (20 mL) was added and extracted with MTBE (5 mL×2). Then the aqueous layer was lyophilized to give a crude, which was purified by prep-HPLC (CH₃CN/H₂O/TFA) to give N-[(1S)-5-amino-1-(1,3-benzothiazole-2-carbonyl)pentyl]-2-(trifluoromethyl)benzamide trifluoroacetate (7; 20 mg, 36.40 μmol, 6.9% yield) as a light yellow solid. MS m/z=437.0 (MH⁺).

Example 13. Preparation of (3S)-1-acetyl-N-(6-amino-1-(benzo[d]thiazol-2-yl)-1-oxohexan-2-yl)piperidine-3-carboxamide (8 and 10)

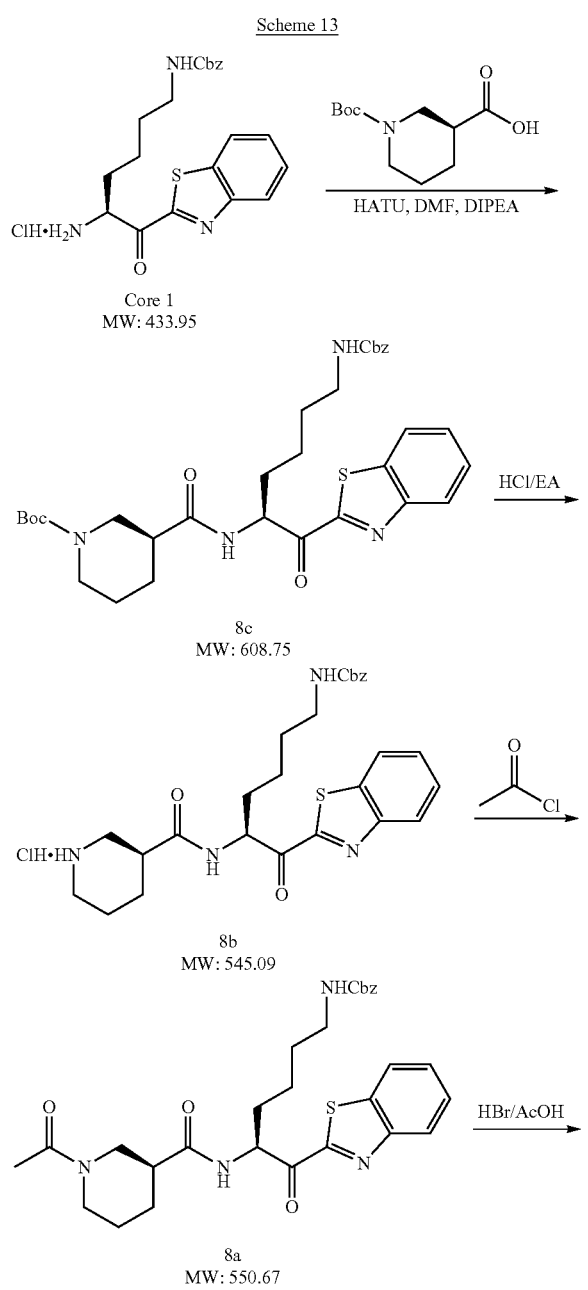

Scheme 13

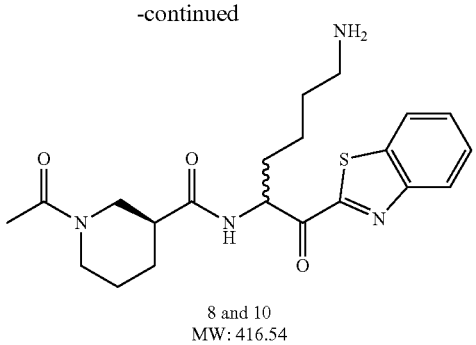

8 and 10
MW: 416.54

Tert-butyl-(3S)-3-[[(1S)-1-(1,3-benzothiazole-2-carbonyl)-5-(benzyloxycarbonylamino)pentyl]carbamoyl]piperidine-1-carboxylate (8c)

A mixture of (3S)-1-tert-butoxycarbonylpiperidine-3-carboxylic acid (693 mg, 3.02 mmol, 1.20 eq), HATU (1.15 g, 3.02 mmol, 1.20 eq), DIPEA (977 mg, 7.56 mmol, 3.00 eq) in DMF (20 mL) was stirred at 0° C. for 1 h. Then benzyl-N-[(5S)-5-amino-6-(1,3-benzothiazol-2-yl)-6-oxohexyl]carbamate hydrochloride (1.00 g, 2.52 mmol, 1.00 eq) was added and the mixture was stirred at 30° C. for 16 h. TLC (PE:EA=3:1) indicated the reaction completed. EA (100 mL) was added and washed with water (50 mL×3), dried over Na₂SO₄, concentrated to give tert-butyl-(3S)-3-[[(1S)-1-(1,3-benzothiazole-2-carbonyl)-5-(benzyloxycarbonylamino)pentyl]carbamoyl]piperidine-1-carboxylate (8c; 1.10 g, 1.81 mmol, 71.7% yield) as a yellow solid.

Benzyl-N-[(5S)-6-(1,3-benzothiazol-2-yl)-6-oxo-5-[[(3S)-piperidine-3-carbonyl]amino]hexyl]carbamate (8b)

To a mixture of tert-butyl-(3S)-3-[[(1S)-1-(1,3-benzothiazole-2-carbonyl)-5-(benzyloxycarbonylamino)pentyl]carbamoyl]piperidine-1-carboxylate (1.10 g, 1.81 mmol, 1.00 eq) in EA (10 mL) was added HCl/EA (4 M, 2 mL) and the reaction mixture was stirred at 30° C. for 2 h. TLC (PE:EA=3:1) indicated the reaction completed and the reaction was filtered to give benzyl-N-[(5S)-6-(1,3-benzothiazol-2-yl)-6-oxo-5-[[(3 S)-piperidine-3-carbonyl]amino]hexyl]carbamate hydrochloride (8b; 700 mg, crude) as a light yellow solid.

Benzyl-N-[(5S)-5-[[(3S)-1-acetylpiperidine-3-carbonyl]amino]-6-(1,3-benzothiazol-2-yl)-6-oxo-hexyl]carbamate (8a)

To a mixture of benzyl-N-[(5S)-6-(1,3-benzothiazol-2-yl)-6-oxo-5-[[(3 S)-piperidine-3-carbonyl]amino]hexyl]carbamate hydrochloride (700 mg, 1.28 mmol, 1.00 eq), TEA (390 mg, 3.85 mmol, 3.00 eq) in DCM (5 mL) was added acetyl chloride (150 mg, 1.93 mmol, 1.50 eq) dropwise at 0° C. under N₂ and the reaction mixture was stirred 0° C. under N₂ for 1 h. TLC (PE:EA=3:1) indicated the reaction completed, then DCM (20 mL) was added and the mixture was washed with water (10 mL×3), dried over Na₂SO₄, concentrated to give benzyl-N-[(5S)-5-[[(3S)-1-acetylpiperidine-3-carbonyl]amino]-6-(1,3-benzothiazol-2-yl)-6-oxo-hexyl]carbamate (8a; 800 mg, crude) as a yellow oil.

(3S)-1-acetyl-N-(6-amino-1-(benzo[d]thiazol-2-yl)-1-oxohexan-2-yl)piperidine-3-carboxamide (8 and 10)

To a mixture of benzyl-N-[(5S)-5-[[(3S)-1-acetylpiperidine-3-carbonyl]amino]-6-(1,3-benzothiazol-2-yl)-6-oxohexyl]carbamate (800 mg, 1.45 mmol, 1.00 eq) in AcOH (5 mL) was added HBr/AcOH (5.5 M, 2 mL). Then the reaction mixture was stirred at 30° C. for 0.5 hr. LC-MS indicated the reaction completed. Water (30 mL) was added and extracted with MTBE (10 mL×2), the aqueous layer was lyophilized to give a crude, which was purified by prep-HPLC (CH₃CN/H₂O/TFA) to give (3S)-1-acetyl-N-[(1S)-5-amino-1-(1,3-benzothiazole-2-carbonyl)pentyl]piperidine-3-carboxamide trifluoroacetate (8; 21.20 mg, 39.96 µmol, 2.8% yield) and (3S)-1-acetyl-N-[(1R)-5-amino-1-(1,3-benzothiazole-2-carbonyl)pentyl]piperidine-3-carboxamide trifluoroacetate (10; 24.20 mg, 45.61 µmol, 3.2% yield) as light yellow solids. MS m/z=417. 1 (MH⁺).

Example 14. Preparation of (3R)-1-acetyl-N-(6-amino-1-(benzo[d]thiazol-2-yl)-1-oxohexan-2-yl)piperidine-3-carboxamide (9 and 11)

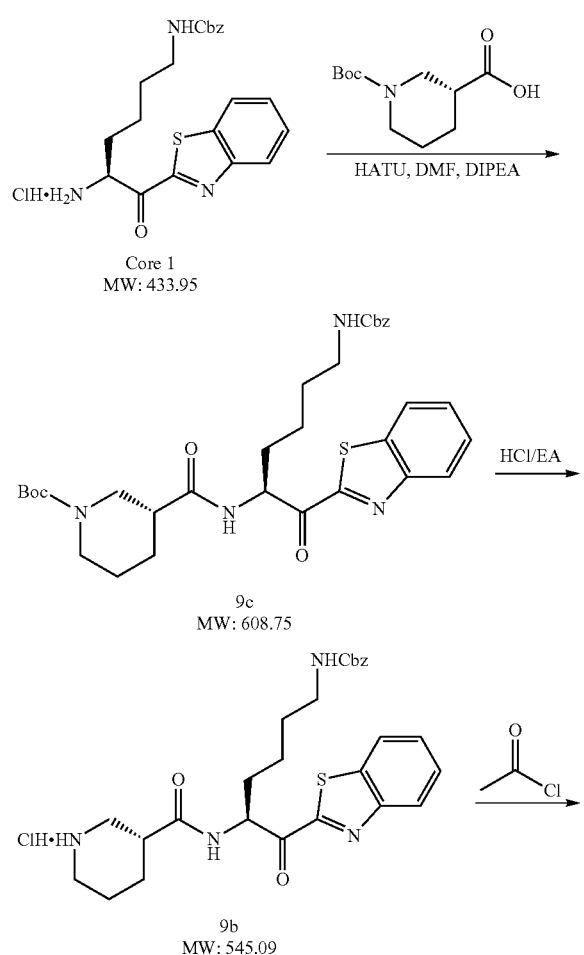

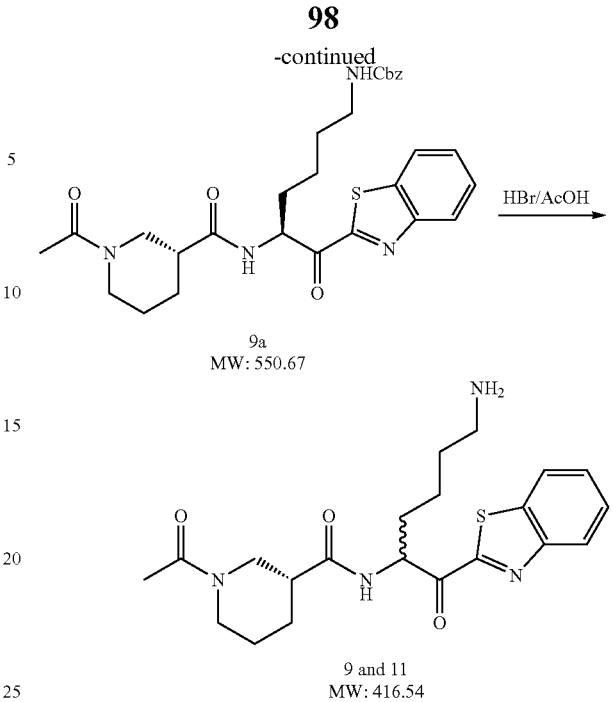

Tert-butyl-(3R)-3-[[(1S)-1-(1,3-benzothiazole-2-carbonyl)-5-(benzyloxycarbonylamino)pentyl]carbamoyl]piperidine-1-carboxylate (9c)

To a solution of (3R)-1-tert-butoxycarbonylpiperidine-3-carboxylic acid (633 mg, 2.76 mmol, 1.20 eq) in DMF (10 mL) were added HATU (2.62 g, 6.90 mmol, 3.00 eq) and DIPEA (892 mg, 6.90 mmol, 3.00 eq) under 0° C. After being stirred for 0.5 h under 0° C., benzyl-N-[(5S)-5-(amino-chloranyl)-6-(1,3-benzothiazol-2-yl)-6-oxo-hexyl]carbamate hydrochloride (1.00 g, 2.30 mmol, 1.00 eq) was added and the resulting mixture was stirred at 30° C. for 6 h. TLC (PE:EA=3:1) indicated the reaction completed. The mixture was diluted with H₂O (15 mL×2) and extracted with EA (20 mL×2). The combined organic layers were washed with H₂O (20 mL×2), dried over Na₂SO₄, filtered and concentrated to give tert-butyl-(3R)-3-[[(1S)-1-(1,3-benzothiazole-2-carbonyl)-5-(benzyloxycarbonylamino)pentyl]carbamoyl]piperidine-1-carboxylate (9c; 1.40 g, crude) as a oil, which was used directly for next step without further purification.

Benzyl-N-[(5S)-6-(1,3-benzothiazol-2-yl)-6-oxo-5-[[(3R)-piperidine-3-carbonyl]amino]hexyl]carbamate (9b)

To a solution of tert-butyl-(3R)-3-[[(1S)-1-(1,3-benzothiazole-2-carbonyl)-5-(benzyloxycarbonylamino)pentyl]carbamoyl]piperidine-1-carboxylate (821.36 µmol, 1.00 eq) (1.4 g, crude) in EA (20.00 mL) was added HCl/EA (4 M, 600.00 uL, 2.92 eq). The reaction mixture was stirred at 30° C. for 4 h. The suspension was filtered and the filter cake was collected to afford benzyl-N-[(5S)-6-(1,3-benzothiazol-2-yl)-6-oxo-5-[[(3R)-piperidine-3-carbonyl]amino]hexyl]carbamate hydrochloride (9b; 2.20 g, crude), which was used directly for next step without purification.

Benzyl-N-[(5S)-5-[[(3R)-1-acetylpiperidine-3-carbonyl]amino]-6-(1,3-benzothiazol-2-yl)-6-oxo-hexyl]carbamate (9a)

To a solution of benzyl-N-[(5S)-6-(1,3-benzothiazol-2-yl)-6-oxo-5-[[(3R)-piperidine-3-carbonyl]amino]hexyl]carbamate hydrochloride (4.04 mmol, 1.00 eq) (2.2 g, crude) in DCM (20 mL) was added TEA (1.23 g, 12.11 mmol, 3.00 eq). The mixture was cooled to 0° C., and then acetyl chloride (475 mg, 6.05 mmol, 1.50 eq) was added dropwise. The resulting mixture was stirred at 0° C. for 30 min. LC-MS indicated the reaction completed. The reaction was quenched by $H_2O$ (30 mL) and extracted with DCM (20 mL×2). The combined organic layers were dried over $Na_2SO_4$, filtered and concentrated to give benzyl-N-[(5S)-5-[[(3R)-1-acetylpiperidine-3-carbonyl]amino]-6-(1,3-benzothiazol-2-yl)-6-oxo-hexyl]carbamate (9a; 1.50 g, crude), which was used directly for next step without purification.

(3R)-1-acetyl-N-(6-amino-1-(benzo[d]thiazol-2-yl)-1-oxohexan-2-yl)piperidine-3-carboxamide (9 and 11)

To a solution of benzyl-N-[5-[[(3R)-1-acetylpiperidine-3-carbonyl]amino]-6-(1,3-benzothiazol-2-yl)-6-oxo-hexyl]carbamate (2.30 mmol, 1.00 eq) (1.5 g, crude) in AcOH (10 mL) was added HBr/AcOH (2.30 mmol, 1.00 eq) (2 mL, 33% purity) under $N_2$. The reaction mixture was stirred at 32° C. for 30 min. LC-MS indicated the desired product was detected. The mixture was diluted with $H_2O$ (100 mL) and MeOH (20 mL), washed with MTBE (50 mL×2). The resulting solution was under lyophilized to give a residue, which was purified by prep-HPLC (mobile phase: $CH_3CN$/$H_2O$/TFA) to give (3R)-1-acetyl-N-[(1S)-5-amino-1-(1,3-benzothiazole-2-carbonyl)pentyl]piperidine-3-carboxamide trifluoroacetate (9; 5.30 mg, 9.99 μmol, 0.4% yield) (yield over 4 steps) and (3R)-1-acetyl-N-[(1R)-5-amino-1-(1,3-benzothiazole-2-carbonyl)pentyl]piperidine-3-carboxamide trifluoroacetate (11; 49.70 mg, 119.32 μmol, 5.2% yield) (yield over 4 steps) as yellow solids. MS m/z=417.1 (MH+).

Example 15. Preparation of N-[(1)-5-amino-1-(1,3-benzothiazole-2-carbonyl)pentyl]pyridine-2-carboxamide (12)

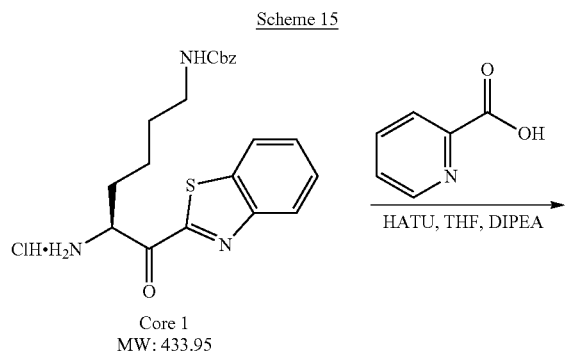

Scheme 15

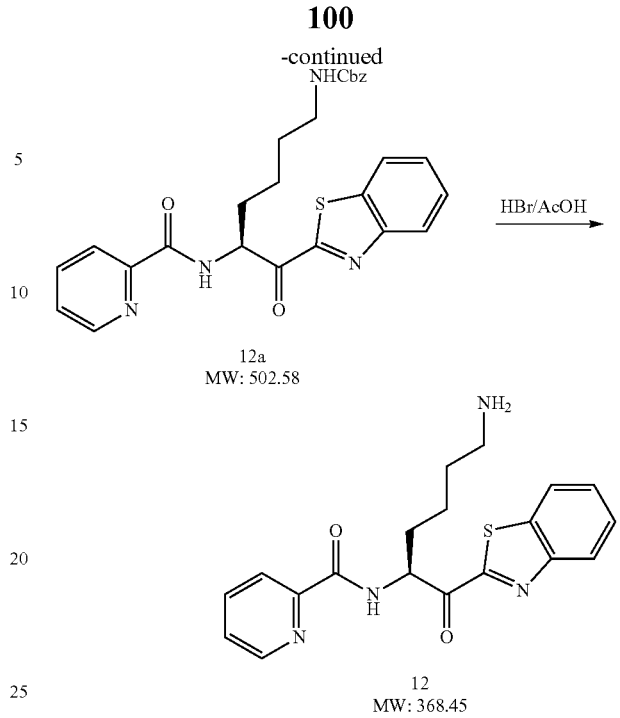

Benzyl-N-[(5S)-6-(1,3-benzothiazol-2-yl)-6-oxo-5-(pyridine-2-carbonylamino)hexyl]carbamate (12a). To a solution of pyridine-2-carboxylic acid (102 mg, 829.58 μmol, 1.20 eq) in THF (8 mL) were added HATU (315 mg, 829.58 μmol, 1.20 eq) and DIPEA (268 mg, 2.07 mmol, 3.00 eq) at 0° C., the resulting mixture was stirred at 0° C. for 15 min. Then benzyl-N-[(5S)-5-amino-6-(1,3-benzothiazol-2-yl)-6-oxo-hexyl]carbamate hydrochloride (300 mg, 691.32 μmol, 1.00 eq) was added at 0° C., the reaction mixture was stirred at 30° C. for another 3 h. LC-MS indicated the starting material was consumed completely. The reaction was quenched by $H_2O$ (30 mL) and then extracted with EA (20 mL×2), the combined organic phase was washed with saturated brine (30 mL) and concentrated to give benzyl-N-[(5S)-6-(1,3-benzothiazol-2-yl)-6-oxo-5-(pyridine-2-carbonylamino)hexyl]carbamate (12a; 698 mg, crude) as a yellow solid.

N-[(1S)-5-amino-1-(1,3-benzothiazole-2-carbonyl)pentyl]pyridine-2-carboxamide (12)

To a solution of benzyl-N-[(5S)-6-(1,3-benzothiazol-2-yl)-6-oxo-5-(pyridine-2-carbonylamino)hexyl]carbamate (682 mg, 1.36 mmol, 1.00 eq) in AcOH (3 mL) was added HBr/AcOH (1 mL, 33% purity) at 20° C., the reaction mixture was stirred at 20° C. for 1 h. LC-MS indicated the starting material was consumed and desired compound was detected. After stirring for another 30 min, the reaction was quenched by $H_2O$ (10 mL) and washed with MTBE (20 mL). The organic phase was extracted with $H_2O$ (20 mL×2) and the aqueous phases were combined and lyophilized to give a crude, which was purified by prep-HPLC ($CH_3CN$/$H_2O$/TFA) to give N-[(1S)-5-amino-1-(1,3-benzothiazole-2-carbonyl)pentyl]pyridine-2-carboxamide trifluoroacetate (12; 67.44 mg, 139.78 μmol, 10.3% yield, 74.4% ee) as a yellow solid. MS m/z=369.1 (MH+).

Example 16. Preparation of N-[(1)-5-amino-1-(1,3-benzothiazole-2-carbonyl)pentyl]pyridine-4-carboxamide (13)

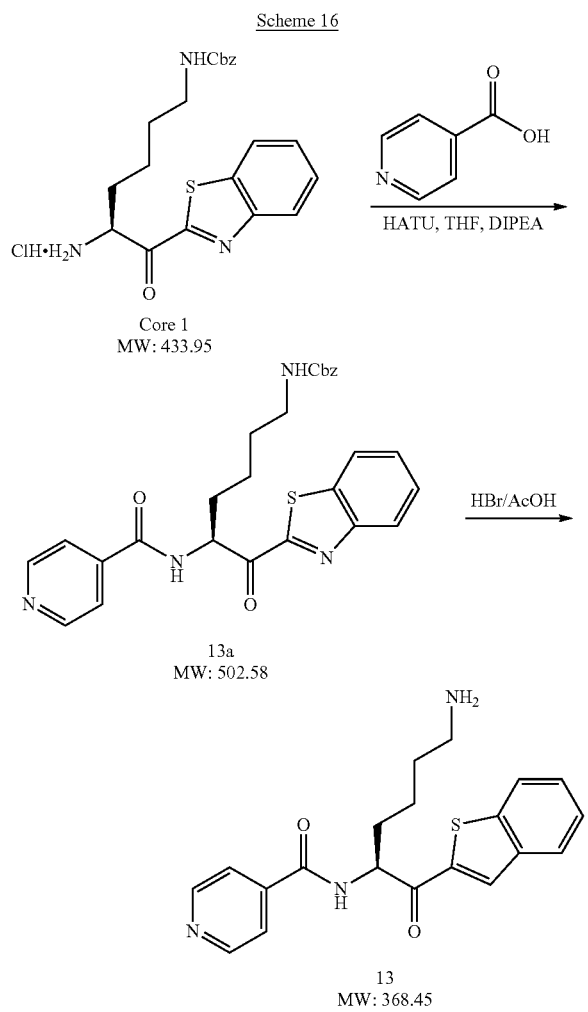

Benzyl-N-[(5S)-6-(1,3-benzothiazol-2-yl)-6-oxo-5-(pyridine-4-carbonylamino)hexyl]carbamate (13a)

To a solution of isonicotinic acid (102 mg, 829.58 μmol, 1.20 eq) in THF (8 mL) were added DIPEA (268 mg, 2.07 mmol, 3.00 eq) and HATU (315.43 mg, 829.58 μmol, 1.20 eq) at 0° C., the reaction mixture was stirred at 0° C. for 15 min. Then benzyl-N-[(5S)-5-amino-6-(1,3-benzothiazol-2-yl)-6-oxo-hexyl]carbamate hydrochloride (300 mg, 691.32 μmol, 1.00 eq) was added at 0° C., the reaction mixture was stirred at 30° C. for another 3 h. LC-MS indicated the starting material was consumed completely. The reaction was quenched by H$_2$O (30 mL) and then extracted with EA (20 mL×2), the combined organic phase was washed with saturated brine (30 mL) and concentrated to give benzyl-N-[(5S)-6-(1,3-benzothiazol-2-yl)-6-oxo-5-(pyridine-4-carbonylamino)hexyl]carbamate (13a; 727 mg, crude) as a red solid, which was used directly without further purification.

N-[(1S)-5-amino-1-(1,3-benzothiazole-2-carbonyl)pentyl]pyridine-4-carboxamide (13)

To a solution of benzyl-N-[(5S)-6-(1,3-benzothiazol-2-yl)-6-oxo-5-(pyridine-4-carbonylamino)hexyl]carbamate (727 mg, 1.45 mmol, 1.00 eq) in AcOH (3 mL) was added HBr/AcOH (1 mL, 33% purity). The reaction mixture was stirred at 20° C. for 3 h. LC-MS indicated the starting material was consumed completely. The reaction was quenched by H$_2$O (10 mL) and washed with MTBE (20 mL). The organic phase was extracted with H$_2$O (20 mL×2) and the aqueous phases were combined and lyophilized to give a crude, which was purified by prep-HPLC (CH$_3$CN/ H$_2$O/TFA) to give N-[(1S)-5-amino-1-(1,3-benzothiazole-2-carbonyl) pentyl]pyridine-4-carboxamide trifluoroacetate (13; 75.78 mg, 157.07 μmol, 10.8% yield, 69.3% ee) as a yellow solid. MS m/z=369.0 (MH$^+$).

Example 17. Preparation of (3R)—N-[5-amino-1-(1,3-benzothiazole-2-carbonyl)pentyl]-1-(3-phenylpropanoyl)piperidine-3-carboxamide (14/15)

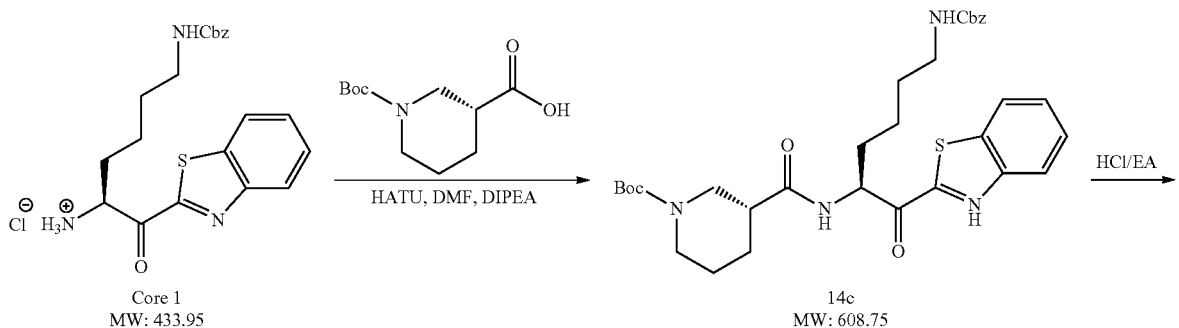

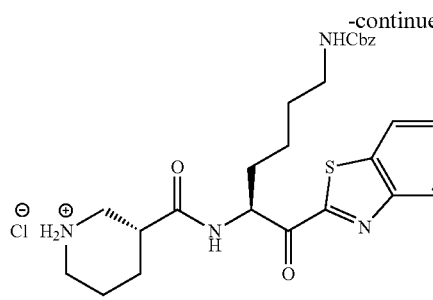
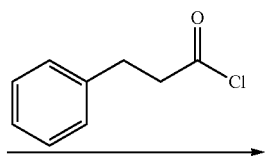

14b
MW: 545.09

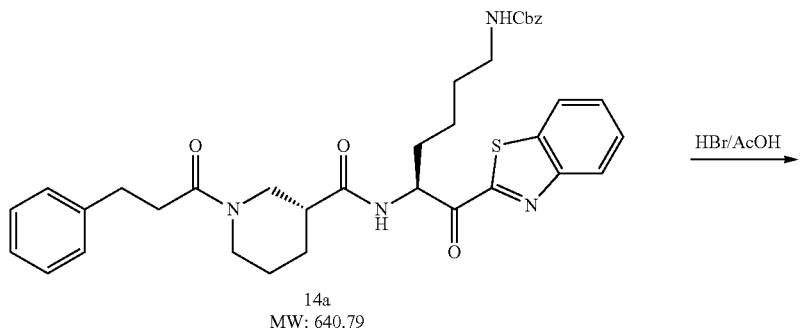

14a
MW: 640.79

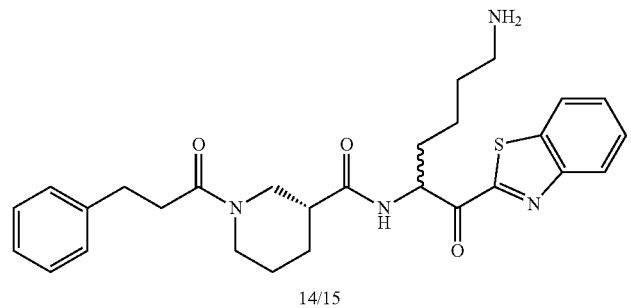

14/15
MW: 506.77

Tert-butyl-(3R)-3-[[(1S)-1-(1,3-benzothiazole-2-carbonyl)-5-(benzyloxycarbonylamino)pentyl]carbamoyl]piperidine-1-carboxylate (14c)

To a solution of (3R)-1-tert-butoxycarbonylpiperidine-3-carboxylic acid (3.17 g, 13.83 mmol, 1.20 eq) in DMF (60 mL) were added HATU (5.34 g, 14.06 mmol, 1.22 eq) and DIPEA (4.45 g, 34.45 mmol, 2.99 eq) under 0° C. After stirring for 0.5 h under 0° C., benzyl-N-[(5S)-5-amino-6-(1,3-benzothiazol-2-yl)-6-oxo-hexyl]carbamate hydrochloride (5.00 g, 11.52 mmol, 1.00 eq) was added and the resulting mixture was stirred at 30° C. for 3 h. TLC (PE:EA=3:1) indicated the reaction completed. The mixture was diluted with $H_2O$ (80 mL×2) and extracted with EA (100 mL×2). The combined organic layers were washed with $H_2O$ (60 mL×2), dried over $Na_2SO_4$, filtered and concentrated to give tert-butyl-(3R)-3-[[(1S)-1-(1,3-benzothiazole-2-carbonyl)-5-(benzyloxycarbonylamino)pentyl]carbamoyl]piperidine-1-carboxylate (9.80 g, crude) as a oil, which was used directly for next step without further purification.

Benzyl-N-[(5S)-6-(1,3-benzothiazol-2-yl)-6-oxo-5-[[(3R)-piperidine-3-carbonyl]amino]hexyl]carbamate (14b)

To a solution of tert-butyl-(3R)-3-[[(1S)-1-(1,3-benzothiazole-2-carbonyl)-5-(benzyloxycarbonylamino)pentyl]carbamoyl]piperidine-1-carboxylate (16.10 mmol, 1.00 eq) (9.8 g, crude) in EA (100 mL) was added HCl/EA (4 M, 20 mL, 4.97 eq). The reaction mixture was stirred at 30° C. for 1 h. The suspension was filtered and the filter cake was collected to afford benzyl-N-[(5S)-6-(1,3-benzothiazol-2-yl)-6-oxo-5-[[(3R)-piperidine-3-carbonyl]amino]hexyl]carbamate hydrochloride (10.90 g, crude), which was used directly for next step without purification.

Benzyl-N-[6-(1,3-benzothiazol-2-yl)-6-oxo-5-[[(3R)-1-(3-phenylpropanoyl)piperidine-3-carbonyl]amino]hexyl]carbamate (14a)

To a solution of benzyl-N-[(5S)-6-(1,3-benzothiazol-2-yl)-6-oxo-5-[[(3R)-piperidine-3-carbonyl]amino]hexyl]carbamate; hydrochloride (20 mmol, 1.00 eq) (10.9 g, crude) in DCM (100 mL) was added TEA (6.07 g, 60.00 mmol, 3.00 eq). The mixture was cooled to 0° C., and then 3-phenyl-propanoyl chloride (5.06 g, 30.00 mmol, 1.50 eq) was added dropwise. The resulting mixture was stirred at 0° C. for 30 min. LC-MS indicated the reaction completed. The reaction was quenched by $H_2O$ (60 mL) and extracted with DCM (100 mL×2). The combined organic layers were dried over $Na_2SO_4$, filtered and concentrated to give a crude, which was purified by column chromatography (PE:EA=8:1 to 3:1) to give benzyl-N-[6-(1,3-benzothiazol-2-yl)-6-oxo-5-

[[(3R)-1-(3-phenylpropanoyl)piperidine-3-carbonyl]amino]hexyl]carbamate (2.77 g, 4.32 mmol, 21.6% yield) as a yellow solid.

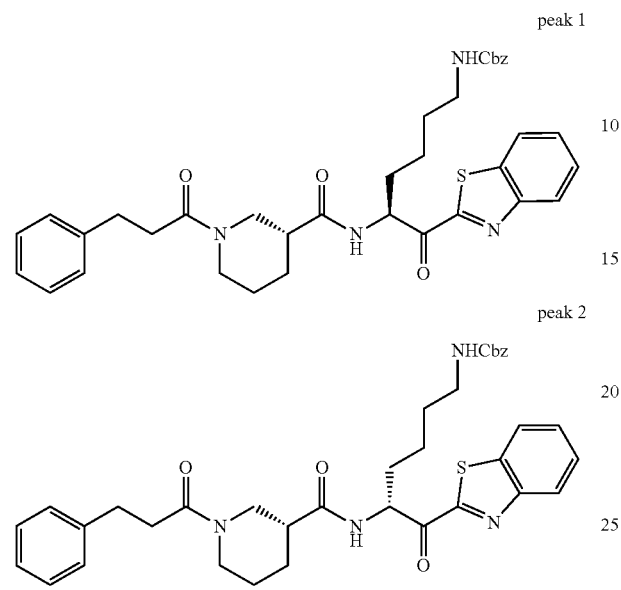

peak 1 peak 2

Benzyl-N-[6-(1,3-benzothiazol-2-yl)-6-oxo-5-[[(3R)-1-(3-phenylpropanoyl)piperidine-3-carbonyl]amino]hexyl]carbamate (1 g) was purified by chiral SFC separation (Chiral SFC separation method: Instrument: SFC 80, Column: AD-10 µm, Mobile phase: A for $CO_2$ and B for EtOH (0.1% $NH_3.H_2O$), Gradient: B 50%, Flow rate: 70 mL/min, Back pressure: 100 bar, Column temperature: 35° C., Wavelength: 220 nm) to give products (peak 1: 0.4 g) as a yellow solid and (peak 2: 0.51 g) as brown oil.

(3R)—N-[5-amino-1-(1,3-benzothiazole-2-carbonyl)pentyl]-1-(3-phenylpropanoyl)piperidine-3-carboxamide; 2,2,2-trifluoroacetic Acid (14/15)

To a solution of benzyl-N-[6-(1,3-benzothiazol-2-yl)-6-oxo-5-[[(3R)-1-(3-phenylpropanoyl) piperidine-3-carbonyl]amino]hexyl]carbamate (400 mg, 624.23 µmol, 1.00 eq) (Peak 1) in AcOH (6 mL) was added HBr/AcOH (624.23 µmol, 1.00 eq) (2 mL, 33% purity) under $N_2$. The reaction mixture was stirred at 30° C. for 1 hr. LC-MS indicated the desired product was detected. The mixture was diluted with $H_2O$ (100 mL) and MeOH (20 mL), washed with MTBE (50 mL×2). The resulting solution was lyophilized to give a residue, which was purified by prep-HPLC (mobile phase: $CH_3CN/H_2O/TFA$) to give (3R)—N-[5-amino-1-(1,3-benzothiazole-2-carbonyl)pentyl]-1-(3-phenylpropanoyl)piperidine-3-carboxamide trifluoroacetate (14; 39 mg, 76.97 µmol, 12.3% yield) as a light yellow solid. MS m/z=507.2 ($MH^+$).

To a solution of benzyl-N-[6-(1,3-benzothiazol-2-yl)-6-oxo-5-[[(3R)-1-(3-phenylpropanoyl) piperidine-3-carbonyl]amino]hexyl]carbamate (510 mg, 795.89 µmol, 1.00 eq) (Peak 2) in AcOH (6 mL) was added HBr/AcOH (795.89 µmol, 1.00 eq) (2 mL, 33% purity) under $N_2$. The reaction mixture was stirred at 30° C. for 1 hr. LC-MS indicated the desired product was detected. The mixture was diluted with $H_2O$ (100 mL) and MeOH (20 mL), washed with MTBE (50 mL×2). The resulting solution was lyophilized to give a residue, which was purified by prep-HPLC (mobile phase: $CH_3CN/H_2O/TFA$) to give (3R)—N-[5-amino-1-(1,3-benzothiazole-2-carbonyl)pentyl]-1-(3-phenylpropanoyl)piperidine-3-carboxamide trifluoroacetate (15; 43 mg, 84.87 µmol, 10.7% yield) as yellow oil. MS m/z=507.2 ($MH^+$).

Example 18. Preparation of N-[(14)-5-amino-1-(1,3-benzothiazole-2-carbonyl)pentyl]tetrahydropyran-3-carboxamide (18/19)

Scheme 18

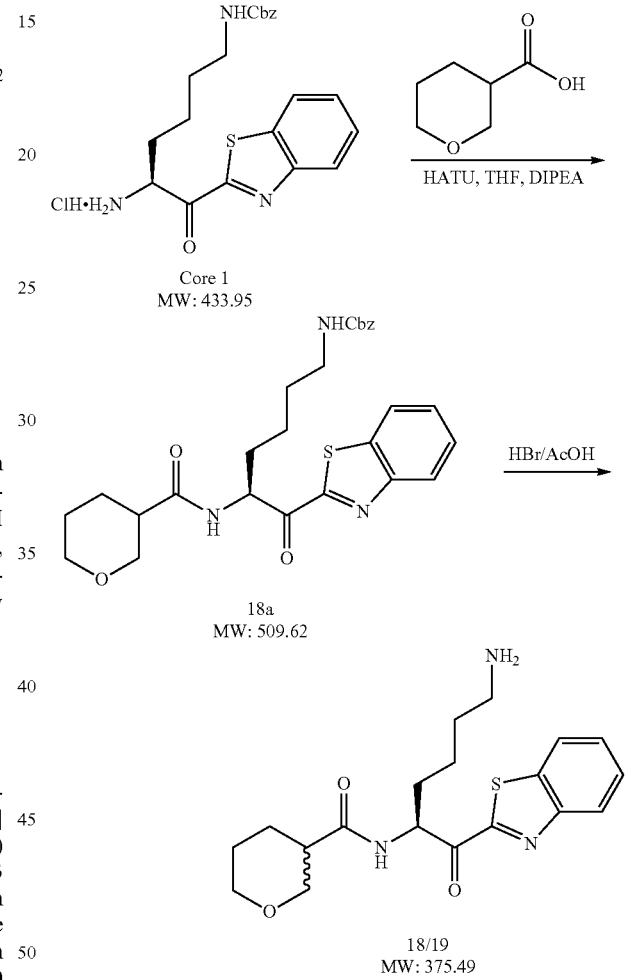

Core 1
MW: 433.95

18a
MW: 509.62

18/19
MW: 375.49

Benzyl-N-[(5S)-6-(1,3-benzothiazol-2-yl)-6-oxo-5-(tetrahydropyran-3-carbonylamino)hexyl]carbamate (18a)

To a solution of tetrahydropyran-3-carboxylic acid (108 mg, 829.58 µmol, 1.20 eq) in THF (5 mL) were added HATU (390 mg, 1.03 mmol, 1.48 eq) and DIPEA (270 mg, 2.09 mmol, 3.02 eq) under 0° C. After being stirred for 0.5 h under 0° C., benzyl-N-[(5S)-5-amino-6-(1,3-benzothiazol-2-yl)-6-oxo-hexyl]carbamate hydrochloride (300 mg, 691.32 µmol, 1.00 eq) was added and the resulting mixture was stirred at 28° C. for 4.5 h. LC-MS indicated the reaction completed. The mixture was diluted with $H_2O$ (15 mL×2) and extracted with EA (20 mL×2). The combined organic layers were washed with H₂O (20 mL), dried over Na₂SO₄, filtered and concentrated to give benzyl-N-[(5S)-6-(1,3-benzothiazol-2-yl)-6-oxo-5-(tetrahydropyran-3-carbonylamino)hexyl]carbamate (700 mg, crude) as a yellow solid. It was used directly for next step without further purification.

N-[(1S)-5-amino-1-(1,3-benzothiazole-2-carbonyl)pentyl]tetrahydropyran-3-carboxamide (18/19)

To a solution of benzyl-N-[(5S)-6-(1,3-benzothiazol-2-yl)-6-oxo-5-(tetrahydropyran-3-carbonylamino)hexyl]carbamate (1.37 mmol, 1.00 eq) (0.7 g, crude) in AcOH (6 mL) was added HBr/AcOH (1.37 mmol, 1.00 eq) (2 mL, 33% purity) under N₂. The reaction mixture was stirred at 28° C. for 1 hr. LC-MS indicated the desired product was detected. The mixture was diluted with H₂O (10 mL) and MeOH (2 mL), washed with MTBE (10 mL×2). The resulting solution was diluted with H₂O and then lyophilized to give a residue, which was purified by prep-HPLC (mobile phase: CH₃CN/H₂O/TFA) to give N-[(1S)-5-amino-1-(1,3-benzothiazole-2-carbonyl)pentyl]tetrahydropyran-3-carboxamide trifluoroacetates (14 mg Peak 1, compound 18) and (15 mg Peak 2, compound 19) as yellow solids. MS m/z=376.1 (MH⁺).

Example 19. Preparation of N-[(1S)-5-amino-1-(1,3-benzothiazole-2-carbonyl)pentyl]tetrahydropyran-4-carboxamide (22)

Scheme 19

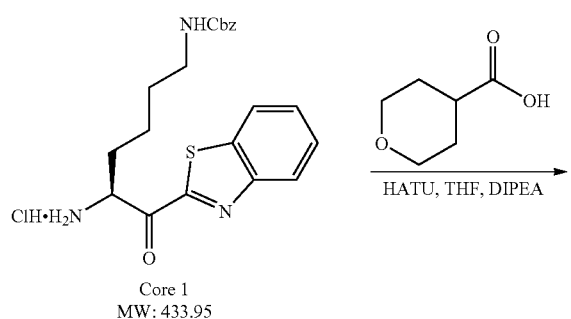

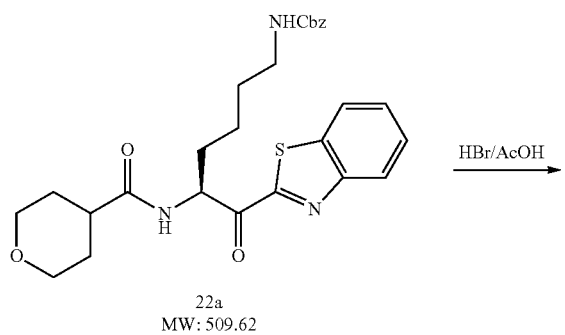

22a
MW: 509.62

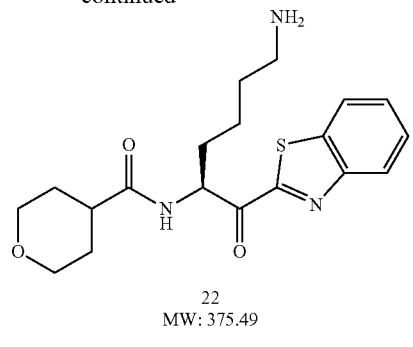

22
MW: 375.49

Benzyl-N-[(5S)-6-(1,3-benzothiazol-2-yl)-6-oxo-5-(tetrahydropyran-4-carbonylamino)hexyl]carbamate (22a)

To a solution of tetrahydropyran-4-carboxylic acid (108 mg, 829.58 μmol, 1.20 eq) in THF (5 mL) were added HATU (390 mg, 1.03 mmol, 1.48 eq) and DIPEA (270 mg, 2.09 mmol, 3.02 eq) under 0° C. After being stirred for 0.5 h under 0° C., benzyl-N-[(5S)-5-amino-6-(1,3-benzothiazol-2-yl)-6-oxo-hexyl]carbamate hydrochloride (300 mg, 691.32 μmol, 1.00 eq) was added and the resulting mixture was stirred at 28° C. for 4.5 h. LC-MS indicated the reaction completed. The mixture was diluted with H₂O (15 mL×2) and extracted with EA (20 mL×2). The combined organic layers were washed with H₂O (20 mL), dried over Na₂SO₄, filtered and concentrated to give benzyl-N-[(5S)-6-(1,3-benzothiazol-2-yl)-6-oxo-5-(tetrahydropyran-4-carbonylamino)hexyl]carbamate (680 mg, crude) as a light yellow solid. It was used directly for next step without further purification.

N-[(1S)-5-amino-1-(1,3-benzothiazole-2-carbonyl)pentyl]tetrahydropyran-4-carboxamide (22)

To a solution of benzyl-N-[(5S)-6-(1,3-benzothiazol-2-yl)-6-oxo-5-(tetrahydropyran-4-carbonylamino)hexyl]carbamate (1.33 mmol, 1.00 eq) (0.68 g, crude) in AcOH (5 mL) was added HBr/AcOH (1.33 mmol, 1.00 eq) (2 mL, 33% purity) under N₂. The reaction mixture was stirred at 30° C. for 30 min. LC-MS indicated the desired product was detected. The mixture was diluted with H₂O (10 mL) and MeOH (2 mL), washed with MTBE (10 mL×2). The resulting solution was lyophilized to give a residue, which was purified by prep-HPLC (mobile phase: CH₃CN/H₂O/TFA) to give N-[(1S)-5-amino-1-(1,3-benzothiazole-2-carbonyl)pentyl]tetrahydropyran-4-carboxamide trifluoroacetate (45 mg) as a yellow solid. MS m/z=376.1 (MH⁺).

Example 20. Preparation of Benzyl-N-[(1S)-5-amino-1-(1,3-benzothiazole-2-carbonyl) pentyl]carbamate (23)

Scheme 20

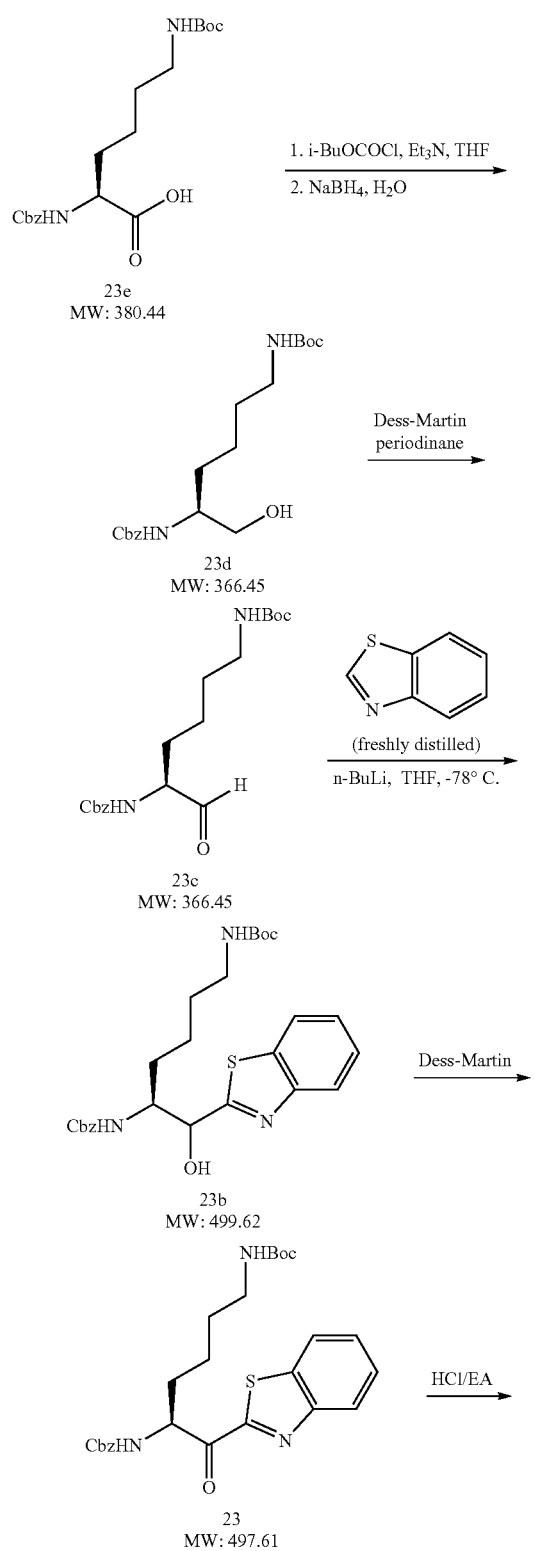

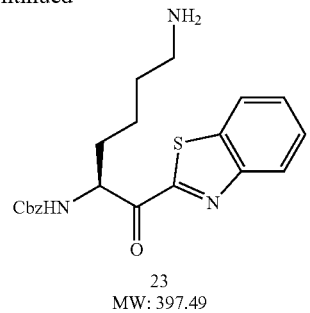

23
MW: 397.49

Tert-butyl-N-[(5S)-5-(benzyloxycarbonylamino)-6-hydroxy-hexyl]carbamate (23d)

To a solution of (2S)-2-(benzyloxycarbonylamino)-6-(tert-butoxycarbonylamino)-hexanoic acid (25.00 g, 65.72 mmol, 1.00 eq) in THF (250 mL) was added TEA (6.65 g, 65.72 mmol, 1.00 eq). The solution was cooled to −10° C. and then dropwise addition of iso-butylchloroformate (9.87 g, 72.27 mmol, 1.10 eq) (It has suspensoid appeared). The resulting suspension was stirred for 2 h at 0° C. The reaction mixture was filtered and cooled to −10° C. NaBH$_4$ (5.22 g, 138.00 mmol, 2.10 eq) was dissolved in water (50 mL) at 0° C. and the solution was added dropwise to the THF solution (heavy CO$_2$ evolution). The reaction mixture was allowed to warm to 30° C. and stirred for 3 hr. The reaction mixture was acidified with 1M HCl solution, and the aqueous phase was extracted with EA (400 mL×2). The combined organic layers were washed with water, saturated aqueous NaHCO$_3$ solution and brine; dried over Na$_2$SO$_4$, concentrated to give a residue, which was purified by flash column chromatography (PE:EA=2:1 to EA) to afford tert-butyl-N-[(5S)-5-(benzyloxycarbonylamino)-6-hydroxy-hexyl]carbamate (19.30 g, 52.67 mmol, 80.1% yield) as a oil.

Tert-butyl-N-[(5S)-5-(benzyloxycarbonylamino)-6-oxo-hexyl]carbamate (23c)

A solution of tert-butyl-N-[(5S)-5-(benzyloxycarbonylamino)-6-hydroxy-hexyl]carbamate (19.20 g, 52.39 mmol, 1.00 eq) in DCM (200 mL) was cooled to 0° C. Then Dess-Martin Periodinane (22.22 g, 52.39 mmol, 1.00 eq) was added in portions. The suspension was allowed to warm to room temperature (30° C.) and stirred 14 hr. TLC indicated the starting material was remained a little. A (100 mL:100 mL) mixture of saturated aqueous NaHCO$_3$ solution and a 1M Na$_2$S$_2$O$_3$ solution was added and the resulting biphasic system was stirred vigorously for 30 min. The organic layer was separated and the aqueous layer was extracted with DCM (200 mL). The combined organic layers were distilled in vacuo and the resulting oil were taken up in EA (100 mL) and washed four times with the NaHCO$_3$/Na$_2$S$_2$O$_3$ mixture, water and brine, dried over Na$_2$SO$_4$ and concentrated in vacuo to give crude tert-butyl-N-[(5S)-5-(benzyloxycarbonylamino)-6-oxo-hexyl]carbamate (17.33 g, crude) as a yellowish oil. It was directly used in the next step without further purification.

Tert-butyl-N-[(5S)-6-(1,3-benzothiazol-2-yl)-5-(benzyloxycarbonylamino)-6-hydroxy-hexyl]carbamate (23b)

A solution of 1,3-benzothiazole (5.56 g, 41.16 mmol, 3.00 eq) in THF (100 mL) was cooled to −78° C. Then n-BuLi (2.5 M, 16.5 mL, 3.01 eq) (2.5 M in THF, 16.5 mL) was added dropwise at −78° C. under N$_2$. After being stirred for 1 h at −78° C., tert-butyl-N-[(5S)-5-(benzyloxycarbonylamino)-6-oxo-hexyl]carbamate (13.72 mmol, 1.00 eq) (5 g, crude) in THF was added dropwise at −78° C. The resulting mixture was stirred for another 3 h at −78° C. LC-MS indicated the starting material disappeared and the desired product was detected. The reaction was quenched by NH$_4$Cl (60 mL) and extracted with EA (100 mL). The organic layer was separated, washed with brine, dried over MgSO$_4$, filtered and concentrated to give a crude product, which was purified by flash column chromatography (PE:EA=5:1 to 3:1) to give tert-butyl-N-[(5S)-6-(1,3-benzothiazol-2-yl)-5-(benzyloxycarbonylamino)-6-hydroxy-hexyl]carbamate (1.77 g, 3.54 mmol, 25.8% yield) as a yellow oil.

Benzyl-N-[(1S)-1-(1,3-benzothiazole-2-carbonyl)-5-(tert-butoxycarbonyl-amino)pentyl]carbamate (23a)

A solution of tert-butyl-N-[(5S)-6-(1,3-benzothiazol-2-yl)-5-(benzyloxycarbonylamino)-6-hydroxy-hexyl]carbamate (500 mg, 1.00 mmol, 1.00 eq) in DCM (6 mL) was cooled to 0° C. Then Dess-Martin (430 mg, 1.01 mmol, 1.01 eq) was added in portions. The suspension was allowed to warm to room temperature (28° C.) and stirred 14 hr. TLC indicated the starting material was consumed completely. A (10 mL:10 mL) mixture of saturated aqueous NaHCO$_3$ solution and a 1M Na$_2$S$_2$O$_3$ solution was added and the resulting biphasic system was stirred vigorously for 30 min. The organic layer was separated and the aqueous layer was extracted with DCM (20 mL). The combined organic layers were distilled in vacuo and the resulting oil were taken up in EA (20 mL) and washed four times with the NaHCO$_3$/Na$_2$S$_2$O$_3$ mixture, water and brine, dried over Na$_2$SO$_4$ and concentrated in vacuo to give a crude, which was purified by flash chromatography to give benzyl-N-[(1S)-1-(1,3-benzothiazole-2-carbonyl)-5-(tert-butoxycarbonyl-amino)pentyl]carbamate (200 mg, 401.92 μmol, 40.2% yield) as a yellow solid.

Benzyl-N-[(1S)-5-amino-1-(1,3-benzothiazole-2-carbonyl)pentyl]carbamate (23)

To a solution of benzyl-N-[(1S)-1-(1,3-benzothiazole-2-carbonyl)-5-(tert-butoxycarbonylamino) pentyl]carbamate (200 mg, 401.92 μmol, 1.00 eq) in EA (6 mL) was added HCl/EA (4 M, 4 mL, 39.81 eq). The resulting mixture was stirred at 28° C. for 14 hr. It was filtered and the filter cake was diluted with deionized water. The solution was lyophilized to give benzyl-N-[(1S)-5-amino-1-(1,3-benzothiazole-2-carbonyl)pentyl]carbamate hydrochloride (43.9 mg) as a yellow solid. MS m/z=398.1 (MH$^+$).

Example 21. Preparation of N-[(1S)-5-amino-1-(1,3-benzothiazole-2-carbonyl)pentyl]cyclopentanecarboxamide (24)

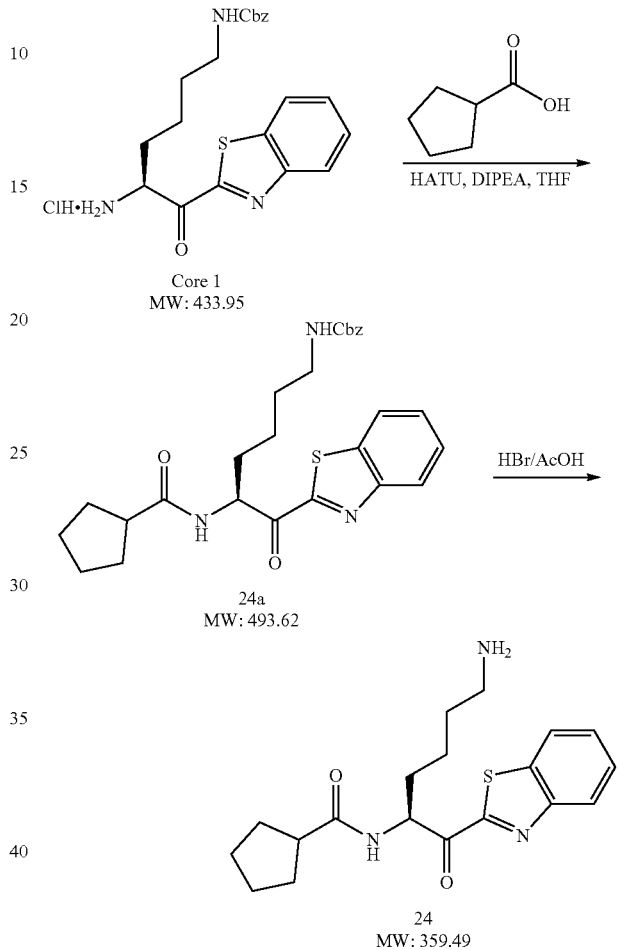

Benzyl-N-[(5S)-6-(1,3-benzothiazol-2-yl)-5-(cyclopentanecarbonylamino)-6-oxo-hexyl]carbamate (24a)

To a mixture of benzyl-N-[(5S)-5-amino-6-(1,3-benzothiazol-2-yl)-6-oxo-hexyl]carbamate hydrochloride (300 mg, 691.32 μmol, 1.00 eq), cyclopentanecarboxylic acid (79 mg, 691.32 μmol, 1.00 eq), DIPEA (268 mg, 2.07 mmol, 3.00 eq) in THF (5 mL) was added HATU (315 mg, 829.58 μmol, 1.20 eq). The mixture was stirred at 30° C. for 16 h. LC-MS indicated the starting material was consumed completely. EA (50 mL) was added and the mixture was washed with water (20 mL×2), dried over Na$_2$SO$_4$, concentrated to give a crude, which was purified by column chromatography on silica gel (PE:EA=5:1) to give benzyl-N-[(5S)-6-(1,3-benzothiazol-2-yl)-5-(cyclopentanecarbonylamino)-6-oxo-hexyl]carbamate (280 mg, 567.24 μmol, 82.1% yield) as a yellow solid.

N-[(1S)-5-amino-1-(1,3-benzothiazole-2-carbonyl)pentyl]cyclopentanecarboxamide (24)

To a mixture of benzyl-N-[(5S)-6-(1,3-benzothiazol-2-yl)-5-(cyclopentanecarbonylamino)-6-oxo-hexyl]carbamate (280 mg, 567.24 μmol, 1.00 eq) in AcOH (3 mL) was added HBr/AcOH (5.5 M, 1 mL). The mixture was stirred at 30° C. for 1 h. LC-MS indicated the starting material was consumed completely. Water (50 mL) was added and extracted with MTBE (10 mL×2). The aqueous layer was lyophilized to give a crude, which was purified by prep-HPLC (CH$_3$CN/H$_2$O/TFA) to give N-[(1S)-5-amino-1-(1,3-benzothiazole-2-carbonyl)pentyl]cyclo-pentanecarboxamide trifluoroacetate (21.63 mg, 60.17 μmol, 10.6% yield) as a white solid. MS m/z=360 (MH$^+$). $^1$H NMR (CD$_3$OD, 400 MHz) d 8.22 (d, J=7.6, 1H), 8.15 (d, J=7.6, 1H), 7.69-7.61 (m, 2H), 5.68 (dd, J=9.6, J=4.0, 1H), 3.07-2.92 (m, 2H), 2.85-2.75 (m, 1H), 2.22-2.12 (m, 1H), 1.95-1.55 (m, 13H).

Example 22. Preparation of N-[(1S)-5-amino-1-(1,3-benzothiazole-2-carbonyl)pentyl]tetrahydropyran-2-carboxamide (25/26)

Scheme 22

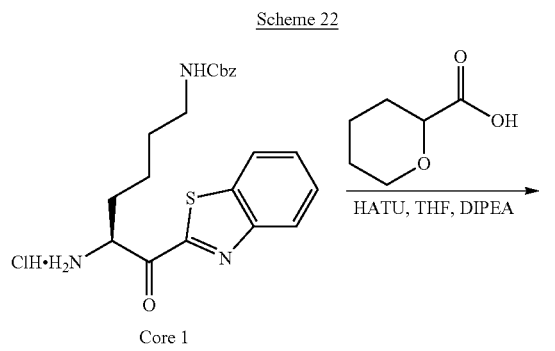

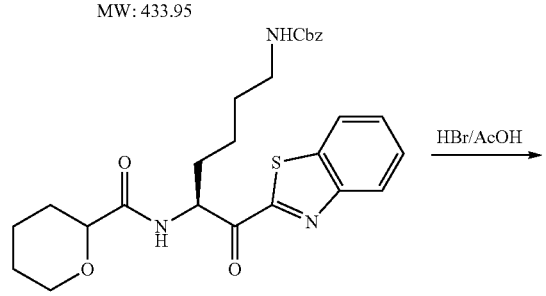

25a
MW: 509.62

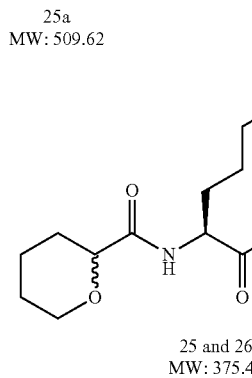

25 and 26
MW: 375.49

Benzyl-N-[(5S)-6-(1,3-benzothiazol-2-yl)-6-oxo-5-(tetrahydropyran-2-carbonylamino)hexyl]carbamate (2)

To a solution of tetrahydropyran-2-carboxylic acid (108 mg, 829.88 μmol, 1.20 eq) in THF (5 mL) were added HATU (395 mg, 1.04 mmol, 1.50 eq) and DIPEA (270 mg, 2.09 mmol, 3.02 eq) under 0° C. After being stirred for 0.5 h under 0° C., benzyl-N-[(5S)-5-amino-6-(1,3-benzothiazol-2-yl)-6-oxo-hexyl]carbamate hydrochloride (300 mg, 691.32 μmol, 1.00 eq) was added and the resulting mixture was stirred at 28° C. for 4.5 h. LC-MS indicated the reaction completed. The mixture was diluted with H$_2$O (10 mL) and extracted with EA (20 mL×2). The combined organic layers were washed with H$_2$O (20 mL), dried over Na$_2$SO$_4$, filtered and concentrated to give benzyl-N-[(5S)-6-(1,3-benzothiazol-2-yl)-6-oxo-5-(tetrahydropyran-2-carbonylamino)hexyl]carbamate (950 mg, crude) as a yellow oil. It was used directly for next step without further purification.

N-[(1S)-5-amino-1-(1,3-benzothiazole-2-carbonyl)pentyl]tetrahydropyran-2-carboxamide (152/153)

To a solution of benzyl-N-[(5S)-6-(1,3-benzothiazol-2-yl)-6-oxo-5-(tetrahydropyran-2-carbonyl-amino)hexyl]carbamate (1.86 mmol, 1.00 eq) (0.95 g, crude) in AcOH (6 mL) was added HBr/AcOH (1.86 mmol, 1.00 eq) (2 mL, 33% purity) under N$_2$. The reaction mixture was stirred at 30° C. for 1 hr. LC-MS indicated the desired product was detected. The mixture was diluted with H$_2$O (10 mL) and MeOH (2 mL), washed with MTBE (10 mL×2). The resulting solution was lyophilized to give a residue, which was purified by prep-HPLC (mobile phase: CH$_3$CN/H$_2$O/TFA) to give N-[(1S)-5-amino-1-(1,3-benzothiazole-2-carbonyl)pentyl]tetrahydropyran-2-carboxamide trifluoroacetates (15 mg; Peak 1, 25) and (13 mg; Peak 2, 26) as yellow solids. MS m/z=376.1 (MH$^+$).

Example 23. Preparation of 4-acetyl-N-[(1S)-5-amino-1-(1,3-benzothiazole-2-carbonyl)pentyl]morpholine-2-carboxamide (29)

Scheme 23

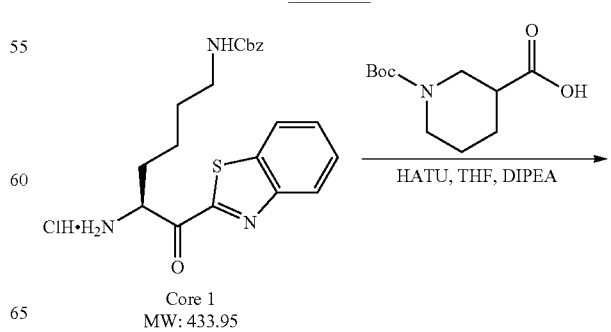

Core 1
MW: 433.95

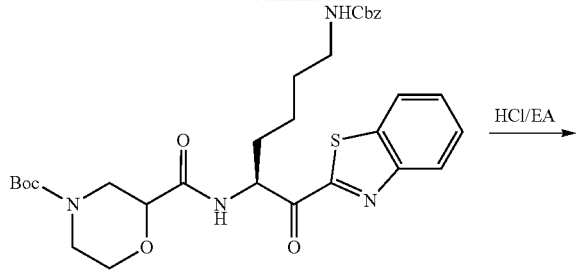

29c
MW: 610.72

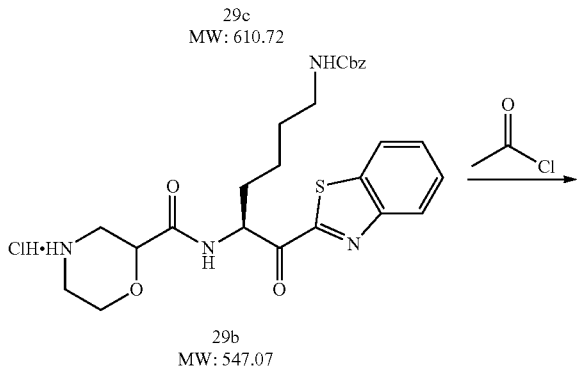

29b
MW: 547.07

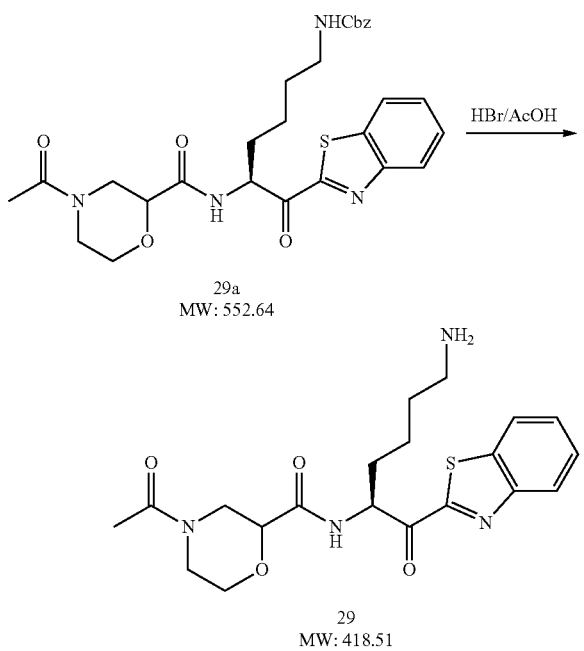

29a
MW: 552.64

29
MW: 418.51

Tert-butyl-2-[[(1S)-1-(1,3-benzothiazole-2-carbonyl)-5-(benzyloxycarbonyl-amino)pentyl]carbamoyl]morpholine-4-carboxylate (29c)

To mixture of 4-tert-butoxycarbonylmorpholine-2-carboxylic acid (320 mg, 1.38 mmol, 1.20 eq), DIPEA (446 mg, 3.45 mmol, 3.00 eq) in THF (10 mL) was added HATU (525 mg, 1.38 mmol, 1.20 eq) at 0° C. and the mixture was stirred at 0° C. for 0.5 h. Then benzyl-N-[(5S)-5-amino-6-(1,3-benzothiazol-2-yl)-6-oxo-hexyl]carbamate hydrochloride (500 mg, 1.15 mmol, 1.00 eq) was added and the mixture was stirred at 30° C. for 3 h. LC-MS indicated the starting material was consumed completely. EA (30 mL) was added and the mixture was washed with water (10 mL×2), dried over $Na_2SO_4$, concentrated to give a crude, which was purified by column chromatography on silica gel (PE:EA=3:1 to PE:EA=1:1) to give tert-butyl-2-[[(1S)-1-(1,3-benzothiazole-2-carbonyl)-5-(benzyloxycarbonylamino)pentyl]carbamoyl]morpholine-4-carboxylate (600 mg, crude) as a yellow solid.

Benzyl-N-[(5S)-6-(1,3-benzothiazol-2-yl)-5-(morpholine-2-carbonylamino)-6-oxo-hexyl]carbamate (29b)

To a mixture of tert-butyl-2-[[(1S)-1-(1,3-benzothiazole-2-carbonyl)-5-(benzyloxycarbonylamino)pentyl]carbamoyl]morpholine-4-carboxylate (600 mg, 982.45 μmol, 1.00 eq) in EA (5 mL) was added HCl/EA (4 M, 1 mL). The mixture was stirred at 30° C. for 2 hr. TLC (PE:EA=1:1) indicated the starting material was consumed completely. The mixture was filtered to give benzyl-N-[(5S)-6-(1,3-benzothiazol-2-yl)-5-(morpholine-2-carbonylamino)-6-oxo-hexyl]carbamate hydrochloride (300 mg, 548.39 μmol, 55.8% yield) as a light yellow solid.

Benzyl-N-[(5S)-5-[(4-acetylmorpholine-2-carbonyl)amino]-6-(1,3-benzothiazol-2-yl)-6-oxo-hexyl]carbamate (29a)

To a mixture of benzyl-N-[(5S)-6-(1,3-benzothiazol-2-yl)-5-(morpholine-2-carbonylamino)-6-oxo-hexyl]carbamate hydrochloride (300 mg, 548.39 μmol, 1.00 eq), TEA (166 mg, 1.65 mmol, 3.00 eq) in DCM (5 mL) was added acetyl chloride (86 mg, 1.10 mmol, 2.00 eq) dropwise at 0° C. under $N_2$. The mixture was stirred at 0° C. under $N_2$ for 10 min. LC-MS indicated the starting material was consumed completely. DCM (20 mL) was added and the mixture was washed with water (10 mL×3), dried over $Na_2SO_4$, concentrated to give benzyl-N-[(5S)-5-[(4-acetylmorpholine-2-carbonyl)amino]-6-(1,3-benzothiazol-2-yl)-6-oxo-hexyl]carbamate (200 mg, 361.90 μmol, 67.0% yield) as a yellow solid.

4-acetyl-N-[(1S)-5-amino-1-(1,3-benzothiazole-2-carbonyl)pentyl]morpholine-2-carboxamide (29)

To a mixture benzyl-N-[(5S)-5-[(4-acetylmorpholine-2-carbonyl)amino]-6-(1,3-benzothiazol-2-yl)-6-oxo-hexyl]carbamate (200 mg, 361.90 μmol, 1.00 eq) in AcOH (3 mL) was added HBr/AcOH (5.5 M, 1 mL). The mixture was stirred at 30° C. for 1 h. LC-MS indicated the starting material was consumed completely. Water (40 mL) was added and the mixture was extracted with MTBE (10 mL×2). The aqueous layer was lyophilized to give a crude, which was purified by prep-HPLC ($CH_3CN/H_2O$/TFA) to give 4-acetyl-N-[(1S)-5-amino-1-(1,3-benzothiazole-2-carbonyl)pentyl]morpholine-2-carboxamide trifluoroacetate (14.46 mg, 27.15 μmol, 7.5% yield) as a white solid. MS m/z=419.1 ($MH^+$).

117

Example 24. Preparation of N-[(1S)-5-amino-1-(1,3-benzothiazole-2-carbonyl)pentyl]pyridine-3-carboxamide (30)

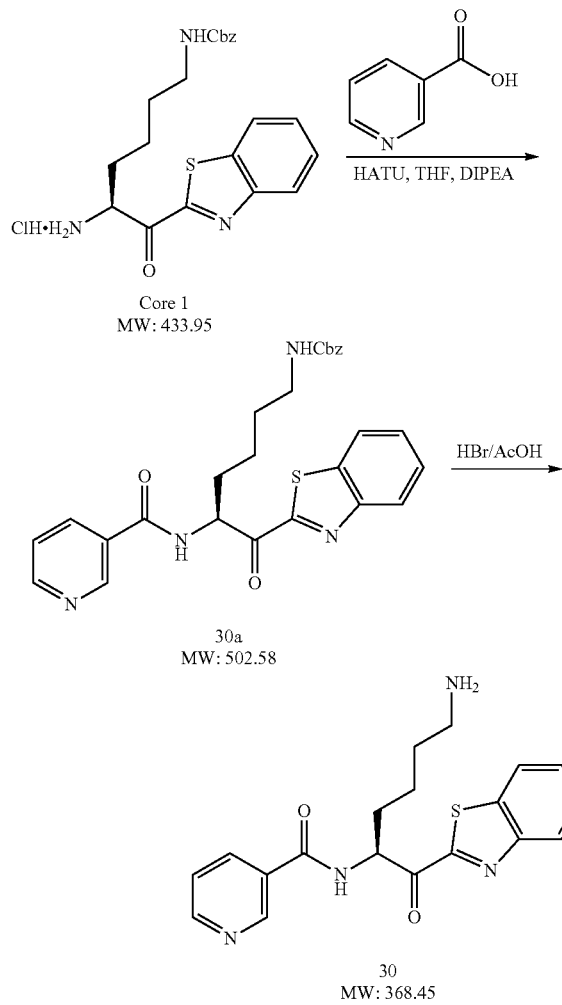

Benzyl-N-[(5S)-6-(1,3-benzothiazol-2-yl)-6-oxo-5-(pyridine-3-carbonylamino)hexyl]carbamate (30a)

To a solution of nicotinic acid (102 mg, 829.58 µmol, 1.20 eq) in THF (8 mL) were added DIPEA (268 mg, 2.07 mmol, 3.00 eq) and HATU (315 mg, 829.58 µmol, 1.20 eq) at 0° C., the reaction mixture was stirred at 0° C. for 15 min. Then benzyl-N-[(5S)-5-amino-6-(1,3-benzothiazol-2-yl)-6-oxohexyl]carbamate hydrochloride (300 mg, 691.32 µmol, 1.00 eq) was added at 0° C., the reaction mixture was stirred at 30° C. for another 3 h. LC-MS indicated the starting material was consumed completely. The reaction was quenched by H₂O (30 mL) and then extracted with EA (20 mL×2), the organic phases were combined, washed with saturated brine (30 mL) and concentrated to give benzyl-N-[(5S)-6-(1,3-benzothiazol-2-yl)-6-oxo-5-(pyridine-3-carbonylamino)hexyl]carbamate (638 mg, crude) as a red solid, which was used directly without further purification.

118

N-[(1S)-5-amino-1-(1,3-benzothiazole-2-carbonyl)pentyl]pyridine-3-carboxamide (30)

To a solution of benzyl-N-[(5S)-6-(1,3-benzothiazol-2-yl)-6-oxo-5-(pyridine-3-carbonylamino)hexyl]carbamate (638 mg, 1.27 mmol, 1.00 eq) in AcOH (3 mL) was added HBr/AcOH (1 mL, 33% purity). The reaction mixture was stirred at 30° C. for 1 h. LC-MS indicated the starting material was consumed completely. The reaction was quenched by H₂O (10 mL) and washed with MTBE (20 mL). The organic phase was extracted with H₂O (20 mL×2) and the aqueous phases were combined and lyophilized to give a crude product, which was purified by prep-HPLC (CH₃CN/H₂O/TFA) to give N-[(1S)-5-amino-1-(1,3-benzothiazole-2-carbonyl)pentyl]pyridine-3-carboxamide trifluoroacetate (50.96 mg, 105.62 µmol, 8.3% yield, 38.2% ee) as a yellow solid. MS m/z=369.1 (MH⁺).

Example 25. Preparation of N-[(1S)-5-amino-1-(1,3-benzothiazole-2-carbonyl)pentyl]tetralin-1-carboxamide (31)

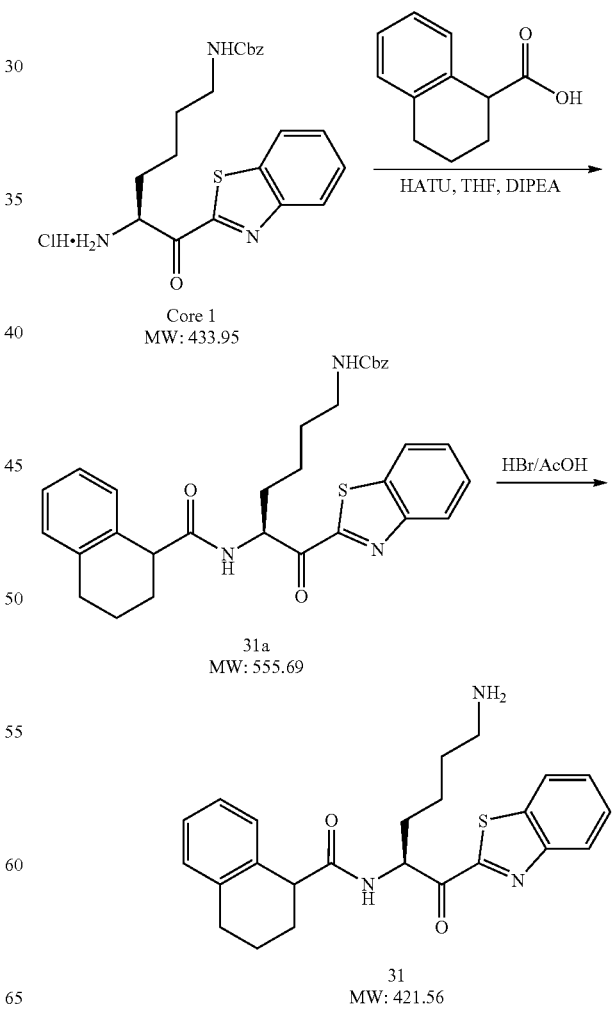

Benzyl-N-[(5S)-6-(1,3-benzothiazol-2-yl)-6-oxo-5-(tetralin-1-carbonylamino)hexyl]carbamate (31a)

To a solution of tetralin-1-carboxylic acid (150 mg, 851.26 μmol, 1.23 eq) in THF (5 mL) were added HATU (390 mg, 1.03 mmol, 1.48 eq) and DIPEA (270 mg, 2.09 mmol, 3.02 eq) under 0° C. After being stirred for 0.5 h under 0° C., benzyl-N-[(5S)-5-amino-6-(1,3-benzothiazol-2-yl)-6-oxo-hexyl]carbamate hydrochloride (300 mg, 691.32 μmol, 1.00 eq) was added and the resulting mixture was stirred at 28° C. for 5.5 h. LC-MS indicated the reaction completed. The mixture was diluted with H$_2$O (10 mL) and extracted with EA (20 mL×2). The combined organic layers were washed with H$_2$O (20 mL), dried over Na$_2$SO$_4$, filtered and concentrated to give benzyl-N-[(5S)-6-(1,3-benzothiazol-2-yl)-6-oxo-5-(tetralin-1-carbonylamino)hexyl]carbamate (660.00 mg, crude) as a yellow oil. It was used directly for next step without further purification.

N-[(1S)-5-amino-1-(1,3-benzothiazole-2-carbonyl)pentyl]tetralin-1-carboxamide (31)

To a solution of benzyl-N-[(5S)-6-(1,3-benzothiazol-2-yl)-6-oxo-5-(tetralin-1-carbonylamino)hexyl]carbamate (1.19 mmol, 1.00 eq) (0.66 g, crude) in AcOH (6 mL) was added HBr/AcOH (1.19 mmol, 1.00 eq) (2 mL, 33% purity) under N$_2$. The reaction mixture was stirred at 28° C. for 1 hr. LC-MS indicated the desired product was detected. The mixture was diluted with H$_2$O (10 mL) and MeOH (2 mL), washed with MTBE (10 mL×2). The resulting solution was diluted with H$_2$O and then lyophilized to give a residue, which was purified by prep-HPLC (CH$_3$CN/H$_2$O/TFA) to give N-[(1S)-5-amino-1-(1,3-benzothiazole-2-carbonyl)pentyl]tetralin-1-carboxamide trifluoroacetate (70 mg) as a yellow solid. MS m/z=422.1 (MH$^+$).

Example 26. Preparation of N-[(1S)-5-amino-1-(1,3-benzothiazole-2-carbonyl)pentyl]tetralin-2-carboxamide (32)

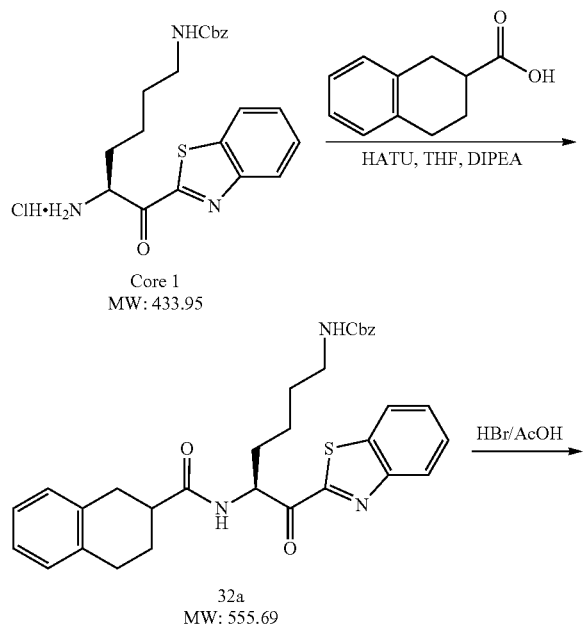

Scheme 26

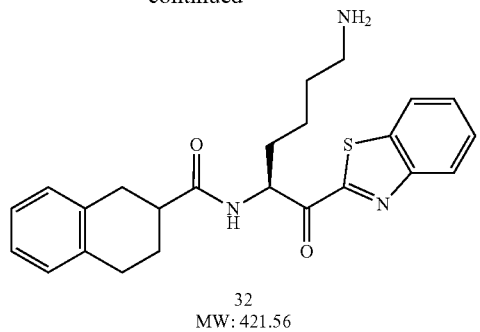

32
MW: 421.56

Benzyl-N-[(5S)-6-(1,3-benzothiazol-2-yl)-6-oxo-5-(tetralin-2-carbonylamino)hexyl]carbamate (32a)

To a solution of tetralin-2-carboxylic acid (150 mg, 851.26 μmol, 1.23 eq) in THF (5 mL) were added HATU (390 mg, 1.03 mmol, 1.48 eq) and DIPEA (270 mg, 2.09 mmol, 3.02 eq) under 0° C. After being stirred for 0.5 h under 0° C., benzyl-N-[(5S)-5-amino-6-(1,3-benzothiazol-2-yl)-6-oxo-hexyl]carbamate hydrochloride (300 mg, 691.32 μmol, 1.00 eq) was added and the resulting mixture was stirred at 28° C. for 5.5 h. LC-MS indicated the reaction completed. The mixture was diluted with H$_2$O (15 mL×2) and extracted with EA (20 mL×2). The combined organic layers were washed with H$_2$O (20 mL), dried over Na$_2$SO$_4$, filtered and concentrated to give benzyl-N-[(5S)-6-(1,3-benzothiazol-2-yl)-6-oxo-5-(tetralin-2-carbonylamino)hexyl]carbamate (700 mg, crude) as a yellow solid. It was used directly for next step without further purification.

N-[(1S)-5-amino-1-(1,3-benzothiazole-2-carbonyl)pentyl]tetralin-2-carboxamide (32)

To a solution of benzyl-N-[(5S)-6-(1,3-benzothiazol-2-yl)-6-oxo-5-(tetralin-2-carbonylamino)hexyl]carbamate (1.26 mmol, 1.00 eq) (0.7 g, crude) in AcOH (5 mL) was added HBr/AcOH (1.26 mmol, 1.00 eq) (2 mL) under N$_2$. The reaction mixture was stirred at 28° C. for 0.5 hr. LC-MS indicated the desired product was detected. The mixture was diluted with H$_2$O (10 mL) and MeOH (2 mL), washed with MTBE (10 mL×2). The resulting solution was diluted with H$_2$O and then lyophilized to give a residue, which was purified by prep-HPLC (CH$_3$CN/H$_2$O/TFA) to give the product, but LC-MS indicated it was not pure enough. So it was further purified by prep-HPLC (CH$_3$CN/H$_2$O/TFA) to give a solution, which was lyophilized to give N-[(1S)-5-amino-1-(1,3-benzothiazole-2-carbonyl)pentyl]tetralin-2-carboxamide trifluoroacetate (52 mg) as a yellow solid. MS m/z=422.2 (MH$^+$).

Example 27. Preparation of N-[(1S)-5-amino-1-(1,3-benzothiazole-2-carbonyl)pentyl]-1-methyl-cyclohexanecarboxamide (33)

Scheme 27.

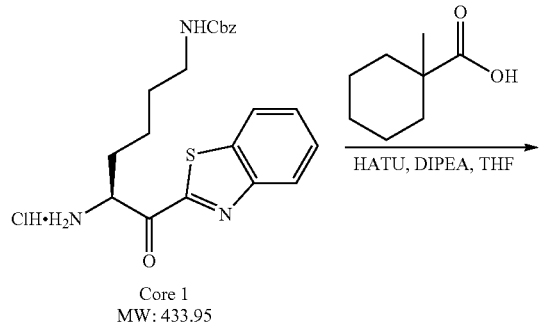
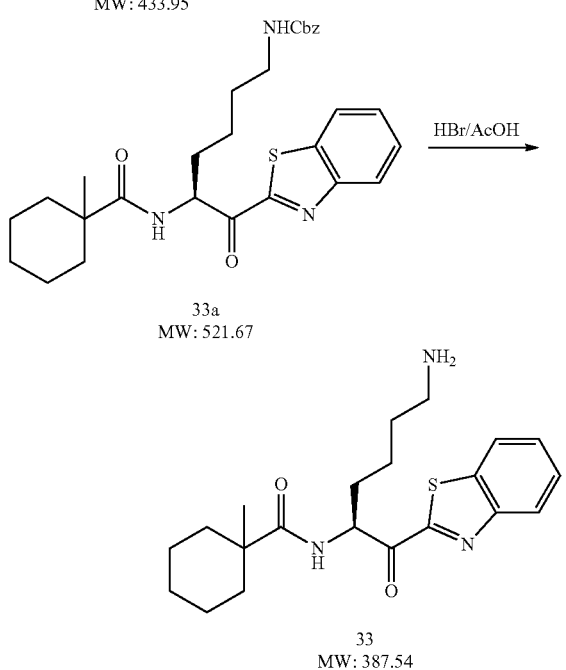

Benzyl-N-[(5S)-6-(1,3-benzothiazol-2-yl)-5-[(1-methylcyclohexanecarbonyl)-amino]-6-oxo-hexyl]carbamate (33a)

To a mixture of 1-methylcyclohexanecarboxylic acid (118 mg, 829.58 μmol, 1.20 eq) and DIPEA (268 mg, 2.07 mmol, 3.00 eq) in THF (5 mL) was added HATU (315 mg, 829.58 μmol, 1.20 eq) at 0° C., the reaction mixture was stirred at 0° C. for 15 min. Then benzyl-N-[(5S)-5-amino-6-(1,3-benzothiazol-2-yl)-6-oxo-hexyl]carbamate hydrochloride (300 mg, 691.32 μmol, 1.00 eq) was added at 0° C., the reaction was stirred at 20° C. for another 3 h. LC-MS indicated the starting material was consumed completely. The reaction was quenched by $H_2O$ (10 mL) and extracted with EA (20 mL×2). The organic layers were combined, washed with saturated brine (20 mL×2) and concentrated to give benzyl-N-[(5S)-6-(1,3-benzothiazol-2-yl)-5-[(1-methylcyclohexanecarbonyl)amino]-6-oxo-hexyl]carbamate (704 mg, crude) as a yellow oil, which was used directly without further purification.

N-[(1S)-5-amino-1-(1,3-benzothiazole-2-carbonyl)pentyl]-1-methyl-cyclohexanecarboxamide (33)

To a solution of benzyl-N-[(5S)-6-(1,3-benzothiazol-2-yl)-5-[(1-methylcyclohexanecarbonyl) amino]-6-oxo-hexyl] carbamate (704 mg, 1.26 mmol, 1.00 eq) in AcOH (3 mL) was added HBr/AcOH (1 mL, 33% purity). The reaction mixture was stirred at 20° C. for 3 h. LC-MS indicated the starting material was consumed completely. The reaction was quenched by $H_2O$ (10 mL) and washed with MTBE (20 mL). The organic phase was extracted with $H_2O$ (20 mL×2) and the aqueous phases were combined and lyophilized to give a crude, which was purified by prep-HPLC ($CH_3CN$/$H_2O$/TFA) to give N-[(1S)-5-amino-1-(1,3-benzothiazole-2-carbonyl)pentyl]-1-methyl-cyclohexanecarboxamide trifluoroacetate (50.68 mg, 101.04 μmol, 8.0% yield, 73.1% ee) as a yellow solid. MS m/z=388 ($MH^+$). $^1H$ NMR ($CD_3OD$, 400 MHz) d 8.19 (d, J=7.6, 1H), 8.12 (d, J=7.6, 1H), 7.66-7.59 (m, 2H), 5.58 (dd, J=10.0, J=4.0, 1H), 3.05-2.94 (m, 2H), 2.23-2.14 (m, 1H), 2.08-2.00 (m, 2H), 1.93-1.71 (m, 3H), 1.62-1.23 (m, 10H), 1.14 (s, 3H).

Example 28. Preparation of N-[(1S)-5-amino-1-(1,3-benzothiazole-2-carbonyl)pentyl]tetrahydrofuran-2-carboxamide (34/35)

Scheme 28

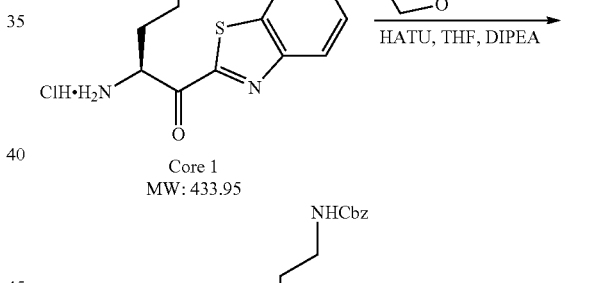
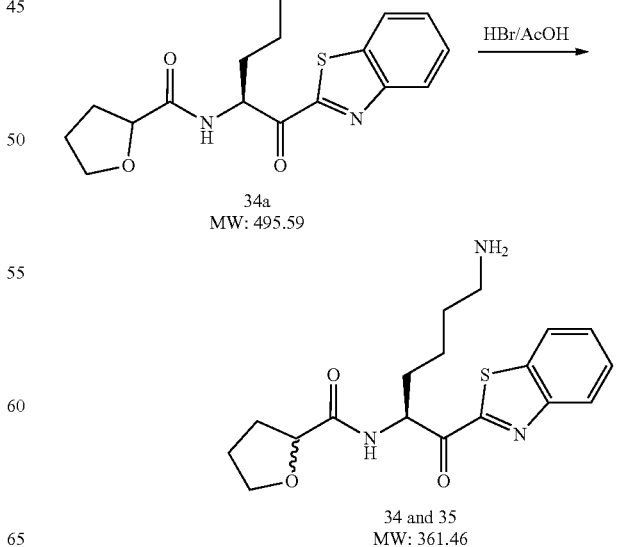

Benzyl-N-[(5S)-6-(1,3-benzothiazol-2-yl)-6-oxo-5-(tetrahydrofuran-2-carbonylamino)hexyl]carbamate (2)

To a mixture of tetrahydrofuran-2-carboxylic acid (96 mg, 829.58 μmol, 1.20 eq) and DIPEA (268 mg, 2.07 mmol, 3.00 eq) in THF (5 mL) was added HATU (315 mg, 829.58 μmol, 1.20 eq) at 0° C., the reaction mixture was stirred at 0° C. for 15 min. Then benzyl-N-[(5S)-5-amino-6-(1,3-benzothiazol-2-yl)-6-oxo-hexyl]carbamate hydrochloride (300 mg, 691.32 μmol, 1.00 eq) was added at 0° C., the mixture was stirred at 20° C. for another 3 h. LC-MS indicated the starting material was consumed completely. The reaction was quenched by $H_2O$ (10 mL) and extracted with EA (20 mL×2), the organic layers were combined, washed with saturated brine (20 mL×2) and concentrated to give benzyl-N-[(5S)-6-(1,3-benzothiazol-2-yl)-6-oxo-5-(tetrahydrofuran-2-carbonylamino)hexyl]carbamate (517 mg, crude) as a yellow oil, which was used without further purification.

N-[(1S)-5-amino-1-(1,3-benzothiazole-2-carbonyl) pentyl]tetrahydrofuran-2-carboxamide (34/35)

To a solution of benzyl-N-[(5S)-6-(1,3-benzothiazol-2-yl)-6-oxo-5-(tetrahydrofuran-2-carbonylamino)hexyl]carbamate (517 mg, 1.04 mmol, 1.00 eq) in AcOH (3 mL) was added HBr/AcOH (1 mL, 33% purity). The reaction mixture was stirred at 20° C. for 1.5 h. LC-MS indicated the starting material was consumed completely. The reaction was quenched by $H_2O$ (10 mL) and washed with MTBE (20 mL). The organic phase was extracted with $H_2O$ (20 mL×2), and the aqueous phases were combined and lyophilized to give a crude, which was purified by prep-HPLC ($CH_3CN/H_2O$/TFA) to give two separated diastereomers of N-[(1S)-5-amino-1-(1,3-benzothiazole-2-carbonyl) pentyl]tetrahydrofuran-2-carboxamide trifluoroacetate as yellow solids. Compound 34 (33.78 mg, 71.04 μmol, 6.8% yield) MS m/z=362 (MH$^+$). $^1$H NMR (CD$_3$OD, 400 MHz) d 8.20 (d, J=7.6, 1H), 8.13 (d, J=7.6, 1H), 7.67-7.60 (m, 2H), 5.65 (dd, J=9.2, J=4.0, 1H), 4.37 (dd, J=8.2, J=4.2, 1H), 4.06-4.04 (m, 1H), 3.93-3.90 (m, 1H), 3.00-2.95 (m, 2H), 2.28-2.15 (m, 2H), 1.97-1.81 (m, 4H), 1.77-1.65 (m, 2H), 1.59-1.51 (m, 2H). Compound 35 (41.00 mg, 86.23 μmol, 8.3% yield) MS m/z=362 (MH$^+$). $^1$H NMR (CD$_3$OD, 400 MHz) d 8.21 (dd, J=7.6, 1H), 8.13 (dd, J=7.6, 1H), 7.68-7.60 (m, 2H), 5.71-5.64 (m, 1H), 4.39 (dd, J=8.2, J=5.4, 1H), 4.03 (q, J=7.0, 1H), 3.89 (q, J=7.4, 1H), 3.01-2.95 (m, 2H), 2.30-2.15 (m, 2H), 2.03-1.82 (m, 4H), 1.77-1.65 (m, 2H), 1.61-1.55 (m, 2H).

Example 29. Preparation of N-[(1S)-5-amino-1-(1,3-benzothiazole-2-carbonyl)pentyl]thiazole-5-carboxamide (38)

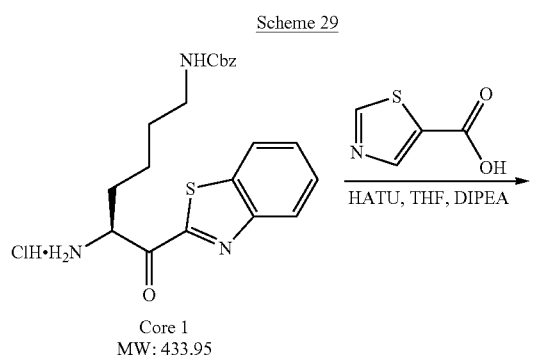

Scheme 29

Core 1
MW: 433.95

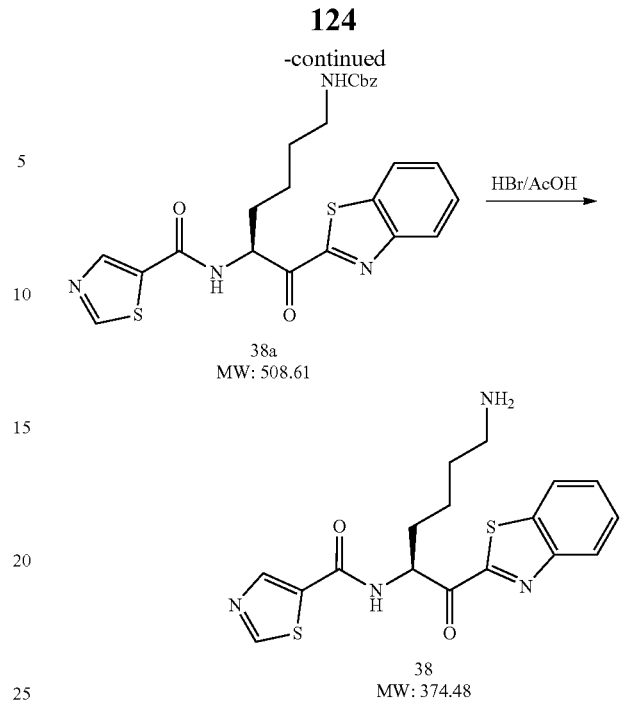

38a
MW: 508.61

38
MW: 374.48

Benzyl-N-[(5S)-6-(1,3-benzothiazol-2-yl)-6-oxo-5-(thiazole-5-carbonylamino)hexyl]carbamate (38a)

To a mixture of thiazole-5-carboxylic acid (107 mg, 829.58 μmol, 1.20 eq) in THF (5 mL) were added HATU (315 mg, 829.58 μmol, 1.20 eq) and DIPEA (268 mg, 2.07 mmol, 3.00 eq) at 0° C., the reaction was stirred at 0° C. for 15 min. Then benzyl-N-[(5S)-5-amino-6-(1,3-benzothiazol-2-yl)-6-oxo-hexyl]carbamate hydrochloride (300 mg, 691.32 μmol, 1.00 eq) was added at 0° C., the reaction mixture was stirred at 20° C. for another 3 h. LC-MS indicated the starting material was consumed completely. The reaction was quenched by $H_2O$ (10 mL), extracted with EA (20 mL×2). The organic layers were combined, washed with saturated brine (20 mL×2) and evaporated to give benzyl-N-[(5S)-6-(1,3-benzothiazol-2-yl)-6-oxo-5-(thiazole-5-carbonylamino)hexyl]carbamate (497 mg, crude) as a red solid.

N-[(1S)-5-amino-1-(1,3-benzothiazole-2-carbonyl) pentyl]thiazole-5-carboxamide (38)

To a solution of benzyl-N-[(5S)-6-(1,3-benzothiazol-2-yl)-6-oxo-5-(thiazole-5-carbonylamino)hexyl]carbamate (497 mg, 977.17 μmol, 1.00 eq) in AcOH (3 mL) was added HBr/AcOH (1 mL, 33% purity) at 0° C. The mixture was stirred at 20° C. for 1 h. LC-MS indicated the reaction completed. $H_2O$ (10 mL) was added, the solution was wash with MTBE (20 mL). The organic phase was extracted with $H_2O$ (20 mL×2) and the aqueous phases were combined and lyophilized to give a residue, which was purified by prep-HPLC ($CH_3CN/H_2O$/TFA), to give N-[(1S)-5-amino-1-(1,3-benzothiazole-2-carbonyl)pentyl]thiazole-5-carboxamide trifluoroacetate (139.46 mg, 285.49 μmol, 29.2% yield, 82.2% ee) as a yellow solid. MS m/z=375.1 (MH$^+$).

Example 30. Preparation of N-[(1S)-5-amino-1-(1,3-benzothiazole-2-carbonyl)pentyl]thiazole-2-carboxamide (39)

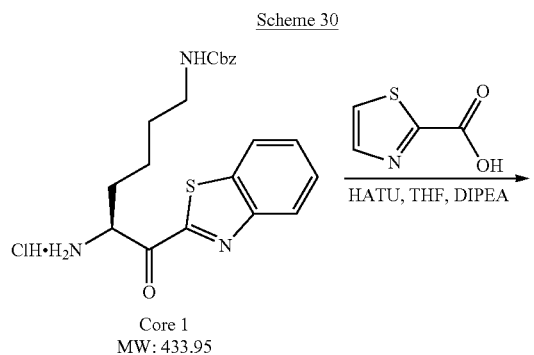

Scheme 30

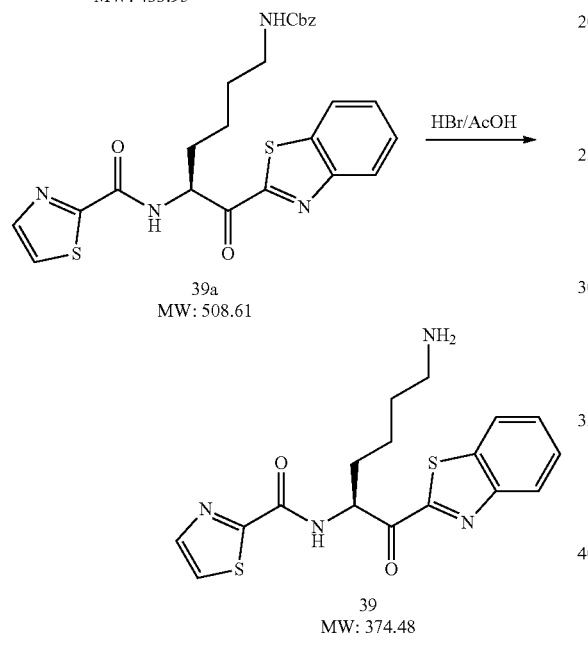

Benzyl-N-[(5S)-6-(1,3-benzothiazol-2-yl)-6-oxo-5-(thiazole-2-carbonylamino)hexyl]carbamate (39a)

To a solution of thiazole-2-carboxylic acid (110 mg, 851.79 µmol, 1.23 eq) in THF (6 mL) were added HATU (390 mg, 1.03 mmol, 1.48 eq) and DIPEA (270 mg, 2.09 mmol, 3.02 eq) under 0° C. After being stirred for 0.5 h under 0° C., benzyl-N-[(5S)-5-amino-6-(1,3-benzothiazol-2-yl)-6-oxo-hexyl]carbamate hydrochloride (300 mg, 691.32 µmol, 1.00 eq, HCl) was added and the resulting mixture was stirred at 28° C. for 14 h. It was diluted with H₂O (10 mL) and extracted with EA (15 mL×2). The organic layers were combined, dried over Na₂SO₄, filtered and concentrated to give benzyl-N-[(5S)-6-(1,3-benzothiazol-2-yl)-6-oxo-5-(thiazole-2-carbonylamino)hexyl]carbamate (510 mg, crude) as a yellow solid. It was used directly for the next step without further purification.

N-[(1S)-5-amino-1-(1,3-benzothiazole-2-carbonyl)pentyl]thiazole-2-carboxamide (39)

To a solution of benzyl-N-[(5S)-6-(1,3-benzothiazol-2-yl)-6-oxo-5-(thiazole-2-carbonylamino)hexyl]carbamate (1.00 mmol, 1.00 eq) (0.51 g, crude) in AcOH (5 mL) was added HBr/AcOH (1.00 mmol, 1.00 eq) (2 mL, 33% purity) under N₂. The reaction mixture was stirred at 28° C. for 1 hr. LC-MS indicated the desired product was detected. The mixture was diluted with H₂O (10 mL) and MeOH (2 mL), washed with MTBE (10 mL×2). The resulting solution was diluted with H₂O (80 mL) and then lyophilized to give a residue, which was purified by prep-HPLC (CH₃CN/H₂O/TFA) to give N-[(1S)-5-amino-1-(1,3-benzothiazole-2-carbonyl) pentyl]thiazole-2-carboxamide trifluoroacetate (20 mg) as a yellow solid. MS m/z=375.0 (MH⁺).

Example 31. Preparation of N-[(1S)-5-amino-1-(1,3-benzothiazole-2-carbonyl)pentyl]-6-oxo-1H-pyridine-2-carboxamide (40)

Scheme 31

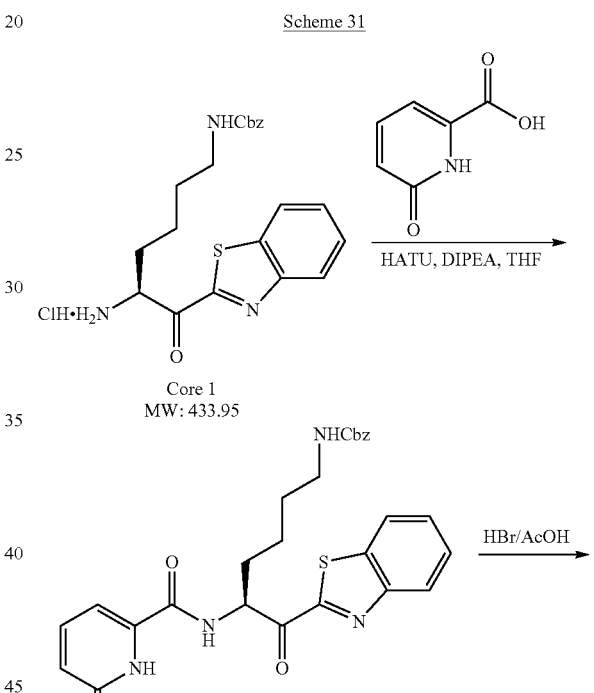

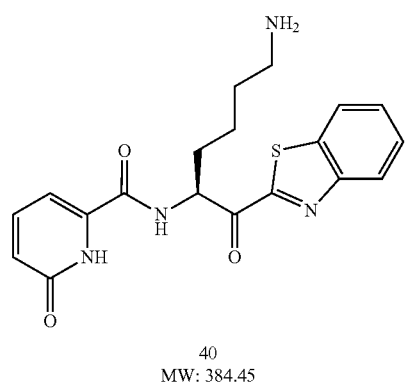

Benzyl-N-[((5S)-6-(1,3-benzothiazol-2-yl)-6-oxo-5-[(6-oxo-1H-pyridine-2-carbonyl)amino]hexyl]-carbamate (40a)

A solution of 6-oxo-1H-pyridine-2-carboxylic acid (115 mg, 829.59 μmol, 1.20 eq), DIPEA (268 mg, 2.07 mmol, 3.00 eq) and HATU (315 mg, 829.58 μmol, 1.20 eq) in THF (3 mL) was stirred at 0° C. for 15 min. Then benzyl-N-[(50292)-5-amino-6-(1,3-benzothiazol-2-yl)-6-oxo-hexyl] carbamate hydrochloride (300 mg, 691.32 μmol, 1.00 eq) was added at 0° C., the resulting mixture was stirred at 25° C. for another 3 h. LC-MS indicated the reaction completed. H₂O (10 mL) was added and extracted with EA (20 mL×2). The combined organic phase was washed with saturated brine (20 mL) and concentrated to give benzyl-N-[(5S)-6-(1,3-benzothiazol-2-yl)-6-oxo-5-[(6-oxo-1H-pyridine-2-carbonyl)amino]hexyl]carbamate (612 mg, crude) as a yellow solid.

N-[(1S)-5-amino-1-(1,3-benzothiazole-2-carbonyl)pentyl]-6-oxo-1H-pyridine-2-carboxamide (40)

To a solution of benzyl-N-[(5S)-6-(1,3-benzothiazol-2-yl)-6-oxo-5-[(6-oxo-1H-pyridine-2-carbonyl)amino]hexyl] carbamate (612 mg, 1.18 mmol, 1.00 eq) in AcOH (3 mL) was added HBr/AcOH (1 mL, 33% purity) at 0° C. The reaction mixture was stirred at 20° C. for 1 h. LC-MS indicated the desired compound was detected. The reaction was quenched by H₂O (10 mL), washed with MTBE (20 mL). The organic phase was extracted with H₂O (20 mL×2) and the aqueous phases were combined and lyophilized to give crude product, which was purified by prep-HPLC (CH₃CN/H₂O/TFA) to give N-[(1S)-5-amino-1-(1,3-benzothiazole-2-carbonyl)pentyl]-6-oxo-1H-pyridine-2-carboxamide trifluoroacetate (51.45 mg, 103.22 μmol, 80.4% yield, 74.1% ee) as a yellow solid. MS m/z=385.1 (MH⁺).

Example 32. Preparation of (S)—N-(6-amino-1-(benzo[d]thiazol-2-yl)-1-oxohexan-2-yl)-1-methoxycyclohexanecarboxamide (41)

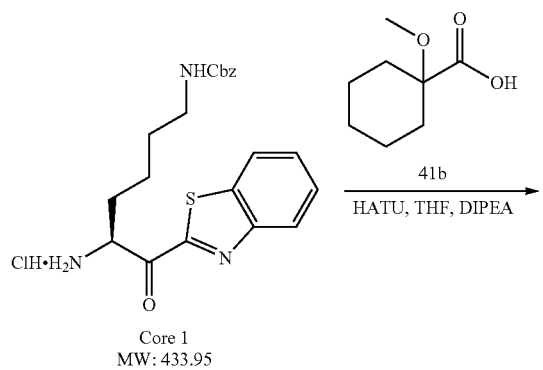

Scheme 32

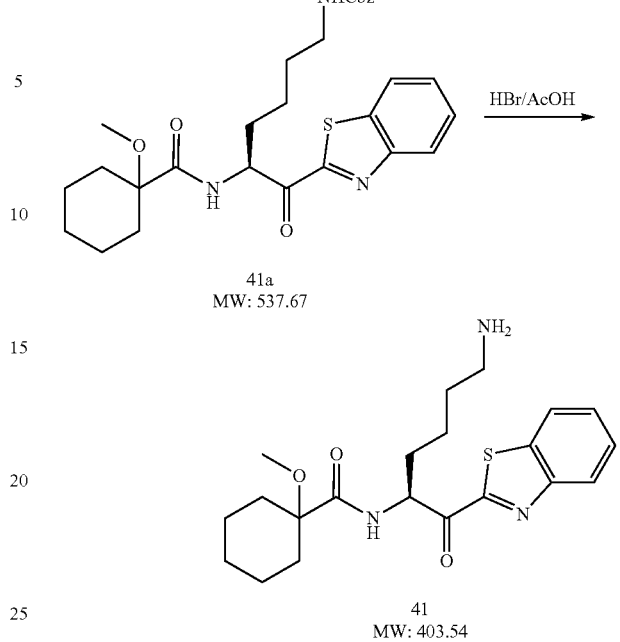

1-methoxycyclohexanecarboxylic Acid (41b)

To a solution of cyclohexanone (2.00 g, 20.38 mmol, 1.00 eq) in CHCl3 (2.43 g, 20.38 mmol, 1.00 eq) (10 mL) was added a solution of KOH (10.00 g, 178.22 mmol, 8.74 eq) in MeOH (10 mL) at 0-5° C. The resulting mixture was stirred at 23° C. for 3 hr. The suspension was filtered and the filtrate was concentrated to give a crude, which was diluted with H₂O (20 mL) and extracted with EA (20 mL×2). Then the aqueous layer was adjusted to pH=5-6 with HCl (1 M). The resulting solution was extracted with DCM (40 mL×2). The organic layers were combined, dried over Na₂SO₄, filtered and concentrated to give 1-methoxycyclohexanecarboxylic acid (1.21 g, 7.65 mmol, 37.53% yield) as a yellow oil.

Benzyl-N-[(5S)-6-(1,3-benzothiazol-2-yl)-5-[(1-methoxycyclohexanecarbonyl)amino]-6-oxo-hexyl] carbamate (41a)

To a solution of 1-methoxycyclohexanecarboxylic acid (164 mg, 1.04 mmol, 1.50 eq) in THF (6 mL) were added HATU (390 mg, 1.03 mmol, 1.48 eq) and DIPEA (300 mg, 2.32 mmol, 3.36 eq) under 0° C. After being stirred for 0.5 h under 0° C., benzyl-N-[(5S)-5-amino-6-(1,3-benzothiazol-2-yl)-6-oxo-hexyl]carbamate hydrochloride (300 mg, 691.32 μmol, 1.00 eq) was added and the resulting mixture was stirred at 20° C. for 14 h. It was diluted with H₂O (10 mL) and extracted with EA (15 mL×2). The organic layers were combined, dried over Na₂SO₄, filtered and concentrated to give benzyl-N-[(5S)-6-(1,3-benzothiazol-2-yl)-5-[(1-methoxycyclo-hexanecarbonyl)amino]-6-oxo-hexyl] carbamate (830 mg, crude) as a yellow solid. It was used directly for the next step without further purification.

(S)—N-(6-amino-1-(benzo[d]thiazol-2-yl)-1-oxohexan-2-yl)-1-methoxycyclohexanecarboxamide (41)

To a solution of benzyl-N-[(5S)-6-(1,3-benzothiazol-2-yl)-5-[(1-methoxycyclohexanecarbonyl) amino]-6-oxohexyl]carbamate (1.00 eq) (0.83 g, crude) in AcOH (5 mL) was added HBr/AcOH (1.00 eq) (1.5 mL, 33% purity) under $N_2$. The reaction mixture was stirred at 18° C. for 1 hr. The mixture was diluted with $H_2O$ (100 mL) and washed with MBTE (40 mL). The aqueous layer was lyophilized to give a residue, which was purified by prep-HPLC ($CH_3CN/H_2O$/TFA) to give a solution. The solution was lyophilized to give N-[(1S)-5-amino-1-(1,3-benzothiazole-2-carbonyl)pentyl]-1-methoxycyclohexanecarboxamide trifluoroacetate (55 mg, 106.27 µmol) as a light yellow solid. MS m/z=404.2 ($MH^+$).

Example 33. Preparation of N-[(1S)-5-amino-1-(thiazole-2-carbonyl)pentyl]cyclopentanecarboxamide (42)

Scheme 33

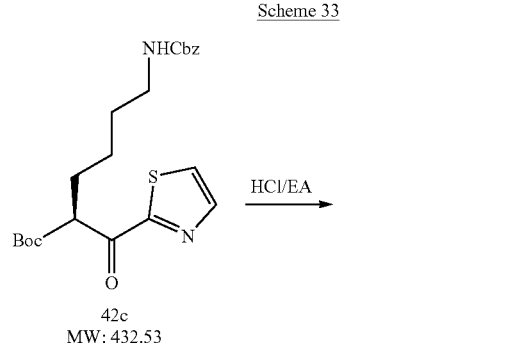

42c
MW: 432.53

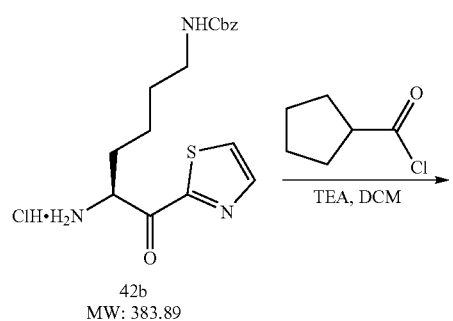

42b
MW: 383.89

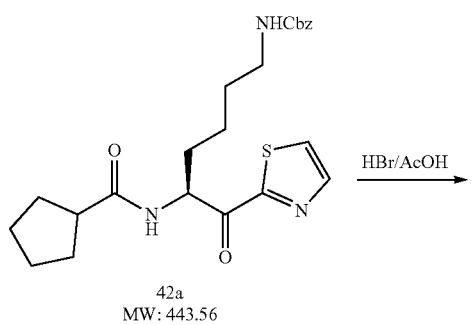

42a
MW: 443.56

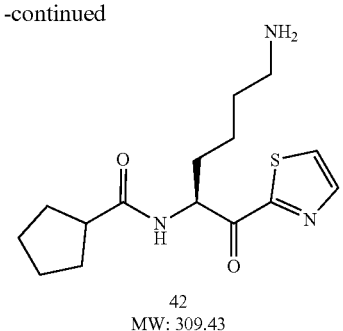

42
MW: 309.43

Benzyl-N-[(5S)-5-amino-6-oxo-6-thiazol-2-yl-hexyl] carbamate (42b)

To a solution of tert-butyl-N-[(1S)-5-(benzyloxycarbonylamino)-1-(thiazole-2-carbonyl)pentyl]carbamate (300 mg, 670.32 µmol, 1.00 eq) in EA (10 mL) was added HCl/EA (4 M, 2 mL, 11.93 eq). The reaction mixture was stirred at 10° C. for 14 hr. LC-MS indicated the starting material was still remained and the desired product was detected. HCl/EA (4 M, 2.00 mL, 11.93 eq) was added. Then the reaction mixture was stirred at 10° C. for another 4 hr. TLC (PE:EA=3:1) indicated the starting material was consumed completely. It was concentrated to give benzyl-N-[(5S)-5-amino-6-oxo-6-thiazol-2-yl-hexyl]carbamate hydrochloride (310 mg, crude, HCl) as a brown solid. It was used directly for next step without further purification.

Benzyl-N-[(5S)-5-amino-6-oxo-6-thiazol-2-yl-hexyl] carbamate (42a)

To a solution of benzyl-N-[(5S)-5-amino-6-oxo-6-thiazol-2-yl-hexyl]carbamate hydrochloride (300 mg, 781.47 µmol, 1.00 eq, HCl) in DCM (10 mL) was added TEA (240 mg, 2.37 mmol, 3.04 eq) and cyclopentanecarbonyl chloride (130 mg, 980.47 µmol, 1.25 eq). The reaction mixture was stirred at 10° C. for 3 hr. LC-MS indicated the starting material was consumed and the major was desired product. The solution was washed with $H_2O$ (15 mL×2). The aqueous layer was extracted with DCM (20 mL×2). The organic layers were combined, washed with sat. brine (100 mL), dried over $Na_2SO_4$, filtered and concentrated to give a crude. The crude was purified by column chromatography (PE:EA=4:1 to 2:1) to give benzyl-N-[(5S)-5-(cyclopentanecarbonylamino)-6-oxo-6-thiazol-2-yl-hexyl]carbamate (230 mg, 482.23 µmol, 61.7% yield, 93% purity) as a yellow solid.

N-[(1S)-5-amino-1-(thiazole-2-carbonyl)pentyl]cyclopentanecarboxamide (42)

To a solution of benzyl-N-[(5S)-5-(cyclopentanecarbonylamino)-6-oxo-6-thiazol-2-yl-hexyl]carbamate (210 mg, 473.44 µmol, 1.00 eq) in AcOH (5 mL) was added HBr/AcOH (2 mL, 33% purity) under $N_2$. The reaction mixture was stirred at 15° C. for 1 hr. LC-MS indicated the starting material was remained and the desired product was detected. The mixture was stirred at 15° C. for another 1 hr. LC-MS indicated the starting material was still remained and the desired product was detected. The mixture was deionized water (20 mL) and MeOH (2 mL), washed with MTBE (20 mL×2). The resulting solution was diluted with deionized water (80 mL) and then lyophilized to give a residue, which was adjusted to pH=7-8 with sat. aq. NaHCO₃. The resulting solution was diluted with deionized water (80 mL) and then lyophilized again to give a residue, which was purified by prep-HPLC (CH₃CN/H₂O/TFA) to give N-[(1S)-5-amino-1-(thiazole-2-carbonyl)pentyl]cyclopentanecarboxamide trifluoroacetate (53 mg) as a yellow solid. MS m/z=304.2 (MH⁺).

Example 34. Preparation of N-[(1S)-5-amino-1-[2-(2,3,5,6-tetrafluorophenoxy)acetyl]-pentyl]cyclopentanecarboxamide (43)

Scheme 34

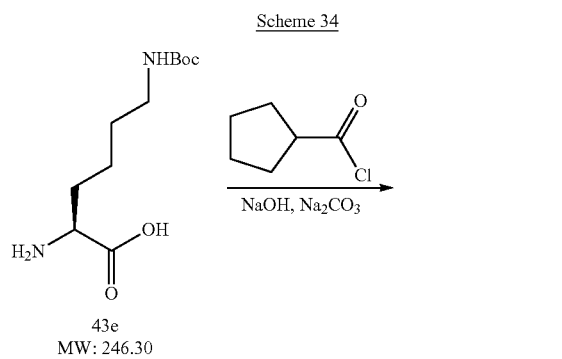

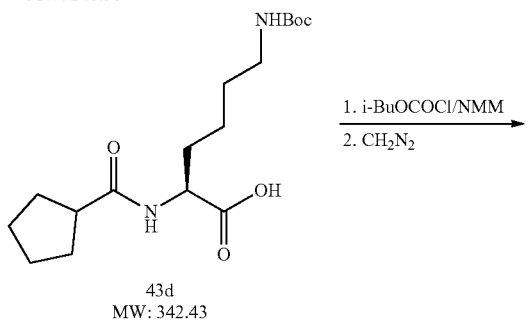

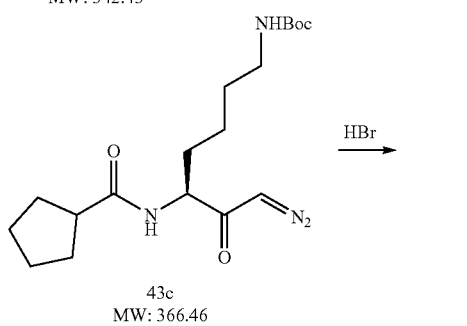

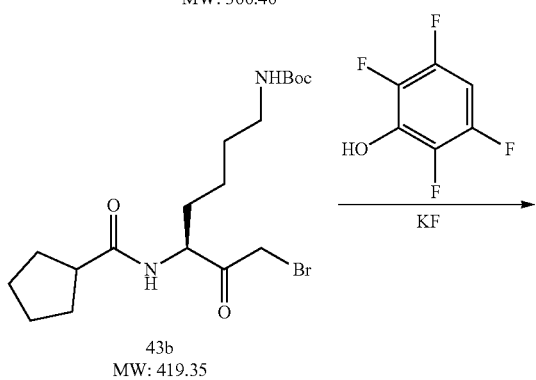

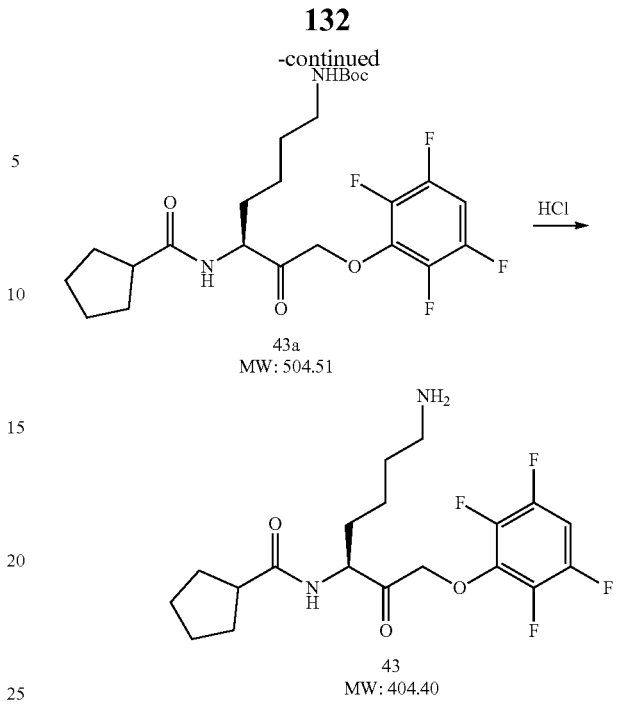

(2S)-6-(tert-butoxycarbonylamino)-2-(cyclopentanecarbonylamino)hexanoic Acid (43d)

To a solution of (2S)-2-amino-6-(tert-butoxycarbonylamino)hexanoic acid (5.00 g, 20.30 mmol, 1.00 eq) in H₂O (40 mL) were added NaOH (820 mg, 20.50 mmol, 1.01 eq) and Na₂CO₃ (2.58 g, 24.36 mmol, 1.20 eq). After being stirred for 10 min, it was cooled to 0° C. and cyclopentanecarbonyl chloride (2.96 g, 22.33 mmol, 1.10 eq) in EA (20 mL) was added under 0° C. The reaction mixture was stirred at 10° C. for 14 h. EA was removed and then solution was cooled to 0° C., the pH was adjusted to 6-7 with solid KHSO₄. The suspension was filtered and the filter cake was washed with PE (60 mL) and dried in vacuo to give (2S)-6-(tert-butoxycarbonylamino)-2-(cyclopentanecarbonylamino)hexanoic acid (4.50 g, crude) as a white solid.

Tert-butyl-N-[(5S)-5-(cyclopentanecarbonylamino)-7-diazo-6-oxo-heptyl]carbamate (43c)

To a solution of (2S)-6-(tert-butoxycarbonylamino)-2-(cyclopentane-carbonylamino)hexanoic acid (2.00 g, 5.84 mmol, 1.00 eq) in THF (20 mL) was added isobutyl chloroformate (798 mg, 5.84 mmol, 1.00 eq) and NMM (591 mg, 5.84 mmol, 1.00 eq). The mixture was stirred at −20° C. for 2 h under N₂. Then diazomethane (491 mg, 11.68 mmol, 2.00 eq) was added. The mixture was stirred at 0° C. for 10 h. The mixture was diluted with H₂O (20 mL), extracted with EA (20 mL×3). The organic layers were combined, dried over Na₂SO₄, filtered and concentrated under reduced pressure to give a residue, which was purified by silica gel chromatography (PE/EA=1/1) to give tert-butyl-N-[(5S)-5-(cyclopentanecarbonylamino)-7-diazo-6-oxo-heptyl]carbamate (2.00 g, 5.46 mmol, 93.4% yield) as a yellow solid.

Tert-butyl-N-[(5S)-7-bromo-5-(cyclopentanecarbonylamino)-6-oxoheptyl]carbamate (43b)

To a solution of tert-butyl-N-[(5S)-5-(cyclopentanecarbonylamino)-7-diazo-6-oxo-heptyl]carbamate (1.00 g, 2.73 mmol, 1.00 eq) in EA (20 mL) was added HBr/AcOH (Purity: 33%, 1 mL). The mixture was stirred at −20° C. for 10 min under $N_2$ and then basified with sat. $NaHCO_3$ till pH=8, extracted with EA (20 mL×3). The organic layers were combined, dried over $Na_2SO_4$, filtered and concentrated to give tert-butyl-N-[(5S)-7-bromo-5-(cyclopentanecarbonylamino)-6-oxoheptyl]carbamate (1.10 g, 2.62 mmol, 96.08% yield) as a yellow solid.

Tert-butyl-N-[(5S)-5-(cyclopentanecarbonylamino)-6-oxo-7-(2,3,5,6-tetrafluorophenoxy)heptyl]carbamate (43a)

To a solution of tert-butyl-N-[(5S)-7-bromo-5-(cyclopentanecarbonylamino)-6-oxo-heptyl]carbamate (1.10 g, 2.62 mmol, 1.00 eq) in DMF (20 mL) was added 2,3,5,6-tetrafluorophenol (523 mg, 3.15 mmol, 1.20 eq) and KF (457 mg, 7.87 mmol, 3.00 eq). The reaction mixture was stirred at 20° C. for 3 h. The mixture was diluted with $H_2O$ (50 mL) and extracted with EA (40 mL×3). The organic layers were combined, washed with brine (50 mL×5), dried over $Na_2SO_4$, filtered and concentrated under reduced pressure. The residue was purified by silica gel chromatography (PE/EA=4/1) to give tert-butyl-N-[(5S)-5-(cyclopentanecarbonylamino)-6-oxo-7-(2,3,5,6-tetrafluorophenoxy)heptyl]carbamate (1.10 g, 2.18 mmol, 83.2% yield) as a white solid.

N-[(1S)-5-amino-1-[2-(2,3,5,6-tetrafluorophenoxy)acetyl]pentyl]cyclopentanecarboxamide (43)

To a solution of tert-butyl-N-[(5S)-5-(cyclopentanecarbonylamino)-6-oxo-7-(2,3,5,6-tetrafluorophenoxy)heptyl]carbamate (500 mg, 991.06 μmol, 1.00 eq) in EA (10 mL) was added HCl/EA (4 M, 5 mL, 20.18 eq). The mixture was stirred at 20° C. for 1 h. The mixture was diluted with $H_2O$ (20 mL), the aqueous layer was separated and lyophilized to give N-[(1S)-5-amino-1-[2-(2,3,5,6-tetrafluorophenoxy)acetyl]pentyl]cyclopentanecarboxamide hydrochloride (280 mg, 635.12 μmol, 64.1% yield) as a white solid. MS m/z=405 (MH$^+$). $^1$H NMR ((CD$_3$)$_2$SO, 400 MHz) d 8.38 (d, J=7.2, 1H), 8.05 (bs, 3H), 7.58 (ddd, J=4.5, J=8.3, J=15.5, 1H), 5.25 (d, J=17.6, 1H), 5.18 (d, J=17.6, 1H), 4.29 (ddd, J=2.4, J=4.6, J=10.6, 1H), 2.77-2.64 (m, 3H), 1.78-1.24 (m, 14H).

Example 35. Preparation of N-[(1S)-5-amino-1-(pyridine-2-carbonyl)pentyl]cyclopentanecarboxamide (44)

Scheme 35

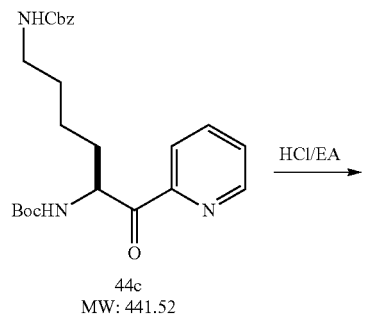

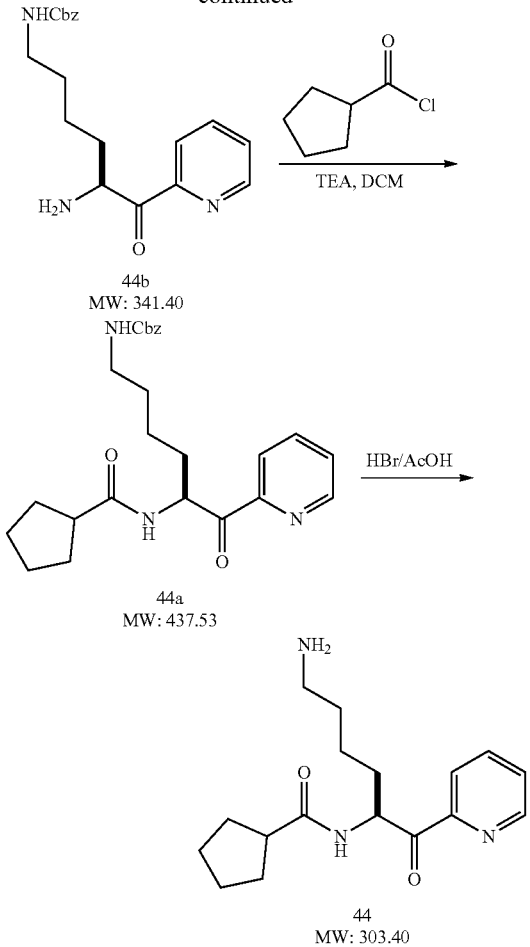

Benzyl-N-[(5S)-5-amino-6-oxo-6-(2-pyridyl)hexyl]carbamate (44b)

To a solution of tert-butyl-N-[(1S)-5-(benzyloxycarbonylamino)-1-(pyridine-2-carbonyl)pentyl]carbamate (480 mg, 1.09 mmol, 1.00 eq) in EA (10 mL) was added HCl/EA (4 M, 4 mL, 14.68 eq). The reaction mixture was stirred at 10° C. for 14 hr. LC-MS indicated the starting material was consumed completely and the desired product was detected. It was concentrated to give benzyl-N-[(5S)-5-amino-6-oxo-6-(2-pyridyl)hexyl]carbamate hydrochloride (400 mg, crude) as a yellow solid. It was used directly for next step without further purification.

Benzyl-N-[(5S)-5-(cyclopentanecarbonylamino)-6-oxo-6-(2-pyridyl)-hexyl]carbamate (44a)

To a solution of benzyl-N-[(5S)-5-amino-6-oxo-6-(2-pyridyl)hexyl]carbamate hydrochloride (400 mg, 1.06 mmol, 1.00 eq) in DCM (10 mL) was added TEA (320 mg, 3.16 mmol, 2.98 eq) and cyclopentanecarbonyl chloride (160 mg, 1.21 mmol, 1.14 eq). The reaction mixture was stirred at 10° C. for 3 hr. LC-MS indicated the starting material was consumed and the major was the desired product. The solution was washed with $H_2O$ (15 mL×2). The aqueous layer was extracted with DCM (20 mL×2). The organic layers were combined, washed with sat. brine (100 mL), dried over $Na_2SO_4$, filtered and concentrated to give a crude, which was purified by column chromatography (PE:EA=4:1 to 2:1) to give benzyl-N-[(5S)-5-(cyclopentanecarbonylamino)-6-oxo-6-(2-pyridyl)hexyl]carbamate (250 mg, 571.39 μmol, 53.9% yield) as a light yellow solid.

N-[(1S)-5-amino-1-(pyridine-2-carbonyl)pentyl]cyclopentanecarboxamide (44)

To a solution of benzyl-N-[(5S)-5-(cyclopentanecarbonylamino)-6-oxo-6-(2-pyridyl) hexyl]carbamate (230 mg, 525.68 μmol, 1.00 eq) in AcOH (5 mL) was added HBr/AcOH (2 mL, 33% purity) under N₂. The reaction mixture was stirred at 15° C. for 1 hr. LC-MS indicated the starting material was still remained and the desired product was detected. The reaction mixture was stirred at 15° C. for another 1 hr. LC-MS indicated the starting material was still remained and the desired product was detected. The mixture was diluted with deionized water (20 mL) and MeOH (2 mL), washed with MTBE (20 mL×2). The resulting solution was diluted with deionized water (80 mL) and then lyophilized to give a residue, which was adjusted to pH=7-8 with sat. aq. NaHCO₃. The resulting solution was diluted with deionized water (80 mL) and then lyophilized again to give a residue. A part of crude was purified by prep-HPLC (CH₃CN/H₂O/NH₃.H₂O) to give the desired product but it contained cyclized product. Other part of crude was purified by prep-HPLC (CH₃CN/H₂O/TFA) to N-[(1S)-5-amino-1-(pyridine-2-carbonyl)pentyl]cyclopentanecarboxamide trifluoroacetate (56 mg) as a yellow solid. MS m/z=304.2 (MH⁺).

Example 36. Preparation of N-[(1S)-5-amino-1-[2-(2,3,5,6-tetrafluorophenoxy)acetyl]-pentyl]-3-azido-benzamide (45)

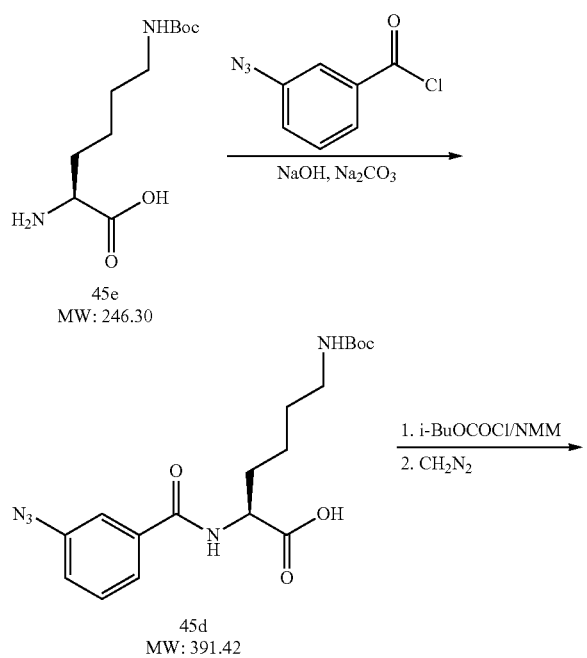

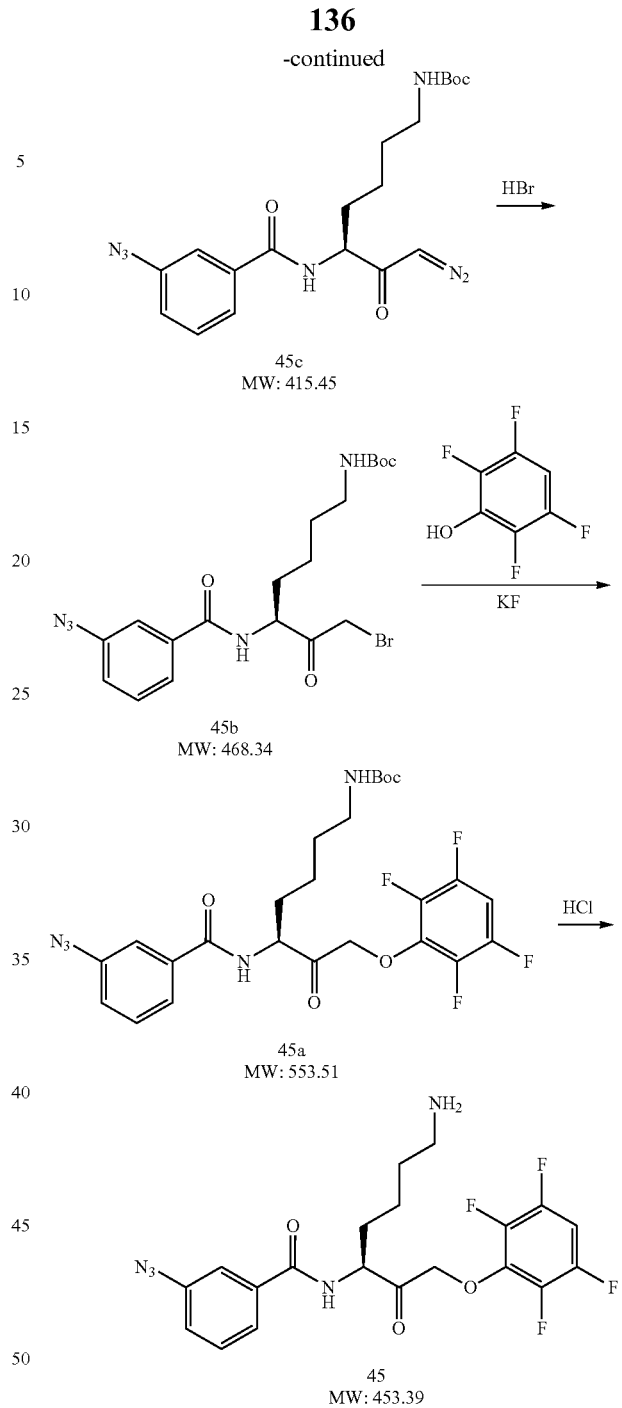

(2S)-2-[(3-azidobenzoyl)amino]-6-(tertbutoxycarbonylamino)hexanoic acid (45d). To a solution of (2S)-2-amino-6-(tert-butoxycarbonylamino)hexanoic acid (10.00 g, 40.60 mmol, 1.00 eq) in EA/H₂O (1/1, 200 mL) were added NaOH (1.62 g, 40.60 mmol, 1.00 eq), Na₂CO₃ (4.30 g, 40.60 mmol, 1.00 eq) and 3-azidobenzoyl chloride (7.37 g, 40.60 mmol, 1.00 eq). The mixture was stirred at 20° C. for 4 h. The mixture was acidified with KHSO₄ till pH=4, concentrated under reduced pressure. The residue was purified by silica gel chromatography eluted with DCM/MeOH=10/1 to give (2S)-2-[(3-azidobenzoyl)amino]-6-(tertbutoxycarbonylamino) hexanoic acid (10.00 g, 25.55 mmol, 62.9% yield) as a yellow solid.

Tert-butyl-N-[(5S)-5-[(3-azidobenzoyl)amino]-7-diazo-6-oxo-heptyl]carbamate (45c)

To a solution of (2S)-2-[(3-azidobenzoyl)amino]-6-(tert-butoxycarbonylamino)hexanoic acid (3.50 g, 8.94 mmol, 1.00 eq) in THF (50 mL) was added NMM (904 mg, 8.94 mmol, 1.00 eq) and isobutyl chloroformate (1.22 g, 8.94 mmol, 1.00 eq). The mixture was stirred at −20° C. for 1 h under $N_2$. Then diazomethane (376 mg, 8.94 mmol, 1.00 eq) was added. The mixture was stirred at −20° C. for 4 h under $N_2$. The mixture was diluted with $H_2O$ (50 mL), extracted with EA (50 mL×3). The organic layers were combined, dried over $Na_2SO_4$, filtered and concentrated under reduced pressure. The residue was purified by silica gel chromatography eluted with PE/EA=1/1 to give tert-butyl-N-[(5S)-5-[(3-azidobenzoyl)amino]-7-diazo-6-oxo-heptyl]carbamate (2.90 g, 6.98 mmol, 78.1% yield) as yellow solid.

Tert-butyl-N-[(5S)-5-[(3-azidobenzoyl)amino]-7-bromo-6-oxo-heptyl]-carbamate (45b)

To a solution of (3-azidobenzoyl)-[(1S)-5-(tert-butoxycarbonylamino)-1-(2-diazoacetyl)pentyl]ammonium (2.90 g, 6.96 mmol, 1.00 eq) in EA (50 mL) was added HBr/AcOH (2.56 g, 10.44 mmol, 1.50 eq, Purity: 33%). The mixture was stirred at −20° C. for 10 min. The mixture was diluted with $H_2O$ (50 mL), extracted with EA (50 mL). The organic layer was washed with brine (50 mL×3), dried over $Na_2SO_4$, filtered and concentrated under reduced pressure to give tert-butyl-N-[(5S)-5-[(3-azidobenzoyl)amino]-7-bromo-6-oxo-heptyl]carbamate (2.90 g, crude, Purity: 62.2%) as a yellow solid.

Tert-butyl-N-[(5S)-5-[(3-azidobenzoyl)amino]-6-oxo-7-(2,3,5,6-tetrafluoro-phenoxy)heptyl]carbamate (45a)

To a solution of tert-butyl-N-[(5S)-5-[(3-azidobenzoyl)-amino]-7-bromo-6-oxo-heptyl]carbamate (2.90 g, 6.19 mmol, 1.00 eq) in DMF (20 mL) were added 2,3,5,6-tetrafluorophenol (1.54 g, 9.29 mmol, 1.50 eq) and KF (1.80 g, 30.95 mmol, 5.00 eq). The mixture was stirred at 20° C. for 12 h. The mixture was diluted with $H_2O$ (100 mL), extracted with EA (100 mL). The organic layer was washed with brine (100 mL×5), dried over $Na_2SO_4$, filtered and concentrated under reduced pressure. The residue was purified by silica gel chromatography eluted with PE:EA=4:1 to give tert-butyl-N-[(5S)-5-[(3-azidobenzoyl)amino]-6-oxo-7-(2,3,5,6-tetrafluorophenoxy)heptyl]carbamate (2.80 g, 5.06 mmol, 81.7% yield) as a white solid.

N-[(1S)-5-amino-1-[2-(2,3,5,6-tetrafluorophenoxy)acetyl]pentyl]-3-azido-benzamide (45)

A solution of tert-butyl-N-[(5S)-5-[(3-azidobenzoyl)amino]-6-oxo-7-(2,3,5,6-tetrafluorophenoxy) heptyl]carbamate (2.20 g, 3.97 mmol, 1.00 eq) in HCl/EA (20 mL, 4 M) was stirred at 20° C. for 30 min. The mixture was diluted with $H_2O$ (20 mL), the aqueous layer was lyophilized to give N-[(1S)-5-amino-1-[2-(2,3,5,6-tetrafluorophenoxy)acetyl]pentyl]-3-azido-benzamide as a white solid. MS m/z=454.1 (MH$^+$).

Example 37. Inhibition of Lysine Gingipain by Compounds of the Invention

The capacities of compounds of the present invention to inhibit the activity of lysine gingipain were measured in a fluorogenic assay similar to those described in Barret *Biochemical Journal.* 1980, 187(3), 909. The specific assay conditions were as follows. Buffer: pH=7.5, 100 mM Tris-HCl, 75 mM NaCl, 2.5 mM CaCl2, 10 mM cysteine, 1% DMSO after all additions. Protein: 0.1 nM Kgp, isolated from culture of *Porphyromonas gingivalis*, as described in Pike et al. J. Biol. Chem. 1994, 269(1), 406, and Potempa and Nguyen. *Current Protocols in Protein Scienc.* 2007, 21.20.1-21.20.27. Fluorogenic substrate: 10 uM Z-His-Glu-Lys-MCA. Time=90 minutes. Temperature=37° C. Each compound: 10 concentrations, starting at either 100 uM or 100 nM, with lower concentrations generated by serial 3-fold dilutions. By testing a range of concentrations for each compound, the concentration required to inhibit the activity of lysine gingipain by 50% (the "$IC_{50}$") was determined. Under the described assay conditions, signal-to-noise was excellent, and Z factor was greater than 0.6.

The inhibitory of activity of compounds described herein was tested against Kgp, RgpB, and trypsin. Kgp $IC_{50}$ values for various compounds are set forth in Table 2. Compound 43 exhibited an RgpB $IC_{50}$ value above 475 nM, and the remaining compounds in Table 2 exhibited RgpB $IC_{50}$ values above 2.5 μM. All of the compounds in Table 2 exhibited trypsin $IC_{50}$ values above 1 μM.

TABLE 2

Lysine gingipain inhibitory activity of compounds of the invention.

| Compound No. | Kgp $IC_{50}$ average |
|---|---|
| 1 | +++ |
| 1 | * |
| 2 | ** |
| 2 | *** |
| 3 | ** |
| 4 | *** |
| 7 | * |
| 8 | ** |
| 9 | *** |
| 10 | ** |
| 11 | *** |
| 12 | +++ |
| 13 | * |
| 14 | *** |
| 15 | *** |
| 18 | ** |
| 19 | ** |
| 22 | ** |
| 23 | ++ |
| 24 | *** |
| 25 | * |
| 26 | * |
| 29 | ** |
| 30 | * |
| 31 | ** |
| 32 | *** |
| 33 | *** |
| 34 | *** |
| 35 | *** |
| 38 | ** |
| 39 | +++ |
| 40 | * |
| 41 | ** |
| 42 | +++ |
| 43 | **** |
| 44 | + |

**** $IC_{50}$ ≤ 1 nM
*** 1 nM < $IC_{50}$ ≤ 10 nM
** 10 nM < $IC_{50}$ ≤ 25 nM
* 25 nM < $IC_{50}$ ≤ 50 nM
+++ 50 nM < $IC_{50}$ ≤ 100 nM
++ 100 nM < $IC_{50}$ ≤ 250 nM
++ 250 nM < $IC_{50}$

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method for treating periodontal disease, the method comprising administering to a subject an effective amount of a compound according to Formula I:

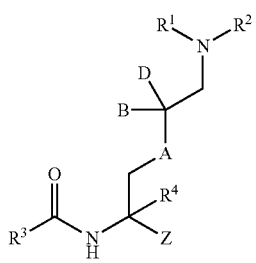

or a pharmaceutically acceptable salt thereof, wherein:
Z is halogen-substituted aryloxymethyl-carbonyl;
A is —CH$_2$—;
B, D, R', and R$^2$ are hydrogen;
R$^3$ is selected from the group consisting of C$_{6-10}$ aryl, 5-to-12 membered heteroaryl, C$_{3-8}$ cycloalkyl, 5-to-12 membered saturated heterocyclyl, and -L-R$^5$, wherein L is selected from the group consisting of —O—, —NR—, C$_{1-4}$ alkylene, and 2- to 4-membered heteroalkylene, wherein R is selected from the group consisting of hydrogen and C$_{1-8}$ alkyl,
R$^5$ is selected from the group consisting of C$_{6-10}$ aryl, 5-to-12 membered heteroaryl, C$_{3-8}$ cycloalkyl, and 5-to-12 membered saturated heterocyclyl,
and wherein R$^3$ is optionally substituted with one or more substituents selected from the group consisting of halo, —CN, —NO$_2$, —N$_3$, —OH, R$^a$, R$^b$, —OR$^a$, —OR$^b$, —(CH$_2$)$_k$C(O)R$^c$, —NR$^d$(CH$_2$)$_u$C(O)R$^c$, —O(CH$_2$)$_u$C(O)R$^c$, —(CH$_2$)$_k$CONR$^d$R$^d$, —(CH$_2$)$_k$NR$^d$C(O)R$^c$, —NR$^d$(CH$_2$)$_u$CONR$^d$R$^d$, —NR$^d$(CH$_2$)$_u$NR$^d$C(O)R$^c$, —O(CH$_2$)$_u$CONR$^d$R$^d$, —O(CH$_2$)$_u$NR$^d$C(O)R$^c$, —(CH$_2$)$_k$S(O)$_2$NR$^d$R$^d$, —(CH$_2$)$_k$NR$^d$S(O)$_2$R$^c$, —(CH$_2$)$_k$S(O)$_2$R$^c$, —(CH$_2$)$_k$S(O)R$^c$, —(CH$_2$)$_k$SR$^d$, —NR$^d$(CH$_2$)$_n$S(O)$_2$NR$^d$R$^d$, —NR$^d$(CH$_2$)$_n$NR$^d$ S(O)$_2$ R$^c$, —NR$^d$(CH$_2$)$_u$S(O)$_2$R$^c$, —NR$^d$(CH$_2$)$_u$S(O)R$^c$, —NR$^d$(CH$_2$)$_u$SR$^d$, —O(CH$_2$)$_u$S(O)$_2$NR$^d$R$^d$, —O(CH$_2$)$_u$NR$^d$S(O)$_2$R$^c$, —O(CH$_2$)$_u$S(O)$_2$R$^c$, —O(CH$_2$)$_u$S(O)R$^c$, and —O(CH$_2$)$_u$SR$^c$, wherein:
each R$^a$ is independently selected from the group consisting of C$_{1-4}$ alkyl and C$_{1-4}$ haloalkyl,
each R$^b$ is independently selected from the group consisting of C$_{3-6}$ cycloalkyl, C$_{3-6}$ halocycloalkyl, C$_{6-10}$ aryl, 5-to-12 membered heteroaryl, and 5-to-12 membered saturated heterocyclyl,
each R$^c$ is independently selected from the group consisting of —OH, C$_{1-8}$ alkyl, C$_{1-8}$ haloalkyl, C$_{3-8}$ cycloalkyl, C$_{3-8}$ halocycloalkyl, C$_{6-10}$ aryl, (C$_{6-10}$ aryl)-(C$_{1-8}$ alkyl), 5-to-12 membered heteroaryl, and 5-to-12 membered saturated heterocyclyl,
each R$^d$ is independently selected from the group consisting of hydrogen and C$_{1-8}$ alkyl, each subscript k is independently selected from 0, 1, 2, 3, 4, 5, and 6, and
each subscript u is independently selected from 1, 2, 3, 4, 5, and 6; and
R$^4$ is selected from the group consisting of hydrogen, halogen, C$_{1-4}$ alkyl, C$_{1-4}$ alkoxy, C$_{1-4}$ haloalkyl, and C$_{1-4}$ haloalkoxy;
provided that when A is —CH$_2$—, and B and D are hydrogen, then R$^3$ is other than (2-phenyl)ethyl or substituted (2-phenyl)ethyl.

2. The method of claim 1, wherein Z is halogen-substituted phenoxymethyl carbonyl.

3. The method of claim 1, wherein R$^3$ is selected from the group consisting of cyclohexyl, cyclopentyl, morpholino, phenyl, piperidinyl, pyridinyl, tetrahydrofuranyl, tetrahydropyranyl, 1,2,3,4-tetrahydronaphthyl, and thiazolyl, each of which is optionally substituted with 1-3 members selected from the group consisting of methyl, methoxy, trifluoromethyl, acetyl, and —N$_3$.

4. The method of claim 1, wherein the compound is a compound according to Formula Id:

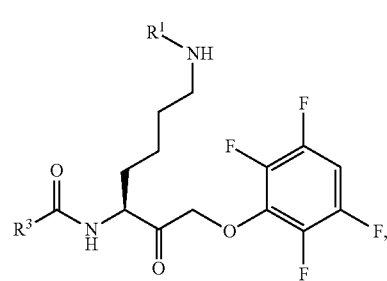

or a pharmaceutically acceptable salt thereof,
wherein R$^3$ is selected from the group consisting of C$_{6-10}$ aryl, 5-to-12 membered heteroaryl, C$_{3-8}$ cycloalkyl, 5-to-12 membered saturated heterocyclyl, and -L-R$^5$,
wherein L is C$_{1-4}$ alkylene.

5. The method of claim 4, wherein
R$^3$ is selected from the group consisting of cyclohexyl, cyclopentyl, morpholino, phenyl, piperidinyl, pyridinyl, tetrahydrofuranyl, tetrahydropyranyl, 1,2,3,4-tetrahydronaphthyl, and thiazolyl,
each of which is optionally substituted with 1-3 members selected from the group consisting of methyl, methoxy, trifluoromethyl, acetyl, and —N$_3$.

6. The method of claim 1, wherein the compound is selected from the group consisting of:

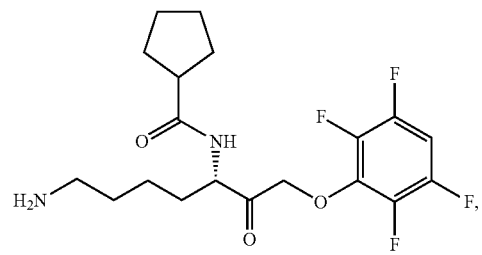

-continued

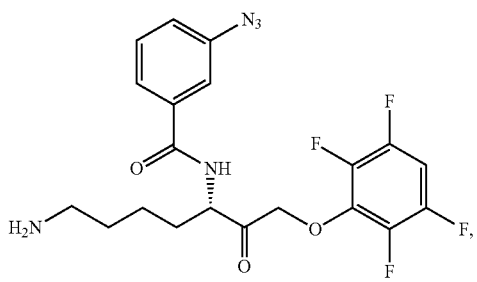

and pharmaceutically acceptable salts thereof.

7. The method of claim 1, wherein the compound is selected from the group consisting of:

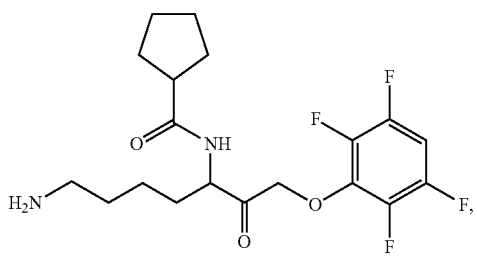

-continued

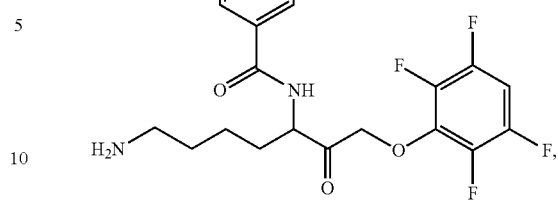

and pharmaceutically acceptable salts thereof.

8. The method of claim 1, wherein $R^4$ is selected from the group consisting of $C_{1-4}$ alkyl and $C_{1-4}$ haloalkyl.

9. The method of claim 8, wherein the compound is

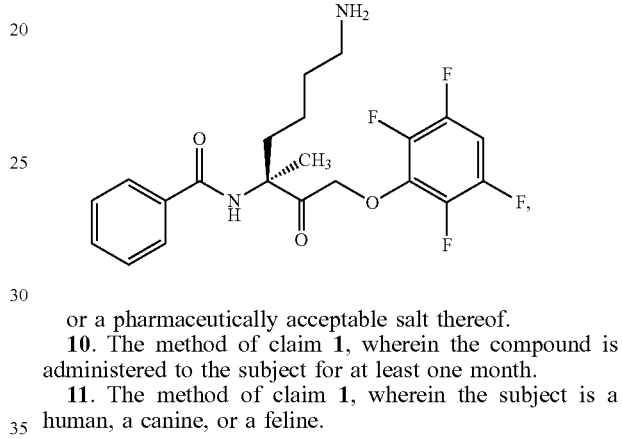

or a pharmaceutically acceptable salt thereof.

10. The method of claim 1, wherein the compound is administered to the subject for at least one month.

11. The method of claim 1, wherein the subject is a human, a canine, or a feline.

* * * * *